US010485806B2

(12) United States Patent
Kerns et al.

(10) Patent No.: US 10,485,806 B2
(45) Date of Patent: Nov. 26, 2019

(54) NRF2 REGULATORS

(71) Applicants: GlaxoSmithKline Intellectual Property Development Limited, Brentford, Middlesex (GB); Astex Therapeutics, Limited, Cambridgeshire (GB)

(72) Inventors: Jeffrey K. Kerns, King of Prussia, PA (US); James Francis Callahan, King of Prussia, PA (US); Hongxing Yan, King of Prussia, PA (US); Thomas Daniel Heightman, Hertfordshire (GB); Jeffrey Charles Boehm, King of Prussia, PA (US); Alison Jo-Anne Woolford, Cambridgeshire (GB)

(73) Assignees: GlaxoSmithKline Intellectual Property Development Limited, Brentford, Middlesex (GB); Astex Therapeutics Limited, Cambridgeshire (GB)

( * ) Notice: Subject to any disclaimer, the term of this patent is extended or adjusted under 35 U.S.C. 154(b) by 0 days.

(21) Appl. No.: 16/375,047

(22) Filed: Apr. 4, 2019

(65) Prior Publication Data
US 2019/0224212 A1    Jul. 25, 2019

Related U.S. Application Data

(63) Continuation of application No. 15/735,977, filed as application No. PCT/IB2016/053545 on Jun. 15, 2016, now Pat. No. 10,272,095.

(60) Provisional application No. 62/175,505, filed on Jun. 15, 2015.

(51) Int. Cl.
| A61K 31/5513 | (2006.01) |
| A61K 31/421  | (2006.01) |
| A61K 31/403  | (2006.01) |
| A61P 11/00   | (2006.01) |
| C07D 403/06  | (2006.01) |
| C07D 413/06  | (2006.01) |
| C07D 413/10  | (2006.01) |
| C07D 267/14  | (2006.01) |
| C07D 498/04  | (2006.01) |
| C07D 519/00  | (2006.01) |

(52) U.S. Cl.
CPC ........ *A61K 31/5513* (2013.01); *A61K 31/403* (2013.01); *A61K 31/421* (2013.01); *A61P 11/00* (2018.01); *C07D 267/14* (2013.01); *C07D 403/06* (2013.01); *C07D 413/06* (2013.01); *C07D 413/10* (2013.01); *C07D 498/04* (2013.01); *C07D 519/00* (2013.01)

(58) Field of Classification Search
CPC .............. A61K 31/5513; A61K 31/403; A61K 31/421; A61P 11/00; C07D 267/14; C07D 403/06; C07D 413/06; C07D 413/10; C07D 498/04; C07D 519/00

USPC ......................................................... 514/411
See application file for complete search history.

(56) References Cited

U.S. PATENT DOCUMENTS

| 2003/0191115 A1 | 10/2003 | Pinto et al. |
| 2004/0157919 A1 | 8/2004  | Wu et al. |
| 2011/0136246 A1 | 6/2011  | Shibata et al. |
| 2015/0018422 A1 | 1/2015  | Miwatashi et al. |

FOREIGN PATENT DOCUMENTS

| EP | 528586 B1        | 2/1995  |
| EP | 0478328 B1       | 1/1996  |
| RU | 2486253 C2       | 6/2013  |
| WO | WO 1993012075 A1 | 6/1993  |
| WO | WO 1995032710 A1 | 12/1995 |
| WO | WO 2001025181 A1 | 4/2001  |
| WO | WO 2001053267 A1 | 7/2001  |
| WO | WO 2002059080 A2 | 8/2002  |
| WO | WO 2002080899 A1 | 10/2002 |
| WO | WO 2002100812 A1 | 12/2002 |
| WO | WO 2003026652 A1 | 4/2003  |
| WO | WO 2004007464 A1 | 1/2004  |
| WO | WO 2004092140 A1 | 10/2004 |
| WO | WO 2006044133 A1 | 4/2006  |
| WO | WO 2006118320 A1 | 11/2006 |
| WO | WO 2008002490 A2 | 1/2008  |
| WO | WO 2009032249 A1 | 3/2009  |
| WO | WO 2010/010672 A1| 1/2010  |
| WO | WO 2010005922 A1 | 1/2010  |
| WO | WO 2010099054 A2 | 9/2010  |
| WO | WO 2011097300 A1 | 8/2011  |
| WO | WO 2012068589 A2 | 5/2012  |
| WO | WO 2013067036 A1 | 5/2013  |
| WO | WO 2013122028 A1 | 8/2013  |
| WO | WO 2013155528 A2 | 10/2013 |
| WO | WO 2014145642 A2 | 9/2014  |
| WO | WO 2015/092713 A1| 6/2015  |
| WO | WO 2015/135091 A1| 9/2015  |
| WO | WO 2015/138220 A1| 9/2015  |

(Continued)

OTHER PUBLICATIONS

TG Davies, et al, "Journal of Medicinal Chemistry Paper—Monoacidic Inhibitors of the Kelch-like ECH-Associated Protein 1: Nuclear Factor Erythroid 2—Related Factor 2 (KEAP1:NRF2) Protein-Protein Interaction with High Cell Potency Identified by Fragment-Based discovery." J Med Chem. Apr. 28, 2016;59(8):3991-4006.

*Primary Examiner* — Kristin A Vajda
(74) *Attorney, Agent, or Firm* — Nora L. Stein; Fang Qian; Edward R. Gimmi

(57) ABSTRACT

The present invention relates to aryl analogs, pharmaceutical compositions containing them and their use as NRF2 regulators.

10 Claims, No Drawings

(56) References Cited

FOREIGN PATENT DOCUMENTS

| WO | WO2016/202253 | 12/2016 |
| WO | WO2016/203400 | 12/2016 |
| WO | WO 2016/203401 A1 | 12/2016 |
| WO | WO2017/060854 | 4/2017 |
| WO | WO2017/060855 | 4/2017 |
| WO | WO 2018/104766 | 6/2018 |
| WO | WO 2018/109643 | 6/2018 |
| WO | WO 2018/109647 | 6/2018 |
| WO | WO 2018/109648 A1 | 6/2018 |

NRF2 REGULATORS

This application is a continuation of application Ser. No. 15/735,977, filed 13 Dec. 2017, which is a 371 national phase entry of PCT/IB2016/053545, filed 15 Jun. 2016, which claims priority from U.S. provisional application 62/175,505, filed 15 Jun. 2015.

FIELD OF THE INVENTION

The present invention relates to aryl analogs, pharmaceutical compositions containing them and their use as NRF2 regulators.

BACKGROUND OF THE INVENTION

NRF2 (NF-E2 related factor 2) is a member of the cap-n-collar (CNC) family of transcription factors containing a characteristic basic-leucine zipper motif. Under basal conditions, NRF2 levels are tightly controlled by the cytosolic actin-bound repressor, KEAP1 (Kelch-like ECH associating protein 1), which binds to NRF2 and targets it for ubiquitylation and proteasomal degradation via the Cul3-based E3-ubiquitin ligase complex. Under conditions of oxidative stress, DJ1 (PARK7) is activated and stabilizes NRF2 protein by preventing NRF2 from interacting with KEAP1. Also, modification of reactive cysteines on KEAP1 can cause a conformational change in KEAP1 that alters NRF2 binding and promotes NRF2 stabilization. Thus, the levels of NRF2 in the cytosol are low in normal conditions but the system is designed to respond immediately to environmental stress by increasing NRF2 activity.

Inappropriately low NRF2 activity in the face of on-going oxidative stress appears to be a pathological mechanism underlying chronic obstructive pulmonary disease (COPD). This may be a result of an altered equilibrium between NRF2 regulators with both inappropriate lack of positive regulators such as DJ1, and overabundance of negative regulators such as Keap1 and Bach1. Therefore, restoration of NRF2 activity in the lungs of COPD patients should result in repair of the imbalance and mitigation of deleterious processes such as apoptosis of structural cells (including alveolar epithelial and endothelial cells) and inflammation. The results of these effects would be enhanced cytoprotection, preservation of lung structure, and structural repair in the COPD lung, thus slowing disease progression. Therefore, NRF2 modulators may treat COPD (Boutten, A., et al. 2011, *Trends Mol. Med.* 17:363-371) and other respiratory diseases, including asthma and pulmonary fibrosis (Cho, H. Y., and Kleeberger, S. R. 2010, *Toxicol. Appl. Pharmacol.* 244:43-56).

An example of inappropriately low NRF2 activity is found in pulmonary macrophages from COPD patients. These cells have impaired bacterial phagocytosis compared with similar cells from control patients, and this effect is reversed by the addition of NRF2 activators in vitro. Therefore, in addition to the effects mentioned above, restoration of appropriate NRF2 activity could also rescue COPD exacerbations by reducing lung infections. This is demonstrated by the NRF2 activator, Sulforaphane, which increases the expression of Macrophage Receptor with Collagenous structure (MARCO) by COPD macrophages and alveolar macrophages from cigarette smoke-exposed mice, thereby improving in these cells bacterial phagocytosis (*Pseudomonas aeruginosa*, non-typable *Haemophilus influenzae*) and bacterial clearance both ex vivo and in vivo. (Harvey, C. J., et al. 2011. *Sci. Transl. Med.* 3:78ra32).

The therapeutic potential of targeting NRF2 in the lung is not limited to COPD. Rather, targeting the NRF2 pathway could provide treatments for other human lung and respiratory diseases that exhibit oxidative stress components such as chronic and acute asthma, lung disease secondary to environmental exposures including but not limited to ozone, diesel exhaust and occupational exposures, fibrosis, acute lung infection (e.g., viral (Noah, T. L. et al. 2014. PLoS ONE 9(6): e98671), bacterial or fungal), chronic lung infection, al antitrypsin disease, and cystic fibrosis (C F, Chen, J. et al. 2008. *PLoS One,* 2008; 3(10):e3367).

A therapy that targets the NRF2 pathway also has many potential uses outside the lung and respiratory system. Many of the diseases for which an NRF2 activator may be useful are autoimmune diseases (psoriasis, IBD, MS), suggesting that an NRF2 activator may be useful in autoimmune diseases in general.

In the clinic, a drug targeting the NRF2 pathway (bardoxolone methyl) has shown efficacy in diabetic patients with diabetic nephropathy/chronic kidney disease (CKD) (Aleksunes, L. M., et al. 2010. *J. Pharmacol. Exp. Ther.* 335:2-12), though phase III trials with this drug in patients with the most severe stage of CKD were terminated. Furthermore, there is evidence to suspect that such a therapy would be effective in sepsis-induced acute kidney injury, other acute kidney injury (AKI) (Shelton, L. M., et al. 2013. *Kidney International,* June 19. doi: 10.1038/ki.2013.248.), and kidney disease or malfunction seen during kidney transplantation.

In the cardiac area, bardoxolone methyl is currently under investigation in patients with Pulmonary Arterial Hypertension and so a drug targeting NRF2 by other mechanisms may also be useful in this disease. Also, it may be useful in a variety of cardiovascular diseases including but not limited to atherosclerosis, hypertension, and heart failure (Oxidative Medicine and Cellular Longevity Volume 2013 (2013), Article ID 104308, 10 pages).

A drug activating the NRF2 pathway could also be useful for treatment of several neurodegenerative diseases including Parkinson's disease (PD), Alzheimer's disease (AD), amyotrophic lateral sclerosis (ALS) (Brain Res. 2012 Mar. 29; 1446:109-18. 2011.12.064. Epub 2012 Jan. 12.) and multiple sclerosis (MS). Multiple in vivo models have shown that NRF2 KO mice are more sensitive to neurotoxic insults than their wild-type counterparts. Treatment of rats with the NRF2 activator tert-butylhydroquinone (tBHQ) reduced cortical damage in rats in a cerebral ischemia-reperfusion model, and cortical glutathione levels were increased in NRF2 wild-type but not KO mice after administration of tBHQ (Shih, A. Y., et al. 2005, *J. Neurosci.* 25: 10321-10335). Tecfidera™ (dimethyl fumarate), which activates NRF2 among other targets, is approved in the U.S. to treat relapsing-remitting multiple sclerosis (MS). Activation of NRF2 may also help treat cases of Friedreich's Ataxia, where increased sensitivity to oxidative stress and impaired NRF2 activation has been reported (Paupe V., et al, 2009. PLoS One; 4(1):e4253.

There is preclinical evidence of the specific protective role of the NRF2 pathway in models of inflammatory bowel disease (IBD, Crohn's Disease and Ulcerative Colitis) and/or colon cancer (Khor, T. O., et al 2008. *Cancer Prev. Res.* (Phila) 1:187-191).

Age-related macular degeneration (AMD) is a common cause of vision loss in people over the age of 50. Cigarette smoking is a major risk factor for the development of non-neovascular (dry) AMD and perhaps also neovascular (wet) AMD. Findings in vitro and in preclinical species support the notion that the NRF2 pathway is involved in the anti-oxidant response of retinal epithelial cells and modulation of inflammation in pre-clinical models of eye injury (Schimel, et al. 2011. *Am. J. Pathol.* 178:2032-2043). Fuchs Endothelial Corneal Dystrophy (FECD) is a progressive, blinding disease characterized by corneal endothelial cells apoptosis. It is a disease of aging and increased oxidative stress related to low levels of NRF2 expression and/or function (Bitar, M. S., et al. 2012. *Invest Ophthalmol. Vis. Sci.*, Aug. 24, 2012 vol. 53 no. 9 5806-5813). In addition, an NRF2 activator may be useful in uveitis or other inflammatory eye conditions.

Non-alcoholic steatohepatitis (NASH) is a disease of fat deposition, inflammation, and damage in the liver that occurs in patients who drink little or no alcohol. In pre-clinical models, development of NASH is greatly accelerated in KO mice lacking NRF2 when challenged with a methionine- and choline-deficient diet (Chowdhry S., et al. 2010. *Free Rad. Biol. & Med.* 48:357-371). Administration of the NRF2 activators oltipraz and NK-252 in rats on a choline-deficient L-amino acid-defined diet significantly attenuated progression of histologic abnormalities, especially hepatic fibrosis (Shimozono R. et al. 2012, *Molecular Pharmacology.* 84:62-70). Other liver diseases that may be amenable to NRF2 modulation are toxin-induced liver disease (e.g., acetaminophen-induced hepatic disease), viral hepatitis, and cirrhosis (Oxidative Medicine and Cellular Longevity Volume 2013 (2013), Article ID 763257, 9 page).

Recent studies have also begun to elucidate the role of ROS in skin diseases such as psoriasis. A study in psoriasis patients showed an increase in serum malondialdehyde and nitric oxide end products and a decrease in erythrocyte-superoxide dismutase activity, catalase activity, and total antioxidant status that correlated in each case with disease severity index (Dipali P. K., et al. Indian J Clin Biochem. 2010 October; 25(4): 388-392). Also, an NRF2 modulator may be useful in treating the dermatitis/topical effects of radiation (Schäfer, M. et al. 2010, *Genes & Devl.* 24:1045-1058), and the immunosuppression due to radiation exposure (Kim J H et al, J. Clin. Invest. 2014 Feb. 3; 124(2): 730-41).

There are also data suggesting that an NRF2 activator may be beneficial in preeclampsia, a disease that occurs in 2-5% of pregnancies and involves hypertension and proteinuria (Annals of Anatomy—Anatomischer Anzeiger Volume 196, Issue 5, September 2014, Pages 268-277).

Preclinical data has shown that compounds with NRF2 activating activity are better at reversing high altitude-induced damage than compounds without NRF2 activity, using animal and cellular models of Acute Mountain Sickness (Lisk C. et al, 2013, Free Radic Biol Med. October 2013; 63: 264-273.)

SUMMARY OF THE INVENTION

In one aspect this invention provides for aryl analogs, pharmaceutically acceptable salts thereof, and pharmaceutical compositions containing them.

In a second aspect, this invention provides for the use of the compounds of Formulas (I) and (II) as NRF2 regulators.

In another aspect, this invention provides for the use of the compounds of Formulas (I) and (II) for treating and preventing conditions associated with NRF2 imbalance.

In one aspect, the invention is provides a pharmaceutical composition comprising a compound of the invention according to Formulas (I) and (II), or a pharmaceutically acceptable salt thereof, and a pharmaceutically acceptable excipient. Particularly, this invention is directed to a pharmaceutical composition for the treatment of an NRF2 regulated disease or disorder, wherein the composition comprises a compound according to Formula (I) or Formula (II), or a pharmaceutically acceptable salt thereof, and a pharmaceutically acceptable excipient.

In a further aspect, this invention provides for a method of treating respiratory and non-respiratory disorders, including COPD, asthma, fibrosis, chronic and acute asthma, lung disease secondary to environmental exposures, acute lung infection, chronic lung infection, al antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness, which comprises administering to a human in need thereof, a compound of Formula (I) or Formula (II).

In yet another aspect, this invention provides for the use of the compounds of Formulas (I) and (II) for the treatment of respiratory and non-respiratory disorders, including COPD, asthma, fibrosis, chronic and acute asthma, lung disease secondary to environmental exposures, acute lung infection, chronic lung infection, al antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

In a further aspect, this invention relates to use of a compound of Formulas (I) and (II) or a pharmaceutically acceptable salt thereof in the manufacture of a medicament for the treatment of respiratory and non-respiratory disorders, including COPD, asthma, fibrosis, chronic and acute asthma, lung disease secondary to environmental exposures, acute lung infection, chronic lung infection, al antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

In a further aspect, this invention relates to a compound of Formulas (I) and (II) or a pharmaceutically acceptable salt thereof, for use in medical therapy.

In a further aspect, this invention relates to a compound of Formulas (I) and (II) or a pharmaceutically acceptable salt thereof, for use in the treatment of respiratory and non-respiratory disorders, including COPD, asthma, fibrosis, chronic and acute asthma, lung disease secondary to environmental exposures, acute lung infection, chronic lung infection, a1 antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

In a further aspect, this invention relates to the use of a compound of Formula (I) or Formula (II) for the treatment of COPD.

In a further aspect, this invention relates to use of a compound of Formula (I) or Formula (II) or a pharmaceutically acceptable salt thereof in the manufacture of a medicament for the treatment of COPD.

In a further aspect, this invention relates to a compound of Formulas (I) and (II) or a pharmaceutically acceptable salt thereof, for use in the treatment COPD.

In a further aspect, this invention relates to a method of treating COPD which comprises administering to a human in need thereof, a compound of Formula (I) or Formula (II).

In a further aspect, this invention relates to the use of a compound of Formula (I) or Formula (II) for the treatment of heart failure.

In a further aspect, this invention relates to a method of treating heart failure which comprises administering to a human in need thereof, a compound of Formula (I) or Formula (II).

In a further aspect, this invention relates to use of a compound of Formula (I) or Formula (II) or a pharmaceutically acceptable salt thereof in the manufacture of a medicament for the treatment of heart failure.

In a further aspect, this invention relates to a compound of Formula (I) or Formula (II) or a pharmaceutically acceptable salt thereof, for use in the treatment of heart failure.

The compounds of Formulas (I) and (II) and pharmaceutically acceptable salts thereof may be used in combination with one or more other agents which may be useful in the prevention or treatment of allergic disease, inflammatory disease, autoimmune disease, for example; antigen immunotherapy, anti-histamines, corticosteroids, (e.g., fluticasone propionate, fluticasone furoate, beclomethasone dipropionate, budesonide, ciclesonide, mometasone furoate, triamcinolone, flunisolide), NSAIDs, leukotriene modulators (e.g., montelukast, zafirlukast, pranlukast), iNOS inhibitors, tryptase inhibitors, IKK2 inhibitors, p38 inhibitors, Syk inhibitors, protease inhibitors such as elastase inhibitors, integrin antagonists (e.g., beta-2 integrin antagonists), adenosine A2a agonists, mediator release inhibitors such as sodium chromoglycate, 5-lipoxygenase inhibitors (zyflo), DP1 antagonists, DP2 antagonists, PI3K delta inhibitors, ITK inhibitors, LP (lysophosphatidic) inhibitors or FLAP (5-lipoxygenase activating protein) inhibitors (e.g. sodium 3-(3-(tert-butylthio)-1-(4-(6-ethoxypyridin-3-yl)benzyl)-5-((5-methylpyridin-2-yl)methoxy)-1H-indol-2-yl)-2,2-dimethylpropanoate), bronchodilators (e.g., muscarinic antagonists, beta-2 agonists), methotrexate, and similar agents; monoclonal antibody therapy such as anti-IgE, anti-TNF, anti-IL-5, anti-IL-6, anti-IL-12, anti-IL-1 and similar agents; cytokine receptor therapies e.g. etanercept and similar agents; antigen non-specific immunotherapies (e.g. interferon or other cytokines/chemokines, chemokine receptor modulators such as CCR3, CCR4 or CXCR2 antagonists, other cytokine/chemokine agonists or antagonists, TLR agonists and similar agents).

The compounds may also be used in combination with agents for aiding transplantation including Cyclosporines, Tacrolimus, Mycophenolate mofetil, Prednisone, Azathioprine, Sirolimus, Daclizumab, Basiliximab, or OKT3.

They may also be used in combination with agents for Diabetes: metformin (biguanides), meglitinides, sulfonylureas, DPP-4 inhibitors, Thiazolidinediones, Alpha-glucosidase inhibitors, Amylin mimetics, Incretin mimetics, and insulin.

The compounds may be used in combination with antihypertensives such as diuretics, ACE inhibitors, ARBS, calcium channel blockers, and beta blockers.

In one embodiment, the invention is directed to the use of a compound of Formula (I) or Formula (II), or a pharmaceutically acceptable salt thereof, as an active therapeutic substance. More specifically, this invention provides for the use of the compounds described herein for the treatment of a respiratory and non-respiratory disorder, specifically, a disease or disorder recited herein. Accordingly, the invention provides for the use of a compound of Formula (I) or Formula (II), or a pharmaceutically acceptable salt thereof, as an active therapeutic substance in the treatment of a human in need thereof with a respiratory and non-respiratory disorder, specifically, a disease or disorder recited herein. Specifically, the invention provides for the use of a compound of Formula (I) or Formula (II), or a pharmaceutically acceptable salt thereof, as an active therapeutic substance in the treatment of COPD.

In one embodiment, the invention is directed to a compound described herein, or a pharmaceutically acceptable salt thereof, in the manufacture of a medicament for treatment of a respiratory and non-respiratory disorder, for example the diseases and disorders recited herein. The invention further provides for the use of a compound of Formula (I) or Formula (II), or a pharmaceutically acceptable salt thereof, in the manufacture of a medicament for use in the treatment of a respiratory and non-respiratory disorder, for example the diseases and disorders recited herein. Specifically, the invention further provides for the use of a compound of Formula (I) or Formula (II), or a pharmaceutically acceptable salt thereof, in the manufacture of a medicament for use in the treatment of COPD.

Other aspects and advantages of the present invention are described further in the following detailed description of the preferred embodiments thereof.

DETAILED DESCRIPTION OF THE INVENTION

The present invention provides for compounds of Formulas (I) and (II):

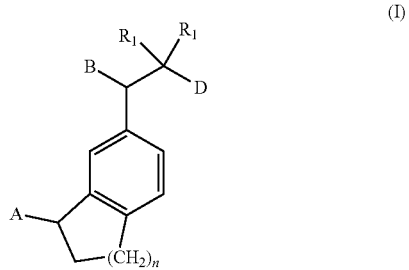

(I)

wherein:
B is benzotriazolyl, phenyl, triazolopyridinyl, or —(CH$_2$)$_2$ triazolyl each of which may be unsubstituted or substituted by 1, 2, or 3 substituents independently chosen from —C$_{1-3}$alkyl, —O—C$_{1-3}$alkyl, CN, —(CH$_2$)$_2$—O—(CH$_2$)$_2$—OR$_4$ and halo;
D is —C(O)OH, —C(O)NHSO$_2$CH$_3$, —SO$_2$NHC(O)CH$_3$, 5-(trifluoromethyl)-4H-1,2,4-triazol-2-yl, or tetrazolyl;
R$_1$ is independently hydrogen, C$_{1-3}$ alkyl, F, C$_{3-6}$spirocycloalkyl, oxetane, or the two R$_1$ groups together with the carbon to which they are attached form a cyclopropyl group; R$_4$ is hydrogen or C$_{1-3}$ alkyl;
A is tetrahydrobenzoxazepinyl, tetrahydrobenzazepinyl, tetrahydroimidazodiazepinyl, or tetrahydro-pyrido-oxazepinyl, all of which may be unsubstituted or substituted by 1, 2, or 3 substituents independently chosen from —C$_{1-3}$ alkyl, halo, CN, —OC$_{1-3}$alkyl, —CH$_2$—O—CH$_3$, C$_{3-6}$spirocycloalkyl, and OH;
n is 1 or 2;
or a pharmaceutically acceptable salt thereof.

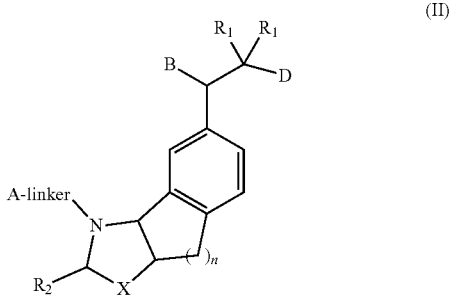

(II)

wherein:
B is benzotriazolyl, phenyl, triazolopyridinyl, or —(CH$_2$)$_2$ triazolyl each of which may be unsubstituted or substituted by 1, 2, or 3 substituents independently chosen from —C$_{1-3}$-alkyl, —O—C$_{1-3}$alkyl, CN, —(CH$_2$)$_2$—O—(CH$_2$)$_2$—OR$_4$ and halo;
D is —C(O)OH, —C(O)NHSO$_2$CH$_3$, —SO$_2$NHC(O)CH$_3$, 5-(trifluoromethyl)-4H-1,2,4-triazol-2-yl, or tetrazolyl;

R$_1$ is independently hydrogen, C$_{1-3}$ alkyl, F, C$_{3-6}$spirocycloalkyl, oxetane, or the two R$_1$ groups together with the carbon to which they are attached form a cyclopropyl group;
R$_2$ is =O or hydrogen;
R$_4$ is hydrogen or —C$_{1-3}$alkyl;
Linker is —CH$_2$—, —O—C(O)—, —CH$_2$—C(O)—, —C(O)—, —CH(CH$_3$)—C(O)—, or —N(CH$_3$)—C(O)—;
A is cyclohexyl, cyclopentyl, phenyl or decahydronapthalenyl; all of which may be unsubstituted or independently substituted by C$_{1-3}$ alkyl, CN, and halo;
or A is C$_{4-5}$ alkyl which may be substituted by —OC$_{1-3}$ alkyl;
n is 1 or 2;
X is CH$_2$ or O;
or a pharmaceutically acceptable salt thereof.

"Alkyl" refers to a monovalent saturated hydrocarbon chain having the specified number of carbon member atoms. For example, C$_{1-4}$ alkyl refers to an alkyl group having from 1 to 4 carbon member atoms. Alkyl groups may be straight or branched. Representative branched alkyl groups have one, two, or three branches. Alkyl includes methyl, ethyl, propyl, (n-propyl and isopropyl), and butyl (n-butyl, isobutyl, s-butyl, and t-butyl).

"C$_{3-6}$ spirocycloalkyl" refers to spiro-cyclopropyl, spiro-cyclobutyl, spiro-cyclopentane and spiro-cyclohexane.

When used herein, the terms 'halogen' and 'halo' include fluorine, chlorine, bromine and iodine, and fluoro, chloro, bromo, and iodo, respectively.

"Substituted" in reference to a group indicates that one or more hydrogen atom attached to a member atom within the group is replaced with a substituent selected from the group of defined substituents. It should be understood that the term "substituted" includes the implicit provision that such substitution be in accordance with the permitted valence of the substituted atom and the substituent and that the substitution results in a stable compound (i.e. one that does not spontaneously undergo transformation such as by rearrangement, cyclization, or elimination and that is sufficiently robust to survive isolation from a reaction mixture). When it is stated that a group may contain one or more substituents, one or more (as appropriate) member atoms within the group may be substituted. In addition, a single member atom within the group may be substituted with more than one substituent as long as such substitution is in accordance with the permitted valence of the atom. Suitable substituents are defined herein for each substituted or optionally substituted group.

The term "independently" means that where more than one substituent is selected from a number of possible substituents, those substituents may be the same or different. That is, each substituent is separately selected from the entire group of recited possible substituents.

The invention also includes various isomers of the compounds of Formulas (I) and (II) and mixtures thereof. "Isomer" refers to compounds that have the same composition and molecular weight but differ in physical and/or chemical properties. The structural difference may be in constitution (geometric isomers) or in the ability to rotate the plane of polarized light (stereoisomers). The compounds according to Formula (I) or Formula (II) contain one or more asymmetric centers, also referred to as chiral centers, and may, therefore, exist as individual enantiomers, diastereomers, or other stereoisomeric forms, or as mixtures thereof. All such isomeric forms are included within the present invention, including mixtures thereof.

Chiral centers may also be present in a substituent such as an alkyl group. Where the stereochemistry of a chiral center present in Formulas (I) and (II), or in any chemical structure illustrated herein, is not specified the structure is intended to encompass any stereoisomer and all mixtures thereof. Thus, compounds according to Formulas (I) and (II) containing one or more chiral centers may be used as racemic mixtures, enantiomerically enriched mixtures, or as enantiomerically pure individual stereoisomers.

Individual stereoisomers of a compound according to Formulas (I) and (II) which contain one or more asymmetric centers may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

As used herein, "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

The skilled artisan will appreciate that pharmaceutically acceptable salts of the compounds according to Formulas (I) and (II) may be prepared. These pharmaceutically acceptable salts may be prepared in situ during the final isolation and purification of the compound, or by separately treating the purified compound in its free acid or free base form with a suitable base or acid, respectively.

In certain embodiments, compounds according to Formulas (I) and (II) may contain an acidic functional group and are, therefore, capable of forming pharmaceutically acceptable base addition salts by treatment with a suitable base. Examples of such bases include a) hydroxides, carbonates, and bicarbonates of sodium, potassium, lithium, calcium, magnesium, aluminum, and zinc; and b) primary, secondary, and tertiary amines including aliphatic amines, aromatic amines, aliphatic diamines, and hydroxy alkylamines such as methylamine, ethylamine, 2-hydroxyethylamine, diethylamine, triethylamine, ethylenediamine, ethanolamine, diethanolamine, and cyclohexylamine.

In certain embodiments, compounds according to Formulas (I) and (II) may contain a basic functional group and are therefore capable of forming pharmaceutically acceptable acid addition salts by treatment with a suitable acid. Suitable acids include pharmaceutically acceptable inorganic acids and organic acids. Representative pharmaceutically acceptable acids include hydrogen chloride, hydrogen bromide, nitric acid, sulfuric acid, sulfonic acid, phosphoric acid, acetic acid, hydroxyacetic acid, phenylacetic acid, propionic acid, butyric acid, valeric acid, maleic acid, acrylic acid, fumaric acid, succinic acid, malic acid, malonic acid, tartaric acid, citric acid, salicylic acid, benzoic acid, tannic acid, formic acid, stearic acid, lactic acid, ascorbic acid, methylsulfonic acid, p-toluenesulfonic acid, oleic acid, lauric acid, and the like.

As used herein, the term "a compound of Formula (I) or (II)" or "the compound of Formula (I) or (II)" refers to one or more compounds according to Formula (I) or (II). The compound of Formula (I) or (II) may exist in solid or liquid form. In the solid state, it may exist in crystalline or noncrystalline form, or as a mixture thereof. The skilled artisan will appreciate that pharmaceutically acceptable solvates may be formed from crystalline compounds wherein solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The subject invention also includes isotopically-labelled compounds, which are identical to those recited in Formulas (I) and (II) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{36}$Cl, $^{123}$I and $^{125}$I.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^{18}$F isotopes are particularly useful in PET (positron emission tomography), and $^{125}$I isotopes are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of Formulas (I) and (II) and following of this invention can generally be prepared by carrying out the procedures disclosed in the Schemes and/or in the Examples below, by substituting a readily available isotopically labeled reagent for a non-isotopically labeled reagent.

Representative Embodiments In one embodiment for compounds of Formula (I):
B is benzotriazolyl, phenyl, triazolopyridinyl, or —$(CH_2)_2$ triazolyl each of which may be unsubstituted or substituted by 1, 2, or 3 substituents independently chosen from —$C_{1-3}$alkyl, —O—$C_{1-3}$alkyl, CN, —$(CH_2)_2$—O—$(CH_2)_2$—$OR_4$ and halo;
D is —C(O)OH, —C(O)$NHSO_2CH_3$, —$SO_2$NHC(O)$CH_3$, 5-(trifluoromethyl)-4H-1,2,4-triazol-2-yl, or tetrazolyl;
$R_1$ is independently hydrogen, $C_{1-3}$ alkyl, F, $C_{3-6}$spirocycloalkyl, oxetane, or the two $R_1$ groups together with the carbon to which they are attached form a cyclopropyl group;
$R_4$ is hydrogen or $C_{1-3}$ alkyl;
A is tetrahydrobenzoxazepinyl, tetrahydrobenzazepinyl, tetrahydroimidazodiazepinyl, or tetrahydro-pyrido-oxazepinyl, all of which may be unsubstituted or substituted by 1, 2, or 3 substituents independently chosen from —$C_{1-3}$ alkyl, halo, CN, —$OC_{1-3}$alkyl, —$CH_2$—O—$CH_3$, $C_{3-6}$spirocycloalkyl, and OH; and
n is 1 or 2;
or a pharmaceutically acceptable salt thereof.

In another embodiment for compounds of Formula (I):
B is benzotriazolyl or —$(CH_2)_2$ triazolyl each of which may be unsubstituted or substituted by 1, 2, or 3 substituents independently chosen from —$C_{1-3}$alkyl and halo;
D is —C(O)OH;
$R_1$ is independently hydrogen or methyl or the two R1 groups together with the carbon to which they are attached form a cyclopropyl group;
A is tetrahydrobenzoxazepinyl, tetrahydrobenzazepinyl, or tetrahydro-pyrido-oxazepinyl, all of which may be unsubstituted or substituted by 1, 2, or 3 substituents independently chosen from —$C_{1-3}$ alkyl, halo or CN, or —$OC_{1-3}$alkyl; and
n is 1 or 2;
or a pharmaceutically acceptable salt thereof.

In yet another embodiment for compounds of Formula (I):
B is benzotriazolyl or phenyl each of which may be unsubstituted or substituted by 1, 2, or 3 substituents independently chosen from —$C_{1-3}$alkyl, halo and CN;
D is —C(O)OH;
$R_1$ is independently hydrogen or $C_{1-3}$ alkyl;
A is tetrahydrobenzoxazepinyl, tetrahydrobenzazepinyl, tetrahydroimidazodiazepinyl, or tetrahydro-pyrido-oxazepinyl, all of which may be unsubstituted or substituted by 1, 2, or 3 substituents independently chosen from —$C_{1-3}$ alkyl, halo, CN, —$OC_{1-3}$alkyl, —$CH_2$—O—$CH_3$, $C_{3-6}$spirocycloalkyl, and OH; and
n is 1;
or a pharmaceutically acceptable salt thereof.

In another embodiment for compounds of Formula (I):
B is benzotriazolyl which may be unsubstituted or substituted by 1, 2, or 3 substituents independently chosen from —$C_{1-3}$alkyl;
D is —C(O)OH;
$R_1$ is independently hydrogen or $C_{1-3}$ alkyl;
A is tetrahydrobenzoxazepinyl which may be unsubstituted or substituted by 1, 2, or 3 substituents independently chosen from: —$C_{1-3}$ alkyl, —$OC_{1-3}$alkyl, CN and halo; and
n is 1;
or a pharmaceutically acceptable salt thereof.

In one embodiment for compounds of Formula (II):
B is benzotriazolyl, phenyl, triazolopyridinyl, or —$(CH_2)_2$ triazolyl each of which may be unsubstituted or substituted by 1, 2, or 3 substituents independently chosen from —$C_{1-3}$alkyl, —O—$C_{1-3}$alkyl, CN, —$(CH_2)_2$—O—$(CH_2)_2$—$OR_4$ and halo;
D is —C(O)OH, —C(O)$NHSO_2CH_3$, —$SO_2$NHC(O)$CH_3$, 5-(trifluoromethyl)-4H-1,2,4-triazol-2-yl, or tetrazolyl;
$R_1$ is independently hydrogen, $C_{1-3}$ alkyl, F, $C_{3-6}$spirocycloalkyl, oxetane, or the two $R_1$ groups together with the carbon to which they are attached form a cyclopropyl group;
$R_2$ is =O or hydrogen;
$R_4$ is hydrogen or $C_{1-3}$ alkyl;
Linker is —$CH_2$—, —O—C(O)—, —$CH_2$—C(O)—, —C(O)—, —CH($CH_3$)—C(O)—, or —N($CH_3$)—C(O)—;
A is cyclohexyl, cyclopentyl, phenyl or decahydronapthalenyl; all of which may be unsubstituted or substituted independently by $C_{1-3}$ alkyl, CN, and halo;
or A is $C_{4-5}$ alkyl which may be substituted by —$OC_{1-3}$ alkyl;
n is 1 or 2; and
X is $CH_2$ or O;
or a pharmaceutically acceptable salt thereof.

In another embodiment for compounds of Formula (II):
B is benzotriazolyl or —$(CH_2)_2$ triazolyl each of which may be unsubstituted or substituted by 1, 2, or 3 substituents independently chosen from —$C_{1-3}$alkyl and halo;
D is —C(O)OH;
$R_1$ is independently hydrogen or methyl or the two $R_1$ groups together with the carbon to which they are attached form a cyclopropyl group;
$R_2$ is =O or hydrogen;
Linker is —$CH_2$—, —O—C(O)—, —CH($CH_3$)—C(O)—, or —N($CH_3$)—C(O)—;
A is cyclohexyl or cyclopentyl, each of which may be unsubstituted or independently substituted by $C_{1-3}$ alkyl, CN, and halo;
n is 1; and
X is $CH_2$ or O;
or a pharmaceutically acceptable salt thereof.

In yet another embodiment for compounds of Formula (II):
B is benzotriazolyl or —$(CH_2)_2$ triazolyl each of which may be unsubstituted or substituted by 1, 2, or 3 substituents independently chosen from —$C_{1-3}$alkyl and —O—$C_{1-3}$alkyl;
D is —C(O)OH;
$R_1$ is independently hydrogen;
$R_2$ is hydrogen;
Linker is —$CH_2$—, —O—C(O)—, —$CH_2$—C(O)—;
A is cyclohexyl, phenyl or decahydronapthalenyl; all of which may be unsubstituted or independently substituted by $C_{1-3}$ alkyl, CN, and halo;
or A is $C_{4-5}$ alkyl which may be substituted by —$OC_{1-3}$ alkyl;
n is 1; and
X is $CH_2$;
or a pharmaceutically acceptable salt thereof.

In still another embodiment for compounds of Formula (II):
B is benzotriazolyl or —$(CH_2)_2$ triazolyl each of which may be unsubstituted or substituted by 1, 2, or 3 substituents independently chosen from —$C_{1-3}$alkyl and —O—$C_{1-3}$alkyl;

D is —C(O)OH;
R₁ is independently hydrogen;
R₂ is =O;
Linker is —CH₂—, —O—C(O)—, —CH₂—C(O)—;
A is cyclohexyl, phenyl or decahydronapthalenyl; all of which may be unsubstituted or independently substituted by C$_{1-3}$ alkyl, CN, and halo;
or A is C$_{4-5}$ alkyl which may be substituted by —OC$_{1-3}$ alkyl;
n is 1; and
X is CH₂ or O;
or a pharmaceutically acceptable salt thereof.

It is to be understood that the present invention covers all combinations of particular groups described hereinabove.

Specific examples of compounds of the present invention include the following:

3-(1,4-dimethyl-1H-1,2,3-benzotriazol-5-yl)-3-[1-(3,3-3-[(3aR,8bS)-1-(cyclohexylmethyl)-2-oxo-1H,2H,3H,3aH,4H,8bH-indeno[1,2-b]pyrrol-7-yl]-3-(1,4-dimethyl-1H-1,2,3-benzotriazol-5-yl)propanoic acid;

3-(1,4-dimethyl-1H-1,2,3-benzotriazol-5-yl)-3-{1-[(4-ethylcyclohexyl)methyl]-2-oxo-1H,2H,3H,3aH,4H,8bH-indeno[1,2-b]pyrrol-7-yl}propanoic acid;

3-[(3aR,8bS)-1-(cyclohexylmethyl)-2-oxo-1H,2H,3H,3aH,4H,8bH-indeno[1,2-b]pyrrol-7-yl]-5-(1-ethyl-1H-1,2,3-triazol-4-yl)pentanoic acid;

3-[1-(decahydronaphthalen-2-ylmethyl)-2-oxo-1H,2H,3H,3aH,4H,8bH-indeno[1,2-b]pyrrol-7-yl]-3-(1,4-dimethyl-1H-1,2,3-benzotriazol-5-yl)propanoic acid;

3-(1,4-dimethyl-1H-1,2,3-benzotriazol-5-yl)-3-{2-oxo-1-[(4-propylcyclohexyl) methyl]-1H,2H,3H,3aH,4H,8bH-indeno[1,2-b]pyrrol-7-yl}propanoic acid;

3-{1-[(tert-butoxy)carbonyl]-1H,2H,3H,3aH,4H,8bH-indeno[1,2-b]pyrrol-7-yl}-3-(1,4-dimethyl-1H-1,2,3-benzotriazol-5-yl)propanoic acid;

3-[1-(2-cyclohexylacetyl)-1H,2H,3H,3aH,4H,8bH-indeno[1,2-b]pyrrol-7-yl]-3-(1,4-dimethyl-1H-1,2,3-benzotriazol-5-yl)propanoic acid;

3-(1,4-dimethyl-1H-1,2,3-benzotriazol-5-yl)-3-[1-(2-phenylpropanoyl)-1H,2H,3H,3aH,4H,8bH-indeno[1,2-b]pyrrol-7-yl]propanoic acid;

3-(1,4-dimethyl-1H-1,2,3-benzotriazol-5-yl)-3-[1-(2-phenylpropanoyl)-1H,2H,3H,3aH,4H,8bH-indeno[1,2-b]pyrrol-7-yl]propanoic acid;

3-(1,4-dimethyl-1H-1,2,3-benzotriazol-5-yl)-3-[1-(2-methylpentanoyl)-1H,2H,3H,3aH,4H,8bH-indeno[1,2-b]pyrrol-7-yl]propanoic acid;

3-{1-[2-(2-chlorophenyl)acetyl]-1H,2H,3H,3aH,4H,8bH-indeno[1,2-b]pyrrol-7-yl}-3-(1,4-dimethyl-1H-1,2,3-benzotriazol-5-yl)propanoic acid;

3-{1-[2-(2-cyanophenyl)acetyl]-1H,2H,3H,3aH,4H,8bH-indeno[1,2-b]pyrrol-7-yl}-3-(1,4-dimethyl-1H-1,2,3-benzotriazol-5-yl)propanoic acid;

dimethylbutanoyl)-1H,2H,3H,3aH,4H,8bH-indeno[1,2-b]pyrrol-7-yl]propanoic acid;

3-{1-[butyl(methyl)carbamoyl]-1H,2H,3H,3aH,4H,8bH-indeno[1,2-b]pyrrol-7-yl}-3-(1,4-dimethyl-1H-1,2,3-benzotriazol-5-yl)propanoic acid;

3-{1-[(tert-butoxy)carbonyl]-1H,2H,3H,3aH,4H,8bH-indeno[1,2-b]pyrrol-7-yl}-3-(7-methoxy-1-methyl-1H-1,2,3-benzotriazol-5-yl)propanoic acid;

3-{1-[(tert-butoxy)carbonyl]-1H,2H,3H,3aH,4H,8bH-indeno[1,2-b]pyrrol-7-yl}-3-(1-ethyl-4-methyl-1H-1,2,3-benzotriazol-5-yl)propanoic acid;

3-{1-[(tert-butoxy)carbonyl]-1H,2H,3H,3aH,4H,8bH-indeno[1,2-b]pyrrol-7-yl}-5-(1-ethyl-1H-1,2,3-triazol-4-yl)pentanoic acid;

3-{1-[(tert-butoxy)carbonyl]-1H,2H,3H,3aH,4H,8bH-indeno[1,2-b]pyrrol-7-yl}-3-(7-methoxy-1,4-dimethyl-1H-1,2,3-benzotriazol-5-yl)propanoic acid;

3-[1-(cyclohexylmethyl)-2-oxo-1H,2H,3H,3aH,4H,5H,9bH-benzo[g]indol-8-yl]-3-(1,4-dimethyl-1H-1,2,3-benzotriazol-5-yl)propanoic acid;

3-[3-(cyclohexylmethyl)-2-oxo-2H,3H,3aH,8H,8aH-indeno[1,2-d][1,3]oxazol-5-yl]-3-(1,4-dimethyl-1H-1,2,3-benzotriazol-5-yl)propanoic acid;

3-[3-(7-chloro-2,2-dimethyl-2,3,4,5-tetrahydro-1,4-benzoxazepin-4-yl)-2,3-dihydro-1H-inden-5-yl]-3-(1,4-dimethyl-1H-1,2,3-benzotriazol-5-yl)propanoic acid;

3-(1,4-dimethyl-1H-1,2,3-benzotriazol-5-yl)-3-[3-(2,2,7-trimethyl-2,3,4,5-tetrahydro-1,4-benzoxazepin-4-yl)-2,3-dihydro-1H-inden-5-yl]propanoic acid;

3-(1,4-dimethyl-1H-1,2,3-benzotriazol-5-yl)-3-[3-(7-methoxy-2,2-dimethyl-2,3,4,5-tetrahydro-1,4-benzoxazepin-4-yl)-2,3-dihydro-1H-inden-5-yl]propanoic acid;

3-(1,4-dimethyl-1H-1,2,3-benzotriazol-5-yl)-3-[3-(2,2,8-trimethyl-2,3,4,5-tetrahydro-1,4-benzoxazepin-4-yl)-2,3-dihydro-1H-inden-5-yl]propanoic acid;

3-(1,4-dimethyl-1H-1,2,3-benzotriazol-5-yl)-3-[3-(8-fluoro-2,2-dimethyl-2,3,4,5-tetrahydro-1,4-benzoxazepin-4-yl)-2,3-dihydro-1H-inden-5-yl]propanoic acid;

3-[3-(2,2-dimethyl-2,3,4,5-tetrahydro-1,4-benzoxazepin-4-yl)-2,3-dihydro-1H-inden-5-yl]-3-(4-fluoro-2-methylphenyl)-2,2-dimethylpropanoic acid;

3-(1,4-dimethyl-1H-1,2,3-benzotriazol-5-yl)-3-[3-(2,2-dimethyl-2,3,4,5-tetrahydro-1,4-benzoxazepin-4-yl)-2,3-dihydro-1H-inden-5-yl]-2,2-dimethylpropanoic acid; formic acid;

3-[3-(7-cyano-2,2-dimethyl-2,3,4,5-tetrahydro-1,4-benzoxazepin-4-yl)-2,3-dihydro-1H-inden-5-yl]-3-(1,4-dimethyl-1H-1,2,3-benzotriazol-5-yl)propanoic acid; formic acid;

3-[3-(2,2-dimethyl-2,3,4,5-tetrahydro-1,4-benzoxazepin-4-yl)-2,3-dihydro-1H-inden-5-yl]-3-(7-methoxy-1,4-dimethyl-1H-1,2,3-benzotriazol-5-yl)propanoic acid;

3-(1,4-dimethyl-1H-1,2,3-benzotriazol-5-yl)-3-{3-[(2R)-2-ethyl-2,3,4,5-tetrahydro-1,4-benzoxazepin-4-yl]-2,3-dihydro-1H-inden-5-yl}-2,2-dimethylpropanoic acid;

3-(1,4-dimethyl-1H-1,2,3-benzotriazol-5-yl)-3-{3-[(2R)-2,7-dimethyl-2,3,4,5-tetrahydro-1,4-benzoxazepin-4-yl]-2,3-dihydro-1H-inden-5-yl}-2,2-dimethylpropanoic acid; formic acid;

3-(1,4-dimethyl-1H-1,2,3-benzotriazol-5-yl)-2,2-dimethyl-3-{3-[(2R)-2-methyl-2,3,4,5-tetrahydro-1,4-benzoxazepin-4-yl]-2,3-dihydro-1H-inden-5-yl}propanoic acid;

3-(1,4-dimethyl-1H-1,2,3-benzotriazol-5-yl)-3-(3-{2,2-dimethyl-2H,3H,4H,5H-pyrido[3,4-f][1,4]oxazepin-4-yl}-2,3-dihydro-1H-inden-5-yl)-2,2-dimethylpropanoic acid;

3-(1,4-dimethyl-1H-1,2,3-benzotriazol-5-yl)-3-(3-{2,2-dimethyl-2H,3H,4H,5H-pyrido[3,2-f][1,4]oxazepin-4-yl}-2,3-dihydro-1H-inden-5-yl)-2,2-dimethylpropanoic acid;

3-[3-(8-cyano-2,2-dimethyl-2,3,4,5-tetrahydro-1,4-benzoxazepin-4-yl)-2,3-dihydro-1H-inden-5-yl]-3-(1,4-dimethyl-1H-1,2,3-benzotriazol-5-yl)propanoic acid; formic acid;

3-(3-{2,2-dimethyl-2H,3H,4H,5H-pyrido[3,4-f][1,4]oxazepin-4-yl}-2,3-dihydro-1H-inden-5-yl)-3-(7-methoxy-1,4-dimethyl-1H-1,2,3-benzotriazol-5-yl)propanoic acid;

3-(1,4-dimethyl-1H-1,2,3-benzotriazol-5-yl)-3-{3-[(2R)-2-ethyl-2H,3H,4H,5H-pyrido[3,4-f][1,4]oxazepin-4-yl]-2,3-dihydro-1H-inden-5-yl}-2,2-dimethylpropanoic acid; formic acid;

3-(1,4-dimethyl-1H-1,2,3-benzotriazol-5-yl)-2,2-dimethyl-3-[3-(2,3,4,5-tetrahydro-1,4-benzoxazepin-4-yl)-2,3-dihydro-1H-inden-5-yl]propanoic acid;

3-{3-[(2R)-2,7-dimethyl-2,3,4,5-tetrahydro-1,4-benzoxazepin-4-yl]-2,3-dihydro-1H-inden-5-yl}-3-(7-methoxy-1,4-dimethyl-1H-1,2,3-benzotriazol-5-yl)propanoic acid; formic acid;

3-(1,4-dimethyl-1H-1,2,3-benzotriazol-5-yl)-3-[3-(2,2-dimethyl-2,3,4,5-tetrahydro-1,4-benzoxazepin-4-yl)-2,3-dihydro-1H-inden-5-yl]propanoic acid;

(3S)-3-(1,4-dimethyl-1H-1,2,3-benzotriazol-5-yl)-3-[(3R)-3-(2,2-dimethyl-2,3,4,5-tetrahydro-1,4-benzoxazepin-4-yl)-2,3-dihydro-1H-inden-5-yl]propanoic acid;

3-(1,4-dimethyl-1H-1,2,3-benzotriazol-5-yl)-2,2-dimethyl-3-{3-[(2R)-2-methyl-2H,3H,4H,5H-pyrido[3,2-f][1,4]oxazepin-4-yl]-2,3-dihydro-1H-inden-5-yl}propanoic acid;

3-[3-(2,2-dimethyl-2,3,4,5-tetrahydro-1,4-benzoxazepin-4-yl)-2,3-dihydro-1H-inden-5-yl]-3-(7-methoxy-1-methyl-1H-1,2,3-benzotriazol-5-yl)propanoic acid;

3-(3-{2,2-dimethyl-2H,3H,4H,5H-pyrido[3,2-f][1,4]oxazepin-4-yl}-2,3-dihydro-1H-inden-5-yl)-3-(7-methoxy-1,4-dimethyl-1H-1,2,3-benzotriazol-5-yl)propanoic acid;

3-{3-[(2R)-2-ethyl-2,3,4,5-tetrahydro-1,4-benzoxazepin-4-yl]-2,3-dihydro-1H-inden-5-yl}-3-(7-methoxy-1,4-dimethyl-1H-1,2,3-benzotriazol-5-yl)propanoic acid;

3-(3-{2,2-dimethyl-2H,3H,4H,5H-pyrido[3,4-f][1,4]oxazepin-4-yl}-2,3-dihydro-1H-inden-5-yl)-3-(7-methoxy-1-methyl-1H-1,2,3-benzotriazol-5-yl)propanoic acid;

3-(1,4-dimethyl-1H-1,2,3-benzotriazol-5-yl)-3-{3-[(2R)-2,7-dimethyl-2,3,4,5-tetrahydro-1,4-benzoxazepin-4-yl]-2,3-dihydro-1H-inden-5-yl}propanoic acid; formic acid;

3-(1,4-dimethyl-1H-1,2,3-benzotriazol-5-yl)-3-(3-{2,2-dimethyl-2H,3H,4H,5H-pyrido[3,4-f][1,4]oxazepin-4-yl}-2,3-dihydro-1H-inden-5-yl)propanoic acid;

3-(1,4-dimethyl-1H-1,2,3-benzotriazol-5-yl)-2,2-dimethyl-3-{3-[(2S)-2-methyl-2H,3H,4H,5H-pyrido[3,2-f][1,4]oxazepin-4-yl]-2,3-dihydro-1H-inden-5-yl}propanoic acid;

3-(1,4-dimethyl-1H-1,2,3-benzotriazol-5-yl)-3-{3-[(2R)-2-ethyl-2,3,4,5-tetrahydro-1,4-benzoxazepin-4-yl]-2,3-dihydro-1H-inden-5-yl}propanoic acid; formic acid;

3-(1,4-dimethyl-1H-1,2,3-benzotriazol-5-yl)-3-(3-{2,2-dimethyl-2H,3H,4H,5H-pyrido[3,2-f][1,4]oxazepin-4-yl}-2,3-dihydro-1H-inden-5-yl)propanoic acid;

3-(7-methoxy-1,4-dimethyl-1H-1,2,3-benzotriazol-5-yl)-3-[3-(2,3,4,5-tetrahydro-1,4-benzoxazepin-4-yl)-2,3-dihydro-1H-inden-5-yl]propanoic acid;

3-(1,4-dimethyl-1H-1,2,3-benzotriazol-5-yl)-3-{3-[(2R)-2-methyl-2,3,4,5-tetrahydro-1,4-benzoxazepin-4-yl]-2,3-dihydro-1H-inden-5-yl}propanoic acid;

3-(1,4-dimethyl-1H-1,2,3-benzotriazol-5-yl)-2,2-dimethyl-3-(3-{2H,3H,4H,5H-pyrido[3,2-f][1,4]oxazepin-4-yl}-2,3-dihydro-1H-inden-5-yl)propanoic acid;

3-(3-{2,2-dimethyl-2H,3H,4H,5H-pyrido[3,2-f][1,4]oxazepin-4-yl}-2,3-dihydro-1H-inden-5-yl)-3-(7-methoxy-1-methyl-1H-1,2,3-benzotriazol-5-yl)propanoic acid;

3-(1,4-dimethyl-1H-1,2,3-benzotriazol-5-yl)-3-{3-[(2S)-2-methyl-2,3,4,5-tetrahydro-1,4-benzoxazepin-4-yl]-2,3-dihydro-1H-inden-5-yl}propanoic acid; formic acid;

3-(1,4-dimethyl-1H-1,2,3-benzotriazol-5-yl)-3-{3-[(2R)-2-ethyl-2H,3H,4H,5H-pyrido[3,4-f][1,4]oxazepin-4-yl]-2,3-dihydro-1H-inden-5-yl}propanoic acid; formic acid;

3-(1,4-dimethyl-1H-1,2,3-benzotriazol-5-yl)-3-[3-(2,3,4,5-tetrahydro-1,4-benzoxazepin-4-yl)-2,3-dihydro-1H-inden-5-yl]propanoic acid; formic acid;

3-(4-cyano-2-methylphenyl)-3-(3-{2,2-dimethyl-2H,3H,4H,5H-pyrido[3,2-f][1,4]oxazepin-4-yl}-2,3-dihydro-1H-inden-5-yl)propanoic acid;

3-(3-{2,2-dimethyl-2H,3H,4H,5H-pyrido[3,2-f][1,4]oxazepin-4-yl}-2,3-dihydro-1H-inden-5-yl)-3-(4-fluoro-2-methylphenyl)propanoic acid;

3-(1,4-dimethyl-1H-1,2,3-benzotriazol-5-yl)-3-{3-[(2R)-2-methyl-2H,3H,4H,5H-pyrido[3,2-f][1,4]oxazepin-4-yl]-2,3-dihydro-1H-inden-5-yl}propanoic acid;

3-(3-{2,2-dimethyl-2H,3H,4H,5H-pyrido[3,2-f][1,4]oxazepin-4-yl}-2,3-dihydro-1H-inden-5-yl)-3-{3-methyl-3H-[1,2,3]triazolo[4,5-c]pyridin-6-yl}propanoic acid; formic acid;

3-[3-(2,2-dimethyl-2,3,4,5-tetrahydro-1,4-benzoxazepin-4-yl)-2,3-dihydro-1H-inden-5-yl]-5-(4-propyl-1H-1,2,3-triazol-1-yl)pentanoic acid; trifluoroacetic acid;

3-[3-(2,2-dimethyl-2,3,4,5-tetrahydro-1,4-benzoxazepin-4-yl)-2,3-dihydro-1H-inden-5-yl]-5-(2-ethyl-2H-1,2,3,4-tetrazol-5-yl)-2,2-dimethylpentanoic acid; formic acid;

3-[3-(2,2-dimethyl-2,3,4,5-tetrahydro-1,4-benzoxazepin-4-yl)-2,3-dihydro-1H-inden-5-yl]-2,2-dimethyl-5-(4-propyl-1H-1,2,3-triazol-1-yl)pentanoic acid;

3-(1,4-Dimethyl-1H-benzo[d][1,2,3]triazol-5-yl)-3-(8-((R)-2-methyl-2,3-dihydrobenzo[f][1,4]oxazepin-4(5H)-yl)-5,6,7,8-tetrahydronaphthalen-2-yl)propanoic acid;

rac-(R)-3-(1,4-Dimethyl-1H-benzo[d][1,2,3]triazol-5-yl)-3-(rac-(S)-3-(2,2-dimethyl-2,3-dihydropyrido[2,3-f][1,4]oxazepin-4(5H)-yl)-2,3-dihydro-1H-inden-5-yl)-2,2-dimethylpropanoic acid, trifluoroacetic acid salt;

rac-(R)-3-(1,4-Dimethyl-1H-benzo[d][1,2,3]triazol-5-yl)-3-(rac-(R)-3-(2,2-dimethyl-2,3-dihydropyrido[2,3-f][1,4]oxazepin-4(5H)-yl)-2,3-dihydro-1H-inden-5-yl)-2,2-dimethylpropanoic acid;

rac-(R)-3-(1,4-Dimethyl-1H-benzo[d][1,2,3]triazol-5-yl)-3-(rac-(R)-3-(2,2-dimethyl-2,3-dihydropyrido[4,3-f][1,4]oxazepin-4(5H)-yl)-2,3-dihydro-1H-inden-5-yl)-2,2-dimethylpropanoic acid, Trifluoroacetic acid salt;

rac-(R)-3-(1,4-Dimethyl-1H-benzo[d][1,2,3]triazol-5-yl)-3-(rac-(S)-3-(2,2-dimethyl-2,3-dihydropyrido[4,3-f][1,4]oxazepin-4(5H)-yl)-2,3-dihydro-1H-inden-5-yl)-2,2-dimethylpropanoic acid, Trifluoroacetic acid salt;

rel-(S)-3-(1,4-Dimethyl-1H-benzo[d][1,2,3]triazol-5-yl)-3-(rel-(R)-3-((R)-2-ethyl-2,3-dihydropyrido[3,4-f][1,4]oxazepin-4(5H)-yl)-2,3-dihydro-1H-inden-5-yl)-2,2-dimethylpropanoic acid;

rel-(S)-3-(1,4-Dimethyl-1H-benzo[d][1,2,3]triazol-5-yl)-3-(rel-(S)-3-((R)-2-ethyl-2,3-dihydropyrido[3,4-f][1,4]oxazepin-4(5H)-yl)-2,3-dihydro-1H-inden-5-yl)-2,2-dimethylpropanoic acid;

rel-(R)-3-(1,4-Dimethyl-1H-benzo[d][1,2,3]triazol-5-yl)-3-(rel-(R)-3-((R)-2-ethyl-2,3-dihydropyrido[3,4-f][1,4]oxazepin-4(5H)-yl)-2,3-dihydro-1H-inden-5-yl)-2,2-dimethylpropanoic acid;

rel-(R)-3-(1,4-Dimethyl-1H-benzo[d][1,2,3]triazol-5-yl)-3-(rel-(S)-3-((R)-2-ethyl-2,3-dihydropyrido[3,4-f][1,4]oxazepin-4(5H)-yl)-2,3-dihydro-1H-inden-5-yl)-2,2-dimethylpropanoic acid;

rel-(S)-3-(1,4-Dimethyl-1H-benzo[d][1,2,3]triazol-5-yl)-3-(rel-(R)-3-((R)-2-ethyl-2,3-dihydropyrido[3,4-f][1,4]oxazepin-4(5H)-yl)-2,3-dihydro-1H-inden-5-yl)-2,2-dimethylpropanoic acid;

rel-(R)-3-(1,4-Dimethyl-1H-benzo[d][1,2,3]triazol-5-yl)-3-(rel-(S)-3-((R)-2-ethyl-2,3-dihydropyrido[3,4-f][1,4]oxazepin-4(5H)-yl)-2,3-dihydro-1H-inden-5-yl)-2,2-dimethylpropanoic acid;

rel-(S)-3-(1,4-Dimethyl-1H-benzo[d][1,2,3]triazol-5-yl)-3-(rel-(R)-3-(2,2-dimethyl-2,3-dihydrobenzo[f][1,4]oxazepin-4(5H)-yl)-2,3-dihydro-1H-inden-5-yl)-2,2-dimethylpropanoic acid;

rel-(S)-3-(1,4-Dimethyl-1H-benzo[d][1,2,3]triazol-5-yl)-3-(rel-(S)-3-(2,2-dimethyl-2,3-dihydrobenzo[f][1,4]oxazepin-4(5H)-yl)-2,3-dihydro-1H-inden-5-yl)-2,2-dimethylpropanoic acid;

rel-(R)-3-(1,4-Dimethyl-1H-benzo[d][1,2,3]triazol-5-yl)-3-(rel-(R)-3-(2,2-dimethyl-2,3-dihydrobenzo[f][1,4]oxazepin-4(5H)-yl)-2,3-dihydro-1H-inden-5-yl)-2,2-dimethylpropanoic acid;

rel-(R)-3-(1,4-Dimethyl-1H-benzo[d][1,2,3]triazol-5-yl)-3-(rel-(S)-3-(2,2-dimethyl-2,3-dihydrobenzo[f][1,4]oxazepin-4(5H)-yl)-2,3-dihydro-1H-inden-5-yl)-2,2-dimethylpropanoic acid;

rel-(S)-3-(1,4-Dimethyl-1H-benzo[d][1,2,3]triazol-5-yl)-3-(rel-(S)-3-((R)-2-ethyl-2,3-dihydrobenzo[f][1,4]oxazepin-4(5H)-yl)-2,3-dihydro-1H-inden-5-yl)propanoic acid;

rel-(S)-3-(1,4-Dimethyl-1H-benzo[d][1,2,3]triazol-5-yl)-3-(rel-(R)-3-((R)-2-ethyl-2,3-dihydrobenzo[f][1,4]oxazepin-4(5H)-yl)-2,3-dihydro-1H-inden-5-yl)propanoic acid;

rel-(R)-3-(1,4-Dimethyl-1H-benzo[d][1,2,3]triazol-5-yl)-3-(rel-(S)-3-((R)-2-ethyl-2,3-dihydrobenzo[f][1,4]oxazepin-4(5H)-yl)-2,3-dihydro-1H-inden-5-yl)propanoic acid;

rel-(R)-3-(1,4-Dimethyl-1H-benzo[d][1,2,3]triazol-5-yl)-3-(rel-(R)-3-((R)-2-ethyl-2,3-dihydrobenzo[f][1,4]oxazepin-4(5H)-yl)-2,3-dihydro-1H-inden-5-yl)propanoic acid;

rel-(S)-3-(1,4-Dimethyl-1H-benzo[d][1,2,3]triazol-5-yl)-3-(rel-(S)-3-((R)-2-ethyl-2,3-dihydropyrido[3,4-f][1,4]oxazepin-4(5H)-yl)-2,3-dihydro-1H-inden-5-yl)-2,2-dimethylpropanoic acid;

3-(1,4-Dimethyl-1H-benzo[d][1,2,3]triazol-5-yl)-3-(3-(2,2-dimethyl-2,3-dihydropyrido[3,4-f][1,4]oxazepin-4(5H)-yl)-2,3-dihydro-1H-inden-5-yl)-2,2-dimethylpropanoic acid; or 5-(1-Ethyl-1H-1,2,3-triazol-4-yl)-3-(3-((R)-2-ethyl-2,3-dihydropyrido[3,4-f][1,4]oxazepin-4(5H)-yl)-2,3-dihydro-1H-inden-5-yl)-2,2-dimethylpentanoic acid;

or a pharmaceutically acceptable salt thereof.

Compound Preparation

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

The synthesis of the compounds of the general Formulas (I) and (II) and pharmaceutically acceptable derivatives and salts thereof may be accomplished as outlined below in Schemes 1-21. In the following description, the groups are as defined above for compounds of Formulas (I) and (II) unless otherwise indicated. Abbreviations are as defined in the Examples section. Starting materials are commercially available or are made from commercially available starting materials using methods known to those skilled in the art.

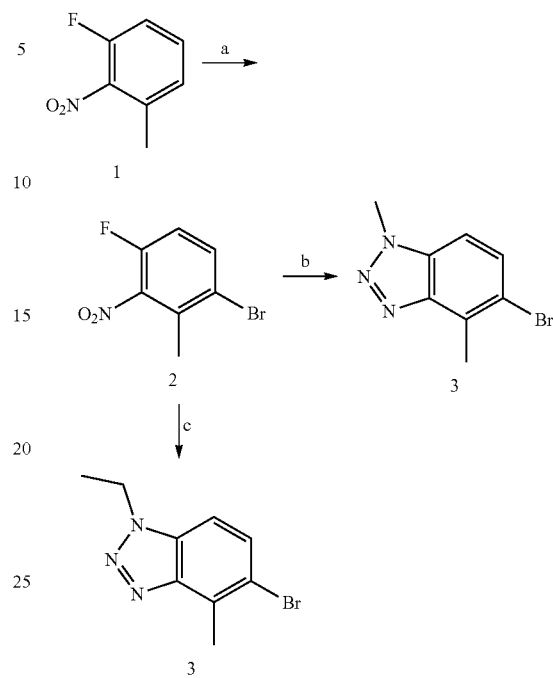

Scheme 1

Conditions:

a) NBS, TFA, $H_2SO_4$; b) i) $MeNH_2$ (or) $EtNH_2THF$; ii) Zn, HOAc; iii) $NaNO_2$, $H_2SO_4$ Scheme 1 shows a general scheme for the preparation of 5-bromo-4-methyl-1-methyl-1H-benzo[d][1,2,3]triazole. Starting with commercially available 1-fluoro-3-methyl-2-nitrobenzene, bromination with NBS provides intermediate 2. Displacement of the fluoride using an appropriate amine followed by zinc metal reduction of the nitro to the aniline and diazotization and cyclization provides the required triazole 3.

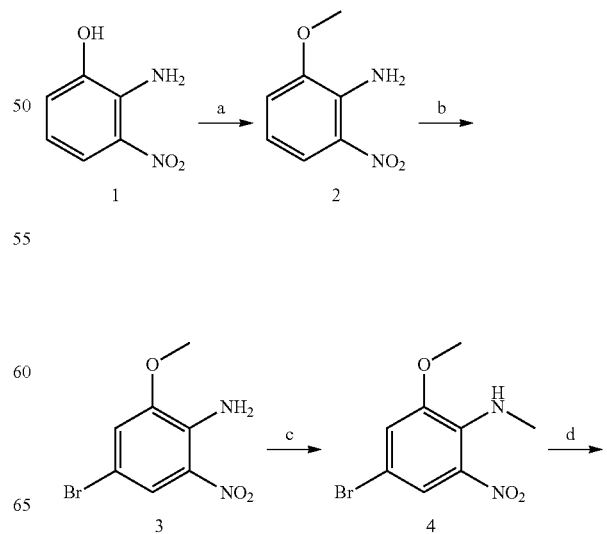

Scheme 2

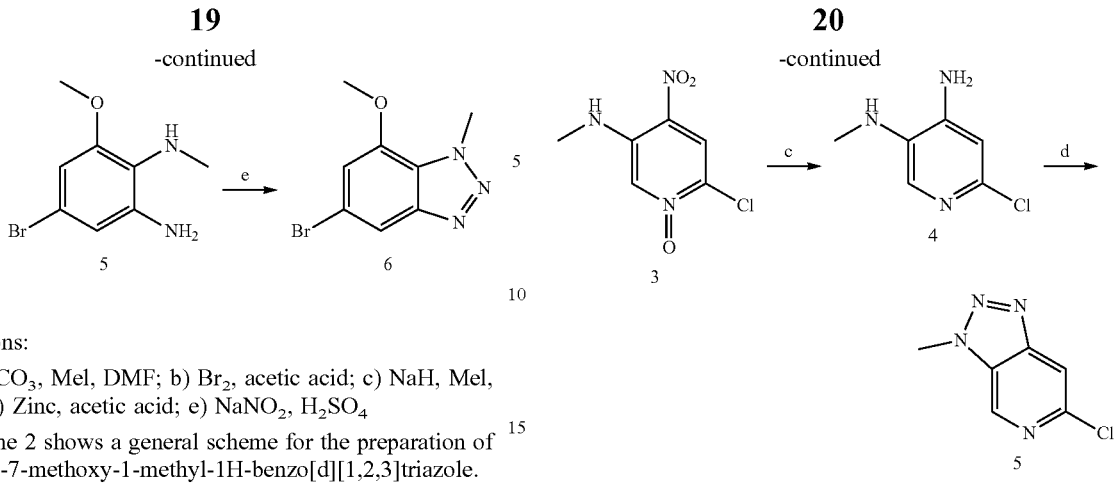

Conditions:

a) $K_2CO_3$, MeI, DMF; b) $Br_2$, acetic acid; c) NaH, MeI, DMF; d) Zinc, acetic acid; e) $NaNO_2$, $H_2SO_4$ Scheme 2 shows a general scheme for the preparation of 5-bromo-7-methoxy-1-methyl-1H-benzo[d][1,2,3]triazole. Starting with commercially available 2-amino-3-nitrophenol, methylation of the phenol using $K_2CO_3$ and MeI (step a) provides intermediate 2 which can be brominated with NBS (step c). Methylation of the aniline (step d) followed by reduction of the nitro group (step d) and diazotization and cyclization (step e) provide the required triazole 5.

Scheme 3

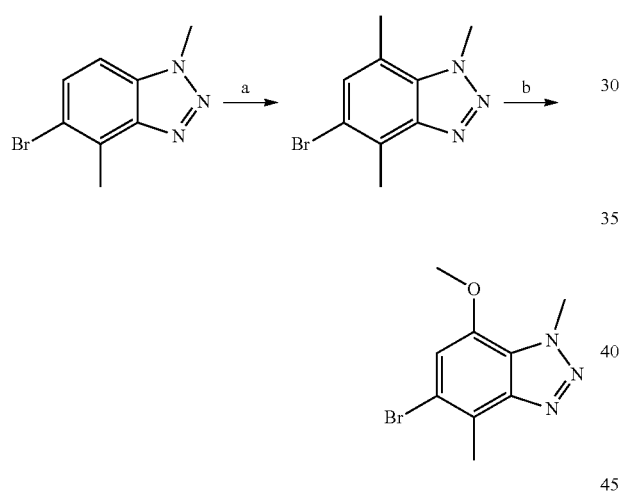

Conditions:

a) $NaIO_4/H_2SO_4$, $I_2$, $Ac_2O/AcOH$; b) CuI, $Cs_2CO_3$, MeOH;

Scheme 3 shows a general scheme for the preparation of 5-bromo-7-methoxy-1,4-dimethyl-1H-benzo[d][1,2,3]triazole This two step process starts with iodination at C7 of 5-bromo-1,4-dimethyl-1H-benzo[d][1,2,3]triazole. Copper mediated replacement of the iodide with methanol provides the desired material.

Scheme 4

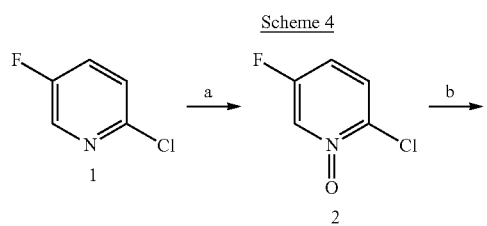

Conditions:

a) $H_2O_2$, TFA; b) (ii) $KNO_3$, $H_2SO_4$; (ii) $CH_3NH_2$; c) Ni, EtOH, 40 psi; d) $NaNO_2$, $H_2SO_4$ Scheme 4 shows a general scheme for the preparation of 6-chloro-3-methyl-3H-[1,2,3]triazolo[4,5-c]pyridine. Starting with commercially available 2-chloro-5-fluoropyridine, oxidation provides intermediate 2. This is subsequently converted to nitro intermediate 3. Displacement of the fluoride using an appropriate amine followed by nickel metal reduction of the nitro to the aniline yields intermediate 4. Diazotization and cyclization provides the required triazole 5.

Scheme 5

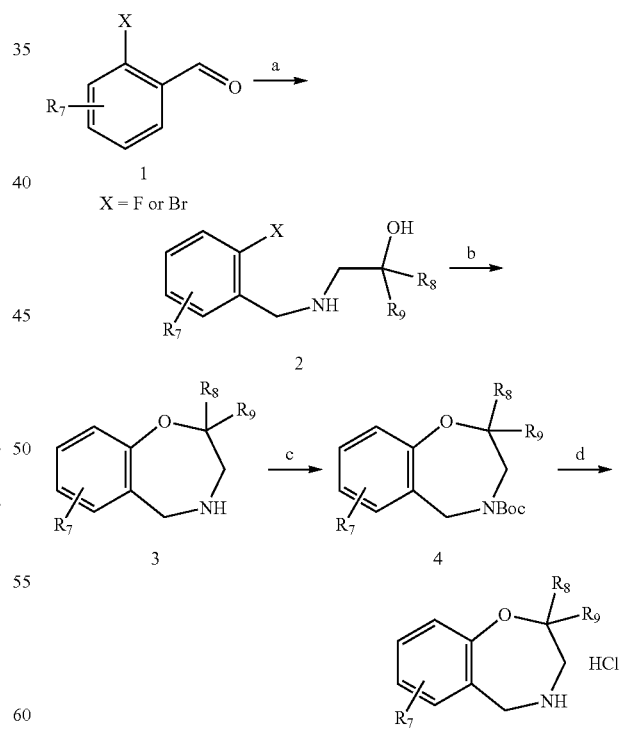

Conditions:

a) $H_2NCH_2C(R_8)(R_9)OH$, $NaBH_4$, NaOH, MeOH; b) $Cs_2CO_3$, CuI, IPA; or KOtBu, DMSO; c) Boc anhydride, $Et_3N$, THF; d) HCl, dioxane Scheme 5 represents a general scheme for the preparation of 2-ethyl-2,3,4,5-tetrahydrobenzo[f][1,4]oxazepines, and 2,2-dimethyl-2,3,4,5-tetrahydrobenzo[f][1,4]oxazepines used in the invention. In Scheme 5 $R_7$ is —$C_{1-3}$ alkyl, halo, CN, —$OC_{1-3}$alkyl, —$CH_2$—O—$CH_3$, or OH; and $R_8$ and $R_9$ are hydrogen, $C_{1-3}$alkyl, or $C_{3-6}$spirocycloalkyl. Substituted 2-bromobenzaldehyde or substituted 2-fluorobenzaldehyde depicted as starting materials are commercially available. Reaction conditions are as described above in the Scheme; however, the skilled artisan will appreciate that certain modifications in the reaction conditions and reagents used are possible.

Reductive amination of the starting aldehyde with the appropriate aminoalcohol followed by displacement of the bromide or fluoro provides the required intermediate 3. This was then protected as the Boc carbamate to facilitate purification. It will be appreciated by the skilled artisan that alternative protecting groups may be used. Deprotection yields the requisite amine 5.

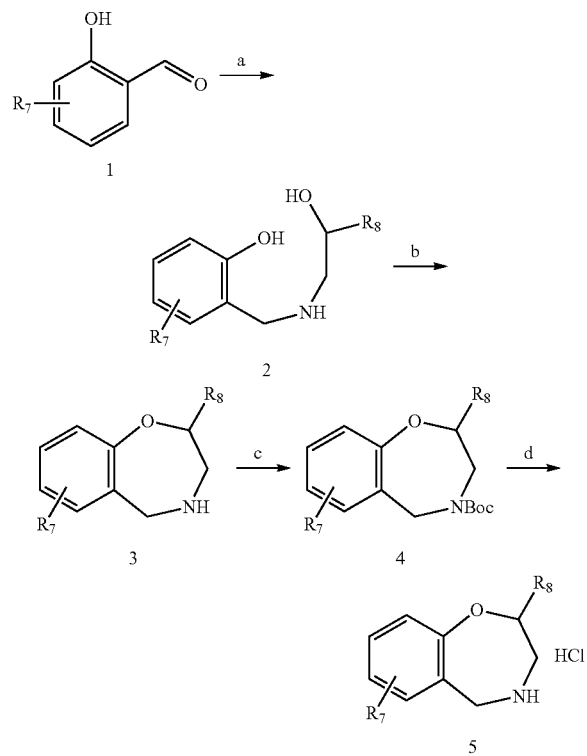

Conditions:
a) $H_2NCH_2CH(R_8)OH$, $NaBH_4$, NaOH, MeOH; b) $PPh_3$, DEAD, THF; c) Boc anhydride, $Et_3N$, THF; d) HCl, dioxane Scheme 6 represents a general scheme for the preparation of (R)-2-ethyl-2,3,4,5-tetrahydrobenzo[f][1,4]oxazepines, and 2,2-dimethyl-2,3,4,5-tetrahydrobenzo[f][1,4]oxazepines used in the invention. In Scheme 6, $R_7$ and $R_8$ are as defined previously. Substituted 2-hydroxybenzaldehyde depicted as starting material is commercially available. Reaction conditions are as described above in the Scheme; however, the skilled artisan will appreciate that certain modifications in the reaction conditions and/or reagents used are possible.

Reductive amination of aldehyde with the appropriate aminoalcohol followed by Mitsunobo reaction provides the required intermediate 3. This was then protected as the Boc carbamate to facilitate purification. It will be appreciated by the skilled artisan that alternative protecting groups may be used. Deprotection yields the requisite amine 5.

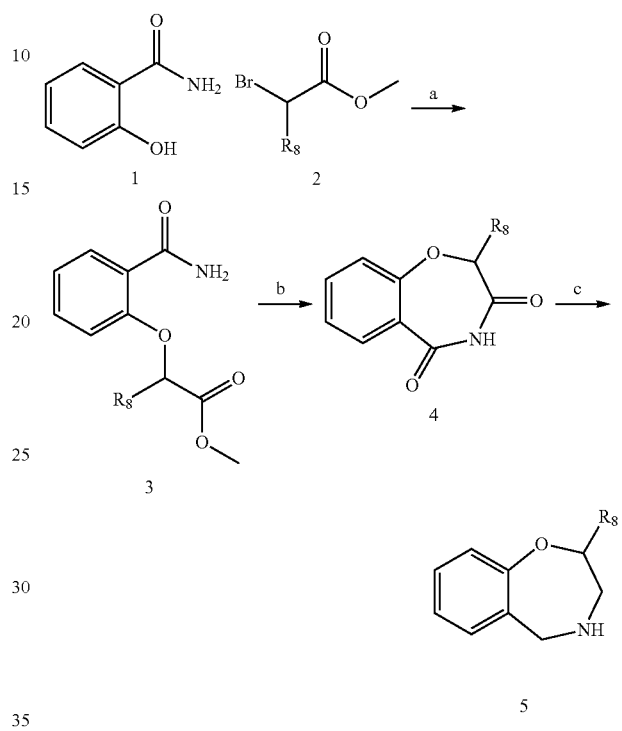

Conditions:
a) $K_2CO_3$, THF; b) NaOMe, DMF; c) LAH, THF

Scheme 7 represents a general scheme for the preparation of substituted-tetrahydrobenzo[f][1,4]oxazepines used in the invention. In scheme 7, $R_8$ is as defined previously. 2-Hydroxybenzamide depicted as starting material is commercially available. Reaction conditions are as described above in the Scheme; however, the skilled artisan will appreciate that certain modifications in the reaction conditions and/or reagents used are possible.

Reaction of 2-hydroxybenzamide with the appropriate bromoacetate yields the intermediate 3. Cyclization under basic conditions followed by reduction of the resulting imide with LAH yields the required amine 5.

Scheme 8

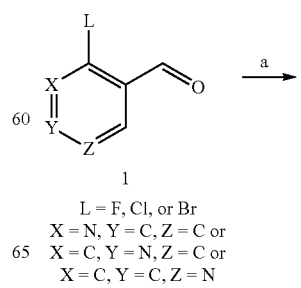

L = F, Cl, or Br
X = N, Y = C, Z = C or
X = C, Y = N, Z = C or
X = C, Y = C, Z = N

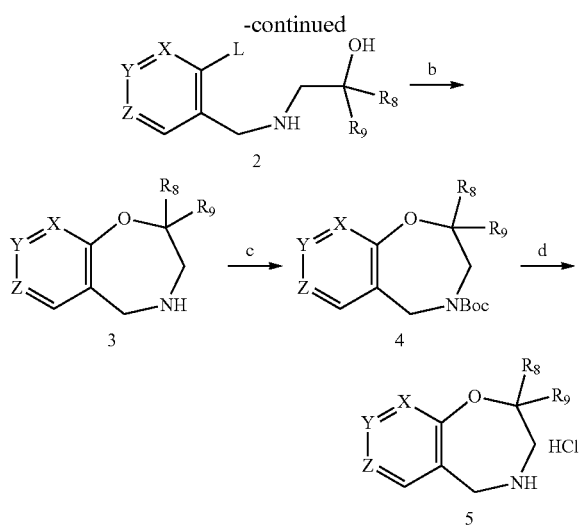

Conditions:

a) H$_2$NCH$_2$C(R$_8$)(R$_9$)OH, NaBH$_4$, NaOH, MeOH; b) Cs$_2$CO$_3$, CuI, IPA; or KOtBu, DMSO; c) Boc anhydride, Et$_3$N, THF; d) HCl, dioxane Scheme 8 represents a general scheme for the preparation of tetrahydropyrido[1,4]oxazepine hydrochloride used in the invention. In Scheme 8, R$_8$ and R$_9$ are as defined previously. Fluoronicotinaldehyde, chloronicotinaldehyde or bromonicotinaldehyde depicted as starting material are commercially available. Reaction conditions are as described above in the Scheme; however, the skilled artisan will appreciate that certain modifications in the reaction conditions and/or reagents used are possible.

Reductive amination of the starting aldehyde with the appropriate aminoalcohol followed by displacement of the bromide or fluoro provides the required intermediate 3. This was then protected as the Boc carbamate to facilitate purification. It will be appreciated by the skilled artisan that alternative protecting groups may be used. Deprotection yields the requisite amine 5 as a hydrochloride salt.

Scheme 9

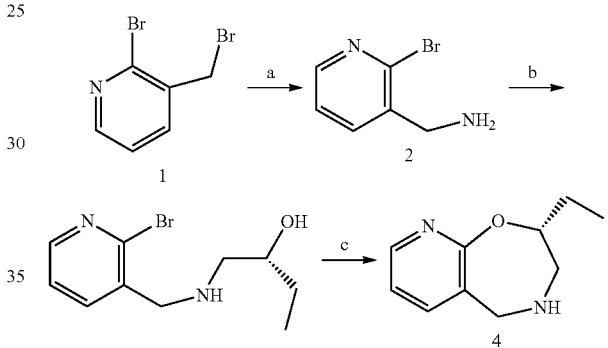

Conditions:

a) H$_2$NCH$_2$CH(R$_8$)OH, NaBH$_4$, NaOH, MeOH; b) PPh$_3$, DEAD, THF; c) Boc anhydride, Et$_3$N, THF; d) HCl, dioxane Scheme 9 represents a general scheme for the preparation of (R)-2-ethyl-2,3,4,5-tetrahydropyrido[2,3-f][1,4]oxazepine hydrochloride, and 2,2-dimethyl-2,3,4,5-tetrahydropyrido[2,3-f][1,4]oxazepine hydrochloride used in the invention. In Scheme 9, R$_8$ is as defined previously. 3-Hydroxypicolinaldehyde depicted as starting material is commercially available. Reaction conditions are as described above in the Scheme; however, the skilled artisan will appreciate that certain modifications in the reaction conditions and/or reagents used are possible.

Reductive amination of the commercially available aldehyde with the appropriate aminoalcohol followed by Mitsunobo reaction provides the required intermediate 3. This was then protected as the Boc carbamate to facilitate purification. It will be appreciated by the skilled artisan that alternative protecting groups may be used. Deprotection yields the requisite amine 5.

Scheme 10

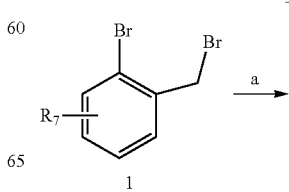

Conditions:

a) NH$_4$OH; b) (R)-(2)-ethyloxirane, EtOH; c) KO$_t$Bu, DMF

Scheme 10 represents a general scheme for the preparation of (R)-2-ethyl-2,3,4,5-tetrahydropyrido[3,2-f][1,4]oxazepine used in the invention. 2-Bromo-3-(bromomethyl)pyridine depicted as starting material is commercially available. Reaction conditions are as described above in the Scheme; however, the skilled artisan will appreciate that certain modifications in the reaction conditions and/or reagents used are possible.

Treatment of commercially available 2-bromo-3-(bromomethyl)pyridine with ammonium hydroxide yields primary amine 2. Alkylation via epoxide opening followed by displacement of the bromide provides intermediate 4.

Scheme 11

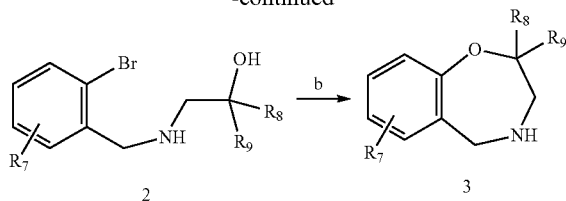

Conditions:

a) amine, $K_2CO_3$, THF, water; b) $Cs_2CO_3$, CuI, IPA

Scheme 11 represents a general scheme for the preparation of 2-ethyl-2,3,4,5-tetrahydrobenzo[f][1,4]oxazepine hydrochloride, and 2,2-dimethyl-2,3,4,5-tetrahydrobenzo[f][1,4]oxazepine hydrochloride used in the invention. In Scheme 11, $R_7$, $R_8$ and $R_9$ are as defined previously. Substituted 1-bromo-2-(bromomethyl)benzene depicted as starting material is commercially available. Reaction conditions are as described above in the Scheme; however, the skilled artisan will appreciate that certain modifications in the reaction conditions and/or reagents used are possible.

Alkylation with the appropriate aminoalcohol followed by displacement of the bromide provides the required intermediate 3.

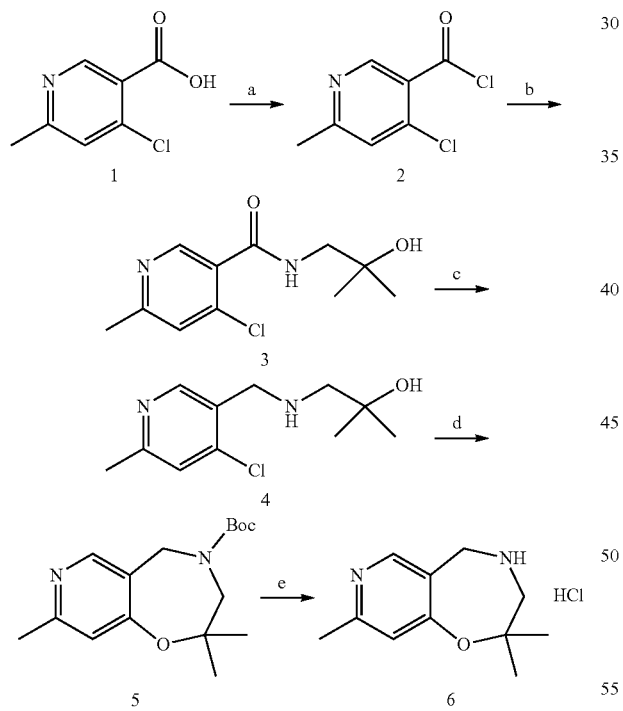

Conditions:

a) $POCl_3$; b) NaOH, DCM; c) borane dimethyl sulfide, THF; d) (i) $KO_tBu$, DMSO; (ii) Boc anhydride, $Et_3N$, THF; d) HCl, dioxane Scheme 12 represents a general scheme for the preparation of 2,2,8-trimethyl-2,3,4,5-tetrahydropyrido[3,4-f][1,4]oxazepine hydrochloride used in the invention. In this, 4-hydroxy-6-methylnicotinic acid depicted as starting material is commercially available. Reaction conditions are as described above in the Scheme; however, the skilled artisan will appreciate that certain modifications in the reaction conditions and/or reagents used are possible.

Commercially available acid 1 was converted to the acid chloride with $POCl_3$, followed by amide formation to give intermediate 3. Reduction of the amide with borane dimethyl sulfide produces amine 4. Cyclization with potassium tert-butoxide as base followed by amine protection as the tert-butylcarbamate group yields compound 5. Deprotection under acidic conditions yields the requisite amine 6.

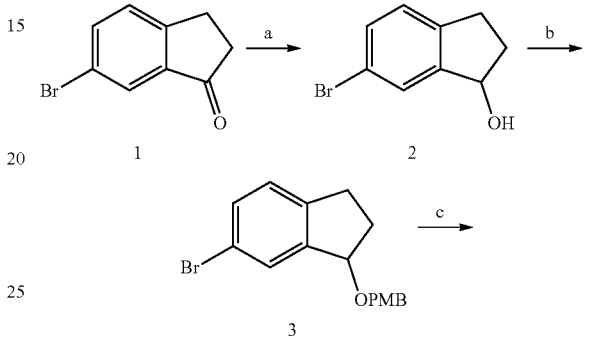

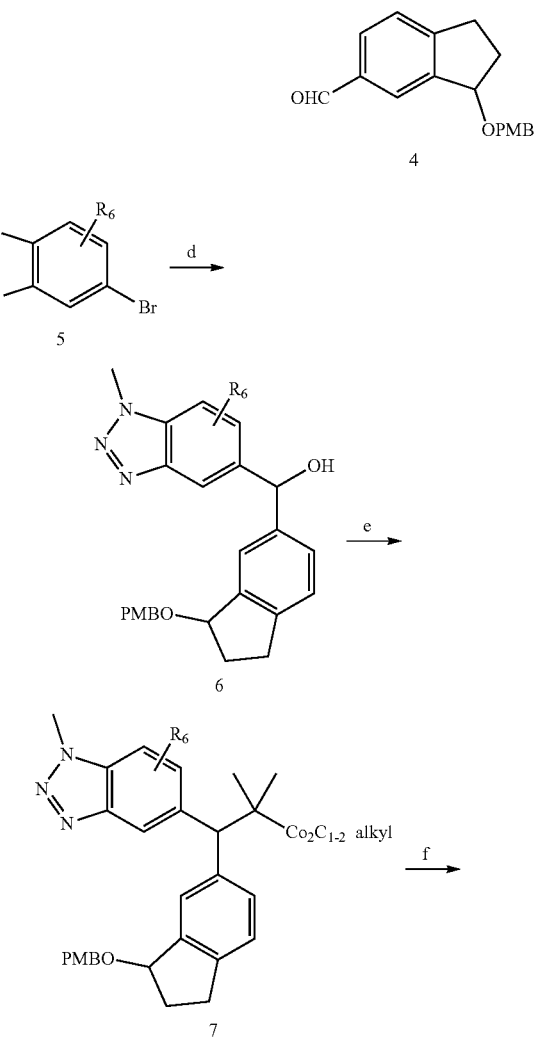

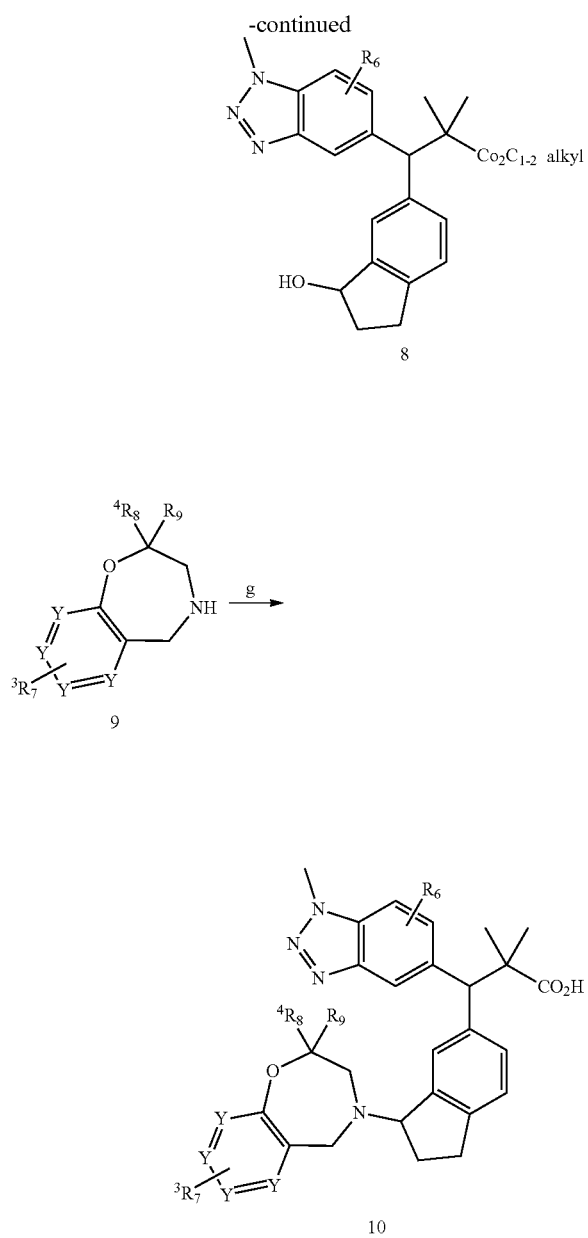

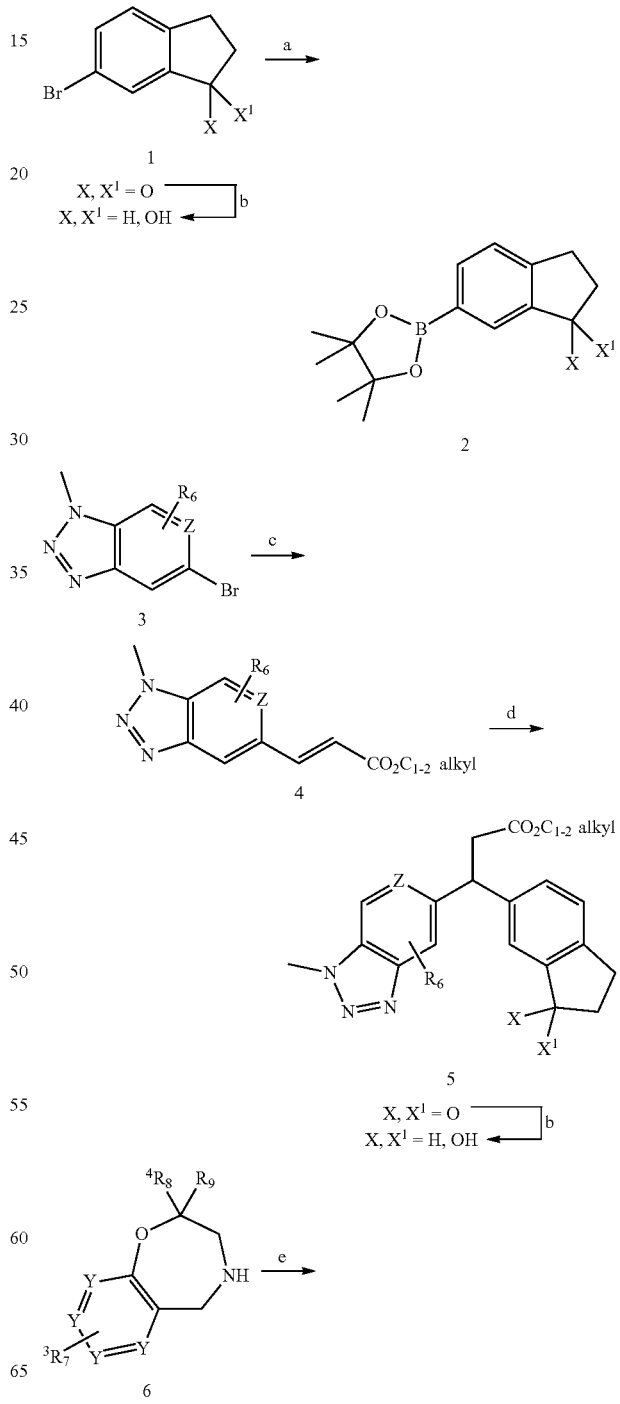

desired intermediate 4. Coupling of 4 and 5 is accomplished by treatment of 5 with t-butyl lithium and intermediate 4 to form alcohol 6. Alcohol 6 was converted to 7 by first treating with $Cl_3CCN$ and DBU followed by the requisite, commercially available silyl ketene acetal in the presence of $Tf_2NH$. The deprotection of intermediate 7 with DDQ formed intermediate 8. The intermediate 8 was first treated with $SOCl_2$ followed by amine 9 and $K_2CO_3$, NaI before hydrolysis with NaOH to form final product 10.

Conditions:

a) $NaBH_4$, MeOH, THF; b) PMBCl, NaH; c) n-BuLi, DMF; d) t-BuLi, 4, THF; e) (i) $Cl_3CCN$, DBU, MeCN; (ii) $Tf_2NH$, $Me_2C=C(OR^2)OTMS$, MeCN; f) DDQ; g) (i) 8, $SOCl_2$, DCM; (ii) 9, $K_2CO_3$, NaI, MeCN (iii) NaOH, MeOH/$H_2O$ Scheme 13 represents a general scheme for the preparation of intermediates 4, 8 and compounds according to Formula (I). In Scheme 13, $R_6$ is $C_{1-3}$alkyl, halo, or —$OC_{1-3}$alkyl, $R_7$, $R_8$ and $R_9$ are as defined previously. Y is independently CH or N.

Starting with commercially available indanone 1, reduction with $NaBH_4$ produces desired alcohol intermediate 2. Intermediate 2 hydroxyl group may be protected as the PMB ether by treating with NaH and PMBCl to give intermediate 3. It will be appreciated by the skilled artisan that the protecting group may vary and is not limited to PMB. Further, transformation of intermediate 3 to the requisite aldehyde by treatment with butyl lithium and DMF yields

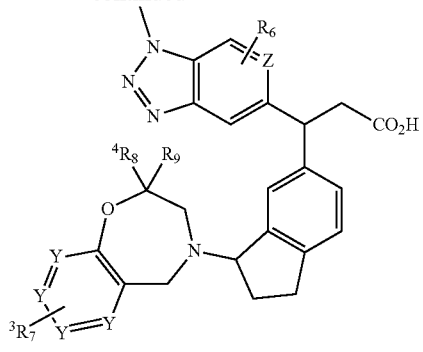

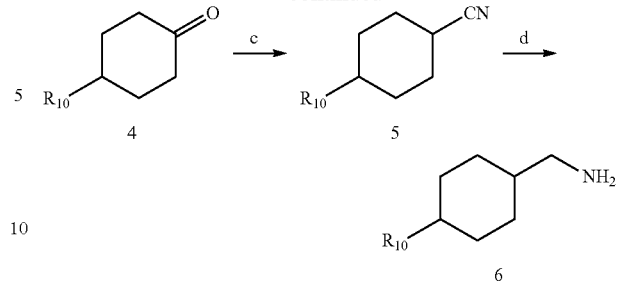

Conditions:

a) Bis(pinacolato)diboron, Pd(dppf)Cl$_2$, KOAc, DMF; b) NaBH$_4$, MeOH; c) CH$_2$=CHCO$_2$C$_{1-2}$ alkyl, Pd(OAc)$_2$, P(o-Tol)$_3$, DMF; d) 2, Rh(cod)Cl$_2$, TEA; e) (i) 5, SOCl$_2$, DCM; (ii) 6, K$_2$CO$_3$, NaI, MeCN (iii) NaOH, MeOH/H$_2$O Scheme 14 represents a general scheme for the preparation of intermediates 2 and 5 and compounds of Formula (I). In Scheme 14, R$_6$, R$_7$, R$_8$, R$_9$ and Y are as previously defined. Z is CH or N.

The commercially available indanone 1 was either first reduced to the hydroxy indane then converted to the boronic ester or converted directly to the boronic ester by treating with bis(pinacolato)diboron in the presence of a palladium catalyst to afford 2. The intermediate 3 was converted to 4 under Heck reaction conditions. (For intermediate 3 for the case where Z=N, a chloride is used for the Heck coupling in the presence of tetrakis(triphenylphosphine) palladium rather than bromide.) Rhodium catalyzed Michael addition of 2 with 4 provides ester 5. Intermediate 5 can be converted to the hydroxy indane by reduction with NaBH$_4$ if necessary and then subsequently to the chloride via treatment with SOCl$_2$. Conversion to the final product 7 is accomplished via treatment of the chloride with 6 and K$_2$CO$_3$, NaI followed by hydrolysis with NaOH.

Scheme 15

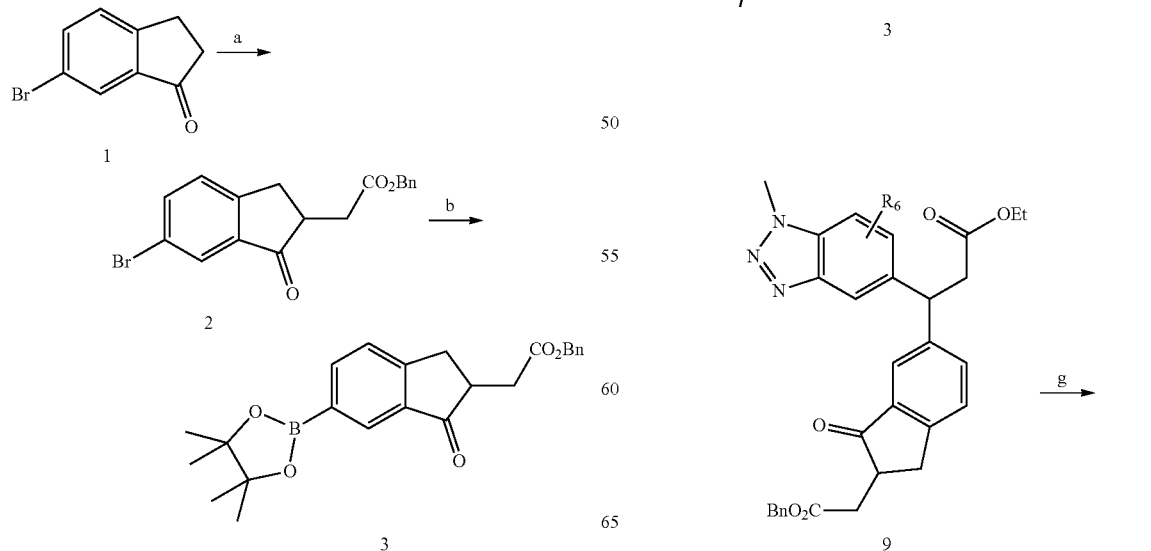

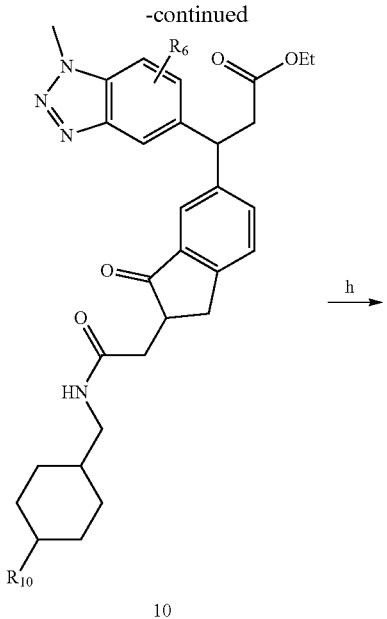

10

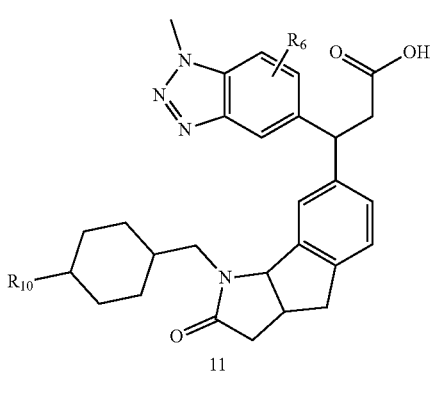

11

Conditions:
a) LiHMDS, BrCH₂CO₂Bn, THF; b) Bis(pinacolato)diboron, PdCl₂(dppf)-CH₂Cl₂, KOAc, 1,4-dioxane; c) p-TolSO₂CH₂NC, KOBu-t, THF; d) LAH, THF; e) Ethyl acrylate, Pd(OAc)₂, P(o-tol)₃, DIEA, DMF; f) [RhCl(cod)]₂, TEA, 1,4-dioxane, H₂O; g) (i) Pd/C, H₂, MeOH; (ii) 6, T3P, TEA, DCM; h) (i) TFA, Et₃SiH, MeCN; (ii) NaOH, MeOH/H₂O Scheme 15 represents a general scheme for the preparation of intermediates 3, 6 and compounds according to Formula (II). In Scheme 15 $R_6$ is defined previously. $R_{10}$ is $C_{1-3}$ alkyl, CN. Reaction of the commercially available indanone 1 with LiHMDS and benzyl bromoacetate in the presence of a suitable solvent produces desired intermediate 2. Further transformation of intermediate 2 with bis(pinacolato)diboron, PdCl₂(dppf)-CH₂Cl₂ and KOAc in a suitable solvent yields desired intermediate 3. Reaction of the commercially available ketone 4 with p-TolSO₂CH₂NC, KOBu-t in suitable solvent produces desired intermediate 5 which can be further converted into amine 6 via LAH reduction. The triazole 7 depicted as starting material may be synthesized from readily available materials. Reaction conditions are as described above in the Scheme; however, the skilled artisan will appreciate that certain modifications in the reaction conditions and/or reagents used are possible. Treatment of triazole 7 with ethyl acrylate in the presence of palladium (II) acetate and diisopropylethyl amine in the presence of a suitable solvent produces the desired Heck cross-coupling product 8. Coupling of 3 and 8 with [RhCl(cod)]₂ under suitable conditions produces intermediate 9 which can be further converted to 10 by hydrogenation with Pd on carbon followed by amide formation with amine 6 using T3P. The intermediate 10 was first cyclized with TFA and Et₃SiH followed by hydrolysis with NaOH to produce desired product 11.

Scheme 16

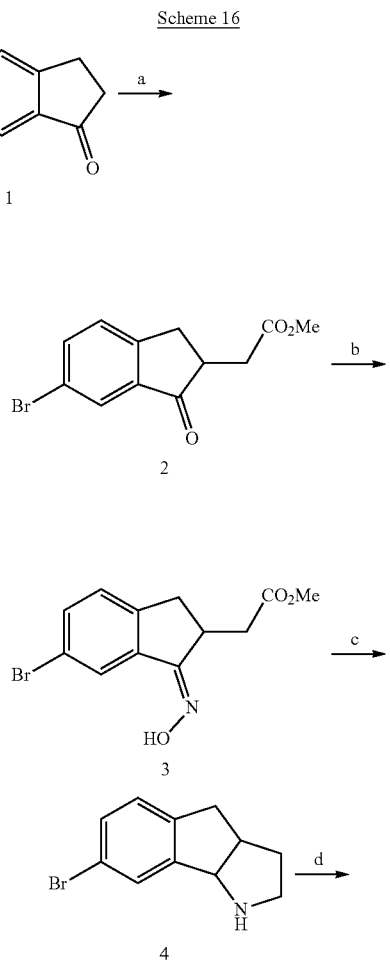

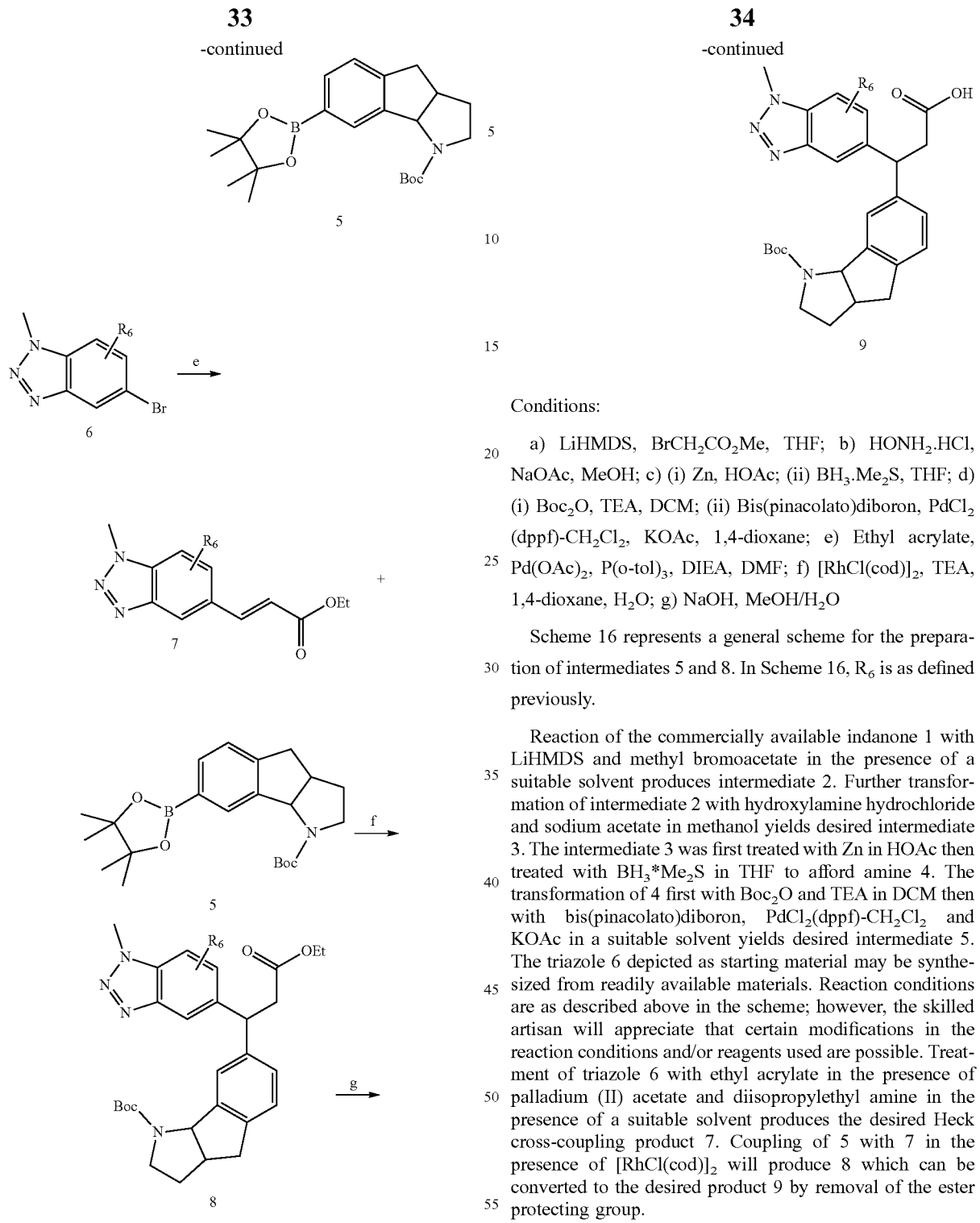

Conditions:

a) LiHMDS, BrCH$_2$CO$_2$Me, THF; b) HONH$_2$.HCl, NaOAc, MeOH; c) (i) Zn, HOAc; (ii) BH$_3$.Me$_2$S, THF; d) (i) Boc$_2$O, TEA, DCM; (ii) Bis(pinacolato)diboron, PdCl$_2$(dppf)-CH$_2$Cl$_2$, KOAc, 1,4-dioxane; e) Ethyl acrylate, Pd(OAc)$_2$, P(o-tol)$_3$, DIEA, DMF; f) [RhCl(cod)]$_2$, TEA, 1,4-dioxane, H$_2$O; g) NaOH, MeOH/H$_2$O Scheme 16 represents a general scheme for the preparation of intermediates 5 and 8. In Scheme 16, R$_6$ is as defined previously.

Reaction of the commercially available indanone 1 with LiHMDS and methyl bromoacetate in the presence of a suitable solvent produces intermediate 2. Further transformation of intermediate 2 with hydroxylamine hydrochloride and sodium acetate in methanol yields desired intermediate 3. The intermediate 3 was first treated with Zn in HOAc then treated with BH$_3$*Me$_2$S in THF to afford amine 4. The transformation of 4 first with Boc$_2$O and TEA in DCM then with bis(pinacolato)diboron, PdCl$_2$(dppf)-CH$_2$Cl$_2$ and KOAc in a suitable solvent yields desired intermediate 5. The triazole 6 depicted as starting material may be synthesized from readily available materials. Reaction conditions are as described above in the scheme; however, the skilled artisan will appreciate that certain modifications in the reaction conditions and/or reagents used are possible. Treatment of triazole 6 with ethyl acrylate in the presence of palladium (II) acetate and diisopropylethyl amine in the presence of a suitable solvent produces the desired Heck cross-coupling product 7. Coupling of 5 with 7 in the presence of [RhCl(cod)]$_2$ will produce 8 which can be converted to the desired product 9 by removal of the ester protecting group.

Scheme 17

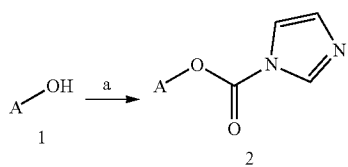

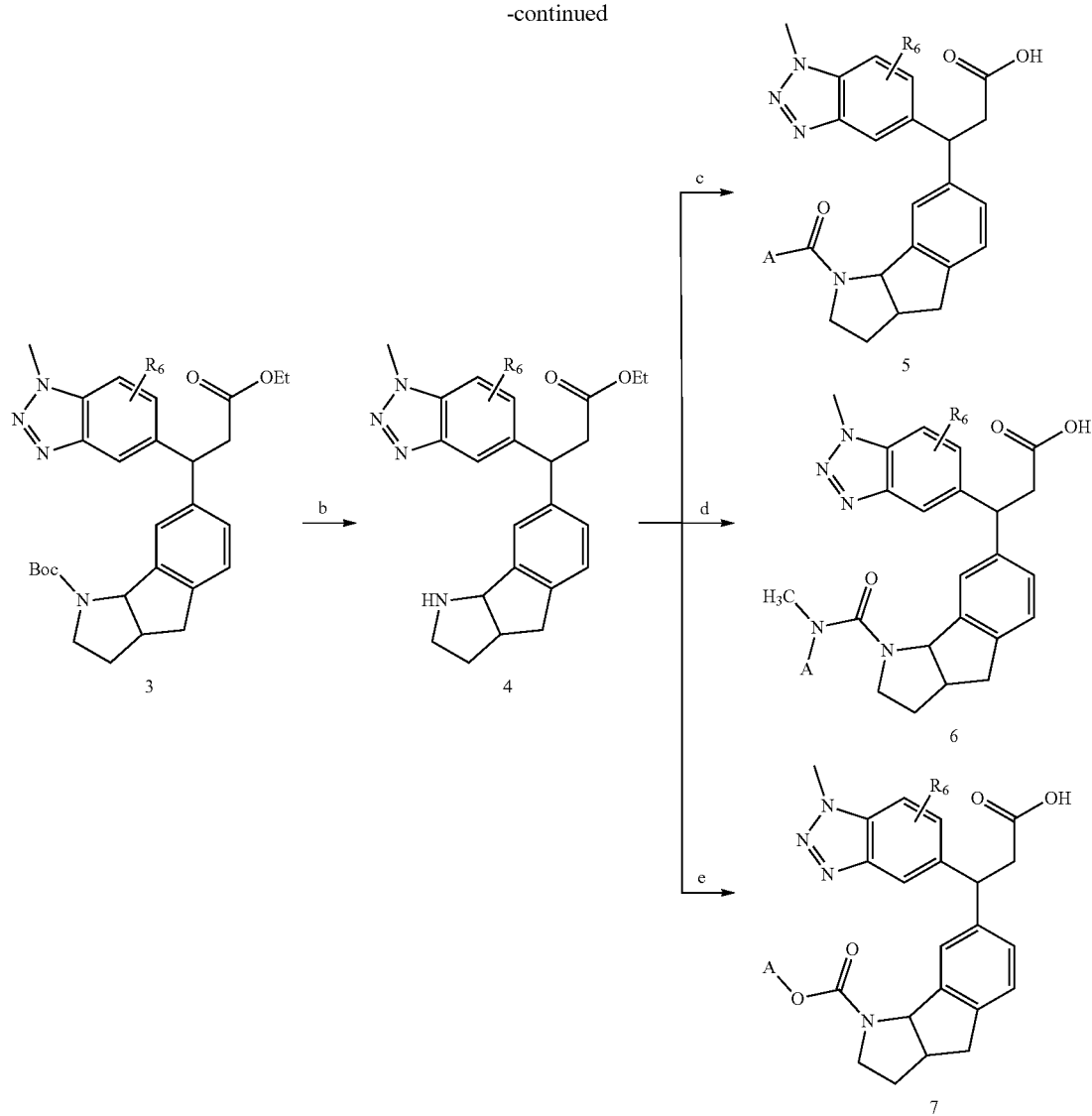

Conditions:

a) CDI, DMAP, DCM; b) HCl, 1,4-dioxane; c) (i) R₂CO₂H, T3P, TEA, DCM; (ii) NaOH, MeOH/H₂O; d) (i) CDI, CH₃A-NH, 1,4-dioxane; (ii) NaOH, MeOH/H₂O; e) (i) 2, MeCN; (ii) NaOH, MeOH/H₂O.

Scheme 17 represents a general scheme for the preparation of intermediates 2 and compounds according to Formula (II). In Scheme 17, $R_6$ and A are as defined previously.

Reaction of the commercially available alcohol 1 with CDI and DMAP produces intermediate 2. The intermediate 3 depicted as starting material may be synthesized from readily available materials as depicted in Scheme 16. The deprotection of Boc group of intermediate 3 with HCl in 1,4-dioxane produces intermediate 4. The intermediate 4 may be converted into amide product 5 by first amide formation using T3P followed by conversion of the ester to the acid. Urea product 6 may be obtained by first treating 4 with CDI followed by treatment with a suitable amine and then conversion of the ester to the acid. Carbamate 7 may be obtained by treatment with intermediate 2 then conversion of the ester to the acid.

Scheme 18

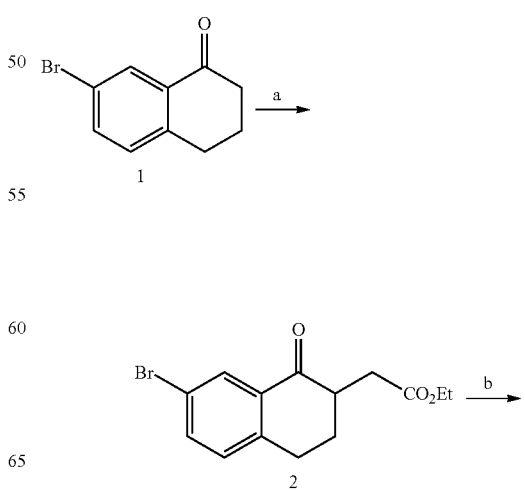

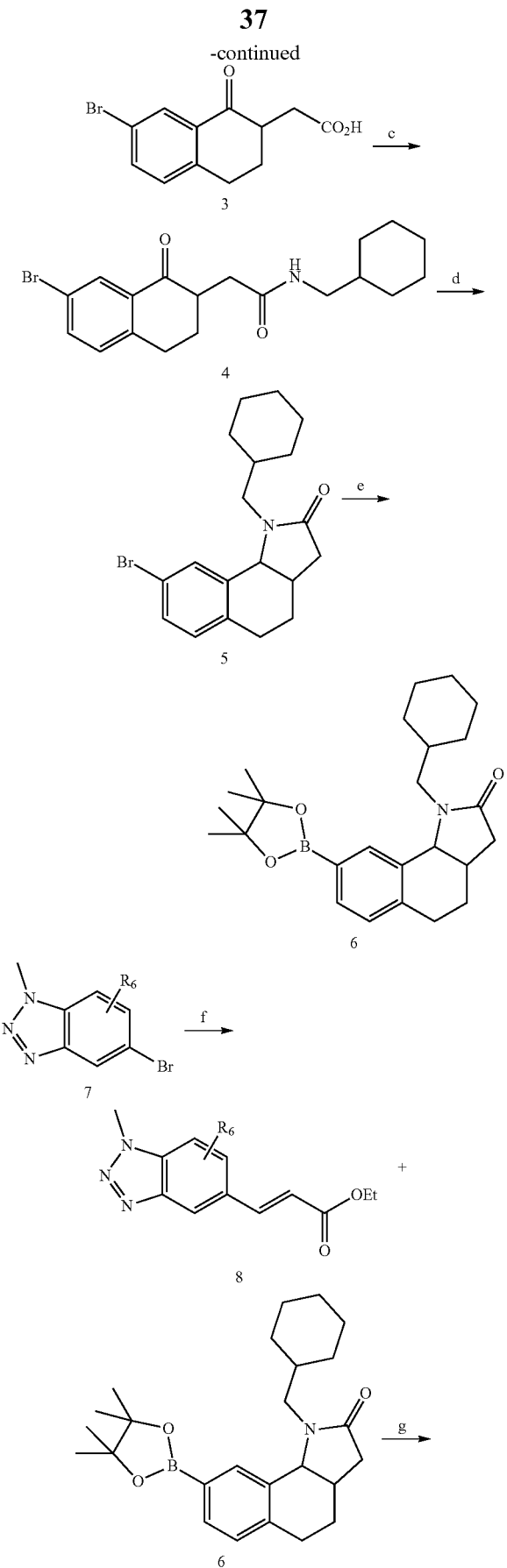
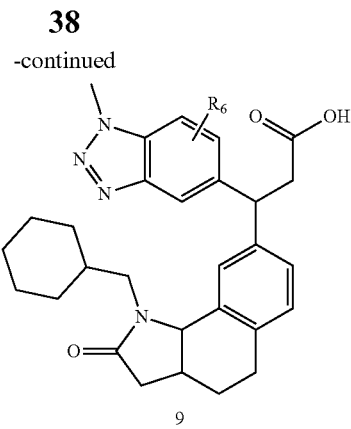

Conditions:

a) LiHMDS, BrCH$_2$CO$_2$Et, THF; b) NaOH, MeOH/H$_2$O; c) C$_6$H$_9$CH$_2$NH$_2$, T3P, TEA, DCM; d) TFA, Et$_3$SiH, MeCN; e) Bis(pinacolato)diboron, PdCl$_2$(dppf), KOAc, DMF; f) Ethyl acrylate, Pd(OAc)$_2$, P(o-tol)$_3$, DIEA, DMF; g) (i) [RhCl(cod)]$_2$, TEA, H$_2$O, 1,4-dioxane; (ii) NaOH, MeOH/H$_2$O.

Scheme 18 represents a general scheme for the preparation of intermediates 6 and compounds according to Formula (II). In Scheme 18, R$_6$ is as defined previously.

Reaction of the commercially available indanone 1 with LiHMDS and ethyl bromoacetate in the presence of a suitable solvent produces desired intermediate 2. Hydrolysis of intermediate 2 with NaOH produces intermediate 3. Conversion to the amide and subsequent cyclization of intermediate 4 with TFA and Et$_3$SiH produces intermediate 5 which was further transformed to intermediate 6 with bis(pinacolato)diboron, PdCl$_2$(dppf) and KOAc in a suitable solvent. The triazole 7 depicted as starting material may be synthesized from readily available materials. Reaction conditions are as described above in the scheme; however, the skilled artisan will appreciate that certain modifications in the reaction conditions and/or reagents used are possible. Treatment of triazole 7 with ethyl acrylate in the presence of palladium (II) acetate and diisopropylethyl amine in the presence of a suitable solvent produces the desired Heck cross-coupling product 8. The coupling of intermediate 6 and intermediate 8 is accomplished in the presence of [RhCl(cod)]$_2$. Conversion of the ester to the acid produces 9.

Scheme 19

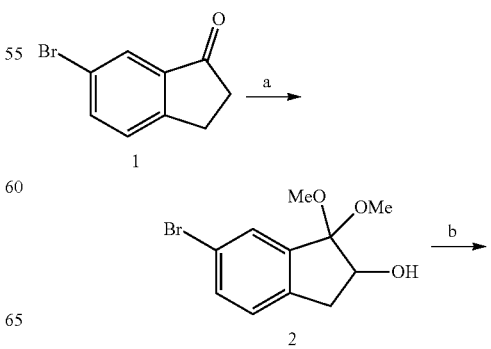

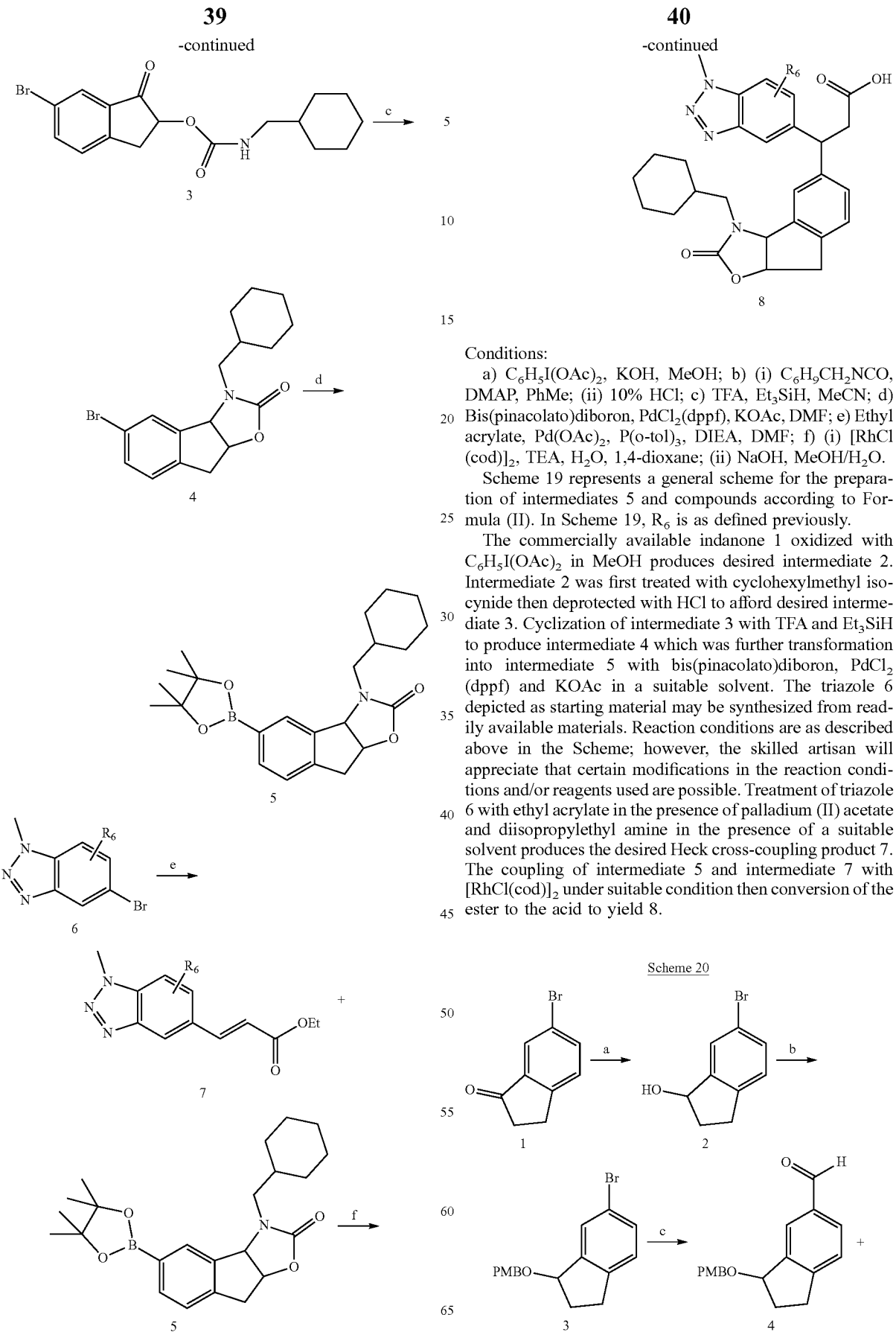

Conditions:
a) $C_6H_5I(OAc)_2$, KOH, MeOH; b) (i) $C_6H_9CH_2NCO$, DMAP, PhMe; (ii) 10% HCl; c) TFA, $Et_3SiH$, MeCN; d) Bis(pinacolato)diboron, $PdCl_2(dppf)$, KOAc, DMF; e) Ethyl acrylate, $Pd(OAc)_2$, $P(o\text{-}tol)_3$, DIEA, DMF; f) (i) [RhCl(cod)]$_2$, TEA, $H_2O$, 1,4-dioxane; (ii) NaOH, MeOH/$H_2O$.

Scheme 19 represents a general scheme for the preparation of intermediates 5 and compounds according to Formula (II). In Scheme 19, $R_6$ is as defined previously.

The commercially available indanone 1 oxidized with $C_6H_5I(OAc)_2$ in MeOH produces desired intermediate 2. Intermediate 2 was first treated with cyclohexylmethyl isocynide then deprotected with HCl to afford desired intermediate 3. Cyclization of intermediate 3 with TFA and $Et_3SiH$ to produce intermediate 4 which was further transformation into intermediate 5 with bis(pinacolato)diboron, $PdCl_2$(dppf) and KOAc in a suitable solvent. The triazole 6 depicted as starting material may be synthesized from readily available materials. Reaction conditions are as described above in the Scheme; however, the skilled artisan will appreciate that certain modifications in the reaction conditions and/or reagents used are possible. Treatment of triazole 6 with ethyl acrylate in the presence of palladium (II) acetate and diisopropylethyl amine in the presence of a suitable solvent produces the desired Heck cross-coupling product 7. The coupling of intermediate 5 and intermediate 7 with [RhCl(cod)]$_2$ under suitable condition then conversion of the ester to the acid to yield 8.

41
-continued
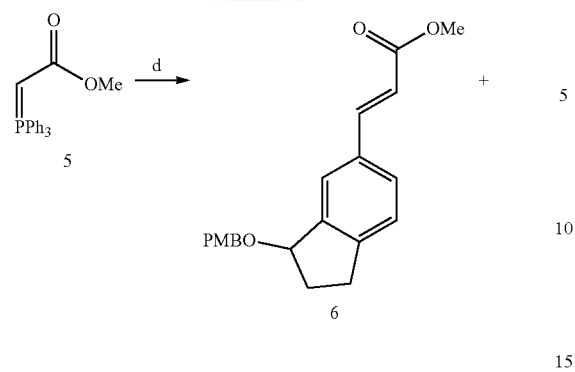
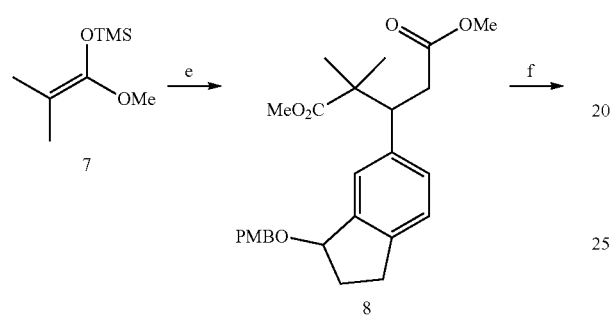
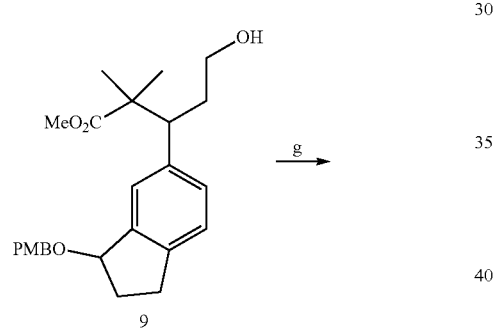

42
-continued
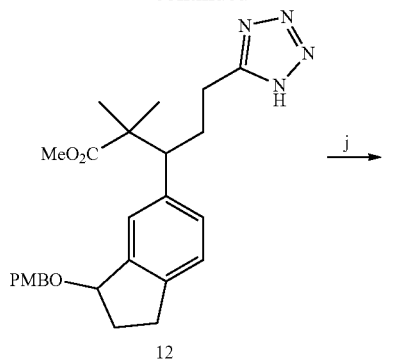
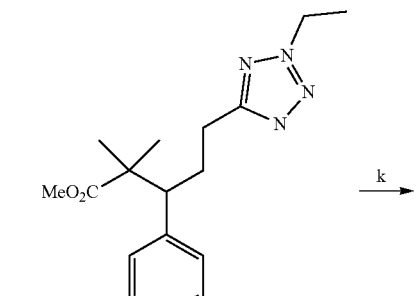
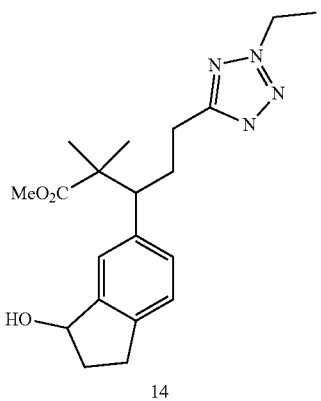
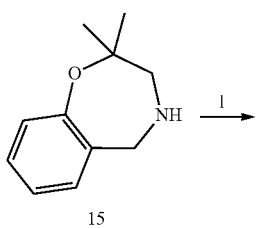

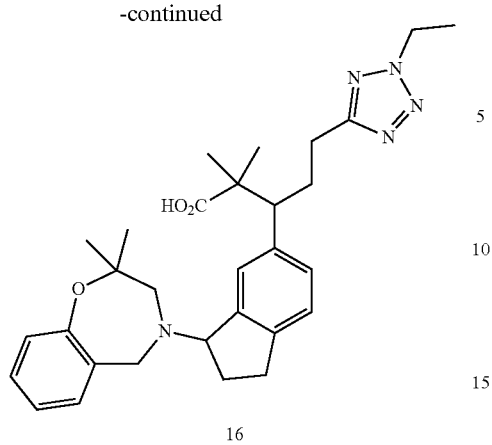

16

Conditions:
a) NaBH$_4$, THF; b) NaH, PMBCl; c) n-BuLi, THF, DMF, -78° C.; d) DCM, 40° C.; e) tetrabutyl ammonium benzoate, THF; f) (i) LiOH, 4:2:1 THF:MeOH:H$_2$O; (ii) BH$_3$.DMS; g) CBr$_4$, polymer-supported PPh$_3$; h) NaCN, 3:1 EtOH:H$_2$O; i) TMSN$_3$, TBAF.3H$_2$O; j) EtI, Et$_3$N; k) DDQ; l) (i) PBr$_3$; (ii) DIPEA, 15, 90° C.; (iii) NaOH, 120° C.

Scheme 20 represents a general scheme for the preparation of compounds according to Formula (I).

Treatment of ketone 1 with sodium borohydride will produce desired alcohol 2 which can be protected using paramethoxybenzylchloride and sodium hydride to afford aryl-bromide 3. By performing a halogen-lithium exchange, aryl-bromide 3 can be transformed into aldehyde 4, which can be converted to α,β-unsaturated ester 6 under standard Wittig olefination conditions with ylide 5. 1,4 addition of ketene-acetal 7 to α,β-unsaturated ester 6 can be accomplished by addition of tetrabutylammonium benzoate in THF to afford methyl-ester 8. One who is skilled in the art will appreciate that selective hydrolosis of methyl-ester 8 and subsequent reduction of the corresponding carboxylic acid will produce alcohol 9. Bromide 10 can be accessed by subjecting alcohol 9 to carbon tetrabromide and polymer supported triphenylphosphine. Displacement of bromide 10 to afford cyano 11 can be accomplished by heating sodium cyanide in the proper ratio of tetrahydrofuran, water, and methanol to the appropriate temperature. The skilled artisan will appreciate that formation of tetrazole 13 can be achieved by heating cyano 11 in the presence of trimethylsilylazide and tetrabutyl ammonium fluoride trihydrate in a microwave reactor, followed by alkylation with iodoethane and triethylamine. Subsequent deprotection will then afford benzylic alcohol 14. Conversion of the benzylic alcohol to the amine is accomplished via bromination and reaction with amine 15. This amine can then be hydrolized under basic microwave reactor conditions to afford 16.

Scheme 21

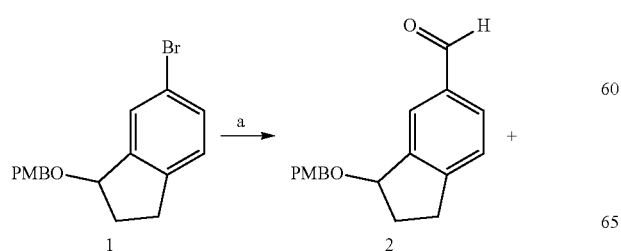

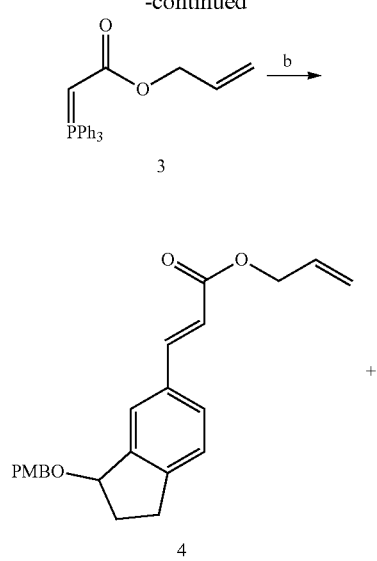

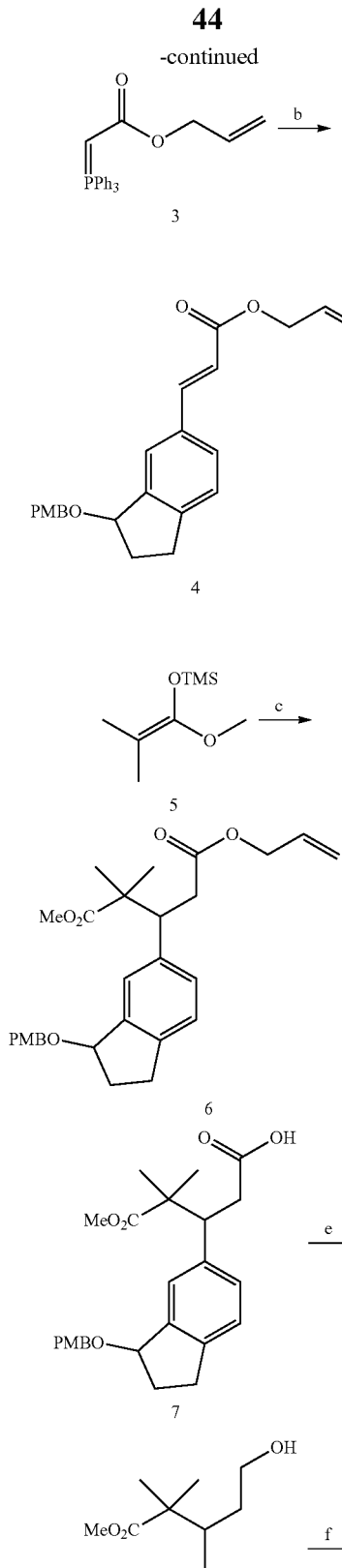

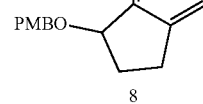

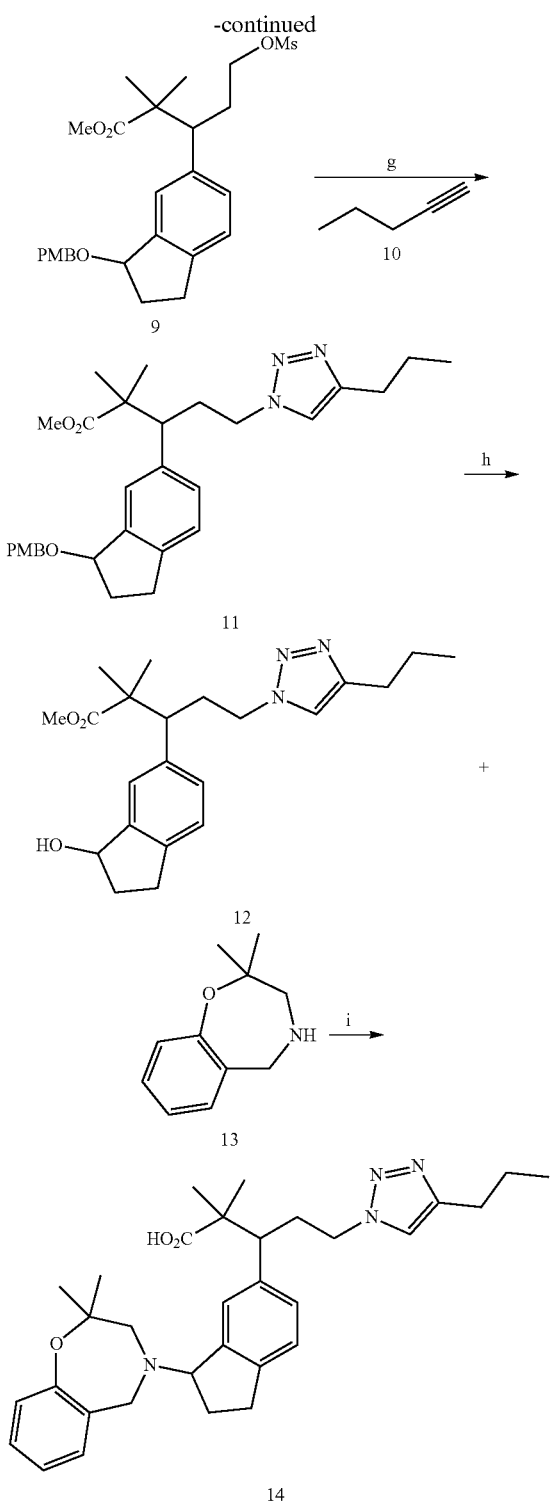

Conditions:

a) n-BuLi, THF, DMF, −78° C.; b) DCM, 40° C.; c) tetrabutyl ammonium benzoate, THF; d) Pd(PPh₃)₄, morpholine; e) BH₃*DMS; f) MsCl, Et₃N; g) NaN₃, CuI, DIPEA; h) DDQ; i) (i) PBr₃; (ii) 13, DIPEA; (iii) NaOH, 120° C.

Scheme 21 represents an alternative general scheme for the preparation of compounds according to Formula (I).

By performing a halogen-lithium exchange, aryl-bromide 1 can be transformed into aldehyde 2, which can be converted to α,β-unsaturated ester 4 under standard Wittig olefination conditions with ylide 3. 1,4 addition of silyl ketene acetal 5 to α,β-unsaturated ester 4 can be accomplished by addition of tetrabutylammonium benzoate in THF to afford allyl-ester 6. One skilled in the art will appreciate that palladium (0) catalyzed deprotection of the allyl group will afford carboxylic acid 7, which can be subsequently reduced to produce alcohol 8. Mesylation, and nucleophilic displacement will lead to an azide, which can be converted to triazole 11 with a copper-catalyzed azide-alkyne cycloaddition and an appropriate alkyne. After oxidative deprotection of the benzylic alcohol, 12 can be converted to amine 14 via bromination with phosphorus tribromide, and reaction with amine 13, followed by basic hydrolysis.

Biological Activity

As stated above, the compounds according to Formulas I and (II) are NRF2 regulators, and are useful in the treatment or prevention of human diseases that exhibit oxidative stress components such as respiratory and non-respiratory disorders, including COPD, asthma, fibrosis, chronic and acute asthma, lung disease secondary to environmental exposures, acute lung infection, chronic lung infection, al antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

The biological activity of the compounds according to Formulas (I) and II can be determined using any suitable assay for determining the activity of a candidate compound as a NRF2 antagonist, as well as tissue and in vivo models.

The biological activity of the compounds of Formulas (I) and (II) are demonstrated by the following tests.

BEAS-2B NQO1 MTT Assay

NAD(P)H:quinone oxidoreductase 1 (NQO1), also called DT diaphorase, is a homodimeric FAD-containing enzyme that catalyzes obligatory NAD(P)H-dependent two-electron reductions of quinones and protects cells against the toxic and neoplastic effects of free radicals and reactive oxygen species arising from one-electron reductions. The transcription of NQO1 is finely regulated by NRF2, and thus NQO1 activity is a good marker for NRF2 activation. On day one, frozen BEAS-2B cells (ATCC) are thawed in a water bath, counted, and re-suspended at a concentration of 250,000 cells/mL. Fifty microliters of cells are plated in 384 well black clear-bottomed plates. Plates are incubated at 37° C., 5% CO₂ overnight. On day two, plates are centrifuged and 50 nL of compound or controls are added to the cells. Plates are then incubated at 37° C., 5% CO₂ for 48 hours. On day four, medium is aspirated from the plate and crude cell lysates are made by adding 13 uL of 1× Cell Signaling Technologies lysis buffer with 1 Complete, Mini, EDTA-free Protease Inhibitor Tablet (Roche) for each 10 mL of lysis buffer. After lysis plates are incubated for 20 minutes at room temperature. Two microliters of lysate are removed for use in Cell Titer Glo assay (Promega) and MTT cocktail is prepared (Prochaska et. al. 1998) for measurement of NQO1 activity. Fifty microliters of MTT cocktail is added to each well, plate is centrifuged, and analyzed on an Envision plate reader (Perkin Elmer) using Absorbance 570 nm label for 30 minutes. Product formation is measured kinetically and the $pEC_{50}$ of NQO1 specific activity induction is calculated by plotting the change in absorbance (Delta OD/min) versus the log of compound concentration followed by 3-parameter fitting.

Beas2B NQO1 MTT Assay

All examples described herein possessed NQO1 specific enzyme activity in BEAS-2B cells with $EC_{50}$s between >10 uM-<1nM unless otherwise noted (see table below). $EC_{50}$s<1 nM (+++++), $EC_{50}$s 10 nM-1 nM (++++), $EC_{50}$s 10-100 nM (+++), $EC_{50}$s 100 nM-1 uM (++), $EC_{50}$s 1 uM-10 uM (+), $EC_{50}$s>10 uM (−), or were not determined (ND).

| Ex. # | EC50 |
|---|---|
| 1 | ++ |
| 2 | +++ |
| 3 | + |
| 4 | +++ |
| 5 | ++++ |
| 6 | ++ |
| 7 | + |
| 8 | + |
| 9 | + |
| 10 | + |
| 11 | + |
| 12 | + |
| 13 | + |
| 14 | + |
| 15 | ++ |
| 16 | ++ |
| 17 | + |
| 18 | +++ |
| 19 | ++ |
| 20 | ++ |
| 21 | ++++ |
| 22 | ++++ |
| 23 | ++++ |
| 24 | ++++ |
| 25 | ++++ |
| 26 | +++ |
| 27# | +++++ |
| 28 | +++++ |
| 29 | +++++ |
| 30 | ++++ |
| 31 | ++++ |
| 32 | ++++ |
| 33 | ++++ |
| 34 | ++++ |
| 35 | ++++ |
| 36 | ++++ |
| 37 | ++++ |
| 38 | ++++ |
| 39 | ++++ |
| 40 | ++++ |
| 41 | ++++ |
| 42 | ++++ |
| 43 | ++++ |
| 44 | ++++ |
| 45 | +++ |
| 46 | +++ |
| 47 | +++ |
| 48 | +++ |
| 49 | +++ |
| 50 | +++ |
| 51 | +++ |
| 52 | +++ |
| 53 | ++ |
| 54 | ++ |
| 55 | ++ |
| 56 | ++ |
| 57 | ++ |
| 58 | ++ |
| 59 | ++ |
| 60 | ++ |
| 61 | + |
| 62 | + |
| 63 | + |
| 64 | +++ |
| 65 | +++ |
| 66 | ++ |
| 67 | +++++ |
| 68 | +++ |
| 69 | +++++ |
| 70 | ++++ |
| 71 | ++++ |
| 72 | ++++ |
| 73 | ++++ |
| 74 | +++ |
| 75 | +++ |
| 76 | + |
| 77 | +++++ |
| 78 | ++++ |
| 79 | ++++ |
| 80 | ++ |
| 81 | +++ |
| 82 | +++ |
| 83 | +++ |
| 84 | + |
| 85 | +++ |
| 86 | +++++ |
| 87 | +++ | in some determinations $pEC_{50}$ values were <170 pM

NRF2-Keap1 FP Assay

One model for the NRF2-Keap1 interaction is through two binding sites in the Neh2 domain on NRF2. The two sites are referred to as the DLG binding motif (latch domain, uM affinity) and the ETGE binding motif (hinge domain, nM affinity). The Keap1 protein consists of an N-terminal region (NTR), a broad complex, tramtrack, and brick a' brac domain (BTB), an intervening region (IVR), a double glycine repeat domain (DGR or Kelch), and a C-terminal region. The DLG and ETGE motifs of NRF2's Neh2 domain bind to the Kelch domain of Keap1 at different affinities. In the Keap1 Kelch fluorescence polarization (FP) assay, a TAMRA-labeled 16 mer peptide (AFFAQLQLDEETGEFL) containing the ETGE motif of NRF2 and the Kelch domain (321-609) of Keap1 is used. The assay determines if a compound interferes with the binding between Keap1 (361-609) and the TAMRA-labeled peptide. Binding of TAMRA-labeled NRF2 peptide to Keap1 (321-609) results in a high FP signal. If a compound interferes with the binding between the peptide and the protein, it will cause the assay signal to decrease. Thus, assay signal is inversely proportional to binding inhibition.

FP Assay:

100 nl of 100× compound dose response curves (serial 3-fold dilutions) in DMSO are stamped using an Echo liquid handling system (Labcyte) into 384-well low volume black assay plates (Greiner, #784076), with DMSO in columns 6 and 18. The top concentration of compound is located in columns 1 and 13. Keap1 (321-609) is diluted to 40 nM (2×) in 1× assay buffer (50 mM Tris, pH 8.0, 100 mM NaCl, 5 mM $MgCl_2$, 1 mM DTT, 2 mM CHAPS, and 0.005% BSA) and 5 ul is added using a Multidrop Combi (Thermo Electron Corporation) equipped with a metal tip dispenser to all wells of the compound plate, except column 18. Column 18 receives only 5 ul of assay buffer. Immediately, 5 uL of 16 nM (2×) of Tamra labeled peptide (AFFAQLQLDEETGEFL, 21$^{st}$ Century Biochemicals) is added to all wells of the plate. The plates are spun at 500 rpm for 1 min, incubated for 1 hr at room temperature, and read on an Analyst GT (Molecular Devices) equipped with excitation (530/25 nm) and emission (580/10 nm) filters designed for Tamra probes. A 561 nm dichroic mirror is also used in the Analyst. The final assay concentrations of Keap1 (321-609) and Tamra labeled peptide are 20 nM and 8 nM, respectively. Fluorescence measurements, represented as mP, are used in the transformation of the data. Compound activity is calculated based on percent inhibition, normalized against controls in the assay (Control 1 contains the Tamra peptide and Keap1 (321-609) together (0% response) and control 2 contains the Tamra peptide alone (100% response)). Data analysis is handled using the software package Abase XE (Surrey, United Kingdom. The % inhibition values are calculated by the equation:

100−(100*((compound response-average control 2)/ (average control 1-average control2))). For calculation of pIC$_{50}$s, Abase XE uses a four parameter equation.

All examples described herein possessed activity in the Keap1/NRF2 FP assay.

NRF2-Keap1 TR-FRET Assay

In the NRF2-Keap1 TR-FRET (time-resolved fluorescence resonance energy transfer) assay, full length NRF2 protein and full length Keap1 protein (Keap1 exists a dimer) are used. The assay detects the ability of compound to displace the binding of FlagHis-tagged Keap1 with biotinylated, Avi-tagged NRF2 protein. Biotin-NRF2 binds to streptavidin-europium (a component of the detection mix) and Keap1-FlagHis is recognized by anti-Flag APC (allophycocyanin) antibody (also a component of the detection mix). If binding occurs between the two proteins, there will be an energy transfer from the Eu+3 (donor) at 615 nm to the APC (acceptor) at 665 nm. A potential Keap1 inhibitor will cause a reduction in the TR-FRET signal by interfering with the binding of Keap1 to NRF2.

One hundred nanoliters of 100× compound dose response curves (serial 3-fold dilutions) in DMSO are stamped using an Echo liquid handling system (Labcyte) into 384-well, low volume, black assay plates (Greiner, #784076), with DMSO in columns 6 and 18. The top concentration of compound is located in columns 1 and 13. All reagents are diluted in assay buffer (50 mM Tris, pH 8.0, 5 mM MgCl2, 100 mM NaCl, 0.005% BSA, 1 mM DTT, and 2 mM CHAPS). The BSA, DTT, and CHAPS are added to the assay buffer on the day of assay. Using a Multidrop Combi (Thermo Electron Corporation) equipped with a metal tip dispenser, 5 ul of 25 nM Keap1-FlagHis protein is added to all wells of the compound plate, with the exception of the wells in column 18. Wells in column 18 receive 5 ul of assay buffer instead. Plates are centrifuged at 500 rpm for 1 minute, covered with a plate lid, and incubated at 37° C. for 2.25 hours. Plates are then removed from the incubator and allowed to cool to RT for 15 minutes. Five microliters of 50 nM biotin-NRF2 protein is then added to all wells of the plates and the plates are spun at 500 rpm for 1 minute, followed by incubating at 4° C. for 1.25 hours. The plates are then allowed to warm to RT for 15 minutes, followed by the addition of 10 ul of detection mix (1 nM Streptavidin Eu+W1024 and 5 ug/ml mouse anti-DYKDDDDK IgG conjugated to SureLight APC antibody; both from Columbia Biosciences) to all wells. Plates are spun at 500 rpm for 1 minute, incubated for 1 hour at RT, and read on an Envision plate reader using a 320 nm excitation filter and 615 nm and 665 nm emission filters. Compound response (% inhibition) and potency (pIC50) are calculated based on the ratio of the two emissions (665 nm/615 nm) and then the transformed data is normalized against controls in the assay (control 1=1% DMSO in the presence of NRF2 and Keap1 protein and control 2=1% DMSO in the absence of protein). Data analysis is handled using the software package Abase XE (Surrey, United Kingdom). The % inhibition values are calculated from the ratio (transformed) data by the equation:

100−(100*(compound response-average control 2)/ (average control 1-average control2)).

For calculation of pIC50s, Abase XE uses a four parameter equation.

NRF2-Keap1 TR-FRET Low Protein Assay

In the NRF2-Keap1 TR-FRET (time-resolved fluorescence resonance energy transfer) low protein assay, full length NRF2 protein and full length Keap1 protein (Keap1 exists a dimer) are used. The assay detects a compound's ability to displace the binding of Keap1 FlagHis with biotinylated Avi-NRF2 protein. Biotin-NRF2 binds to streptavidin-europium (a component of the detection mix) and Keap1 FlagHis is recognized by anti-Flag APC (allophycocyanin) antibody (also a component of the detection mix). If binding occurs between the two proteins, there will be an energy transfer from the Eu+3 (donor) at 615 nm to the APC (acceptor) at 665 nm. A potential NRF2 inhibitor will cause a reduction in the TR-FRET signal by interfering with the binding of Keap1 to NRF2.

Ten nanoliters of 100× compound dose response curves (serial 3-fold dilutions) in DMSO are stamped using an Echo liquid handling system (Labcyte) into 384-well, low volume, black assay plates (Greiner, #784076), with DMSO in columns 6 and 18. An additional 90 nl DMSO is added to each well, to bring the total volume to 100 nl per well. The top concentration of compound is located in columns 1 and 13, with the serial dilutions going across the row. All reagents are diluted in assay buffer (50 mM Tris, pH 8.0, 5 mM MgCl2, 100 mM NaCl, 0.005% BSA, 1 mM DTT, and 2 mM CHAPS. The BSA, DTT, and CHAPS are added to the assay buffer on the day of assay. Using a Multidrop Combi (Thermo Electron Corporation) equipped with a metal tip dispenser, 5 ul of 1.25 nM Keap1 FlagHis protein is added to all wells of the compound plate, with the exception of the wells in column 18. Wells in column 18 receive 5ul of assay buffer instead. Plates are centrifuged at 500 rpm for 1 minute, covered with a plate lid, and incubated at 37° C. for 2.25 hours. Plates are then removed from the incubator and allowed to cool to RT for 15 minutes. Five microliters of 2.5 nM biotin-NRF2 protein is then added to all wells of the plates and the plates are spun at 500 rpm for 1 minute, followed by incubating at 4° C. for 1.25 hours. The plates are then allowed to warm to RT for 15 minutes, followed by the addition of 10 ul of detection mix (1 nM Streptavidin Eu+W1024 and 5 ug/ml mouse anti-DYKDDDDK IgG conjugated to SureLight APC antibody; both from Columbia Biosciences) to all wells. Plates are spun at 500 rpm for 1 minute, incubated for 1 hour at RT, and read on an Envision plate reader using a 320 nm excitation filter and 615 nm and 665 nm emission filters. Compound response (% inhibition) and potency (pIC50) are calculated based on the ratio of the two emissions (665 nm/615 nm) and then the transformed data is normalized against controls in the assay (control 1=1% DMSO in the presence of NRF2 and Keap1 protein and control 2=1% DMSO in the presence of only the NRF2 protein). Data analysis is handled using the software package Abase XE (Surrey, United Kingdom). The % inhibition values are calculated from the ratio (transformed) data by the equation:

$$100-(100*(\text{compound response-average control 2})/(\text{average control 1-average control2})).$$

For calculation of pIC50s, Abase XE uses a four parameter equation.

Methods of Use

The compounds of the invention are NRF2 regulators, and are useful in the treatment or prevention of respiratory disorders, including COPD, asthma, fibrosis, lung infection, diabetic nephropathy/chronic kidney disease, autoimmune diseases (e.g., multiple sclerosis and inflammatory bowel disease), eye diseases (e.g., AMD, Fuchs, and uveitis), cardiovascular diseases, Non-alcoholic steatohepatitis (NASH), Parkinson's, Alzheimer's, psoriasis, acute kidney injury, topical effects of radiation, and kidney transplant.

Accordingly, in another aspect the invention is directed to methods of treating such conditions.

The methods of treatment of the invention comprise administering a safe and effective amount of a compound according to Formula I or a pharmaceutically-acceptable salt thereof to a patient in need thereof.

As used herein, "treat" in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "safe and effective amount" in reference to a compound of the invention or other pharmaceutically-active agent means an amount of the compound sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the condition being treated; the severity of the condition being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient" refers to a human or other animal.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin as well as intraocular, otic, intravaginal, and intranasal administration.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical dosages for oral administration range from 1 mg to 1000 mg per person per 5 day. Preferred dosages are 1-500 mg once daily, more preferred is 1-100 mg per person per day. IV dosages range form 0.1-000 mg/day, preferred is 0.1-500 mg/day, and more preferred is 0.1-100 mg/day. Inhaled daily dosages range from 10 ug-10 mg/day, with preferred 10 ug-2 mg/day, and more preferred 50 uug-500 ug/day.

Additionally, the compounds of the invention may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, ethers, esters, thioesters, carbonates, and carbamates, are well known to those skilled in the art.

Compositions

The compounds of the invention will normally, but not necessarily, be formulated into pharmaceutical compositions prior to administration to a patient. Accordingly, in another aspect the invention is directed to pharmaceutical compositions comprising a compound of the invention and one or more pharmaceutically-acceptable excipient.

The pharmaceutical compositions of the invention may be prepared and packaged in bulk form wherein a safe and effective amount of a compound of the invention can be extracted and then given to the patient such as with powders or syrups. Alternatively, the pharmaceutical compositions of the invention may be prepared and packaged in unit dosage form wherein each physically discrete unit contains a safe and effective amount of a compound of the invention. When prepared in unit dosage form, the pharmaceutical compositions of the invention typically contain from 1 mg to 1000 mg.

The pharmaceutical compositions of the invention typically contain one compound of the invention. However, in certain embodiments, the pharmaceutical compositions of the invention contain more than one compound of the invention. For example, in certain embodiments the pharmaceutical compositions of the invention contain two compounds of the invention. In addition, the pharmaceutical compositions of the invention may optionally further comprise one or more additional pharmaceutically active compounds.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically-acceptable.

The compound of the invention and the pharmaceutically-acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as dry powders, aerosols, suspensions, and solutions; and (6) topical administration such as creams, ointments, lotions, solutions, pastes, sprays, foams, and gels.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting of the compound or compounds of the invention once administered to the patient from one organ, or portion of the body, to another organ, or portion of the body. Certain pharmaceutically-acceptable excipients may be chosen for their ability to enhance patient compliance.

Suitable pharmaceutically-acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmellose, alginic acid, and sodium carboxymethyl cellulose. The oral solid dosage form may further comprise a lubricant. Suitable lubricants include stearic acid, magnesium stearate, calcium stearate, and talc.

In another aspect, the invention is directed to a dosage form adapted for administration to a patient parenterally including subcutaneous, intramuscular, intravenous or intradermal. Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

In another aspect, the invention is directed to a dosage form adapted for administration to a patient by inhalation. For example, the compound of the invention may be inhaled into the lungs as a dry powder, an aerosol, a suspension, or a solution.

Dry powder compositions for delivery to the lung by inhalation typically comprise a compound of the invention as a finely divided powder together with one or more pharmaceutically acceptable excipients as finely divided powders. Pharmaceutically acceptable excipients particularly suited for use in dry powders are known to those skilled in the art and include lactose, starch, mannitol, and mono-, di-, and polysaccharides.

The dry powder compositions for use in accordance with the present invention are administered via inhalation devices. As an example, such devices can encompass capsules and cartridges of for example gelatin, or blisters of, for example, laminated aluminum foil. In various embodiments, each capsule, cartridge or blister may contain doses of composition according to the teachings presented herein. Examples of inhalation devices can include those intended for unit dose or multi-dose delivery of composition, including all of the devices set forth herein. As an example, in the case of multi-dose delivery, the formulation can be pre-metered (e.g., as in Diskus®, see GB2242134, U.S. Pat. Nos. 6,032,666, 5,860,419, 5,873,360, 5,590,645, 6,378,519 and 6,536,427 or Diskhaler, see GB 2178965, 2129691 and 2169265, U.S. Pat. Nos. 4,778,054, 4,811,731, 5,035,237) or metered in use (e.g. as in Turbuhaler, see EP 69715, or in the devices described in U.S. Pat. No. 6,321,747). An example of a unit-dose device is Rotahaler (see GB 2064336). In one embodiment, the Diskus® inhalation device comprises an elongate strip formed from a base sheet having a plurality of recesses spaced along its length and a lid sheet peelably sealed thereto to define a plurality of containers, each container having therein an inhalable formulation containing the compound optionally with other excipients and additive taught herein. The peelable seal is an engineered seal, and in one embodiment the engineered seal is a hermetic seal. Preferably, the strip is sufficiently flexible to be wound into a roll. The lid sheet and base sheet will preferably have leading end portions which are not sealed to one another and at least one of the leading end portions is constructed to be attached to a winding means. Also, preferably the engineered seal between the base and lid sheets extends over their whole width. The lid sheet may preferably be peeled from the base sheet in a longitudinal direction from a first end of the base sheet.

A dry powder composition may also be presented in an inhalation device which permits separate containment of two different components of the composition. Thus, for example, these components are administrable simultaneously but are stored separately, e.g. in separate pharmaceutical compositions, for example as described in WO 03/061743 A1 WO 2007/012871 A1 and/or WO2007/068896. In one embodiment an inhalation device permitting separate containment of components is an inhaler device having two peelable blister strips, each strip containing pre-metered doses in blister pockets arranged along its length, e.g., multiple containers within each blister strip. Said device has an internal indexing mechanism which, each time the device is actuated, peels opens a pocket of each strip and positions the blisters so that each newly exposed dose of each strip is adjacent to the manifold which communicates with the mouthpiece of the device. When the patient inhales at the mouthpiece, each dose is simultaneously drawn out of its associated pocket into the manifold and entrained via the mouthpiece into the patient's respiratory tract. A further device that permits separate containment of different components is DUOHALER™ of Innovata. In addition, various structures of inhalation devices provide for the sequential or separate delivery of the pharmaceutical composition(s) from the device, in addition to simultaneous delivery.

Aerosols may be formed by suspending or dissolving a compound of the invention in a liquefied propellant. Suitable propellants include halocarbons, hydrocarbons, and other liquefied gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of the invention will typically be administered to a patient via a metered dose inhaler (MDI). Such devices are known to those skilled in the art.

The aerosol may contain additional pharmaceutically acceptable excipients typically used with multiple dose inhalers such as surfactants, lubricants, cosolvents and other excipients to improve the physical stability of the formulation, to improve valve performance, to improve solubility, or to improve taste.

Suspensions and solutions comprising a compound of the invention may also be administered to a patient via a nebulizer. The solvent or suspension agent utilized for nebulization may be any pharmaceutically acceptable liquid such as water, aqueous saline, alcohols or glycols, e.g., ethanol, isopropyl alcohol, glycerol, propylene glycol, polyethylene glycol, etc. or mixtures thereof. Saline solutions utilize salts which display little or no pharmacological activity after administration. Both organic salts, such as alkali metal or ammonium halogen salts, e.g., sodium chloride, potassium chloride or organic salts, such as potassium, sodium and ammonium salts or organic acids, e.g., ascorbic acid, citric acid, acetic acid, tartaric acid, etc. may be used for this purpose.

Other pharmaceutically acceptable excipients may be added to the suspension or solution. The compound of the invention may be stabilized by the addition of an inorganic acid, e.g., hydrochloric acid, nitric acid, sulfuric acid and/or phosphoric acid; an organic acid, e.g., ascorbic acid, citric acid, acetic acid, and tartaric acid, etc., a complexing agent such as EDTA or citric acid and salts thereof; or an antioxidant such as antioxidant such as vitamin E or ascorbic acid. These may be used alone or together to stabilize the compound of the invention. Preservatives may be added such as benzalkonium chloride or benzoic acid and salts thereof. Surfactant may be added particularly to improve the physical stability of suspensions. These include lecithin, disodium dioctylsulphosuccinate, oleic acid and sorbitan esters.

The compounds of Formulas (I) and (II) and pharmaceutically acceptable salts thereof may be used in combination with one or more other agents which may be useful in the prevention or treatment of allergic disease, inflammatory disease, autoimmune disease, for example; antigen immunotherapy, anti-histamines, corticosteroids, (eg fluticasone propionate, fluticasone furoate, beclomethasone dipropionate, budesonide, ciclesonide, mometasone furoate, triamcinolone, flunisolide), NSAIDs, leukotriene modulators (e.g. montelukast, zafirlukast, pranlukast), iNOS inhibitors, tryptase inhibitors, IKK2 inhibitors, p38 inhibitors, Syk inhibitors, protease inhibitors such as elastase inhibitors, integrin antagonists (e.g., beta-2 integrin antagonists), adenosine A2a agonists, mediator release inhibitors such as sodium chromoglycate, 5-lipoxygenase inhibitors (zyflo), DP1 antagonists, DP2 antagonists, PI3K delta inhibitors, ITK inhibitors, LP (lysophosphatidic) inhibitors or FLAP (5-lipoxygenase activating protein) inhibitors (e.g. sodium 3-(3-(tert-butylthio)-1-(4-(6-ethoxypyridin-3-yl)benzyl)-5-((5-methylpyridin-2-yl)methoxy)-1H-indol-2-yl)-2,2-dimethylpropanoate), bronchodilators (e.g., muscarinic antagonists, beta-2 agonists), methotrexate, and similar agents;

monoclonal antibody therapy such as anti-IgE, anti-TNF, anti-IL-5, anti-IL-6, anti-IL-12, anti-IL-1 and similar agents; cytokine receptor therapies e.g. etanercept and similar agents; antigen non-specific immunotherapies (e.g. interferon or other cytokines/chemokines, chemokine receptor modulators such as CCR3, CCR4 or CXCR2 antagonists, other cytokine/chemokine agonists or antagonists, TLR agonists and similar agents).

The compounds may also be used in combination with agents for aiding transplantation including Cyclosporines, Tacrolimus, Mycophenolate mofetil, Prednisone, Azathioprine, Sirolimus, Daclizumab, Basiliximab, or OKT3.

They may also be used in combination with agents for Diabetes: metformin (biguanides), meglitinides, sulfonylureas, DPP-4 inhibitors, Thiazolidinediones, Alpha-glucosidase inhibitors, Amylin mimetics, Incretin mimetics, and insulin.

The compounds may be used in combination with anti-hypertensives such as diuretics, ACE inhibitors, ARBS, calcium channel blockers, and beta blockers.

One embodiment of the invention encompasses combinations comprising one or two other therapeutic agents. It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates to optimize the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical formulation and thus pharmaceutical formulations comprising a combination as defined above together with a pharmaceutically acceptable diluent or carrier represent a further aspect of the invention.

The individual compounds of such combinations may be administered either sequentially or simultaneously in separate or combined pharmaceutical formulations. In one embodiment, the individual compounds will be administered simultaneously in a combined pharmaceutical formulation. Appropriate doses of known therapeutic agents will readily be appreciated by those skilled in the art.

The invention thus provides, in a further aspect, a pharmaceutical composition comprising a combination of a compound of the invention together with another therapeutically active agent.

EXAMPLES

The invention will now be described by reference to the following examples which are merely illustrative and are not to be construed as a limitation of the scope of the present invention. All temperatures are given in degrees Celsius, all solvents are highest available purity and all reactions run under anhydrous conditions in an argon (Ar) or nitrogen ($N_2$) atmosphere where necessary.

Analtech Silica Gel GF and E. Merck Silica Gel 60 F-254 thin layer plates were used for thin layer chromatography. Both flash and gravity chromatography were carried out on silica gel 230-400, 100-200 & 60-120 Cilicant Brand. The CombiFlash® system used for purification in this application was purchased from Isco, Inc. CombiFlash® purification was carried out using prepacked silica gel columns, a detector with UV wavelength at 254 nm and a variety of solvents or solvent combinations.

Preparative HPLC was performed using a Gilson or Waters Preparative System with variable wavelength UV detection or an Agilent Mass Directed AutoPrep (MDAP) system or Shimadzu PREP LC 20AP with both mass and variable wavelength UV detection. A variety of reverse phase columns, e.g., Luna C18(2), SunFire C18, XBridge C18, Atlantics T3, Kromasil C18, Xbridge Phenyl-Hexyl columns were used in the purification with the choice of column support dependent upon the conditions used in the purification. The compounds were eluted using a gradient of $CH_3CN$ or methanol and water. Neutral conditions used an $CH_3CN$ and water gradient with no additional modifier, acidic conditions used an acid modifier, usually 0.1% TFA or 0.1% formic acid and basic conditions used a basic modifier, usually 0.1% $NH_4OH$ (added to the water) or 10 mM ammonium bicarbonate (added to the water), or 0.05% $NH_4HCO_3$ (added to water).

Analytical HPLC was run using an Agilent system or Waters Alliance HPLC with 2996 PDA detector, Waters Acquity UPLC-MS or Agilent Infinity 1290 with PDA or conducted on a Sunfire C18 column, alternative on XSELECT CSH C18 column using reverse phase chromatography with a $CH_3CN$ and water gradient with 0.1% formic acid modifier (added to each solvent) and basic conditions used a basic modifier, usually 5 mM ammonium bicarbonate or 10 mM ammonium bicarbonate in water adjusted pH to 10 with ammonia solution. The compound was analyzed by LCMS using a Shimadzu LC system with UV 214 nm wavelength detection and $H_2O$—$CH_3CN$ gradient elution (4-95% over 1.9 min.) acidified to 0.02% TFA. The reversed-phase column was a 2.1×20 mm Thermo Hypersil Gold C18 (1.9u particles) at 50° C. The single quadrupole MS detector was either a Sciex 150EX or a Waters ZQ operated in positive-ion. Alternatively, LC-MS was determined using either a PE Sciex Single Quadrupole 150EX LC-MS, or Waters ZQ Single Quadrupole, Waters 3100 Single Quadrupole, Agilent 6130 SQD or Agilent 6120 Single Quadrupole LC-MS instruments. The compound is analyzed using a reverse phase column, e.g., Thermo Hypersil Gold C18 and/or Luna C18 eluted using a gradient of $CH_3CN$ and water with a low percentage of an acid modifier such as 0.02% or 0.1% TFA.

Preparative Chiral SFC was performed using a Thar/Waters Preparative SFC System with single wavelength UV detection system. A variety of chiral SFC columns, e.g. Chiralpak IA, IC, AY, AD, IF, OJ were used in the purification. The compounds are eluted using supercritical fluid $CO_2$ and co-solvents, such as MeOH, EtOH, IPA, and combination of these solvent in different ratio based on the compound. Modifiers (0.1% to 0.4% of TFA, $NH_4OH$, DEA, TEA) can be used as needed. Normal phase chromatography is performed using the above mentioned chiral columns & pyridyl amide, ethyl pyridine achiral columns are used for chiral & achiral purifications respectively. Modifiers (0.1% of TFA, $NH_4OH$, DEA) would be used as needed. K PREP Lab 100 G—YMC instruments are used in normal phase preparative scale purifications.

Analytical Chiral SFC was run using a Thar/Waters SFC system with variable wavelength UV detection. A variety of chiral SFC columns, e.g. Chiralpak IA, IB, IC, ID, IF, AY, AD, OD, C2, AS, OJ, CCL4 were used in the purification. The compounds are eluted using supercritical fluid $CO_2$ and co-solvents, such as MeOH, EtOH, IPA, and combination of these solvent in different ratio based on the compound selectivity. Modifiers (0.1% to 0.4% of TFA, $NH_4OH$, DEA, TEA) would be used as needed.

Celite® is a filter aid composed of acid-washed diatomaceous silica, and is a registered trademark of Manville Corp., Denver, Colo. Isolute® is a functionalized silica gel based sorbent, and is a registered trademark of Biotage AB Corp., Sweden.

Nuclear magnetic resonance spectra were recorded at 400 MHz using a Bruker AVANCE 400 or Brucker DPX400 spectrometer or Varian MR400 spectrometer. CDCl3 is deuteriochloroform, DMSO-$D_6$ is hexadeuteriodimethylsulfoxide, and MeOD is tetradeuteriomethanol, $CD_2Cl_2$ is deuteriodichloromethane. Chemical shifts are reported in parts per million (δ) downfield from the internal standard tetramethylsilane (TMS) or calibrated to the residual proton signal in the NMR solvent (e.g., $CHCl_3$ in $CDCl_3$). Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz.

Heating of reaction mixtures with microwave irradiation was carried out on a Biotage Initiator® microwave reactor, typically employing the high absorbance setting.

Cartridges or columns containing polymer based functional groups (acid, base, metal chelators, etc) can be used as part of compound workup. The "amine" columns or cartridges are used to neutralize or basify acidic reaction mixtures or products. These include $NH_2$ Aminopropyl SPE-ed SPE Cartridges available from Applied Separations and diethylamino SPE cartridges available from United Chemical Technologies, Inc.

Table of Abbreviations

| | |
|---|---|
| [Rh(cod)Cl]2 or [RhCl(cod)]2: di-μ-chlorido-bis[η2,η2-(cycloocta-1,5-diene)rhodium | MeCN: acetonitrile |
| ®T3P: 2,4,6-tripropyl-1,3,5,2,4,6-trioxatriphosphorinane 2,4,6-trioxide | MeI: methyl iodide |
| ° C.: degree Celsius | MeOH: methanol |
| AcOH: acetic acid | mg: milligram(s) |
| ADDP: (E)-diazene-1,2-diylbis(piperidin-1-ylmethanone) | $MgCl_2$: magnesium chloride |
| aq = aqueous | $MgSO_4$: magnesium sulfate |
| BINAP: 2,2'-bis(diphenylphosphino)-1,1'-binaphthalene | MHz: megahertz |
| CDI: Carbonyl dimidazole | min: minute(s) |
| $CH_2Cl_2$: dichloromethane | mL: milliliter(s) |
| $CH_3CN$: acetonitrile | mmol: millimole(s) |
| $CH_3CN$: acetonitrile | MS: mass spectroscopy |
| $CHCl_3$: chloroform | $N_2$: nitrogen gas |
| $Cs_2CO_3$: cesium carbonate | $Na_2CO_3$: sodium carbonate |
| DBU: 1,8-diazabicyclo[5.4.0]undec-7-ene | $Na_2SO_4$: sodium sulfate |
| DCE: dichloroethane | $NaBH_3CN$ or $NaCNBH3$: sodium cyanoborohydride |
| DCM: dichloromethane | NaCl: sodium chloride |
| DIPEA or DIEA: diisopropylethylamine | NaH: sodium hydride |
| DME: dimethyl ether | $NaHCO_3$: sodium bicarbonate |
| DMF: N,N-dimethylformamide | NaHMDS: sodium hexamethyldisilazane |
| DMF-DMA or DMF-dimethyl acetal: N,N-dimethylformaide-dimethyl acetal | $NaHSO_4$: sodium bisulfate |
| DMSO: dimethyl sulfoxide | NaOAc: sodium acetate |
| EDC: 1-ethyl-3-(3-dimethylaminopropyl)carbodiimide | NaOH: sodium hydroxide |
| $Et_2O$: diethyl ether | NBS: N-Bromosuccinimide |
| $Et_3N$: triethylamine | nBuLi: n-butyl lithium |
| EtOAc: ethyl acetate | $NH_4Cl$: ammonium chloride |
| EtOH: ethanol | NMR: nuclear magnetic resonance |
| g: gram(s) | $P(tBu)_3$: tri-t-butyl phosphine |

Table of Abbreviations

| | |
|---|---|
| h: hour(s) | $Pd(PhP_3)4$: tetrakistriphenylphosphine palladium |
| HATU: O-(7-azabenzotriazol-1-yl)-N,N,N',N'-tetramethyluronium hexafluorophosphate | Pd/C: pallidium on carbon |
| HBTU: N,N,N',N'-tetramethyl-O-(1H-benzotriazol-1-yl)uronium hexafluorophosphate | $Pd_2(dba)_3$: tris(dibenzylideneacetone)-dipalladium(0) |
| HCl: hydrochloric acid | $PdCl_2$(dppf) or Pd(dppf)Cl2: [1,1'-bis(diphenylphosphino)-ferrocene]dichloropalladium(II) |
| HOAt: 1-hydroxy-7-azabenzotriazole | Petrol: petroleum ether |
| HPLC: high performance liquid chromatography | $PS-PPh_3$: polymer supported triphenylphosphine |
| IPA: isopropyl alcohol | $PtO_2$: platinum(IV) oxide |
| $K_2CO_3$: potassium carbonate | RT: room temperature |
| KOAc: Potassium acetate | T3P: 2,4,6-tripropy1-1,3,5,2,4,6-trioxatriphosphorinane-2,4,6-trioxide solution |
| LAH: lithium aluminum hydride | TEA: triethylamine |
| LC: liquid chromatography | TFA: trifluoroacetic acid |
| LC-MS: liquid chromatography-mass spectroscopy | TFFH: Tetrafluoroformamidinium hexafluorophosphate |
| $LiBH_4$: lithium borohydride | THF: tetrahydrofuran |
| LiHMDS: lithium hexamethyldisilazane | triflic anhydride: trifluoromethanesulfonic anhydride |
| LiOH: lithium hydroxide | TsOH: p-toluenesulfonic acid |
| M: molar | wt %: weight percent |

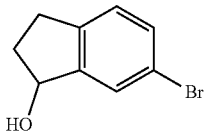 [SMILES: OC1CCc2ccc(Br)cc21]

To a solution of 6-bromo-2,3-dihydro-1H-inden-1-one (5 g, 23.69 mmol) in methanol (50 mL) was added sodium borohydride (0.896 g, 23.69 mmol) under $N_2$ protection. The reaction mixture was stirred for 2 h at ambient temperature. Then the solvent was removed by reduced pressure. The residue was dissolved in 100 mL of ethyl acetate and 20 mL of 1 N HCl. The organic layer was separated and the aqueous layer was extracted with EtOAc (3×30 mL). The combined organic layer was washed with brine (30 mL), dried over anhydrous $Na_2SO_4$ and concentrated to afford the title compound 6-bromo-2,3-dihydro-1H-inden-1-ol (5.0 g, 23.47 mmol, 99%). LC-MS m/z 195.0 (M–OH)+, 1.46 min (ret. time).

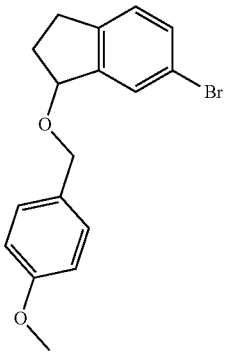 [SMILES: COc1ccc(COC2CCc3ccc(Br)cc32)cc1]

To a solution of 6-bromo-2,3-dihydro-1H-inden-1-ol (7 g, 32.9 mmol) in N,N-dimethylformamide (80 mL) was added NaH (1.314 g, 32.9 mmol) at 0° C. The reaction mixture was stirred at 0° C. for 30 min under N₂ protection, then 1-(chloromethyl)-4-methoxybenzene (5.15 g, 32.9 mmol) was added to the reaction and the reaction mixture was continuously stirred for 2 h at ambient temperature after which it was quenched with 300 mL of H₂O and extracted with EtOAc (3×100 mL). The combined organic layer was washed with water (100 mL), brine (100 mL), dried over anhydrous Na₂SO₄ and concentrated. The residue was purified by silica gel chromatography (petroleum ether/ethyl acetate=10:1) to afford the title compound 6-bromo-1-((4-methoxybenzyl)oxy)-2,3-dihydro-1H-indene (9.2 g, 27.1 mmol, 82%). ¹H NMR (400 MHz, CDCl₃) δ=7.48 (s, 1H), 7.35-7.28 (m, 3H), 7.10 (d, J=8 Hz, 1H), 6.88 (d, J=8.4 Hz, 2H), 4.95 (t, J=6 Hz, 1H), 4.59-4.51 (q, J=21.6 Hz, J=11.4 Hz, 2H), 3.79 (s, 3H), 2.99-2.97 (m, 1H), 2.74-2.73 (m, 1H), 2.35-2.32 (m, 1H), 2.11-2.04 (m, 1H).

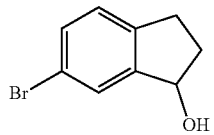 [SMILES: OC1CCc2ccc(Br)cc21]

To a solution of 6-bromo-2,3-dihydro-1H-inden-1-one (30 g, 142 mmol) in methanol (100 mL) and was added NaBH₄ (10.76 g, 284 mmol) portion wise at 0° C. The reaction mixture was stirred for 1 h at ambient temperature. The reaction mixture was concentrated under reduced pressure and quenched with saturated NaHCO₃ solution then extracted with EtOAc (2×), dried over Na₂SO₄ and filtered. The filtrate was concentrated under reduced pressure and purified by flash chromatography by using (2:8) EtOAc: Hexane. The product fractions were concentrated to afford the title compound (23 g, 76% yield). ¹H NMR (400 MHz, CDCl₃) δ ppm=7.54 (s, 1H), 7.37 (dd, J=1.8, 7.9 Hz, 1H), 7.11 (d, J=7.9 Hz, 1H), 5.22 (q, J=5.8 Hz, 1H), 2.99 (ddd, J=4.5, 8.6, 16.1 Hz, 1H), 2.76 (td, J=7.7, 15.9 Hz, 1H), 2.51 (dddd, J=4.6, 7.0, 8.3, 13.2 Hz, 1H), 2.00-1.90 (m, 1H), 1.73 (br d, J=6.4 Hz, 1H), 0.51-0.51 (m, 1H).

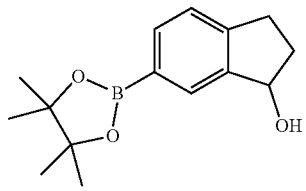 [SMILES: CC1(C)OB(c2ccc3c(c2)C(O)CC3)OC1(C)C]

To a solution of 6-bromo-2,3-dihydro-1H-inden-1-ol (12 g, 56.3 mmol) in 1,4-dioxane (100 mL) was added bis(pinacolato)diboron (18.59 g, 73.2 mmol), potassium acetate (13.82 g, 141 mmol) and the mixture was degassed with argon for 20 min in a sealed tube. PdCl₂(dppf) (2.060 g, 2.82 mmol) was added and the reaction mixture was stirred at 90° C. for 2 h. The reaction mixture was filtered through celite and washed with ethyl acetate. The filtrate was concentrated under reduced pressure to afford a crude residue. The crude residue was purified by column chromatography using 20% ethyl acetate in n-hexane as eluent. The eluted fractions were concentrated under reduced pressure to afford the title compound (12 g, 82% yield). ¹H NMR (400 MHz, CDCl₃) δ ppm=7.88 (s, 1H), 7.72 (d, J=7.7 Hz, 1H), 7.28 (s, 1H), 5.25 (br t, J=5.8 Hz, 1H), 3.08 (ddd, J=5.0, 8.4, 16.4 Hz, 1H), 2.88-2.78 (m, 1H), 2.51-2.41 (m, 1H), 2.01-1.91 (m, 1H), 1.68 (br s, 1H), 1.37-1.27 (m, 12H).

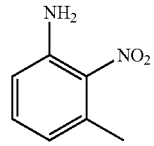

To a mixture of NaOH (2.220 g, 55.5 mmol) in water (12 mL), Br₂ (0.322 mL, 6.26 mmol) was added at 0° C. Then 3-methyl-2-nitrobenzamide (1 g, 5.55 mmol) was added in one portion, and the mixture is warmed slowly in a water bath. The material soon darkens in color, and at 50-55° C. (internal temperature) oil droplets begin to separate. The temperature is raised gradually to 70° and maintained at this point for one hour. A solution of 0.7 g. of NaOH in 4 mL. of water was added slowly and the temperature is increased to 80° C. for an additional hour. The reaction was cooled to ambient temperature and extracted with EtOAc (3×50 mL). The combined organic layer was dried and concentrated to give of the title compound (0.7 g, 90%). LC-MS m/z 153.1 (M+H)⁺, 1.65 min (ret. time).

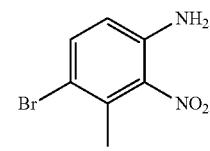

A mixture of NBS (51.5 g, 289 mmol), 3-methyl-2-nitroaniline (44 g, 289 mmol) and acetic acid (450 mL) was stirred at 110° C. for 1 h. The mixture was cooled to ambient temperature and poured into water (100 mL). The solid was collected to afford the title compound (55 g, 78%). LC-MS m/z 230.9 (M+H)⁺, 1.78 min (ret. time).

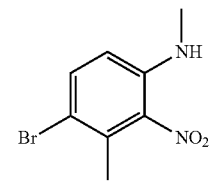

To a solution of 4-bromo-3-methyl-2-nitroaniline (20 g, 87 mmol) in N,N-dimethylformamide (200 mL), NaH (3.81 g, 95 mmol) was added at 25° C. The reaction mixture was stirred at 25° C. for 30 minutes. Then iodomethane (12.90 g, 91 mmol) was added. The reaction mixture was stirred for 12 h. The reaction mixture was poured into water and the solid was collected to give of the title compound (18 g, 59.4%). LC-MS m/z 247.0 (M+H)⁺, 1.90 min (ret. time).

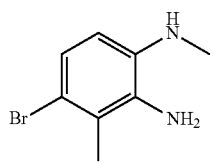

To a solution of 4-bromo-N,3-dimethyl-2-nitroaniline (65 g, 265 mmol) in ethanol (600 mL) and water (300 mL) was added ammonium chloride (142 g, 2652 mmol) followed by addition of iron (59.2 g, 1061 mmol) at ambient temperature. The reaction mixture was stirred at 90° C. for 4 h. The reaction mixture was cooled to ambient temperature and filtered through a celite pad, washed with EtOAc (100 mL) and the filtrate was evaporated under vacuum. The residue was diluted with a NaHCO$_3$ solution (500 mL) and extracted with EtOAc (2×500 mL). The combined organic layers were washed with a brine solution (500 mL) and dried over Na$_2$SO$_4$, filtered and the solvent was evaporated under vacuum. The crude residue was purified through column chromatography by using EtOAc:Hexane (3:7). The eluted fractions were evaporated under vacuum to afford 4-bromo-N1,3-dimethylbenzene-1,2-diamine (46 g, 61.7% yield). LC-MS m/z 214.9 (M+H)$^+$, 2.54 min (ret. time).

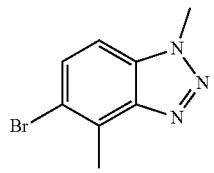

To 4-bromo-N1,3-dimethylbenzene-1,2-diamine (30 g, 139 mmol) in 17 ml of 10% H$_2$SO$_4$ at 0° C., sodium nitrite (13.47 g, 195 mmol) was added in small portions over a 20 minute period. After the reaction mixture was stirred for 30 minutes further, 200 mL of water was added. The resulting precipitate was collected by filtration, washed with water and dried. The mother liquid was left to stand 16 h and a second batch of precipitate formed, which was collected as before. The combined solids were columned in EtOAc to remove inorganic salts to afford the title compound (10 g, 21.57%). LC-MS m/z 226.0 (M+H)$^+$, 1.71 min (ret. time).

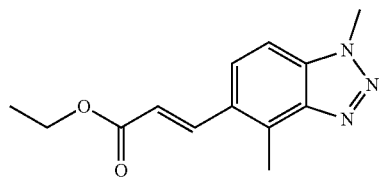 [SMILES: CCOC(=O)/C=C/c1ccc2c(nnn2C)c1C]

To a solution of 5-bromo-1,4-dimethyl-1H-benzo[d][1,2,3]triazole (10 g, 44.2 mmol) in N,N-dimethylformamide (20 mL), tri-o-tolylphosphine (2.69 g, 8.85 mmol), methyl acrylate (7.62 g, 88 mmol) and DIPEA (23.18 mL, 133 mmol) were added. Then Pd(OAc)$_2$ (0.993 g, 4.42 mmol) was added. The reaction mixture was stirred at 100° C. for 12 h. The mixture was poured into water and extracted with EtOAc (30 mL). The organic layer was dried and concentrated to get crude product. It was purified by silica gel chromatography column (petroleum ether: ethyl acetate=4:1) to afford the title compound (8.2 g, 76%). LC-MS m/z 246.1 (M+H)$^+$, 1.68 min (ret. time).

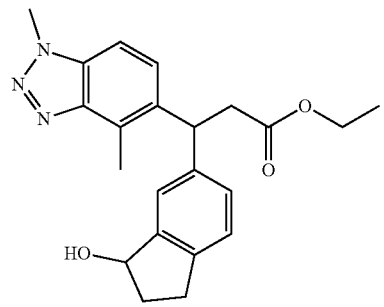 [SMILES: CCOC(=O)CC(c1ccc2c(c1)C(O)CC2)c1ccc2c(nnn2C)c1C]

To a solution of (E)-ethyl 3-(1,4-dimethyl-1H-benzo[d][1,2,3]triazol-5-yl)acrylate (3.5 g, 14.27 mmol) in 1,4-dioxane (10 mL)/water (10.00 mL) was added 6-(4,4,5,5-tetramethyl-1,3,2-dioxaborolan-2-yl)-2,3-dihydro-1H-inden-1-ol (4.83 g, 18.55 mmol), 6-(4,4,5,5-tetramethyl-1,3,2-dioxaborolan-2-yl)-2,3-dihydro-1H-inden-1-ol (4.83 g, 18.55 mmol) in a sealed tube. The mixture was flushed with argon for 20 min, followed by the addition of chloro(1,5-cyclooctadiene)rhodium(I) dimer (0.704 g, 1.427 mmol). The reaction mixture was stirred at 95° C. for 16 h. The reaction mixture was quenched with cold water, extracted with EtOAc (2×), and brine. The organic layer was dried over anhydrous Na$_2$SO$_4$ and filtered. The filtrate was evaporated under reduced pressure and combined with the same crude compound prepared on a 3.5 g scale in another experiment. The combined crude compound was purified by column chromatography by using EtOAc:Hexane (40:60) to afford the title compound (3 g, 55.4% yield). LC-MS m/z 380 (M+H)$^+$, 2.09 min (ret. time).

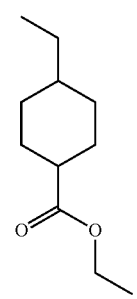

To a solution of 4-ethylcyclohexanecarboxylic acid (15 g, 96 mmol) in ethanol (200 mL) was added H$_2$SO$_4$ (1 mL, 18.76 mmol) slowly under nitrogen at ambient temperature. The reaction mixture was stirred at 80° C. for 16 h. The reaction was then diluted with water (100 mL) and extracted with EtOAc (3×200 mL). The mixture was concentrated under a stream of nitrogen at 50° C. to afford the title compound (15 g, 76% yield) which was used in the next step without further purification. LC-MS m/z 185 (M+H)$^+$, 2.32 min (ret. time).

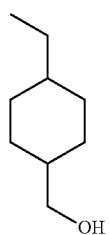

To a solution of ethyl 4-ethylcyclohexanecarboxylate (15 g, 81 mmol) in THF (200 mL) was slowly added LiAlH$_4$ (5 g, 132 mmol) under nitrogen at 0° C. The mixture was stirred at ambient temperature for 4 h. The reaction was then cooled to 0° C., and the reaction was quenched successively with water (5 mL), 10% NaOH (5 mL), and water (15 mL). The reaction was filtered and concentrated it to afford the title compound (11.5 g, 94% yield). LC-MS m/z 125 (M−OH)$^+$, 1.94 min (ret. time).

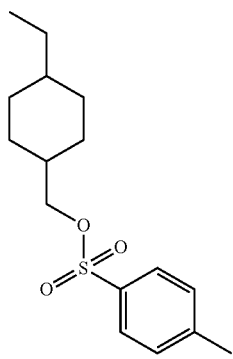 [SMILES: CCC1CCC(COS(=O)(=O)c2ccc(C)cc2)CC1]

To a solution of (4-ethylcyclohexyl)methanol (11.5 g, 81 mmol) in DCM (500 mL) was added to 4-methylbenzene-1-sulfonyl chloride (15.41 g, 81 mmol), TEA (22.54 mL, 162 mmol) and DMAP (0.988 g, 8.09 mmol) slowly under nitrogen at 10° C. The reaction mixture was stirred at 10° C. for 16 h. The reaction was diluted with water (10 mL) and extracted with EtOAc (3×30 mL), Isolute was added to the combined organic layers, and the mixture was concentrated under a stream of nitrogen at 50° C. The Isolute-adsorbed crude product was purified by flash chromatography and was eluted with (hexane:ethyl acetate=20:1) to afford the title compound (4-ethylcyclohexyl)methyl 4-methylbenzenesulfonate (18 g, 71.4% yield) as a solid. LC-MS m/z 319 (M+23)$^+$, 2.38 min (ret. time).

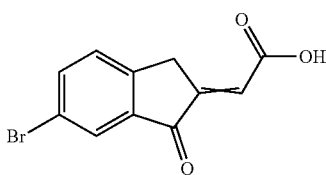 [SMILES: O=C(O)C=C1Cc2ccc(Br)cc2C1=O]

To a solution of 6-bromo-2,3-dihydro-1H-inden-1-one (5 g, 23.69 mmol) in 1,4-dioxane (20 mL) was added 2-oxoacetic acid (35.1 g, 237 mmol), H$_2$SO$_4$ (5 mL, 94 mmol) slowly under nitrogen at ambient temperature. The reaction mixture was stirred at 100° C. for 4 h. The reaction was cooled to ambient temperature and water (100 mL) was added to the reaction. The reaction was filtered and the white solid was dried on high vacuum to afford the title compound (5.6 g, 84% yield). LC-MS m/z 268 (M+H)$^+$, 1.56 min (ret. time).

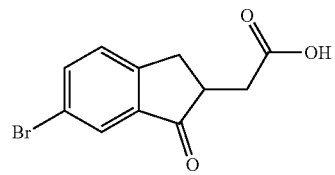 [SMILES: O=C(O)CC1Cc2ccc(Br)cc2C1=O]

To a solution of 2-(6-bromo-1-oxo-1H-inden-2(3H)-ylidene)acetic acid (5.6 g, 20.97 mmol) in acetic acid (50 mL) and water (15 mL) was added zinc (3.43 g, 52.4 mmol) slowly under nitrogen at ambient temperature. The reaction mixture was stirred at 100° C. for 0.5 h. water 50 mL) was added to the reaction and it was extracted with EtOAc (3×100 mL). The mixture was concentrated under a stream of nitrogen at 50° C. to afford the title compound (5 g, 84% yield) as a white solid. LC-MS m/z 269 (M+H)$^+$, 1.47 min (ret. time).

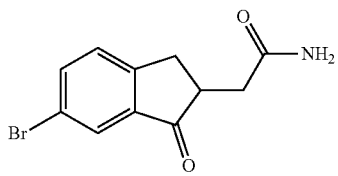 [SMILES: NC(=O)CC1Cc2ccc(Br)cc2C1=O]

To a solution of 2-(6-bromo-1-oxo-2,3-dihydro-1H-inden-2-yl)acetic acid (24 g, 89 mmol) in toluene (200 mL) was added oxalyl chloride (78 mL, 892 mmol) slowly under nitrogen at 20° C. The reaction mixture was stirred at 20° C. for 16 h. The reaction was concentrated and diluted with DCM (300 mL). The reaction mixture was cooled to 0° C. and ammonia (50 mL, 647 mmol) was added dropwise and stirred at ambient temperature for 4 h. The reaction was then extracted with DCM (3×200 mL), and the organic solvents were concentrated. The residue was triturated with ethyl acetate and hexane (1:1) to afford the title compound as a white solid (14 g, 54.4% yield). LC-MS m/z 268 (M+H)$^+$, 1.63 min (ret. time).

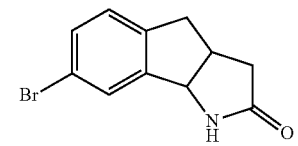 [SMILES: O=C1CC2Cc3ccc(Br)cc3C2N1]

To a solution of 2-(6-bromo-1-oxo-2,3-dihydro-1H-inden-2-yl)acetamide (14 g, 52.2 mmol) in acetonitrile (250 mL) was added TFA (20.12 mL, 261 mmol) and triethylsilane (78 mL, 522 mmol) slowly under nitrogen at ambient temperature. The reaction mixture was stirred at 100° C. for 16 h. The solvent was concentrated and the residue was triturated with hexane to afford the title compound (9.8 g, 63.3% yield) which was used in the next step without further purification. LC-MS m/z 252 (M+H)$^+$, 1.60 min (ret. time).

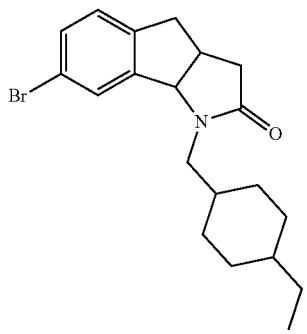 [SMILES: CCC1CCC(CN2C(=O)CC3Cc4ccc(Br)cc4C32)CC1]

To a solution of 7-bromo-1,3a,4,8b-tetrahydroindeno[1,2-b]pyrrol-2(3H)-one (4 g, 15.87 mmol) in N,N-dimethylformamide (100 mL) was added NaH (2.54 g, 63.5 mmol) slowly under nitrogen at 10° C. The reaction mixture was stirred at 10° C. for 1 h. Afterwards, (4-ethylcyclohexyl)methyl 4-methylbenzenesulfonate (9.41 g, 31.7 mmol) was added to the solution in 50 mL of DMF and stirred at 80° C. for 4 h. The reaction was diluted with water (100 mL) and extracted with EtOAc (3×100 mL). Isolute was added to the combined organic layers, and the mixture was concentrated under a stream of nitrogen at 50° C. The Isolute-adsorbed crude product was purified by flash chromatography and was eluted with (hexane:ethyl acetate=4:1) to afford the title compound (2.6 g, 31.8% yield). LC-MS m/z 376 (M+H)$^+$, 2.00 min (ret. time).

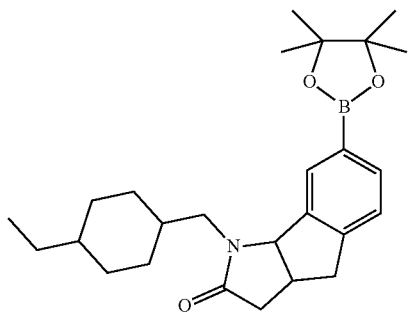 [SMILES: CCC1CCC(CN2C(=O)CC3Cc4ccc(B5OC(C)(C)C(C)(C)O5)cc4C32)CC1]

To a solution of 5-bromo-3-((4-ethylcyclohexyl)methyl)-3,3a,8,8a-tetrahydrocyclopenta[a]inden-2(1H)-one (4.3 g, 11.46 mmol) in 1,4-dioxane (50 mL) was added potassium acetate (3.37 g, 34.4 mmol), and bis(pinacolato)diboron (3.78 g, 14.89 mmol). The reaction mixture was degassed with argon for 30 min and then PdCl$_2$(dppf)-CH$_2$Cl$_2$ adduct (0.936 g, 1.146 mmol) was added to the reaction mixture and stirred at 100° C. for 16 h. The reaction was then cooled and filtered through celite and the filtrate was concentrated under vacuum. The crude residue was purified on flash column chromatography by using EtOAc:Hexane (1:2) as eluent to afford the title compound (3.1 g, 59.4% yield). LC-MS m/z 424 (M+H)$^+$, 2.04 min (ret. time).

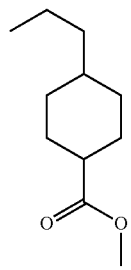

To a solution of 4-propylcyclohexanecarboxylic acid (15 g, 88 mmol) in methanol (100 mL) was added H$_2$SO$_4$ (1 mL, 18.76 mmol) slowly under nitrogen at ambient temperature. The reaction mixture was stirred at 70° C. for 16 h. water 30 mL) was added and the reaction was extracted with EtOAc (3×50 mL). The mixture was concentrated under a stream of nitrogen at 50° C. to afford the title compound (15.2 g, 94% yield) which was used in the next step without further purification. LC-MS m/z 185 (M+H)$^+$, 2.32 min (ret. time).

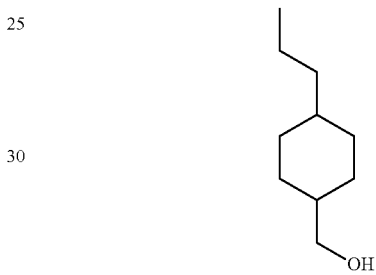

To a solution of methyl 4-propylcyclohexanecarboxylate (15 g, 81 mmol) in THF (200 mL) was slowly added LiAlH$_4$ (5 g, 132 mmol) under nitrogen at 0° C. The mixture was stirred at ambient temperature for 4 h. The reaction was cooled to 0° C., and the reaction was quenched successively with water (5 mL), 10% NaOH (5 mL), and water (15 mL). The reaction was filtered and concentrated to afford title compound (12 g, 90% yield) as a oil. LC-MS m/z 139 (M+H)$^+$, 2.07 min (ret. time).

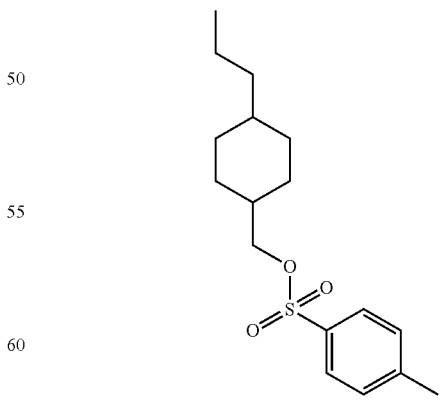

To a solution of (4-propylcyclohexyl)methanol (12 g, 77 mmol) in DCM (200 mL) was added to 4-methylbenzene-1-sulfonyl chloride (14.64 g, 77 mmol), TEA (21.41 mL, 154 mmol) and DMAP (0.938 g, 7.68 mmol) slowly under nitrogen at 10° C. The reaction mixture was stirred at 10° C. for 16 h. water 200 mL) was added and the mixture extracted with EtOAc (3×200 mL). Isolute was added to the combined organic layers, and the mixture was concentrated under a stream of nitrogen at 50° C. The Isolute-adsorbed crude product was purified by flash chromatography and was eluted with (hexane:ethyl acetate=20:1) to afford the title compound (15 g, 57.9% yield) as a white solid. LC-MS m/z 333 (M+23)$^+$, 2.02 min (ret. time).

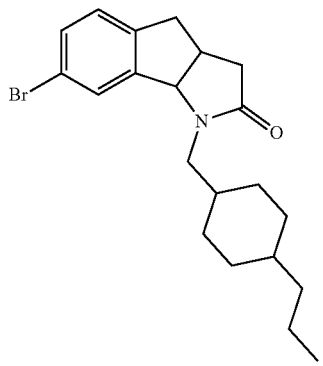 [SMILES: CCCC1CCC(CN2C(=O)CC3Cc4ccc(Br)cc4C32)CC1]

To a solution of 7-bromo-1,3a,4,8b-tetrahydroindeno[1,2-b]pyrrol-2(3H)-one (5 g, 19.83 mmol) in N,N-dimethylformamide (50 mL) was added 60% NaH (3.17 g, 79 mmol) slowly under nitrogen at 20° C. The reaction mixture was stirred at 20° C. for 1 h. (4-propylcyclohexyl)methyl 4-methylbenzenesulfonate (12.31 g, 39.7 mmol) in DMF (2 mL) was then added and stirred at 80° C. for 4 h. water 100 mL) was added and the mixture extracted with EtOAc (3×100 mL). Isolute was added to the combined organic layers, and the mixture was concentrated under a stream of nitrogen at 50° C. The Isolute-adsorbed crude product was purified by flash chromatography and was eluted with (hexane:ethyl acetate=4:1) to afford the title compound (3.3 g, 31.1% yield). LC-MS m/z 390 (M+H)$^+$, 2.49 min (ret. time).

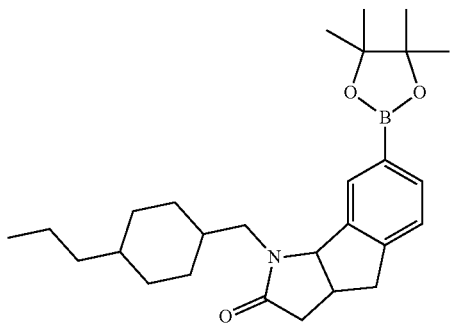 [SMILES: CCCC1CCC(CN2C(=O)CC3Cc4ccc(B5OC(C)(C)C(C)(C)O5)cc4C32)CC1]

To a solution of 5-bromo-3-((4-propylcyclohexyl)methyl)-3,3a,8,8a-tetrahydrocyclopenta[a]inden-2(1H)-one (3.2 g, 8.22 mmol) in 1,4-dioxane (50 mL) was added potassium acetate (2.420 g, 24.66 mmol) and bis(pinacolato)diboron (2.71 g, 10.68 mmol). The reaction mixture was degassed with argon for 30 min and then PdCl$_2$(dppf)-CH$_2$Cl$_2$ adduct (0.671 g, 0.822 mmol) was added to the reaction mixture and stirred at 100° C. for 16 h. The reaction was cooled and filtered through celite and the filtrate was concentrated under vacuum.

The crude residue was purified on flash column chromatography by using EtOAc:Hexane (1:2) as eluent to afford a crude product, which was then crystallised from hexane to afford the title compound (2.6 g, 67.3% yield) as white solid. LC-MS m/z 396 (M+Na)$^+$, 2.11 min (ret. time).

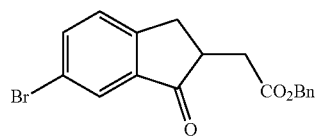 [SMILES: O=C(CC1Cc2ccc(Br)cc2C1=O)OCc1ccccc1]

To a solution of 6-bromo-2,3-dihydro-1H-inden-1-one (2.0 g, 9.48 mmol) in THF (10 mL) under N$_2$ atmosphere was added LiHMDS (11.37 mL, 11.37 mmol) dropwise at −78° C. After the addition, the reaction mixture was allowed to slowly warm up to 0° C. and stirred for 8 h at this temperature. The mixture was recooled to −78° C. and benzyl 2-bromoacetate (1.651 mL, 10.42 mmol) was added dropwise. The reaction mixture was stirred for 30 min and slowly allowed to warm to ambient temperature. The reaction was quenched with water and extracted with ethyl acetate. The organic layer was washed with water and brine, dried and concentrated. The crude residue was purified by flash chromatography eluting with petroleum ether:EtOAc (10:1) to afford the title compound (700 mg, 20.56% yield). LC-MS m/z 359 (M+H)$^+$, 1.78 min (ret. time).

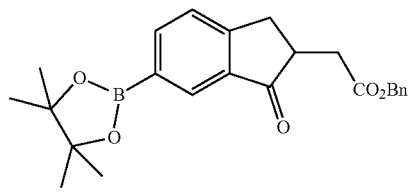 [SMILES: CC1(C)OB(c2ccc3c(c2)C(=O)C(CC(=O)OCc2ccccc2)C3)OC1(C)C]

To a solution of benzyl 2-(6-bromo-1-oxo-2,3-dihydro-1H-inden-2-yl)acetate (8.51 g, 23.69 mmol) in 1,4-dioxane (100 mL) was added potassium acetate (5.81 g, 59.2 mmol), and bis(pinacolato)diboron (7.82 g, 30.8 mmol). The reaction mixture was degassed with argon for 30 min and then PdCl$_2$(dppf)-CH$_2$Cl$_2$ adduct (1.935 g, 2.369 mmol) was added to the reaction mixture and stirred at 100° C. for 16 h. The reaction was cooled and filtered through celite and the filtrate was concentrated under vacuum. The crude residue was purified on flash column chromatography by using EtOAc:Hexane (1:3) as eluent to afford a crude product which was then crystallised from hexane to afford the title compound (5.0 g, 46.8% yield) as white solid.

LC-MS m/z 407 (M+H)$^+$, 1.94 min (ret. time).

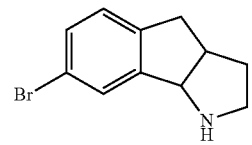 [SMILES: Brc1ccc2c(c1)C1NCCC1C2]

To a solution of 7-bromo-1,3a,4,8b-tetrahydroindeno[1,2-b]pyrrol-2(3H)-one (3.5 g, 13.88 mmol) in THF (60 mL) was added 2 M BH$_3$*DMS (48.6 mL, 97 mmol) at 0° C. The reaction mixture was stirred at reflux overnight and was then cooled to 0° C. The reaction mixture was quenched by the slow addition of MeOH (2 mL) and then 3 N HCl. The reaction mixture was allowed to stir at reflux for 3 h, then concentrated. Water was added to the residue and the pH of the solution was adjusted to pH>9 with 4 N NaOH. The solution was extracted with diethyl ether. The organic layers were combined, dried over Na$_2$SO$_4$, filtered and concentrated afford the title compound (3.05 g, 92% yield). LC-MS m/z 238 (M+H)$^+$, 1.15 min (ret. time).

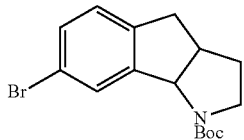 [SMILES: CC(C)(C)OC(=O)N1CCC2Cc3ccc(Br)cc3C21]

To a solution of 7-bromo-1,2,3,3a,4,8b-hexahydroindeno [1,2-b]pyrrole (3.05 g, 12.81 mmol) in DCM (30 mL), was added TEA (3.57 mL, 25.6 mmol) and Boc$_2$O (4.46 mL, 19.21 mmol). The reaction mixture was stirred at ambient temperature for 6 h. The reaction was cool to ambient temperature, water was added, the mixture was extracted with ethyl acetate. The organic layer was washed with water and brine, dried and concentrated to afford the title compound (2.5 g, 57.7% yield). LC-MS m/z 360 (M+H)$^+$, 2.04 min (ret. time).

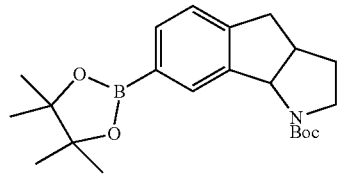 [SMILES: CC(C)(C)OC(=O)N1CCC2Cc3ccc(B4OC(C)(C)C(C)(C)O4)cc3C21]

To a solution of tert-butyl 7-bromo-2,3,3a,4-tetrahydroindeno[1,2-b]pyrrole-1(8bH)-carboxylate (2.9 g, 8.57 mmol) in 1,4-dioxane (200 mL) was added potassium acetate (2.104 g, 21.43 mmol), and bis(pinacolato)diboron (2.83 g, 11.15 mmol). The reaction mixture was degassed with argon for 30 min and then PdCl$_2$(dppf)-CH$_2$Cl$_2$ adduct (0.350 g, 0.429 mmol) was added to the reaction mixture and stirred at 100° C. for 16 h. The reaction was cooled and filtered through celite and the filtrate was concentrated under vacuum. The crude residue was purified by flash column chromatography by using EtOAc:Hexane (15:1) as eluent to afford the crude product, which was then crystallised from hexane to afford the title compound (2.05 g, 56.1% yield) as white solid. LC-MS m/z 408 (M+H)$^+$, 1.99 min (ret. time).

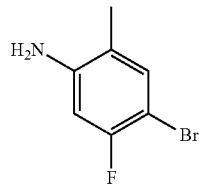

A mixture of NBS (14.22 g, 80 mmol), 5-fluoro-2-methylaniline (10 g, 80 mmol) and N,N-dimethylformamide (200 mL) was stirred at 25° C. for 12 h. The mixture was then poured into water and the solid was filtered to afford the title compound (13 g, 71% yield) as yellow solid. LC-MS m/z 204 (M+H)$^+$, 1.68 min (ret. time).

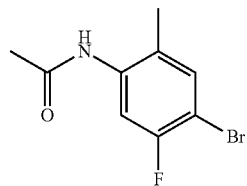

To neat acetic anhydride (4.62 mL, 49.0 mmol) was added 4-bromo-5-fluoro-2-methylaniline (1 g, 4.90 mmol) at 25° C. under N$_2$ atmosphere. The reaction was stirred at 25° C. for 30 min. The mixture was poured into water and the solid was filtered to afford the title compound (1.1 g, 4.02 mmol) as yellow solid. LC-MS m/z 246 (M+H)$^+$, 1.57 min (ret. time).

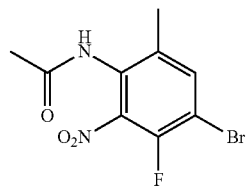 [SMILES: CC(=O)Nc1c(C)cc(Br)c(F)c1[N+](=O)[O-]]

A mixture of nitric acid (200 mL, 4475 mmol), N-(4-bromo-5-fluoro-2-methylphenyl)acetamide (30 g, 122 mmol) and H$_2$SO$_4$ (200 mL, 3752 mmol) was stirred at 0° C. under N$_2$ atmosphere and the mixture was stirred at 0° C. for 2 h. The reaction was poured into water and the solid was filtered to afford the title compound as pale yellow solid (30.1 g, 72% yield). LC-MS m/z 291 (M+H)$^+$, 1.53 min (ret. time).

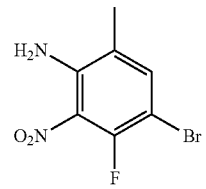

HCl (10.44 mL, 344 mmol) was added to N-(4-bromo-3-fluoro-6-methyl-2-nitrophenyl)acetamide (20 g, 68.7 mmol). The resulting mixture was stirred at 100° C. for 4 h. Then the solvent was removed, and the residue was adjusted to pH 8 with aq NaHCO$_3$. The aqueous mixture was extracted with EtOAc (3×50 mL) and the solvent was concentrated in vacuo. The residue was purified by silica gel chromatography eluting with (petroleum ether:EtOAc=10:1) to afford the title compound (5 g, 20% yield). LC-MS m/z 249 (M+H)$^+$, 1.71 min (ret. time).

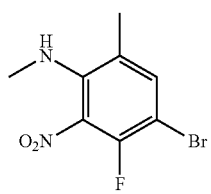

To a solution of 4-bromo-3-fluoro-6-methyl-2-nitroaniline (15 g, 60.2 mmol) in N,N-dimethylformamide (50 mL)

was added sodium hydride (2.168 g, 90 mmol) at 0° C. The mixture was stirred at 0° C. for 10 min, then iodomethane (4.52 mL, 72.3 mmol) was added to the reaction. The resulting mixture was stirred at 0° C. for 20 min, then NH₄Cl (aq.) was added to consume the excess NaH and the aqueous layer was extracted with EtOAc (3×50 mL) and the solvent was concentrated in vacuo to afford the title compound (16 g, 31% yield). LC-MS m/z 263 (M+H)⁺, 1.84 min (ret. time).

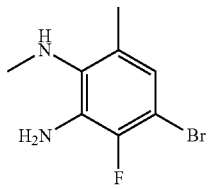

To a solution of 4-bromo-3-fluoro-N,6-dimethyl-2-nitroaniline (16 g, 60.8 mmol) in acetic acid (4 mL) was added zinc (150 mg, 2.294 mmol). The mixture was stirred at 65° C. for 2 h. The reaction was then filtered and concentrated in vacuo. The residue was purified by silical gel chromatography eluting with (petroleum ether:EtOAc=10:1) to afford the title compound (5.3 g, 36% yield). LC-MS m/z 233 (M+H)⁺, 1.45 min (ret. time).

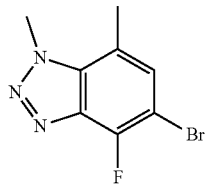

A stirred suspension of 4-bromo-3-fluoro-N1,6-dimethylbenzene-1,2-diamine (5 g, 21.45 mmol) in sulfuric acid (4.57 mL, 85.8 mmol) was treated with a solution of sodium nitrite (1.480 g, 21.45 mmol) in water (30 mL). The mixture was stirred at 0° C. for 2 h, then filtered to afford the title compound (2 g, 36.7% yield). ¹H-NMR (400 MHz, CDCl3) δ ppm 7.30-7.28 (m, 1H), 4.49 (s, 3H), 2.71 (q, J=1.2, 3H).

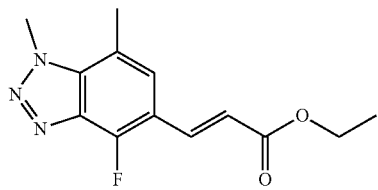 [SMILES: CCOC(=O)/C=C/c1cc(C)c2c(nnn2C)c1F]

To a mixture of 5-bromo-4-fluoro-1,7-dimethyl-1H-benzo[d][1,2,3]triazole (2 g, 8.19 mmol), 3-ethoxy-3-oxoprop-1-en-1-ylium (1.624 g, 16.39 mmol), triphenylphosphine (0.430 g, 1.639 mmol) and TEA (2.284 mL, 16.39 mmol) in N-methyl-2-pyrrolidone (NMP) (20 mL) was added diacetoxypalladium (0.368 g, 1.639 mmol). The resulting mixture was stirred at 135° C. overnight. The reaction was then cooled to ambient temperature, filtered, and extracted with EtOAc (3×50 mL), then concentrated in-vacuo. The residue was purified by silical gel chromatography (petroleum ether:EtOAc=3:1) to afford the title compound (1 g, 38.7% yield). LC-MS m/z 234 (M+H)⁺, 1.66 min (ret. time).

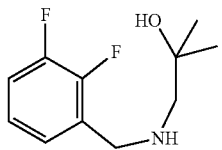

To a solution of 2,3-difluorobenzaldehyde (10 g, 70.4 mmol) in methanol (100 mL) was added 1-amino-2-methylpropan-2-ol (6.27 g, 70.4 mmol) and NaOH (7.04 mL, 7.04 mmol). It was stirred under nitrogen atmosphere for 1 h, and then NaBH₄ (1.065 g, 28.1 mmol) was added portion wise over 10 min. The reaction was stirred at ambient temperature for 24 h. The crude product was purified by silica gel chromatography. The fractions were concentrated to give the title compound (10 g, 44.0 mmol, 62.5% yield) as an off-white solid. LC-MS: m/z: 216.13 (M+H)⁺, 1.915 min (ret. time).

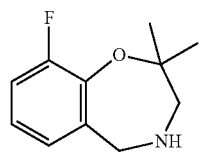

To a solution of 1-((2,3-difluorobenzyl)amino)-2-methylpropan-2-ol (2 g, 9.29 mmol) in dimethyl sulfoxide (DMSO) (20 mL) was added potassium tert-butoxide (2.085 g, 18.58 mmol) and the reaction mixture was stirred at 80° C. for 2 h. The reaction mixture was poured in ice water (100 mL) and extracted with ethyl acetate (2×100 mL). The combined organic layer was washed with water (2×100 mL), brine (100 mL) and then dried over Na₂SO₄. It was filtered and concentrated. The crude residue was purified with silica gel chromatography to give the title compound (2 g, 5.77 mmol, 62.1% yield) as gummy liquid. LC-MS: m/z:196.09 (M+H)⁺, 1.875 min (ret. time).

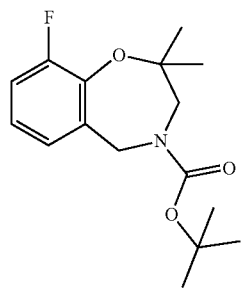 [SMILES: CC(C)(C)OC(=O)N1Cc2cccc(F)c2OC(C)(C)C1]

To a solution of 9-fluoro-2,2-dimethyl-2,3,4,5-tetrahydrobenzo[f][1,4]oxazepine (5 g, 25.6 mmol) in dichloromethane (DCM) (50 mL) at 0° C. was added TEA (7.14 mL, 51.2 mmol) and Boc-anhydride (7.73 mL, 33.3 mmol). The reaction was stirred at ambient temperature for 3 h, diluted with water (100 mL) and extracted with ethyl acetate (2×100 mL), washed with brine solution (100 mL), dried over anhydrous Na₂SO₄, filtered and concentrated. The crude residue was purified with silica gel chromatography to give the title compound (6.5 g, 21.47 mmol, 84% yield) as an off-white solid. LC-MS: m/z: 239.94 (M−56)⁺, 6.256 min (ret. time).

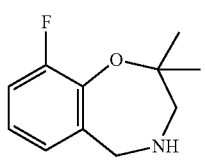

To a solution of tert-butyl 9-fluoro-2,2-dimethyl-2,3-dihydrobenzo[f][1,4]oxazepine-4(5H)-carboxylate (6.5 g, 22.01 mmol) in dichloromethane (DCM) (20 mL) at 10° C. was added 4 M HCl in 1,4-dioxane (16.51 mL, 66.0 mmol). It was stirred for 1 h. The obtained precipitate was filtered and triturated with hexane, dried well to give the title compound (4.47 g, 18.99 mmol, 86% yield) as an off-white solid. LC-MS m/z: 196.0 (M−HCl)+, 3.335 min (ret. time).

The compounds in the following Table 1 were prepared by a method similar to the one described for the preparation of 9-Fluoro-2,2-dimethyl-2,3,4,5-tetrahydrobenzo[f][1,4]oxazepine hydrochloride. As is appreciated by those skilled in the art, these analogous examples may involve variations in general reaction conditions.

Benzyl 2-(6-bromo-1-oxo-2,3-dihydro-1H-inden-2-yl)acetate

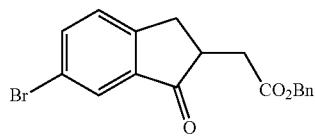

To a solution of 6-bromo-2,3-dihydro-1H-inden-1-one (2.0 g, 9.48 mmol) in THF (10 mL) under N₂ atmosphere was added LiHMDS (11.37 mL, 11.37 mmol) dropwise at −78° C. After the addition, the reaction mixture was allowed to slowly warm up to 0° C. and stirred for 8 h at this temperature. The mixture was recooled to −78° C. and benzyl 2-bromoacetate (1.651 mL, 10.42 mmol) was added dropwise. The reaction mixture was stirred for 30 min and slowly allowed to warm to ambient temperature. The reaction was quenched with water and extracted with ethyl acetate. The organic layer was washed with water and brine, dried and concentrated. The crude residue was purified by flash chromatography eluting with petroleum ether:EtOAc (10:1) to afford the title compound (700 mg, 20.56% yield). LC-MS m/z 359 (M+H)+, 1.78 min (ret. time).

TABLE 1

| Reagent | Product Name | Product Structure | (M + H)+ | Ret. Time (min) |
|---|---|---|---|---|
|  | 2,2-Dimethyl-2,3,4,5-tetrahydropyrido[2,3-f][1,4]oxazepine hydrochloride |  | 178.92 | 1.057 |

Example 1

3-[(3aR,8bS)-1-(cyclohexylmethyl)-2-oxo-1H,2H,3H,3aH,4H,8bH-indeno[1,2-b]pyrrol-7-yl]-3-(1,4-dimethyl-1H-1,2,3-benzotriazol-5-yl)propanoic Acid

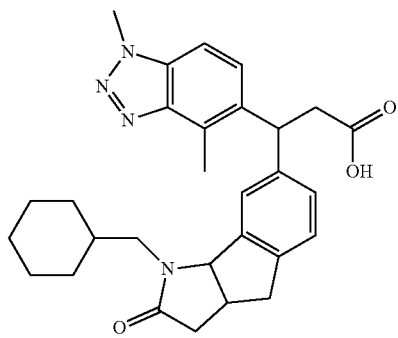 [SMILES: Cc1c(C(CC(=O)O)c2ccc3c(c2)C2C(CC(=O)N2CC2CCCCC2)C3)ccc2c1nnn2C]

Benzyl 2-(1-oxo-6-(4,4,5,5-tetramethyl-1,3,2-dioxaborolan-2-yl)-2,3-dihydro-1H-inden-2-yl)acetate

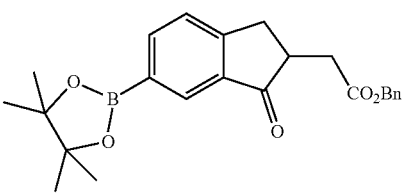 [SMILES: CC1(C)OB(c2ccc3c(c2)C(=O)C(CC(=O)OCc2ccccc2)C3)OC1(C)C]

To a solution of benzyl 2-(6-bromo-1-oxo-2,3-dihydro-1H-inden-2-yl)acetate (8.51 g, 23.69 mmol) in 1,4-dioxane (100 mL) was added potassium acetate (5.81 g, 59.2 mmol), and bis(pinacolato)diboron (7.82 g, 30.8 mmol). The reaction mixture was degassed with argon for 30 min and then PdCl₂(dppf)-CH₂Cl₂ adduct (1.935 g, 2.369 mmol) was added to the reaction mixture and stirred at 100° C. for 16 h. The reaction was cooled and filtered through celite and the filtrate was concentrated under vacuum. The crude residue was purified on flash column chromatography by using EtOAc:Hexane (1:3) as eluent to afford a crude product which was then crystallised from hexane to afford the title compound (5.0 g, 46.8% yield) as white solid. LC-MS m/z 407 (M+H)+, 1.94 min (ret. time).

Ethyl 3-(2-(2-(benzyloxy)-2-oxoethyl)-3-oxo-2,3-dihydro-1H-inden-5-yl)-3-(1,4-dimethyl-1H-benzo[d][1,2,3]triazol-5-yl)propanoate

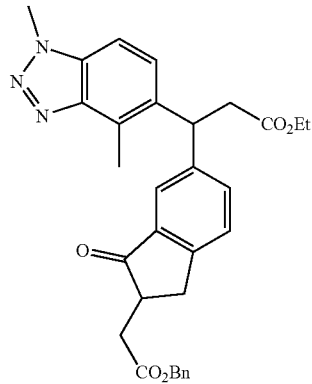 [SMILES: CCOC(=O)CC(c1ccc2c(c1)C(=O)C(CC(=O)OCc1ccccc1)C2)c1ccc2c(nnn2C)c1C]

To a solution of (E)-ethyl 3-(1,4-dimethyl-1H-benzo[d][1,2,3]triazol-5-yl)acrylate (1.0 g, 4.08 mmol) in 1,4-dioxane (30 mL) and water (10 mL) was added benzyl 2-(1-oxo-6-(4,4,5,5-tetramethyl-1,3,2-dioxaborolan-2-yl)-2,3-dihydro-1H-inden-2-yl)acetate (1.656 g, 4.08 mmol), TEA (1.705 mL, 12.23 mmol) and [Rh(cod)Cl]$_2$ (0.101 g, 0.204 mmol). The resulting reaction mixture was stirred at 90° C. for 18 h. The reaction mixture was extracted with EtOAc (3×30 mL). The combined organic layer was dried over MgSO$_4$, filtered, concentrated under reduced pressure, and purified via silica gel chromatography to afford the desired product ethyl 3-(2-(2-(benzyloxy)-2-oxoethyl)-3-oxo-2,3-dihydro-1H-inden-5-yl)-3-(1,4-dimethyl-1H-benzo[d][1,2,3]triazol-5-yl)propanoate (2.1099 g, 2.128 mmol, 52.2% yield). LC-MS m/z 526.5 (M+H)+, 1.12 min (ret. time).

Ethyl 3-(2-(2-((cyclohexylmethyl)amino)-2-oxoethyl)-3-oxo-2,3-dihydro-1H-inden-5-yl)-3-(1,4-dimethyl-1H-benzo[d][1,2,3]triazol-5-yl)propanoate

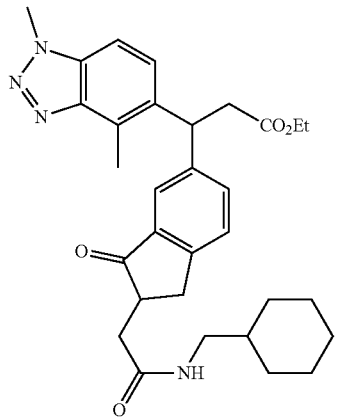 [SMILES: CCOC(=O)CC(c1ccc2c(c1)C(=O)C(CC(=O)NCC1CCCCC1)C2)c1ccc2c(nnn2C)c1C]

To a solution of ethyl 3-(2-(2-(benzyloxy)-2-oxoethyl)-3-oxo-2,3-dihydro-1H-inden-5-yl)-3-(1,4-dimethyl-1H-benzo[d][1,2,3]triazol-5-yl)propanoate (298 mg, 0.3 mmol) in methanol (15 mL) was added 10% Pd/C (63.9 mg, 0.060 mmol). The resulting suspension was stirred under a H$_2$ atmosphere at ambient temperature for 90 min. The reaction mixture was filtered and the filter cake was washed with MeOH (2×5 mL). The combined filtrate was concentrated under reduced pressure before it was dissolved in DCM (6 mL) after which cyclohexylmethanamine (0.078 mL, 0.600 mmol), TEA (0.084 mL, 0.600 mmol) and T3P (50% wt in EtOAc) (0.179 mL, 0.600 mmol) were added. The resulting reaction mixture was stirred at ambient temperature for 17 h. The reaction mixture was concentrated under reduced pressure, and purified via silica gel chromatography to afford the desired product ethyl 3-(2-(2-((cyclohexylmethyl)amino)-2-oxoethyl)-3-oxo-2,3-dihydro-1H-inden-5-yl)-3-(1,4-dimethyl-1H-benzo[d][1,2,3]triazol-5-yl)propanoate (103.5 mg, 0.195 mmol, 65.0% yield). LC-MS m/z 531.3 (M+H)+, 1.06 min (ret. time).

3-[(3aR,8bS)-1-(cyclohexylmethyl)-2-oxo-1H,2H,3H,3aH,4H,8bH-indeno[1,2-b]pyrrol-7-yl]-3-(1,4-dimethyl-1H-1,2,3-benzotriazol-5-yl)propanoic Acid

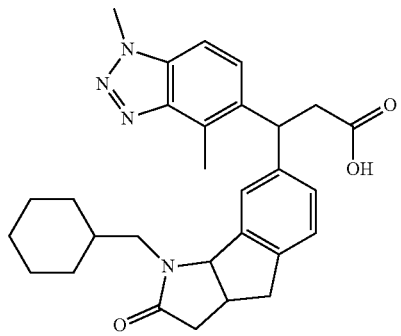 [SMILES: Cc1c(C(CC(=O)O)c2ccc3c(c2)C2C(CC(=O)N2CC2CCCCC2)C3)ccc2c1nnn2C]

To a solution ethyl 3-(2-(2-((cyclohexylmethyl)amino)-2-oxoethyl)-3-oxo-2,3-dihydro-1H-inden-5-yl)-3-(1,4-dimethyl-1H-benzo[d][1,2,3]triazol-5-yl)propanoate (150 mg, 0.283 mmol) in acetonitrile (2.0 mL) and THF (1.0 mL) was added triethylsilane (0.226 mL, 1.413 mmol) and TFA (0.065 mL, 0.848 mmol). The resulting reaction mixture was heated with microwave at 100° C. for 1 h, heated again with microwave at 120° C. for 1 h. The reaction mixture was concentrated under reduced pressure, dissolved in methanol (3 mL) and then NaOH (3.0 N) (0.754 mL, 2.261 mmol) was added. The reaction mixture was heated with microwave at 80° C. for 20 min. The reaction mixture was concentrated under reduced pressure, and purified with reverse phase HPLC to afford the desired product 3-(1-(cyclohexylmethyl)-2-oxo-1,2,3,3a,4,8b-hexahydroindeno[1,2-b]pyrrol-7-yl)-3-(1,4-dimethyl-1H-benzo[d][1,2,3]triazol-5-yl)propanoic acid (64.5 mg, 0.133 mmol, 46.9% yield). LC-MS m/z 487.4 (M+H)+, 0.89 min (ret. time)

Example 2

3-(1,4-Dimethyl-1H-1,2,3-benzotriazol-5-yl)-3-{1-[(4-ethylcyclohexyl)methyl]-2-oxo-1H,2H,3H,3aH,4H,8bH-indeno[1,2-b]pyrrol-7-yl}propanoic acid

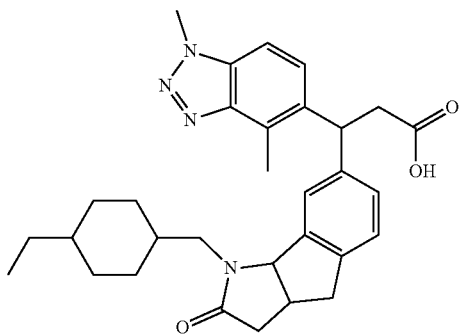 [SMILES: CCC1CCC(CN2C(=O)CC3Cc4ccc(C(CC(=O)O)c5ccc6c(nnn6C)c5C)cc4C32)CC1]

Ethyl 3-(1,4-dimethyl-1H-benzo[d][1,2,3]triazol-5-yl)-3-(2-(2-(((4-ethylcyclohexyl)methyl) amino)-2-oxoethyl)-3-oxo-2,3-dihydro-1H-inden-5-yl)propanoate

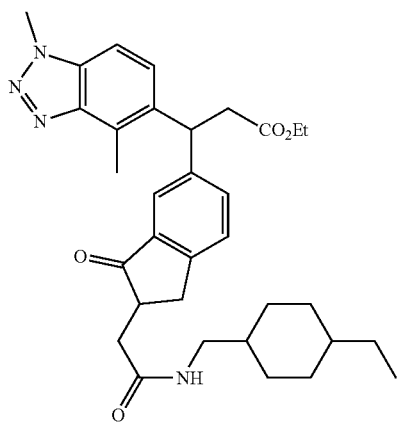 [SMILES: CCOC(=O)CC(c1ccc2c(c1)C(=O)C(CC(=O)NCC1CCC(CC)CC1)C2)c1ccc2c(nnn2C)c1C]

To a solution of ethyl 3-(2-(2-(benzyloxy)-2-oxoethyl)-3-oxo-2,3-dihydro-1H-inden-5-yl)-3-(1,4-dimethyl-1H-benzo[d][1,2,3]triazol-5-yl)propanoate (298 mg, 0.3 mmol) in methanol (15 mL) and THF (5 mL) was added 10% Pd/C (63.9 mg, 0.060 mmol). The resulting suspension was stirred under a H₂ atmosphere at ambient temperature for 30 min. The reaction mixture was filtered and the filter cake was washed with MeOH (2×5 mL). The combined filtrate was concentrated under reduced pressure to afford the crude intermediate. This intermediate was dissolved in DCM (6 mL) after which (4-ethylcyclohexyl)methanamine (85 mg, 0.600 mmol), TEA (0.084 mL, 0.600 mmol) and then T3P (50% wt in EtOAc) (0.179 mL, 0.600 mmol) were added. The resulting reaction mixture was stirred at ambient temperature for 43 h after which TEA (0.042 mL, 0.300 mmol) and T3P (50% wt in EtOAc) (0.089 mL, 0.300 mmol) was added and stirred at ambient temperature for another 94 h. The reaction mixture was concentrated under reduced pressure, and purified via silica gel chromatography to afford the desired product ethyl 3-(1,4-dimethyl-1H-benzo[d][1,2,3]triazol-5-yl)-3-(2-(2-(((4-ethylcyclohexyl)methyl)amino)-2-oxoethyl)-3-oxo-2,3-dihydro-1H-inden-5-yl)propanoate (136.7 mg, 0.245 mmol, 82% yield). LC-MS m/z 559.3 (M+H)⁺, 1.08 min (ret. time).

3-(1,4-dimethyl-1H-1,2,3-benzotriazol-5-yl)-3-{1-[(4-ethylcyclohexyl)methyl]-2-oxo-1H,2H,3H,3aH 4H,8bH-indeno[1,2-b]pyrrol-7-yl}propanoic Acid

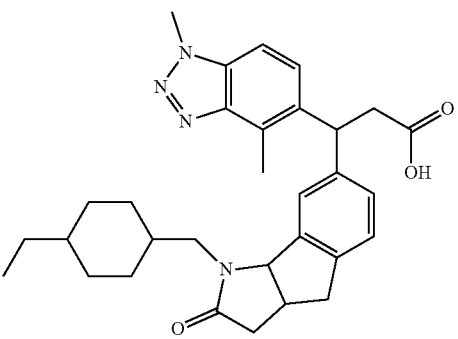 [SMILES: CCC1CCC(CN2C(=O)CC3Cc4ccc(C(CC(=O)O)c5ccc6c(nnn6C)c5C)cc4C32)CC1]

To a solution of ethyl 3-(1,4-dimethyl-1H-benzo[d][1,2,3]triazol-5-yl)-3-(2-(2-(((4-ethylcyclohexyl)methyl)amino)-2-oxoethyl)-3-oxo-2,3-dihydro-1H-inden-5-yl)propanoate (130 mg, 0.233 mmol) in acetonitrile (2 mL) was added triethylsilane (0.186 mL, 1.163 mmol) and TFA (0.054 mL, 0.698 mmol). The resulting reaction mixture was heated with microwave at 100° C. for 2 h. The reaction mixture was concentrated under reduced pressure, dissolved in methanol (3 mL) then NaOH (3.0 N) (0.620 mL, 1.861 mmol) was added and the mixture heated with microwave at 80° C. for 20 min. The reaction mixture was concentrated under reduced pressure, and purified with reverse phase HPLC to afford the desired product 3-(1,4-dimethyl-1H-benzo[d][1,2,3]triazol-5-yl)-3-(1-((4-ethylcyclohexyl)methyl)-2-oxo-1,2,3,3a,4,8b-hexahydroindeno[1,2-b]pyrrol-7-yl)propanoic acid (64.5 mg, 0.125 mmol, 53.9% yield). LC-MS m/z 515.4 (M+H)⁺, 0.99 min (ret. time).

Example 3

3-[(3aR,8bS)-1-(cyclohexylmethyl)-2-oxo-1H,2H,3H,3aH,4H,8bH-indeno[1,2-b]pyrrol-7-yl]-5-(1-ethyl-1H-1,2,3-triazol-4-yl)pentanoic Acid

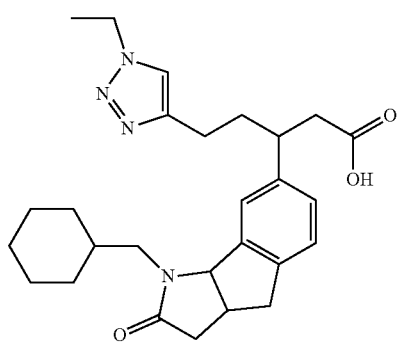 [SMILES: CCn1cc(CCC(CC(=O)O)c2ccc3c(c2)C2C(CC(=O)N2CC2CCCCC2)C3)nn1]

(E)-Ethyl hept-2-en-6-ynoate

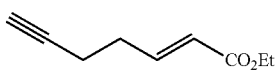

Sodium hydride (1.056 g, 26.4 mmol) was added in small portions to a solution of ethyl 2-(diethoxyphosphoryl)acetate (3.03 mL, 14.4 mmol) in DCM (15 mL). The mixture was stirred at 23° C. for 5 min, crude pent-4-ynal (~1 mL, 12 mmol) in DCM (10 mL) was added slowly, and the mixture was stirred at 23° C. for 30 min. NH₄Cl (saturated aqueous) was added and the solution was extracted with DCM. The crude product was then purified on a silica cartridge (12 g) with a flash chromatography, eluting at 30 mL/min with a gradient running from 0-60% EtOAc/hexane over 20 min. The product containing fractions were combined and the solvent removed under reduced pressure giving 1.32 g (72%) of the title compound. LC-MS m/z 153.0 (M+H)$^+$, 0.82 (ret. time).

(E)-Ethyl 5-(1-ethyl-1H-1,2,3-triazol-4-yl)pent-2-enoate

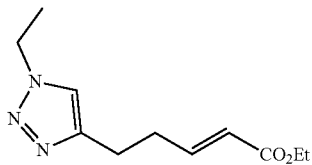 [SMILES: CCOC(=O)/C=C/CCc1cn(CC)nn1]

NaN₃ (0.085 g, 1.31 mmol), CuI (0.25 mg, 1.31 umol) and iodoethane (0.090 mL, 1.31 mmol) was added to a solution of (E)-ethyl hept-2-en-6-ynoate (0.2 g, 1.31 mmol) in water (5 mL), the mixture was stirred at 70° C. for 14 h. The mixture was concentrated and purified over silica gel (12 g) with flash chromatography eluting at 30 mL/min with a gradient running from 0-30% MeOH/DCM over 20 min to afford the title compound (100 mg, 34%). LC-MS m/z 224.1 (M+H)$^+$, 0.65 min (ret. time).

Ethyl 5-(1-ethyl-1H-1,2,3-triazol-4-yl)-3-(3-(hydroxymethyl)-4-methylphenyl)pentanoate

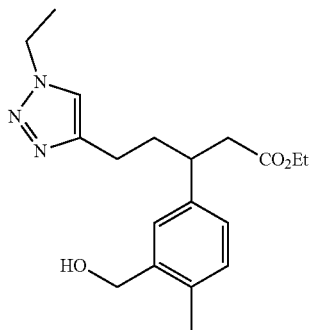 [SMILES: CCOC(=O)CC(CCc1cn(CC)nn1)c1ccc(C)c(CO)c1]

(3-(Hydroxymethyl)-4-methylphenyl)boronic acid (0.11 g, 0.67 mmol), TEA (0.094 mL, 0.67 mmol) and [RhCl(cod)]₂ (11 mg, 0.022 mmol) were added to a solution of (E)-ethyl 5-(1-ethyl-1H-1,2,3-triazol-4-yl)pent-2-enoate (0.1 g, 0.45 mmol) in 1,4-dioxane (1 mL) and water (0.5 mL). The reaction was heated in a microwave at 140° C. (high absorption) for 4 h. The mixture was concentrated and purified over silica gel (12 g) with flash chromatography eluting at 30 mL/min with a gradient running from 0-10% MeOH/DCM over 20 min giving 64 mg (41%) of the title compound and 50 mg recovered (E)-ethyl 5-(1-ethyl-1H-1,2,3-triazol-4-yl)pent-2-enoate. LC-MS m/z 346.2 (M+H)$^+$, 0.81 min (ret. time).

Ethyl 3-(2-(2-(benzyloxy)-2-oxoethyl)-3-oxo-2,3-dihydro-1H-inden-5-yl)-5-(1-ethyl-1H-1,2,3-triazol-4-yl)pentanoate

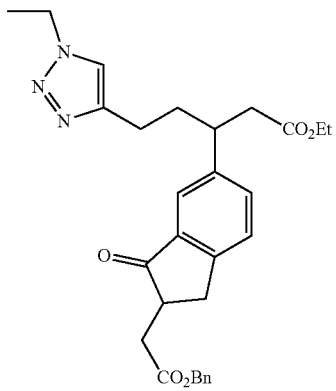 [SMILES: CCOC(=O)CC(CCc1cn(CC)nn1)c1ccc2c(c1)C(=O)C(CC(=O)OCc1ccccc1)C2]

To a solution of (E)-ethyl 5-(1-ethyl-1H-1,2,3-triazol-4-yl)pent-2-enoate (0.3 g, 1.344 mmol) in 1,4-dioxane (12 mL) and water (4 mL) was added benzyl 2-(1-oxo-6-(4,4,5,5-tetramethyl-1,3,2-dioxaborolan-2-yl)-2,3-dihydro-1H-inden-2-yl)acetate (0.819 g, 2.015 mmol), TEA (0.562 mL, 4.03 mmol) and [Rh(cod)Cl]₂ (0.033 g, 0.067 mmol). The resulting reaction mixture was stirred at 90° C. for 17 h. The reaction mixture was extracted with EtOAc (3×30 mL). The combined organic layer was dried over MgSO₄, filtered, concentrated under reduced pressure, and purified via silica gel chromatography to afford the desired product ethyl 3-(2-(2-(benzyloxy)-2-oxoethyl)-3-oxo-2,3-dihydro-1H-inden-5-yl)-5-(1-ethyl-1H-1,2,3-triazol-4-yl)pentanoate (403.9 mg, 0.802 mmol, 59.7% yield). LC-MS m/z 504.1 (M+H)$^+$, 1.05 min (ret. time).

Ethyl 3-(2-(2-((cyclohexylmethyl)amino)-2-oxo-ethyl)-3-oxo-2,3-dihydro-1H-inden-5-yl)-5-(1-ethyl-1H-1,2,3-triazol-4-yl)pentanoate

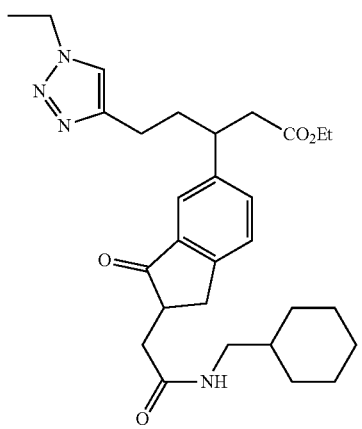 [SMILES: CCOC(=O)CC(CCc1cn(CC)nn1)c1ccc2c(c1)C(=O)C(CC(=O)NCC1CCCCC1)C2]

To a solution of ethyl 3-(2-(2-(benzyloxy)-2-oxoethyl)-3-oxo-2,3-dihydro-1H-inden-5-yl)-5-(1-ethyl-1H-1,2,3-triazol-4-yl)pentanoate (0.20 g, 0.397 mmol) in methanol (15 mL) was added 10% Pd/C (0.085 g, 0.079 mmol). The resulting suspension was stirred under a H₂ atmosphere at ambient temperature for 66 h. The reaction mixture was filtered. To the filtrate was added 10% Pd/C (0.085 g, 0.079 mmol) and the suspension stirred at ambient temperature under a H₂ atmosphere for 90 min. The reaction mixture was filtered and the filter cake was washed with MeOH (2×5 mL). The combined filtrate was concentrated under reduced pressure. This intermediate was dissolved in DCM (6 mL) after which cyclohexylmethanamine (0.103 mL, 0.794 mmol), TEA (0.111 mL, 0.794 mmol) and then T3P (50% wt in EtOAc) (0.236 mL, 0.794 mmol) was added. The resulting reaction mixture was stirred at ambient temperature for 19 h. To the reaction mixture was added more cyclohexylmethanamine (0.052 mL, 0.397 mmol), TEA (0.055 mL, 0.397 mmol) and T3P (50% wt in EtOAc) (0.236 mL, 0.397 mmol). The resulting reaction mixture was stirred at ambient temperature for another 5 h. The reaction mixture was purified via silica gel chromatography to afford the desired product ethyl 3-(2-(2-((cyclohexylmethyl)amino)-2-oxo-ethyl)-3-oxo-2,3-dihydro-1H-inden-5-yl)-5-(1-ethyl-1H-1,2,3-triazol-4-yl)pentanoate (119.8 mg, 0.236 mmol, 59.3% yield). LC-MS m/z 509.3 (M+H)⁺, 0.99 min (ret. time).

3-[(3aR,8bS)-1-(cyclohexylmethyl)-2-oxo-1H,2H,3H,3aH,4H,8bH-indeno[1,2-b]pyrrol-7-yl]-5-(1-ethyl-1H-1,2,3-triazol-4-yl)pentanoic Acid

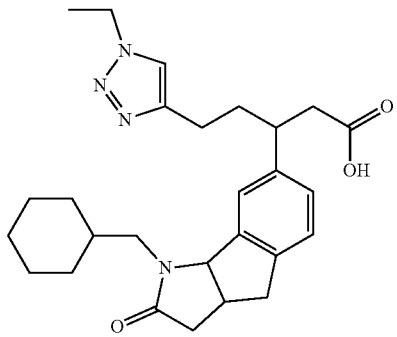 [SMILES: CCn1cc(CCC(CC(=O)O)c2ccc3c(c2)C2C(CC(=O)N2CC2CCCCC2)C3)nn1]

To a solution of ethyl 3-(2-(2-((cyclohexylmethyl)amino)-2-oxoethyl)-3-oxo-2,3-dihydro-1H-inden-5-yl)-5-(1-ethyl-1H-1,2,3-triazol-4-yl)pentanoate (119 mg, 0.234 mmol) in acetonitrile (2.0 mL) and THF (1.0 mL) was added triethylsilane (0.187 mL, 1.170 mmol) and TFA (0.054 mL, 0.702 mmol). The resulting reaction mixture was heated with microwave at 120° C. for 1 h; heated again with microwave at 120° C. for 2 h; heated again with microwave at 130° C. for 1 h. The reaction mixture was concentrated under reduced pressure, dissolved in methanol (3 mL) and then NaOH (3.0 N) (0.624 mL, 1.872 mmol) was added. The resulting reaction mixture was heated with microwave at 80° C. for 20 min. The reaction mixture was concentrated under reduced pressure on under vacuum and purified with reverse phase HPLC to afford the desired product 3-(1-(cyclohexylmethyl)-2-oxo-1,2,3,3a,4,8b-hexahydroindeno[1,2-b]pyrrol-7-yl)-5-(1-ethyl-1H-1,2,3-triazol-4-yl)pentanoic acid (57.5 mg, 0.124 mmol, 52.9% yield). LC-MS m/z 465.2 (M+H)⁺, 0.86 min (ret. time).

Example 4

3-[1-(Decahydronaphthalen-2-ylmethyl)-2-oxo-1H,2H,3H,3aH,4H,8bH-indeno[1,2-b]pyrrol-7-yl]-3-(1,4-dimethyl-1H-1,2,3-benzotriazol-5-yl)propanoic Acid

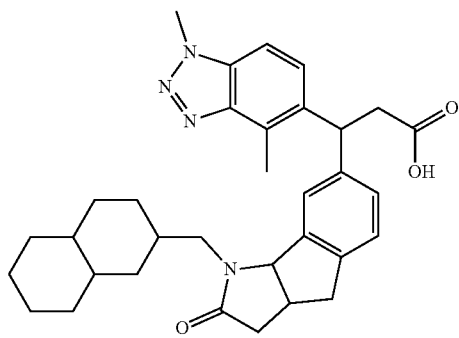 [SMILES: Cc1c(C(CC(=O)O)c2ccc3c(c2)C2C(CC(=O)N2CC2CCC4CCCCC4C2)C3)ccc2c1nnn2C]

Decahydronaphthalene-2-carbonitrile

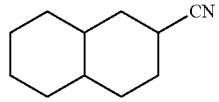 [SMILES: N#CC1CCC2CCCCC2C1]

To a solution of 2-decalone (2.332 mL, 15 mmol) and p-toluenesulfonylmethyl isocyanide (3.51 g, 18.00 mmol) in THF (50 mL) was added KOtBu (3.37 g, 30.0 mmol) slowly at 0° C. The resulting reaction mixture was stirred at 0° C. for 1 h then at ambient temperature for 2 h. The reaction mixture was concentrated under reduced pressure before adding water (150 mL) and then extracted with hexane (3×100 mL). The combined organic layer was dried over $MgSO_4$, filtered, concentrated under reduced pressure, and purified via silica gel chromatography to afford the desired product decahydronaphthalene-2-carbonitrile (1.9881 g, 12.18 mmol, 81% yield). LC-MS m/z 164.3 $(M+H)^+$, 1.05 min (ret. time).

(Decahydronaphthalen-2-yl)methanamine

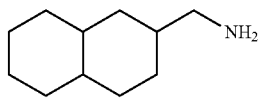 [SMILES: NCC1CCC2CCCCC2C1]

To a suspension of LAH (0.690 g, 18.19 mmol) in THF (40 mL) was added decahydronaphthalene-2-carbonitrile (1.98 g, 12.13 mmol) in THF (5 mL) slowly at ambient temperature. The resulting reaction mixture was stirred at ambient temperature for 1 h. The reaction mixture was quenched slowly with $Na_2SO_4$ (sat. aq.), filtered, and concentrated under reduced pressure to afford the desired product (decahydronaphthalen-2-yl)methanamine (1.9205 g, 11.48 mmol, 95% yield). LC-MS m/z 168.1 $(M+H)^+$, 0.69 min (ret. time).

Ethyl 3-(2-(2-(((decahydronaphthalen-2-yl)methyl)amino)-2-oxoethyl)-3-oxo-2,3-dihydro-1H-inden-5-yl)-3-(1,4-dim ethyl-1H-benzo[d][1,2,3]triazol-5-yl)propanoate

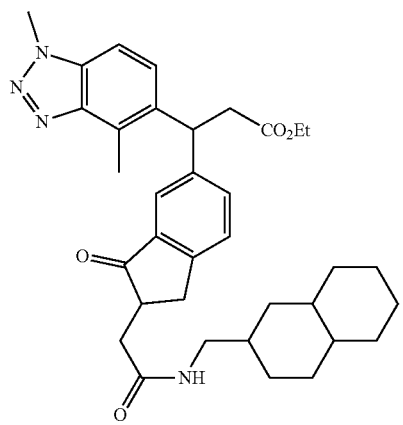 [SMILES: CCOC(=O)CC(c1ccc2c(c1)C(=O)C(CC(=O)NCC1CCC3CCCCC3C1)C2)c1ccc2c(nnn2C)c1C]

To a solution of ethyl 3-(2-(2-(benzyloxy)-2-oxoethyl)-3-oxo-2,3-dihydro-1H-inden-5-yl)-3-(1,4-dimethyl-1H-benzo[d][1,2,3]triazol-5-yl)propanoate (298 mg, 0.3 mmol) in methanol (15 mL) was added 10% Pd/C (63.9 mg, 0.060 mmol). The resulting suspension was stirred under a $H_2$ atmosphere at ambient temperature for 30 min. The reaction mixture was filtered and the filter cake was washed with MeOH (2×5 mL). The combined filtrate was evaporated under vacuum. This intermediate was dissolved in DCM (6 mL) after which (decahydronaphthalen-2-yl)methanamine (100 mg, 0.600 mmol), TEA (0.084 mL, 0.600 mmol) and then T3P (50% wt in EtOAc) (0.357 mL, 0.600 mmol) was added. The resulting reaction mixture was stirred at ambient temperature for 2 h before adding more T3P (50% wt in EtOAc) (0.179 mL, 0.300 mmol) and TEA (0.042 mL, 0.300 mmol). The resulting reaction mixture was stirred at ambient temperature for another 30 min. The reaction mixture was concentrated under reduced pressure, and purified via silica gel chromatography to afford the desired product ethyl 3-(2-(2-(((decahydronaphthalen-2-yl)methyl)amino)-2-oxoethyl)-3-oxo-2,3-dihydro-1H-inden-5-yl)-3-(1,4-dimethyl-1H-benzo[d][1,2,3]triazol-5-yl)propanoate (156.4 mg, 0.267 mmol, 89% yield). LC-MS m/z 585.4 $(M+H)^+$, 1.26 min (ret. time).

3-[1-(Decahydronaphthalen-2-ylmethyl)-2-oxo-1H, 2H,3H,3aH,4H,8bH-indeno[1,2-b]pyrrol-7-yl]-3-(1, 4-dimethyl-1H-1,2,3-benzotriazol-5-yl)propanoic Acid

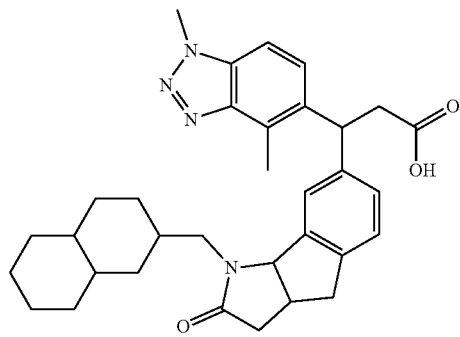 [SMILES: Cc1c(C(CC(=O)O)c2ccc3c(c2)C2C(CC(=O)N2CC2CCC4CCCCC4C2)C3)ccc2c1nnn2C]

To a solution of ethyl 3-(2-(2-(((decahydronaphthalen-2-yl)methyl)amino)-2-oxoethyl)-3-oxo-2,3-dihydro-1H-inden-5-yl)-3-(1,4-dimethyl-1H-benzo[d][1,2,3]triazol-5-yl)propanoate (150 mg, 0.257 mmol) in acetonitrile (3 mL) was added triethylsilane (0.205 mL, 1.283 mmol) and TFA (0.059 mL, 0.770 mmol). The resulting reaction mixture was heated with microwave at 120° C. for 1 h. The reaction mixture was concentrated under reduced pressure, dissolved in methanol (3 mL) and then NaOH (3.0 N) (0.684 mL, 2.052 mmol) was added. The resulting reaction mixture was heated with microwave at 80° C. for 20 min. The reaction mixture was concentrated under reduced pressure, and purified with reverse phase HPLC to afford the desired product 3-(1-(((decahydronaphthalen-2-yl)methyl)-2-oxo-1,2,3,3a,4,8b-hexahydroindeno[1,2-b]pyrrol-7-yl)-3-(1,4-dimethyl-1H-benzo[d][1,2,3]triazol-5-yl)propanoic acid (85.2 mg, 0.158 mmol, 61.4% yield). LC-MS m/z 541.4 $(M+H)^+$, 1.04 min (ret. time).

Example 5

3-(1,4-Dimethyl-1H-1,2,3-benzotriazol-5-yl)-3-{2-oxo-1-[(4-propylcyclohexyl)methyl]-1H,2H,3H,3aH,4H,8bH-indeno[1,2-b]pyrrol-7-yl}propanoic Acid

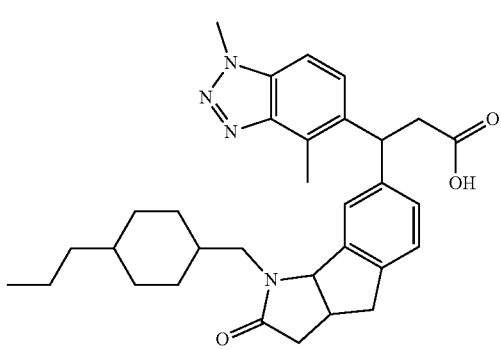 [SMILES: CCCC1CCC(CN2C(=O)CC3Cc4ccc(C(CC(=O)O)c5ccc6c(nnn6C)c5C)cc4C32)CC1]

Ethyl 3-(1,4-dimethyl-1H-benzo[d][1,2,3]triazol-5-yl)-3-(3-oxo-2-(2-oxo-2-(((4-propylcyclohexyl)methyl)amino)ethyl)-2,3-dihydro-1H-inden-5-yl)propanoate

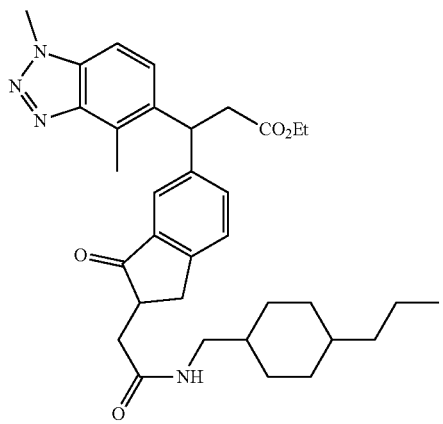

To a solution of ethyl 3-(2-(2-(benzyloxy)-2-oxoethyl)-3-oxo-2,3-dihydro-1H-inden-5-yl)-3-(1,4-dimethyl-1H-benzo[d][1,2,3]triazol-5-yl)propanoate (298 mg, 0.3 mmol) in methanol (15 mL) was added 10% Pd/C (63.9 mg, 0.060 mmol). The resulting suspension was stirred under a $H_2$ atmosphere at ambient temperature for 30 min. The reaction mixture was filtered and the filter cake was washed with MeOH (2×5 mL). The combined filtrate was evaporated under vacuum. This intermediate was dissolved in DCM (6 mL) after which (4-propylcyclohexyl)methanamine (93 mg, 0.600 mmol), TEA (0.084 mL, 0.600 mmol) and then T3P (50% wt in EtOAc) (0.357 mL, 0.600 mmol) was added. The resulting reaction mixture was stirred at ambient temperature for 2 h before adding more T3P (50% wt in EtOAc) (0.179 mL, 0.300 mmol) and TEA (0.042 mL, 0.300 mmol). The resulting reaction mixture was stirred at ambient temperature for another 68 h. To the reaction mixture was added more (4-propylcyclohexyl)methanamine (46.6 mg, 0.300 mmol), T3P (50% wt in EtOAc) (0.179 mL, 0.300 mmol) and TEA (0.042 mL, 0.300 mmol). The resulting reaction mixture was stirred at ambient temperature for 6 h before adding more T3P (50% wt in EtOAc) (0.179 mL, 0.300 mmol) and TEA (0.042 mL, 0.300 mmol). The resulting reaction mixture was stirred at ambient temperature for another 19 h. The reaction mixture was purified via silica gel chromatography to afford the desired product ethyl 3-(1,4-dimethyl-1H-benzo[d][1,2,3]triazol-5-yl)-3-(3-oxo-2-(2-oxo-2-(((4-propylcyclohexyl) methyl)amino)ethyl)-2,3-dihydro-1H-inden-5-yl)propanoate (146.2 mg, 0.255 mmol, 85% yield). LC-MS m/z 573.4 (M+H)$^+$, 1.25 min (ret. time).

4-Propylcyclohexanecarbonitrile

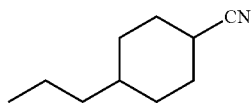

To a solution of 4-propylcyclohexanone (2.319 mL, 15 mmol) and p-toluenesulfonylmethyl isocyanide (3.51 g, 18.00 mmol) in THF (50 mL) was added KOtBu (3.37 g, 30.0 mmol) slowly at 0° C. The resulting reaction mixture was stirred at 0° C. for 1 h then at ambient temperature for 2 h. The reaction mixture was concentrated under reduced pressure, diluted with water (100 mL) and then extracted with hexane (3×80 mL). The combined organic layer was dried over MgSO$_4$, filtered, concentrated under reduced pressure, and purified via silica gel chromatography to afford the desired product 4-propylcyclohexanecarbonitrile (1.2419 g, 8.21 mmol, 54.7% yield). $^1$H NMR (400 MHz, CHLOROFORM-d) □ ppm 0.84-0.94 (m, 4H), 1.13-1.39 (m, 6H), 1.49-1.56 (m, 1H), 1.57-1.61 (m, 1H), 1.67-1.87 (m, 2H), 1.93-2.15 (m, 2H), 2.29-2.94 (m, 1H).

(4-Propylcyclohexyl)methanamine

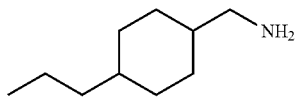

To a suspension of LAH (0.452 g, 11.90 mmol) in THF (20 mL) was added 4-propylcyclohexanecarbonitrile (1.2 g, 7.93 mmol) in THF (5 mL) slowly at ambient temperature. The resulting reaction mixture was stirred at ambient temperature for 1 h. The reaction mixture was quenched slowly with Na$_2$SO$_4$ (sat. aq.), filtered, and concentrated under reduced pressure to afford the desired product (4-propylcyclohexyl)methanamine (1.1512 g, 7.41 mmol, 93% yield). LC-MS m/z 156.0 (M+H)$^+$, 0.69 min (ret. time).

3-(1,4-Dimethyl-1H-benzo[d][1,2,3]triazol-5-yl)-3-(2-oxo-1-((4-propylcyclohexyl)methyl)-1,2,3,3a,4,8b-hexahydroindeno[1,2-b]pyrrol-7-yl)propanoic Acid

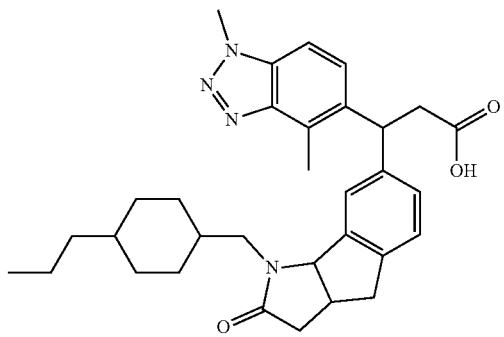 [SMILES: CCCC1CCC(CN2C(=O)CC3Cc4ccc(C(CC(=O)O)c5ccc6c(nnn6C)c5C)cc4C32)CC1]

To a solution of ethyl 3-(1,4-dimethyl-1H-benzo[d][1,2,3]triazol-5-yl)-3-(3-oxo-2-(2-oxo-2-(((4-propylcyclohexyl)methyl)amino)ethyl)-2,3-dihydro-1H-inden-5-yl)propanoate (145 mg, 0.253 mmol) in acetonitrile (3 mL) was added triethylsilane (0.202 mL, 1.266 mmol) and TFA (0.059 mL, 0.760 mmol). The resulting reaction mixture was heated with microwave at 120° C. for 1 h. The reaction mixture was concentrated under reduced pressure, dissolved in methanol (3 mL) after which NaOH (3.0 N) (0.675 mL, 2.025 mmol) was added. The resulting reaction mixture was heated with microwave at 80° C. for 20 min. The reaction mixture was concentrated under reduced pressure, and purified with reverse phase HPLC to afford the desired product 3-(1,4-dimethyl-1H-benzo[d][1,2,3]triazol-5-yl)-3-(2-oxo-1-((4-propylcyclohexyl)methyl)-1,2,3,3a,4,8b-hexahydroindeno[1,2-b]pyrrol-7-yl)propanoic acid (83.2 mg, 0.157 mmol, 62.2% yield). LC-MS m/z 529.3 (M+H)$^+$, 1.06 min (ret. time).

Example 6

3-{1-[(tert-Butoxy)carbonyl]-1H,2H,3H,3aH,4H,8bH-indeno[1,2-b]pyrrol-7-yl}-3-(1,4-dimethyl-1H-1,2,3-benzotriazol-5-yl)propanoic Acid

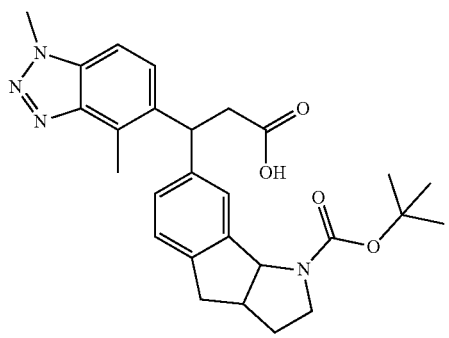 [SMILES: Cc1c(C(CC(=O)O)c2ccc3c(c2)C2C(CCN2C(=O)OC(C)(C)C)C3)ccc2c1nnn2C]

Methyl 2-(6-bromo-1-oxo-2,3-dihydro-1H-inden-2-yl)acetate

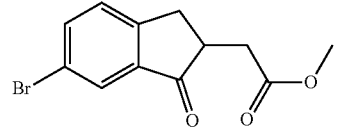 [SMILES: COC(=O)CC1Cc2ccc(Br)cc2C1=O]

To a solution of 6-bromo-2,3-dihydro-1H-inden-1-one (15 g, 71.1 mmol) in THF (300 mL), LiHMDS (85 mL, 85 mmol) was added dropwise at −78° C. Then the reaction mixture was allowed to warm up to 0° C. and was cooled to −78° C. again. Methyl 2-bromoacetate (7.38 mL, 78 mmol) was added dropwise at −78° C. The reaction mixture was warmed to ambient temperature. Water was added and extracted with ethyl acetate. The organic layer was washed with water and brine, dried with MgSO$_4$ and concentrated to give crude product which was purified through silica gel column chromatography (petroleum ether: ethyl acetate=10:1) to afford methyl 2-(6-bromo-1-oxo-2,3-dihydro-1H-inden-2-yl)acetate (8.1 g, 28.6 mmol, 40.3% yield). LC-MS m/z 285.0 (M+H)$^+$, 1.68 min (ret. time).

(Z)-Methyl 2-(6-bromo-1-(hydroxyimino)-2,3-dihydro-1H-inden-2-yl)acetate

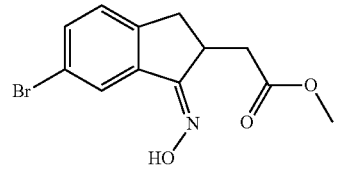 [SMILES: COC(=O)CC1Cc2ccc(Br)cc2/C1=N\O]

To a solution of methyl 2-(6-bromo-1-oxo-2,3-dihydro-1H-inden-2-yl)acetate (8.1 g, 28.6 mmol) in methanol (100 mL), hydroxylamine hydrochloride (2.98 g, 42.9 mmol) and sodium acetate (3.52 g, 42.9 mmol) were added. The reaction mixture was stirred at 65° C. for 6 h. Water was added and the mixture extracted with ethyl acetate. The organic layer was washed with water and brine, dried with Na$_2$SO$_4$ and concentrated to give (Z)-methyl 2-(6-bromo-1-(hydroxyimino)-2,3-dihydro-1H-inden-2-yl)acetate (7.6 g, 25.5 mmol, 89% yield). LC-MS m/z 300.0 (M+H)$^+$, 1.59 min (ret. time).

7-Bromo-1,3a,4,8b-tetrahydroindeno[1,2-b]pyrrol-2(3H)-one

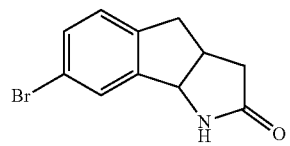 [SMILES: O=C1CC2Cc3ccc(Br)cc3C2N1]

To a solution of (Z)-methyl 2-(6-bromo-1-(hydroxyimino)-2,3-dihydro-1H-inden-2-yl)acetate (7.6 g, 25.5 mmol) in acetic acid (100 mL), zinc (8.3 g, 127 mmol) was added at ambient temperature. The reaction mixture was stirred at 60° C. for 1 hr after which time it was cooled to ambient temperature, filtered, and concentrated. Water was added and the mixture extracted with ethyl acetate. The organic layer was washed with water and brine, dried with Na₂SO₄ and concentrated to give crude product which was purified through silica gel chromatography (petroleum ether: ethyl acetate=1:2) to afford 7-bromo-1,3a,4,8b-tetrahydroindeno[1,2-b]pyrrol-2(3H)-one (3.5 g, 13.88 mmol, 54.5% yield). LC-MS m/z 253.9 (M+H)⁺, 1.09 min (ret. time).

7-Bromo-1,2,3,3a,4,8b-hexahydroindeno[1,2-b]pyrrole

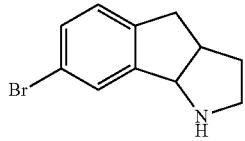 [SMILES: Brc1ccc2c(c1)C1NCCC1C2]

To a solution of 7-bromo-1,3a,4,8b-tetrahydroindeno[1,2-b]pyrrol-2(3H)-one (3.5 g, 13.88 mmol) in THF (60 mL) was added BH₃.DMS (48.6 mL, 97 mmol) at 0° C. The reaction mixture was allowed to stir under refluxing for 16 h and then was cooled to 0° C. The reaction mixture was quenched by the slow addition of MeOH (2 mL) and then 3 N of HCl. The reaction mixture was allowed to stir under refluxing for another 3 h then concentrated. Water was added to the residue and the pH of the solution was adjusted to >9 with 4N NaOH. The solution was extracted with diethyl ether. The organic layer was dried over Na₂SO₄ and concentrated to afford 7-bromo-1,2,3,3a,4,8b-hexahydroindeno[1,2-b]pyrrole (3.05 g, 12.81 mmol, 92% yield). LC-MS m/z 238.0 (M+H)⁺, 1.12 min (ret. time).

Tert-butyl 7-bromo-2,3,3a,4-tetrahydroindeno[1,2-b]pyrrole-1(8bH)-carboxylate

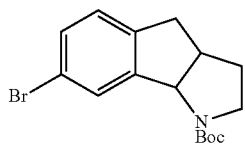 [SMILES: CC(C)(C)OC(=O)N1CCC2Cc3ccc(Br)cc3C21]

To a solution of 7-bromo-1,2,3,3a,4,8b-hexahydroindeno[1,2-b]pyrrole (3.05 g, 12.81 mmol) in DCM (30 mL), TEA (3.57 mL, 25.6 mmol) and Boc₂O (4.46 mL, 19.21 mmol) were added. The reaction mixture was stirred at ambient temperature for 6 h. Water was added and the mixture extracted with ethyl acetate. The organic layer was washed with water and brine, dried with Na₂SO₄ and concentrated to afford tert-butyl 7-bromo-2,3,3a,4-tetrahydroindeno[1,2-b]pyrrole-1(8bH)-carboxylate (2.5 g, 7.39 mmol, 57.7% yield). LC-MS m/z 260.0 (M+H)⁺, 2.04 min (ret. time).

Tert-butyl 7-(4,4,5,5-tetramethyl-1,3,2-dioxaborolan-2-yl)-2,3,3a,4-tetrahydroindeno[1,2-b]pyrrole-1(8bH)-carboxylate

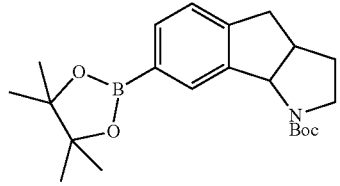 [SMILES: CC(C)(C)OC(=O)N1CCC2Cc3ccc(B4OC(C)(C)C(C)(C)O4)cc3C21]

To a solution of tert-butyl 7-bromo-2,3,3a,4-tetrahydroindeno[1,2-b]pyrrole-1(8bH)-carboxylate (2.9 g, 8.57 mmol) in 1,4-dioxane (200 mL) was added potassium acetate (2.104 g, 21.43 mmol), bis(pinacolato)diboron (2.83 g, 11.15 mmol) and the reaction mixture was degassed with argon for 30 min after which PdCl₂(dppf)-CH₂Cl₂ adduct (0.350 g, 0.429 mmol) was added. The reaction mixture and stirred at 100° C. for 16 h, cooled to ambient temperature, and filtered through celite. The filtrate was concentrated under vacuum. The crude residue was purified via silica gel chromatography by using EtOAc:hexane (15:1) to get a crude product which was crystallized from hexane to afford tert-butyl 7-(4,4,5,5-tetramethyl-1,3,2-dioxaborolan-2-yl)-2,3,3a,4-tetrahydroindeno[1,2-b]pyrrole-1(8bH)-carboxylate (2.05 g, 4.81 mmol, 56.1% yield). LC-MS m/z 408.2 (M+H)⁺, 1.99 min (ret. time).

Tert-butyl 7-(1-(1,4-dimethyl-1H-benzo[d][1,2,3]triazol-5-yl)-3-ethoxy-3-oxopropyl)-2,3,3a,4-tetrahydroindeno[,2-b]pyrrole-1(8bH)-carboxylate

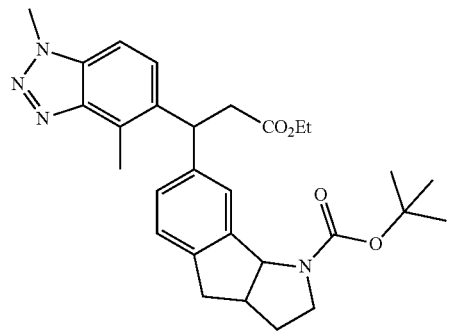 [SMILES: CCOC(=O)CC(c1ccc2c(c1)C1C(CCN1C(=O)OC(C)(C)C)C2)c1ccc2c(nnn2C)c1C]

To a solution of (E)-ethyl 3-(1,4-dimethyl-1H-benzo[d][1,2,3]triazol-5-yl)acrylate (0.491 g, 2 mmol) in 1,4-dioxane (12 mL) and water (4 mL) was added tert-butyl 7-(4,4,5,5-tetramethyl-1,3,2-dioxaborolan-2-yl)-2,3,3a,4-tetrahydroindeno[1,2-b]pyrrole-1 (8bH)-carboxylate (1.156 g, 3.00 mmol), TEA (1.115 mL, 8.00 mmol) and [Rh(cod)Cl]₂ (0.049 g, 0.100 mmol). The resulting reaction mixture was stirred at 90° C. for 65 h. The reaction mixture was concentrated under reduced pressure and purified via silica gel chromatography to afford the desired product tert-butyl 7-(1-(1,4-dimethyl-1H-benzo[d][1,2,3]triazol-5-yl)-3-ethoxy-3-oxopropyl)-2,3,3a,4-tetrahydroindeno[1,2-b]pyrrole-1(8bH)-carboxylate (1.0056 g, 1.993 mmol, 100% yield). LC-MS m/z 505.3 (M+H)⁺, 1.19 min (ret. time).

3-{1-[(tert-Butoxy)carbonyl]-1H,2H,3H,3aH,4H,8bH-indeno[1,2-b]pyrrol-7-yl}-3-(1,4-dimethyl-1H-1,2,3-benzotriazol-5-yl)propanoic Acid

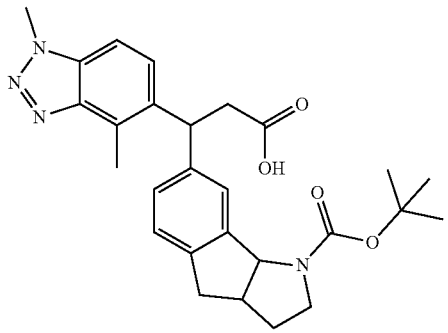 [SMILES: Cc1c(C(CC(=O)O)c2ccc3c(c2)C2C(CCN2C(=O)OC(C)(C)C)C3)ccc2c1nnn2C]

To a solution of tert-butyl 7-(1-(1,4-dimethyl-1H-benzo[d][1,2,3]triazol-5-yl)-3-ethoxy-3-oxopropyl)-2,3,3a,4-tetrahydroindeno[1,2-b]pyrrole-1(8bH)-carboxylate (30 mg, 0.059 mmol) in methanol (1 mL) was added NaOH (3.0 N) (0.099 mL, 0.297 mmol). The resulting reaction mixture was heated with microwave at 80° C. for 20 min. The reaction mixture was acidified with HCl (3 N) slowly to pH~3 then concentrated under reduced pressure, and purified with reverse phase HPLC to afford the desired product 3-(1-(tert-butoxycarbonyl)-1,2,3,3a,4,8b-hexahydroindeno[1,2-b]pyrrol-7-yl)-3-(1,4-dimethyl-1H-benzo[d][1,2,3]triazol-5-yl)propanoic acid (24.6 mg, 0.052 mmol, 87% yield). LC-MS m/z 421.2 (M+H)$^+$, 0.98 min (ret. time).

Example 7

3-[1-(2-Cyclohexylacetyl)-1H,2H,3H,3aH,4H,8bH-indeno[1,2-b]pyrrol-7-yl]-3-(1,4-dimethyl-1H-1,2,3-benzotriazol-5-yl)propanoic Acid

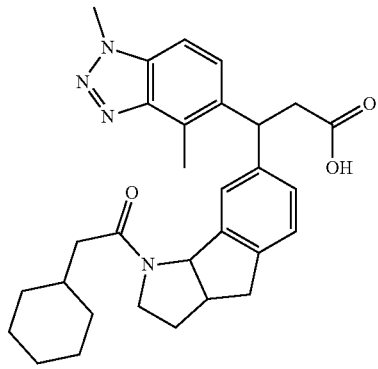 [SMILES: Cc1c(C(CC(=O)O)c2ccc3c(c2)C2C(CCN2C(=O)CC2CCCCC2)C3)ccc2c1nnn2C]

Ethyl 3-(1,4-dimethyl-1H-benzo[d][1,2,3]triazol-5-yl)-3-(1,2,3,3a,4,8b-hexahydroindeno[1,2-b]pyrrol-7-yl)propanoate, Hydrochloride

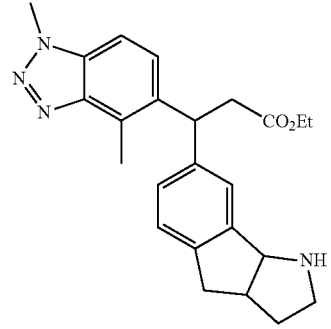 [SMILES: CCOC(=O)CC(c1ccc2c(c1)C1NCCC1C2)c1ccc2c(nnn2C)c1C]

To a solution of tert-butyl 7-(1-(1,4-dimethyl-1H-benzo[d][1,2,3]triazol-5-yl)-3-ethoxy-3-oxopropyl)-2,3,3a,4-tetrahydroindeno[1,2-b]pyrrole-1 (8bH)-carboxylate (970 mg, 1.922 mmol) in 1,4-dioxane (2.5 mL) was added HCl (4 M in 1,4-dioxane) (2.403 mL, 9.61 mmol). The resulting reaction mixture was stirred at ambient temperature for 1 h. The reaction mixture was concentrated under reduced pressure to afford the desired product ethyl 3-(1,4-dimethyl-1H-benzo[d][1,2,3]triazol-5-yl)-3-(1,2,3,3a,4,8b-hexahydroindeno[1,2-b]pyrrol-7-yl)propanoate, hydrochloride (971.6 mg, 2.203 mmol, 115% yield). LC-MS m/z 405.4 (M+H)$^+$, 0.73 min (ret. time).

3-[1-(2-Cyclohexylacetyl)-1H,2H,3H,3aH,4H,8bH-indeno[1,2-b]pyrrol-7-yl]-3-(1,4-dimethyl-1H-1,2,3-benzotriazol-5-yl)propanoic Acid

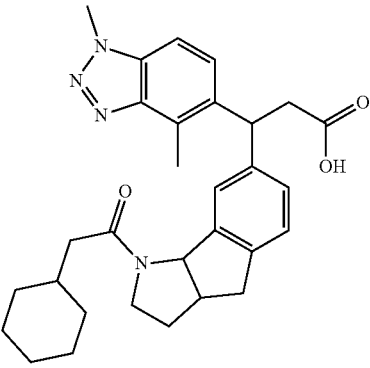 [SMILES: Cc1c(C(CC(=O)O)c2ccc3c(c2)C2C(CCN2C(=O)CC2CCCCC2)C3)ccc2c1nnn2C]

To a solution of ethyl 3-(1,4-dimethyl-1H-benzo[d][1,2,3]triazol-5-yl)-3-(1,2,3,3a,4,8b-hexahydroindeno[1,2-b]pyrrol-7-yl)propanoate, hydrochloride (50 mg, 0.113 mmol) in THF (2 mL) was added 2-cyclohexylacetic acid (17.74 mg, 0.125 mmol), TEA (0.047 mL, 0.340 mmol) and then T3P (50% wt in EtOAc) (0.101 mL, 0.170 mmol). The resulting reaction mixture was stirred at ambient temperature for 70 min before adding more T3P (50% wt in EtOAc) (0.034 mL, 0.113 mmol) and TEA (0.016 mL, 0.113 mmol). The resulting reaction mixture was stirred at ambient temperature for another 3 h. To the reaction mixture was added more T3P (50% wt in EtOAc) (0.034 mL, 0.113 mmol) and TEA (0.032 mL, 0.227 mmol). The resulting reaction mixture was stirred at ambient temperature for 50 min more before adding more 2-cyclohexylacetic acid (17.74 mg, 0.125 mmol). The resulting reaction mixture was stirred at ambient temperature for another 18 h. The reaction mixture was concentrated under reduced pressure, dissolved in methanol (2.000 mL) then was added NaOH (3 N) (0.378 mL, 1.134 mmol). The resulting reaction mixture was heated with microwave at 80° C. for 20 min. To the reaction mixture was added more NaOH (3 N) (0.378 mL, 1.134 mmol). The resulting reaction mixture was heated with microwave at 80° C. for another 20 min. To the reaction mixture was added more NaOH (3 N) (0.113 mL, 0.340 mmol). The resulting reaction mixture was heated with microwave at 80° C. for 20 min, heated again with microwave at 80° C. for 20 min. The reaction mixture was acidified with HCl (3 N) to pH 3-4 concentrated under reduced pressure and purified with reverse phase HPLC to afford the desired product 3-(1-(2-cyclohexylacetyl)-1,2,3,3a,4,8b-hexahydroindeno[1,2-b]pyrrol-7-yl)-3-(1,4-dimethyl-1H-benzo[d][1,2,3]triazol-5-yl)propanoic acid (20.7 mg, 0.041 mmol, 36.5% yield). LC-MS m/z 501.4 (M+H)⁺, 1.03 min (ret. time).

Example 8

3-(1,4-Dimethyl-1H-1,2,3-benzotriazol-5-yl)-3-[1-(2-phenylpropanoyl)-1H,2H,3H,3aH,4H,8bH-indeno[12-b]pyrrol-7-yl]propanoic Acid

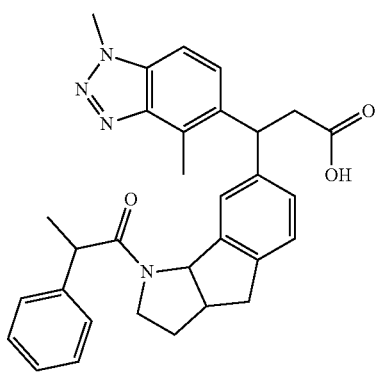

ISOMER 1

To a solution of ethyl 3-(1,4-dimethyl-1H-benzo[d][1,2,3]triazol-5-yl)-3-(1,2,3,3a,4,8b-hexahydroindeno[1,2-b]pyrrol-7-yl)propanoate, hydrochloride (50 mg, 0.113 mmol) in THF (2 mL) was added 2-phenylpropanoic acid (0.017 mL, 0.125 mmol), TEA (0.047 mL, 0.340 mmol) and then T3P (50% wt in EtOAc) (0.101 mL, 0.170 mmol). The resulting reaction mixture was stirred at ambient temperature for 50 min. To the reaction mixture was added more T3P (50% wt in EtOAc) (0.067 mL, 0.113 mmol) and TEA (0.016 mL, 0.113 mmol). The resulting reaction mixture was stirred at ambient temperature for another 3 h. To the reaction mixture was added more T3P (50% wt in EtOAc) (0.067 mL, 0.113 mmol) and TEA (0.032 mL, 0.227 mmol). The resulting reaction mixture was stirred at ambient temperature for another 50 min. To the reaction mixture was added more 2-phenylpropanoic acid (0.017 mL, 0.125 mmol). The resulting reaction mixture was stirred at ambient temperature for another 18 h. The reaction mixture was then heated with microwave at 80° C. for 30 min. To the reaction mixture was added more T3P (50% wt in EtOAc) (0.067 mL, 0.113 mmol) and TEA (0.032 mL, 0.227 mmol). The resulting reaction mixture was stirred at ambient temperature for another 71 h. The reaction mixture was then heated with microwave at 80° C. for 30 min. The reaction mixture was concentrated under reduced pressure, dissolved in methanol (2.000 mL) then was added NaOH (3 N) (0.756 mL, 2.268 mmol). The resulting reaction mixture was heated with microwave at 80° C. for 20 min. To the reaction mixture was added more NaOH (3 N) (0.378 mL, 1.134 mmol). The resulting reaction mixture was heated with microwave at 80° C. for 20 min. The reaction mixture was acidified with HCl (3 N) to pH 3-4 then concentrated under reduced pressure and purified with reverse phase HPLC to afford the desired product 3-(1,4-dimethyl-1H-1,2,3-benzotriazol-5-yl)-3-[1-(2-phenylpropanoyl)-1H,2H,3H,3aH,4H,8bH-indeno[1,2-b]pyrrol-7-yl]propanoic acid (isomer 1) (8.4 mg, 0.017 mmol, 14.57% yield). LC-MS m/z 509.3 (M+H)⁺, 0.96 min (ret. time).

Example 9

3-(1,4-Dimethyl-1H-1,2,3-benzotriazol-5-yl)-3-[1-(2-phenylpropanoyl)-1H,2H,3H,3aH,4H,8bH-indeno[1,2-b]pyrrol-7-yl]propanoic Acid

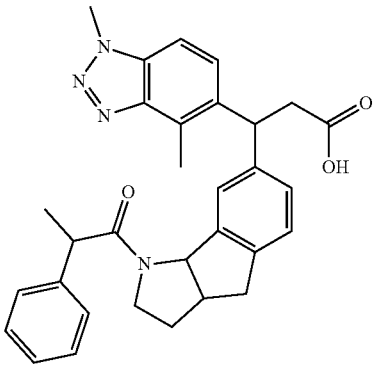

ISOMER 2

To a solution of ethyl 3-(1,4-dimethyl-1H-benzo[d][1,2,3]triazol-5-yl)-3-(1,2,3,3a,4,8b-hexahydroindeno[1,2-b]pyrrol-7-yl)propanoate, hydrochloride (50 mg, 0.113 mmol) in THF (2 mL) was added 2-phenylpropanoic acid (0.017 mL, 0.125 mmol), TEA (0.047 mL, 0.340 mmol) and then T3P (50% wt in EtOAc) (0.101 mL, 0.170 mmol). The resulting reaction mixture was stirred at ambient temperature for 50 min. To the reaction mixture was added more T3P (50% wt in EtOAc) (0.067 mL, 0.113 mmol) and TEA (0.016 mL, 0.113 mmol). The resulting reaction mixture was stirred at ambient temperature for another 3 h. To the reaction mixture was added more T3P (50% wt in EtOAc) (0.067 mL, 0.113 mmol) and TEA (0.032 mL, 0.227 mmol). The resulting reaction mixture was stirred at ambient temperature for another 50 min. To the reaction mixture was added more 2-phenylpropanoic acid (0.017 mL, 0.125 mmol). The resulting reaction mixture was stirred at ambient temperature for another 18 h. The reaction mixture was then heated with microwave at 80° C. for 30 min. To the reaction mixture was added more T3P (50% wt in EtOAc) (0.067 mL, 0.113 mmol) and TEA (0.032 mL, 0.227 mmol). The resulting reaction mixture was stirred at ambient temperature for another 71 h. The reaction mixture was then heated with microwave at 80° C. for 30 min. The reaction mixture was concentrated under reduced pressure, dissolved in methanol (2.000 mL) then was added NaOH (3 N) (0.756 mL, 2.268 mmol). The resulting reaction mixture was heated with microwave at 80° C. for 20 min. To the reaction mixture was added more NaOH (3 N) (0.378 mL, 1.134 mmol). The resulting reaction mixture was heated with microwave at 80° C. for 20 min. The reaction mixture was acidified with HCl (3 N) to pH 3-4, concentrated under reduced pressure, and purified with reverse phase HPLC to afford the desired product 3-(1,4-dimethyl-1H-1,2,3-benzotriazol-5-yl)-3-[1-(2-phenylpropanoyl)-1H,2H,3H,3aH,4H,8bH-indeno[1,2-b]pyrrol-7-yl]propanoic acid (isomer 2) (15.1 mg, 0.030 mmol, 26.2% yield). LC-MS m/z 509.3 (M+H)$^+$, 1.01 min (ret. time).

Example 10

3-(1,4-Dimethyl-1H-1,2,3-benzotriazol-5-yl)-3-[1-(2-methyl pentanoyl)-1H,2H,3H,3aH,4H,8bH-indeno[1,2-b]pyrrol-7-yl]propanoic Acid

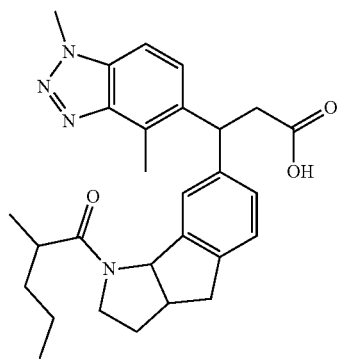 [SMILES: CCCC(C)C(=O)N1CCC2Cc3ccc(C(CC(=O)O)c4ccc5c(nnn5C)c4C)cc3C21]

To a solution of ethyl 3-(1,4-dimethyl-1H-benzo[d][1,2,3]triazol-5-yl)-3-(1,2,3,3a,4,8b-hexahydroindeno[1,2-b]pyrrol-7-yl)propanoate, hydrochloride (50 mg, 0.113 mmol) in THF (2 mL) was added 2-methylvaleric acid (0.016 mL, 0.125 mmol), TEA (0.047 mL, 0.340 mmol) and then T3P (50% wt in EtOAc) (0.101 mL, 0.170 mmol). The resulting reaction mixture was stirred at ambient temperature for 70 min. To the reaction mixture was added more T3P (50% wt in EtOAc) (0.067 mL, 0.113 mmol) and TEA (0.016 mL, 0.113 mmol). The resulting reaction mixture was stirred at ambient temperature for 3 h. To the reaction mixture was added more T3P (50% wt in EtOAc) (0.067 mL, 0.113 mmol) and TEA (0.032 mL, 0.227 mmol). The resulting reaction mixture was stirred at ambient temperature for 50 min. To the reaction mixture was added more 2-methylvaleric acid (0.016 mL, 0.125 mmol). The resulting reaction mixture was stirred at ambient temperature for 18 h. The reaction mixture was then heated with microwave at 80° C. for 30 min (33-8). To the reaction mixture was added more T3P (50% wt in EtOAc) (0.067 mL, 0.113 mmol), TEA (0.032 mL, 0.227 mmol). The resulting reaction mixture was stirred at ambient temperature for 71 h. The reaction mixture was concentrated under reduced pressure before being dissolved in methanol (2.000 mL) then added NaOH (3 N) (0.756 mL, 2.268 mmol). The resulting reaction mixture was heated with microwave at 80° C. for 20 min before adding more NaOH (3 N) (0.378 mL, 1.134 mmol) then heated with microwave at 80° C. for 20 min. The reaction mixture was acidified with HCl (3 N) to pH 3-4, concentrated under reduced pressure, and purified with reverse phase HPLC to afford the desired product 3-(1,4-dimethyl-1H-benzo[d][1,2,3]triazol-5-yl)-3-(1-(2-methylpentanoyl)-1,2,3,3a,4,8b-hexahydroindeno[1,2-b]pyrrol-7-yl)propanoic acid (16.6 mg, 0.035 mmol, 30.8% yield). LC-MS m/z 475.3 (M+H)$^+$, 0.96/0.98 min (ret. time).

Example 11

3-{1-[2-(2-Chlorophenyl)acetyl]-1H,2H,3H,3aH,4H,8bH-indeno[1,2-b]pyrrol-7-yl}-3-(1,4-dimethyl-1H-1,2,3-benzotriazol-5-yl)propanoic Acid

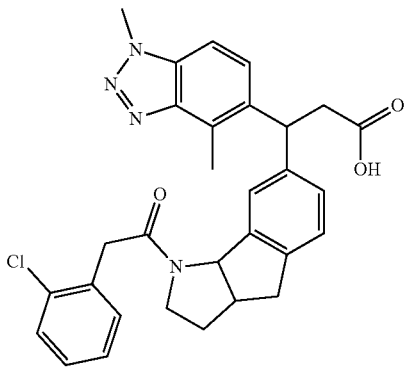 [SMILES: Cc1c(C(CC(=O)O)c2ccc3c(c2)C2C(CCN2C(=O)Cc2ccccc2Cl)C3)ccc2c1nnn2C]

To a solution of ethyl 3-(1,4-dimethyl-1H-benzo[d][1,2,3]triazol-5-yl)-3-(1,2,3,3a,4,8b-hexahydroindeno[1,2-b]pyrrol-7-yl)propanoate, hydrochloride (50 mg, 0.113 mmol) in DCM (2 mL) was added 2-(2-chlorophenyl)acetic acid (23.21 mg, 0.136 mmol), TEA (0.063 mL, 0.454 mmol) and then T3P (50% wt in EtOAc) (0.101 mL, 0.170 mmol). The resulting reaction mixture was stirred at ambient temperature for 40 min. The reaction mixture was concentrated under reduced pressure and dissolved in methanol (2.000 mL), after which NaOH (3 N) (0.378 mL, 1.134 mmol) was added. The resulting reaction mixture was heated with microwave at 80° C. for 20 min. The reaction mixture was acidified with HCl (3 N) to pH 3-4 then concentrated under reduced pressure and purified with reverse phase HPLC to afford the desired product 3-(1-(2-(2-chlorophenyl)acetyl)-1,2,3,3a,4,8b-hexahydroindeno[1,2-b]pyrrol-7-yl)-3-(1,4-dimethyl-1H-benzo[d][1,2,3]triazol-5-yl)propanoic acid (31.8 mg, 0.060 mmol, 53.0% yield). LC-MS m/z 529.2 (M+H)$^+$, 0.97 min (ret. time).

Example 12

3-{1-[2-(2-Cyanophenyl)acetyl]-1H,2H,3H,3aH,4H,8bH-indeno[1,2-b]pyrrol-7-yl}-3-(1,4-dimethyl-1H-1,2,3-benzotriazol-5-yl)propanoic Acid

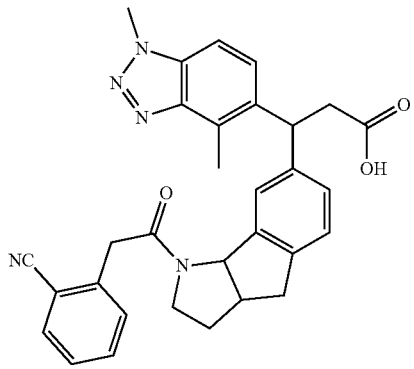 [SMILES: Cc1c(C(CC(=O)O)c2ccc3c(c2)C2C(CCN2C(=O)Cc2ccccc2C#N)C3)ccc2c1nnn2C]

To a solution of ethyl 3-(1,4-dimethyl-1H-benzo[d][1,2,3]triazol-5-yl)-3-(1,2,3,3a,4,8b-hexahydroindeno[1,2-b]pyrrol-7-yl)propanoate, hydrochloride (50 mg, 0.113 mmol) in DCM (2 mL) was added 2-(2-cyanophenyl)acetic acid (21.93 mg, 0.136 mmol), TEA (0.063 mL, 0.454 mmol) and then T3P (50% wt in EtOAc) (0.101 mL, 0.170 mmol). The resulting reaction mixture was stirred at ambient temperature for 30 min. The reaction mixture was concentrated under reduced pressure and dissolved in methanol (2.000 mL) after which was added NaOH (3 N) (0.378 mL, 1.134 mmol). The resulting reaction mixture was heated with microwave at 100° C. for 20 min. The reaction mixture was acidified with HCl (3 N) to pH 3-4 then concentrated under reduced pressure, and purified with reverse phase HPLC to afford the desired product 3-(1-(2-(2-cyanophenyl)acetyl)-1,2,3,3a,4,8b-hexahydroindeno[1,2-b]pyrrol-7-yl)-3-(1,4-dimethyl-1H-benzo[d][1,2,3]triazol-5-yl)propanoic acid (32.4 mg, 0.062 mmol, 55.0% yield). LC-MS m/z 520.3 (M+H)+, 0.90 min (ret. time).

Example 13

3-(1,4-Dimethyl-1H-1,2,3-benzotriazol-5-yl)-3-[1-(3,3-dimethyl butanoyl)-1H,2H,3H,3aH,4H,8bH-indeno[1,2-b]pyrrol-7-yl]propanoic Acid

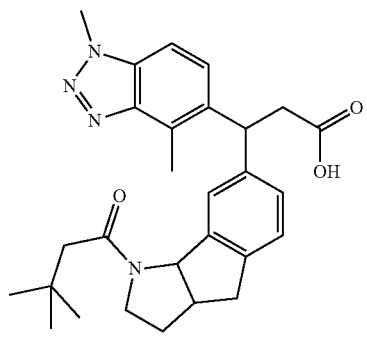 [SMILES: Cc1c(C(CC(=O)O)c2ccc3c(c2)C2C(CCN2C(=O)CC(C)(C)C)C3)ccc2c1nnn2C]

To a solution of ethyl 3-(1,4-dimethyl-1H-benzo[d][1,2,3]triazol-5-yl)-3-(1,2,3,3a,4,8b-hexahydroindeno[1,2-b]pyrrol-7-yl)propanoate, hydrochloride (50 mg, 0.113 mmol) in DCM (2 mL) was added 3,3-dimethylbutanoic acid (0.017 mL, 0.136 mmol), TEA (0.063 mL, 0.454 mmol) and then T3P (50% wt in EtOAc) (0.101 mL, 0.170 mmol). The resulting reaction mixture was stirred at ambient temperature for 30 min. The reaction mixture was concentrated under reduced pressure and dissolved in methanol (2.000 mL) after which NaOH (3 N) (0.378 mL, 1.134 mmol) was added. The resulting reaction mixture was heated with microwave at 80° C. for 20 min. The reaction mixture was acidified with HCl (3 N) to pH 3-4 then concentrated under reduced pressure and purified with reverse phase HPLC to afford the desired product 3-(1,4-dimethyl-1H-benzo[d][1,2,3]triazol-5-yl)-3-(1-(3,3-dimethylbutanoyl)-1,2,3,3a,4,8b-hexahydroindeno[1,2-b]pyrrol-7-yl)propanoic acid (26.0 mg, 0.055 mmol, 48.3% yield). LC-MS m/z 475.2 (M+H)+, 0.94 min (ret. time).

Example 14

3-{1-[Butyl(methyl)carbamoyl]-1H,2H,3H,3aH,4H,8bH-indeno[1,2-b]pyrrol-7-yl}-3-(1,4-dimethyl-1H-1,2,3-benzotriazol-5-yl)propanoic Acid

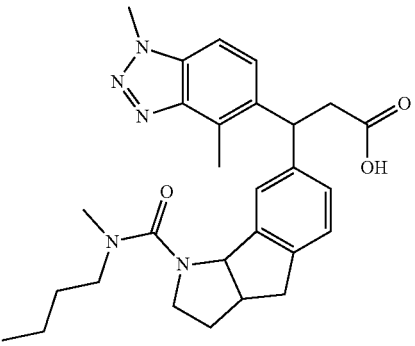 [SMILES: CCCCN(C)C(=O)N1CCC2Cc3ccc(C(CC(=O)O)c4ccc5c(nnn5C)c4C)cc3C21]

To a solution of ethyl 3-(1,4-dimethyl-1H-benzo[d][1,2,3]triazol-5-yl)-3-(1,2,3,3a,4,8b-hexahydroindeno[1,2-b]pyrrol-7-yl)propanoate, hydrochloride (50 mg, 0.113 mmol) in DCM (2 mL) was added CDI (22.06 mg, 0.136 mmol), TEA (0.032 mL, 0.227 mmol). The resulting reaction mixture was stirred at ambient temperature for 1 h before adding N-methylbutan-1-amine (0.020 mL, 0.170 mmol). The resulting reaction mixture was stirred at ambient temperature for 100 min then heated with microwave at 80° C. for 30 min. To the reaction mixture was added more N-methylbutan-1-amine (0.027 mL, 0.227 mmol) then heated with microwave at 80° C. for 30 min. The reaction mixture was concentrated under reduced pressure, dissolved in 1,4-dioxane (0.5 mL) then added more N-methylbutan-1-amine (0.5 mL, 4.22 mmol). The resulting reaction mixture was heated with microwave at 80° C. for 30 min; heated again with microwave at 100° C. for 30 min; heated again with microwave at 120° C. for 60 min; heated again with microwave at 130° C. for 60 min. The reaction mixture was concentrated under reduced pressure and dissolved in methanol (2.000 mL) after which NaOH (3 N) (0.227 mL, 0.680 mmol) was added. The resulting reaction mixture was heated with microwave at 80° C. for 20 min before adding more NaOH (3 N) (0.227 mL, 0.680 mmol) then heated with microwave at 80° C. for 20 min. The reaction mixture was acidified with HCl (3 N) to pH 3-4 then concentrated under reduced pressure and purified with reverse phase HPLC to afford the desired product 3-(1-(butyl(methyl)carbamoyl)-1,2,3,3a,4,8b-hexahydroindeno[1,2-b]pyrrol-7-yl)-3-(1,4-dimethyl-1H-benzo[d][1,2,3]triazol-5-yl)propanoic acid (23.3 mg, 0.048 mmol, 42.0% yield). LC-MS m/z 490.4 (M+H)⁺, 0.97 min (ret. time).

Example 15

3-{1-[(tert-Butoxy)carbonyl]-1H,2H,3H,3aH,4H,8bH-indeno[1,2-b]pyrrol-7-yl}-3-(7-methoxy-1-methyl-1H-1,2,3-benzotriazol-5-yl)propanoic Acid

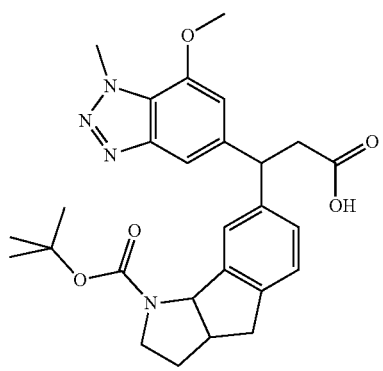 [SMILES: COc1cc(C(CC(=O)O)c2ccc3c(c2)C2C(CCN2C(=O)OC(C)(C)C)C3)cc2nnn(C)c12]

2-Methoxy-6-nitroaniline

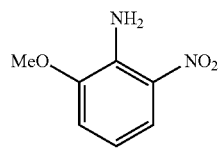

To a solution of 2-amino-3-nitrophenol (2.55 g, 16.55 mmol) dissolved in N,N-dimethylformamide (35 mL) was added potassium carbonate (2.52 g, 18.20 mmol). The mixture was stirred for 5 min before iodomethane (1.138 mL, 18.20 mmol) was added and the reaction allowed to stir at ambient temperature for 2 h. water 75 mL) was added to quench the reaction and the precipitate product was collected by filtration, washed with water to afford the title compound 2-methoxy-6-nitroaniline (2.26 g, 81%). LC-MS m/z 168.9 (M+H)⁺, 0.74 min (ret. time)

4-Bromo-2-methoxy-6-nitroaniline

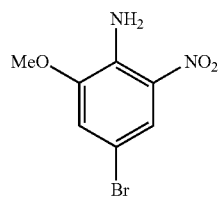 [SMILES: COc1cc(Br)cc([N+](=O)[O-])c1N]

To a solution of 2-methoxy-6-nitroaniline (2.26 g, 13.44 mmol) dissolved in acetic acid (50 mL) was added sodium acetate (1.654 g, 20.16 mmol) and bromine (0.762 mL, 14.78 mmol) and the mixture was stirred at ambient temperature for 30 min. Water was added (75 mL) to quench the reaction and the precipitate product was collected by filtration, washed with water and dried over vacuum to give 2.78 g of 4-bromo-2-methoxy-6-nitroaniline (84%). LC-MS m/z 246.9/248.9 (M+H)⁺, 0.93 min (ret. time).

4-Bromo-2-methoxy-N-methyl-6-nitroaniline

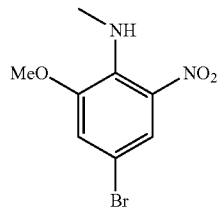

To a solution of 4-bromo-2-methoxy-6-nitroaniline (2.76 g, 11.17 mmol) dissolved in N,N-dimethylformamide (50 mL) was added sodium hydride (300 mg, 12.50 mmol) slowly at 0° C. and the reaction mixture was stirred for 30 min. Then methyl iodide (0.768 mL, 12.29 mmol) was added. Water was added (60 mL) to quench the reaction and the precipitate product was collected by filtration, washed with water and dried over vacuum to afford the title compound 4-bromo-2-methoxy-N-methyl-6-nitroaniline (2.82 g, 97%). LC-MS m/z 260.9/263 (M+H)⁺, 1.03 min (ret. time).

5-Bromo-7-methoxy-1-methyl-1H-benzo[d][1,2,3]triazole

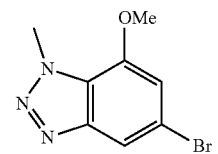

To a solution of 4-bromo-2-methoxy-N-methyl-6-nitroaniline (2.82 g, 10.80 mmol) dissolved in glacial acetic acid (100 ml, 1747 mmol) was added zinc (4.94 g, 76 mmol) and the reaction mixture was stirred at ambient temperature for 2 h 30 min. Zinc (150 mg, 2.294 mmol) was added to the mixture and the solution was stirred until the orange color disappeared (around 30 min). The mixture was filtered and the solid was washed with ethyl acetate, then the filtrate was concentrated. The crude product was dissolved in sulfuric acid (10%) (50 mL, 10.80 mmol), sodium nitrite was added (0.745 g, 10.80 mmol) in small portions at 0° C. and the mixture was stirred at 0° C. for 1 h, 45 min. water 100 mL) was added to quench the reaction and the precipitate product was collected by filtration, washed with water and dried under vacuum to afford the title compound 5-bromo-7-methoxy-1-methyl-1H-benzo[d][1,2,3]triazole (1.28 g, 49%). LC-MS m/z 241.9/243.9 (M+H)⁺, 0.83 min (ret. time).

(E)-ethyl 3-(7-methoxy-1-methyl-1H-benzo[d][1,2,3]triazol-5-yl)acrylate

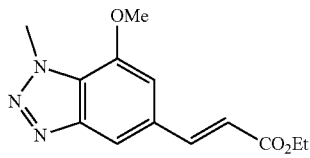 [SMILES: CCOC(=O)/C=C/c1cc(OC)c2c(c1)nnn2C]

To a solution of 5-bromo-7-methoxy-1-methyl-1H-benzo[d][1,2,3]triazole (974 mg, 4.02 mmol) dissolved into DMF (15 mL) was added DIPEA (2.108 mL, 12.07 mmol), ethyl acrylate (4.29 mL, 40.2 mmol), diacetoxypalladium (271 mg, 1.207 mmol) and tri-o-tolylphosphine (980 mg, 3.22 mmol) and the reaction mixture was put in microwave at 150° C. for 2 h. Water was added (50 mL) to quench the reaction. Ethyl acetate was added and the layers were separated. The aqueous layer was then extracted with ethyl acetate twice and the combined organic layer was dried with MgSO$_4$, concentrated then purified by silica gel chromatography to give of (E)-ethyl 3-(7-methoxy-1-methyl-1H-benzo[d][1,2,3]triazol-5-yl)acrylate (820 mg, 78%). LC-MS m/z 262 (M+H)$^+$, 0.90 min (ret. time).

3-(1-(tert-Butoxycarbonyl)-1,2,3,3a,4,8b-hexahydroindeno[1,2-b]pyrrol-7-yl)-3-(7-methoxy-1-methyl-1H-benzo[d][1,2,3]triazol-5-yl)propanoic Acid

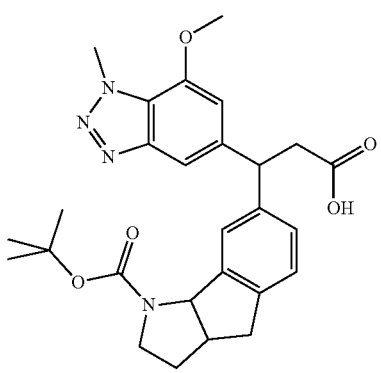 [SMILES: COc1cc(C(CC(=O)O)c2ccc3c(c2)C2C(CCN2C(=O)OC(C)(C)C)C3)cc2nnn(C)c12]

To a solution of tert-butyl 7-(4,4,5,5-tetramethyl-1,3,2-dioxaborolan-2-yl)-2,3,3a,4-tetrahydroindeno[1,2-b]pyrrole-1(8bH)-carboxylate (66.4 mg, 0.172 mmol) in 1,4-dioxane (2 mL) and water (0.7 mL) was added (E)-ethyl 3-(7-methoxy-1-methyl-1H-benzo[d][1,2,3]triazol-5-yl)acrylate (30 mg, 0.115 mmol), TEA (0.048 mL, 0.344 mmol) and [RhCl(cod)]$_2$ (2.83 mg, 5.74 µmol). The resulting reaction mixture was heated at 90° C. for 100 min. The reaction mixture was concentrated under reduced pressure and dissolved in methanol (2.000 mL) after which NaOH (3 N) (0.306 mL, 0.919 mmol) was added. The resulting reaction mixture was heated with microwave at 80° C. for 20 min. The reaction mixture was acidified with HCl (3 N) to pH 3-4 then concentrated under reduced pressure and purified with reverse phase HPLC to afford the desired product 3-(1-(tert-butoxycarbonyl)-1,2,3,3a,4,8b-hexahydroindeno[1,2-b]pyrrol-7-yl)-3-(7-methoxy-1-methyl-1H-benzo[d][1,2,3]triazol-5-yl)propanoic acid (35.8 mg, 0.073 mmol, 63.3% yield). LC-MS m/z 493.3 (M+H)$^+$, 1.00 min (ret. time).

Example 16

3-(1-(tert-Butoxycarbonyl)-1,2,3,3a,4,8b-hexahydroindeno[1,2-b]pyrrol-7-yl)-3-(1-ethyl-4-methyl-1H-benzo[d][1,2,3]triazol-5-yl)propanoic Acid

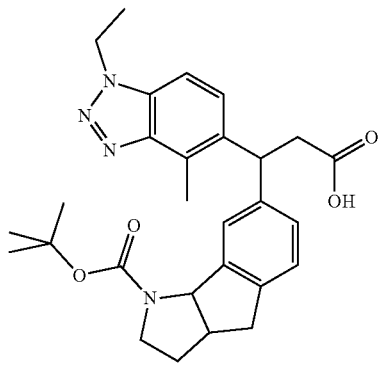 [SMILES: CCn1nnc2c(C)c(C(CC(=O)O)c3ccc4c(c3)C3C(CCN3C(=O)OC(C)(C)C)C4)ccc21]

To a solution of tert-butyl 7-(4,4,5,5-tetramethyl-1,3,2-dioxaborolan-2-yl)-2,3,3a,4-tetrahydroindeno[1,2-b]pyrrole-1(8bH)-carboxylate (66.9 mg, 0.174 mmol) in 1,4-dioxane (2 mL) and water (0.7 mL) was added (E)-ethyl 3-(1-ethyl-4-methyl-1H-benzo[d][1,2,3]triazol-5-yl)acrylate (30 mg, 0.116 mmol), TEA (0.048 mL, 0.347 mmol) and [RhCl(cod)]$_2$ (2.85 mg, 5.78 µmol). The resulting reaction mixture was heated at 90° C. for 100 min. The reaction mixture was concentrated under reduced pressure and dissolved in methanol (2.000 mL) after which NaOH (3 N) (0.309 mL, 0.926 mmol) was added. The resulting reaction mixture was heated with microwave at 80° C. for 20 min. The reaction mixture was acidified with HCl (3 N) to pH 3-4 then concentrated under reduced pressure and purified with reverse phase HPLC to afford the desired product 3-(1-(tert-butoxycarbonyl)-1,2,3,3a,4,8b-hexahydroindeno[1,2-b]pyrrol-7-yl)-3-(1-ethyl-4-methyl-1H-benzo[d][1,2,3]triazol-5-yl)propanoic acid (25.3 mg, 0.052 mmol, 44.6% yield). LC-MS m/z 435.3 (M+H)$^+$, 1.02 min (ret. time).

Example 17

3-(1-(tert-Butoxycarbonyl)-1,2,3,3a,4,8b-hexahydroindeno[1,2-b]pyrrol-7-yl)-5-(1-ethyl-1H-1,2,3-triazol-4-yl)pentanoic Acid

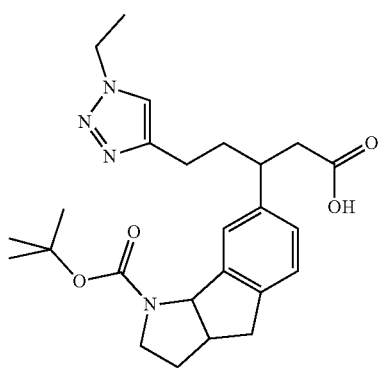 [SMILES: CCn1cc(CCC(CC(=O)O)c2ccc3c(c2)C2C(CCN2C(=O)OC(C)(C)C)C3)nn1]

To a solution of tert-butyl 7-(4,4,5,5-tetramethyl-1,3,2-dioxaborolan-2-yl)-2,3,3a,4-tetrahydroindeno[1,2-b]pyrrole-1(8bH)-carboxylate (78 mg, 0.202 mmol) in 1,4-dioxane (2 mL) and water (0.7 mL) was added (E)-ethyl 5-(1-ethyl-1H-1,2,3-triazol-4-yl)pent-2-enoate (30 mg, 0.134 mmol), TEA (0.056 mL, 0.403 mmol) and [RhCl(cod)]$_2$ (3.31 mg, 6.72 pmol). The resulting reaction mixture was heated at 90° C. for 100 min. The reaction mixture was concentrated under reduced pressure and dissolved in methanol (2.000 mL) after which NaOH (3 N) (0.358 mL, 1.075 mmol) was added. The resulting reaction mixture was heated with microwave at 80° C. for 20 min. The reaction mixture was acidified with HCl (3 N) to pH 3-4 then concentrated under reduced pressure and purified with reverse phase HPLC to afford the desired product 3-(1-(tert-butoxycarbonyl)-1,2,3,3a,4,8b-hexahydroindeno[1,2-b]pyrrol-7-yl)-5-(1-ethyl-1H-1,2,3-triazol-4-yl)pentanoic acid (32.4 mg, 0.071 mmol, 53.0% yield). LC-MS m/z 455.2 (M+H)$^+$, 0.94 min (ret. time).

Example 18

3-(1-(tert-Butoxycarbonyl)-1,2,3,3a,4,8b-hexahydroindeno[1,2-b]pyrrol-7-yl)-3-(7-methoxy-1,4-dimethyl-1H-benzo[d][1,2,3]triazol-5-yl)propanoic Acid

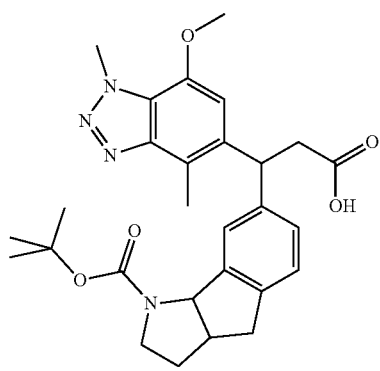 [SMILES: COc1cc(C(CC(=O)O)c2ccc3c(c2)C2C(CCN2C(=O)OC(C)(C)C)C3)c(C)c2nnn(C)c12]

To a solution of tert-butyl 7-(4,4,5,5-tetramethyl-1,3,2-dioxaborolan-2-yl)-2,3,3a,4-tetrahydroindeno[1,2-b]pyrrole-1(8bH)-carboxylate (66.4 mg, 0.172 mmol) in 1,4-dioxane (2 mL) and water (0.7 mL) was added (E)-methyl 3-(7-methoxy-1,4-dimethyl-1H-benzo[d][1,2,3]triazol-5-yl)acrylate (30 mg, 0.115 mmol), TEA (0.048 mL, 0.344 mmol) and [RhCl(cod)]$_2$ (2.83 mg, 5.74 µmol). The resulting reaction mixture was heated at 90° C. for 66 h. The reaction mixture was concentrated under reduced pressure and dissolved in methanol (2.000 mL) after which NaOH (3 N) (0.306 mL, 0.919 mmol) was added. The resulting reaction mixture was heated with microwave at 80° C. for 20 min. The reaction mixture was acidified with HCl (3 N) to pH 3-4 then concentrated under reduced pressure, and purified with reverse phase HPLC to afford the desired product 3-(1-(tert-butoxycarbonyl)-1,2,3,3a,4,8b-hexahydroindeno[1,2-b]pyrrol-7-yl)-3-(7-methoxy-1,4-dimethyl-1H-benzo[d][1,2,3]triazol-5-yl)propanoic acid (35.9 mg, 0.071 mmol, 61.7% yield). LC-MS m/z 507.2 (M+H)$^+$, 1.01 min (ret. time).

Example 19

3-(1-(Cyclohexylmethyl)-2-oxo-2,3,3a,4,5,9b-hexahydro-1H-benzo[g]indol-8-yl)-3-(1,4-dimethyl-1H-benzo[d][1,2,3]triazol-5-yl)propanoic Acid

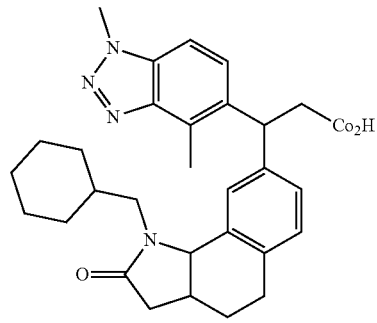

Ethyl 2-(7-bromo-1-oxo-1,2,3,4-tetrahydronaphthalen-2-yl)acetate

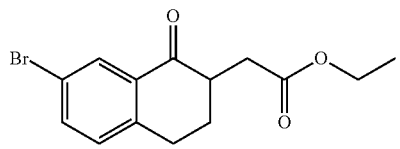 [SMILES: CCOC(=O)CC1CCc2ccc(Br)cc2C1=O]

LiHMDS (1.0 M in THF) (11.00 mL, 11.00 mmol) was added to a solution of 7-bromo-3,4-dihydronaphthalen-1(2H)-one (2.251 g, 10 mmol) in THF (10 mL) slowly (over 10 min) at −78° C. The resulting reaction mixture was allowed to warm to 0° C. and stirred at this temperature for 30 min, then cooled to −78° C. To this reaction mixture was added ethyl 2-bromoacetate (1.391 mL, 11.00 mmol) in THF (2 mL) slowly at −78° C. The resulting mixture was stirred at −78° C. for 1 h then warmed to ambient temperature and stirred for 18 h. The reaction mixture was quenched with 10 mL of saturated solution of NH$_4$Cl and diluted with H$_2$O (10 mL). The mixture was extracted with EtOAc (3×30 mL). The combined organic layer was washed with brine (30 mL), dried over MgSO$_4$, filtered, concentrated under reduced pressure, and purified via silica gel chromatography to afford the title compound (1.6881 g, 2.170 mmol, 21.70% yield) as a colorless oil. LC-MS m/z 310.9 (M+H)$^+$, 1.09 min (ret. time).

2-(7-Bromo-1-oxo-1,2,3,4-tetrahydronaphthalen-2-yl)acetic Acid

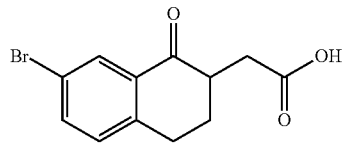

To a solution of ethyl 2-(7-bromo-1-oxo-1,2,3,4-tetrahydronaphthalen-2-yl)acetate (1.6881 g, 5.42 mmol) in methanol (5 mL) was added 10 mL of 2M NaOH (20.0 mmol). The resulting solution was heated via microwave irradiation at 80° C. for 30 min. The reaction mixture was acidified with HCl (1 N) to pH~5 and extracted with EtOAc (3×40 mL). The combined organic phase was concentrated under reduced pressure to afford the title compound 2-(7-bromo-1-oxo-1,2,3,4-tetrahydronaphthalen-2-yl)acetic acid (1.4661 g, 3.26 mmol, 60.1% yield) as a solid. LC-MS m/z 282.9 (M+H)$^+$, 0.86 min (ret. time).

2-(7-Bromo-1-oxo-1,2,3,4-tetrahydronaphthalen-2-yl)-N-(cyclohexyl methyl)acetamide

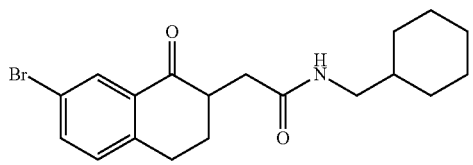 [SMILES: O=C(CC1CCc2ccc(Br)cc2C1=O)NCC1CCCCC1]

To a solution of 2-(7-bromo-1-oxo-1,2,3,4-tetrahydronaphthalen-2-yl)acetic acid (0.400 g, 1.413 mmol) in DCM (3 mL) were added TEA (0.788 ml, 5.65 mmol), T3P (50% wt in EtOAc) (1.682 ml, 2.826 mmol) and cyclohexylmethanamine (0.552 ml, 4.245 mmol). The resulting mixture was stirred at ambient temperature for 3 h. The reaction mixture was concentrated under reduced pressure and purified via silica gel chromatography to afford the title compound (0.2483 g, 0.446 mmol, 31.6% yield) as a solid. LC-MS m/z 378.1 (M+H)$^+$, 1.14 min (ret. time).

8-Bromo-1-(cyclohexyl methyl)-3,3a,4,5-tetrahydro-1H-benzo[g]indol-2(9bH)-one

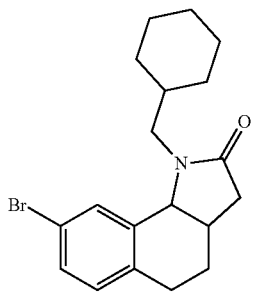

To a solution of 2-(7-bromo-1-oxo-1,2,3,4-tetrahydronaphthalen-2-yl)-N-(cyclohexylmethyl)acetamide (0.2483 g, 0.656 mmol) in acetonitrile (8 mL) was added triethylsilane (0.524 ml, 3.28 mmol) and TFA (0.152 ml, 1.969 mmol). The resulting solution was heated via microwave irradiation at 100° C. for 2 h. The reaction mixture was concentrated under reduced pressure, and purified via silica gel chromatography to afford the title compound (0.1449 g, 0.400 mmol, 60.9% yield) as a colorless oil. LC-MS m/z 362.0 (M+H)$^+$, 1.24 min (ret. time).

1-(Cyclohexylmethyl)-8-(4,4,5,5-tetramethyl-1,3,2-dioxaborolan-2-yl)-3,3a,4,5-tetrahydro-1H-benzo[g]indol-2(9bH)-one

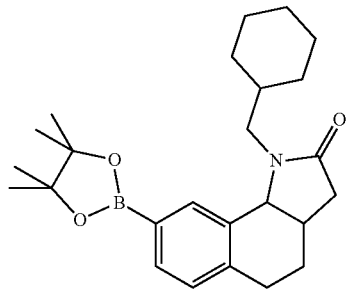 [SMILES: CC1(C)OB(c2ccc3c(c2)C2C(CC3)CC(=O)N2CC2CCCCC2)OC1(C)C]

To a solution of 8-bromo-1-(cyclohexylmethyl)-3,3a,4,5-tetrahydro-1H-benzo[g]indol-2(9bH)-one (0.1449 g, 0.400 mmol) in N,N-dimethylformamide (2 mL) was added bis(pinacolato)diboron (0.152 g, 0.600 mmol), KOAc (0.079 g, 0.800 mmol) and PdCl$_2$(dppf) (0.015 g, 0.020 mmol). The resulting solution was heated via microwave irradiation at 100° C. for 1 h. The reaction mixture was concentrated under reduced pressure, and purified via silica gel chromatography to afford the title compound (0.1287 g, 0.314 mmol, 79% yield) as an oil. LC-MS m/z 410.3 (M+H)$^+$, 1.32 min (ret. time).

3-(1-(Cyclohexylmethyl)-2-oxo-2,3,3a,4,5,9b-hexahydro-1H-benzo[g]indol-8-yl)-3-(1,4-dimethyl-1H-benzo[d][1,2,3]triazol-5-yl)propanoic Acid

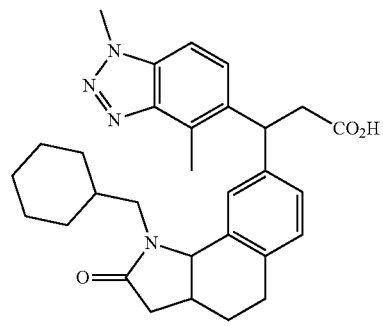 [SMILES: Cc1c(C(CC(=O)O)c2ccc3c(c2)C2C(CC3)CC(=O)N2CC2CCCCC2)ccc2c1nnn2C]

To a solution of (E)-ethyl 3-(1,4-dimethyl-1H-benzo[d][1,2,3]triazol-5-yl)acrylate (0.049 g, 0.2 mmol) in 1,4-dioxane (1.5 mL) and water (0.5 mL) was added 1-(cyclohexylmethyl)-8-(4,4,5,5-tetramethyl-1,3,2-dioxaborolan-2-yl)-3,3a,4,5-tetrahydro-1H-benzo[g]indol-2(9bH)-one (0.1287 g, 0.314 mmol), TEA (0.084 ml, 0.600 mmol) and [Rh(cod)Cl]$_2$ (4.93 mg, 10.00 µmol). The resulting solution was stirred at 90° C. for 5 h. The reaction mixture was concentrated under reduced pressure, and purified via silica gel chromatography to afford the intermediate ethyl 3-(1-(cyclohexylmethyl)-2-oxo-2,3,3a,4,5,9b-hexahydro-1H-benzo[g]indol-8-yl)-3-(1,4-dimethyl-1H-benzo[d][1,2,3]triazol-5-yl)propanoate. This intermediate was re-dissolved in methanol (2 mL). To the resulting solution was added 2M NaOH (0.5 mL, 1.000 mmol). After being heated via microwave irradiation at 80° C. for 30 min, the reaction mixture was acidified with HCl (1 N) to pH~5, concentrated under reduced pressure and purified with preparative HPLC to afford the title compound (20 mg, 0.040 mmol, 19.97% yield) as a white solid. LC-MS m/z 501.3 (M+H)+, 0.90 min (ret. time). ¹H NMR (400 MHz, chloroform-d) δ=0.53-0.74 (m, 2H), 0.89-1.33 (m, 6H), 1.44-1.60 (m, 3H), 1.73 (br. s., 2H), 2.19-2.96 (m, 10H), 3.05-3.23 (m, 3H), 4.27 (d, J=2.76 Hz, 3H), 4.58 (t, J=7.78 Hz, 1H), 4.95-5.07 (m, 1H), 6.94-7.06 (m, 1H), 7.12 (dd, J=13.30, 7.78 Hz, 1H), 7.21 (dd, J=19.07, 7.78 Hz, 1H), 7.31 (s, 1H), 7.33-7.45 (m, 1H).

Example 20

3-(3-(Cyclohexylmethyl)-2-oxo-3,3a,8,8a-tetrahydro-2H-indeno[1,2-d]oxazol-5-yl)-3-(1,4-dimethyl-1H-benzo[d][1,2,3]triazol-5-yl)propanoic Acid

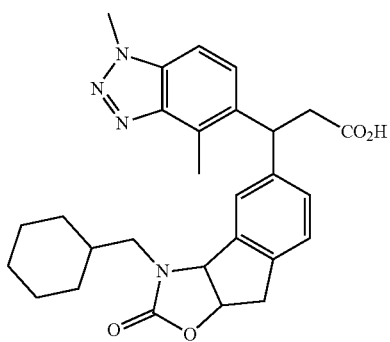 [SMILES: Cc1c(C(CC(=O)O)c2ccc3c(c2)C2C(C3)OC(=O)N2CC2CCCCC2)ccc2c1nnn2C]

6-Bromo-1,1-dimethoxy-2,3-dihydro-1H-inden-2-ol

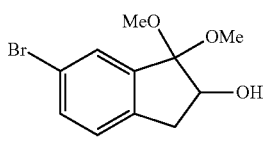

A solution of 6-bromo-2,3-dihydro-1H-inden-1-one (1.055 g, 5 mmol) and KOH (3.09 g, 55.0 mmol) in methanol (25 mL) was stirred for 10 min at 0° C. after which time (diacetoxyiodo) benzene (1.933 g, 6.00 mmol) was added. The resulting solution was stirred at 0° C. for 1 h and at ambient temperature for 2 h. The reaction mixture was then concentrated under reduced pressure and purified via silica gel chromatography to afford the title compound (0.7734 g, 2.61 mmol, 52.1% yield) as a dark red gum. LC-MS m/z 273.0 (M+H)+, 0.84 min (ret. time).

6-Bromo-1-oxo-2,3-dihydro-1H-inden-2-yl (cyclohexylmethyl)carbamate

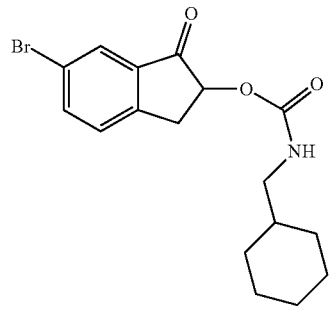 [SMILES: O=C(NCC1CCCCC1)OC1Cc2ccc(Br)cc2C1=O]

To a solution of 6-bromo-1,1-dimethoxy-2,3-dihydro-1H-inden-2-ol (0.3385 g, 1.239 mmol) and DMAP (0.227 g, 1.859 mmol) in toluene (12 mL) was added (isocyanatomethyl)cyclohexane (0.443 mL, 3.10 mmol) dropwise. The resulting solution was heated via microwave irradiation at 100° C. for 5 h. The reaction mixture was concentrated under reduced pressure to afford the crude intermediate 6-bromo-1,1-dimethoxy-2,3-dihydro-1H-inden-2-yl (cyclohexylmethyl)carbamate. The crude intermediate was redissolved in 10 mL of 10% solution of HCl. The resulting mixture was stirred at ambient temperature for 3 h. The reaction mixture was concentrated under reduced pressure and purified via silica gel chromatography to afford the title compound (0.5234 g, 1.429 mmol, 115% yield) as a white solid. LC-MS m/z 366.0 (M+H)+, 1.17 min (ret. time).

5-Bromo-3-(cyclohexylmethyl)-3,3a,8,8a-tetrahydro-2H-indeno[1,2-d]oxazol-2-one

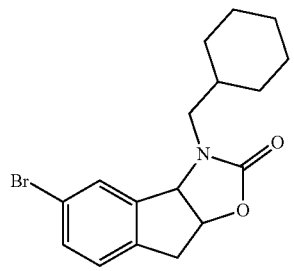 [SMILES: O=C1OC2Cc3ccc(Br)cc3C2N1CC1CCCCC1]

To a solution of 6-bromo-1-oxo-2,3-dihydro-1H-inden-2-yl (cyclohexylmethyl)carbamate (0.5234 g, 1.429 mmol) in acetonitrile (12 mL) were added triethylsilane (2.283 ml, 14.29 mmol) and TFA (0.330 ml, 4.29 mmol). The resulting solution was heated via microwave irradiation at 120° C. for 4 h. The reaction mixture was concentrated under reduced pressure and purified via silica gel chromatography to afford the title compound (0.3618 g, 1.033 mmol, 72.3% yield) as a colorless oil. LC-MS m/z 349.9 (M+H)+, 1.16 min (ret. time).

3-(Cyclohexylmethyl)-5-(4,4,5,5-tetramethyl-1,3,2-dioxaborolan-2-yl)-3,3a,8,8a-tetrahydro-2H-indeno[1,2-d]oxazol-2-one

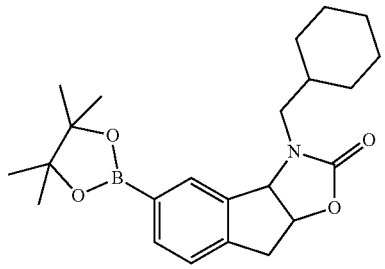 [SMILES: CC1(C)OB(c2ccc3c(c2)C2C(C3)OC(=O)N2CC2CCCCC2)OC1(C)C]

To a solution of 5-bromo-3-(cyclohexylmethyl)-3,3a,8,8a-tetrahydro-2H-indeno[1,2-d]oxazol-2-one (0.3618 g, 1.033 mmol) in N,N-dimethylformamide (5 mL) was added bis(pinacolato)diboron (0.393 g, 1.549 mmol), KOAc (0.203 g, 2.066 mmol) and PdCl$_2$(dppf) (0.038 g, 0.052 mmol). The resulting solution was heated via microwave irradiation at 100° C. for 1 h. The reaction mixture was concentrated under reduced pressure, and purified via silica gel chromatography to afford the title compound (0.298 g, 0.750 mmol, 72.6% yield) as a colorless oil. LC-MS m/z 398.2 (M+H)$^+$, 1.30 min (ret. time). 3-(3-(Cyclohexylmethyl)-2-oxo-3,3a,8,8a-tetrahydro-2H-indeno[1,2-d]oxazol-5-yl)-3-(1,4-dimethyl-1H-benzo[d][1,2,3]triazol-5-yl)propanoic acid

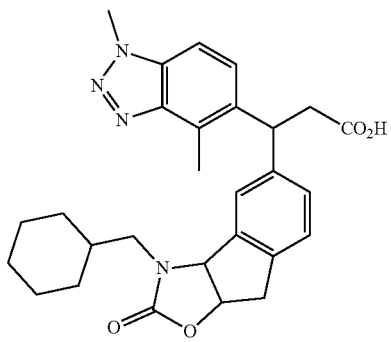 [SMILES: Cc1c(C(CC(=O)O)c2ccc3c(c2)C2C(C3)OC(=O)N2CC2CCCCC2)ccc2c1nnn2C]

To a solution of (E)-ethyl 3-(1,4-dimethyl-1H-benzo[d][1,2,3]triazol-5-yl)acrylate (0.120 g, 0.489 mmol) in 1,4-dioxane (3 mL) and water (1 mL) were added 3-(cyclohexylmethyl)-5-(4,4,5,5-tetramethyl-1,3,2-dioxaborolan-2-yl)-3,3a,8,8a-tetrahydro-2H-indeno[1,2-d]oxazol-2-one (0.298 g, 0.750 mmol), TEA (0.205 ml, 1.468 mmol) and [Rh(cod)Cl]$_2$ (0.012 g, 0.024 mmol). The resulting solution was stirred at 90° C. for 3 h. The reaction mixture was concentrated under reduced pressure, and purified via silica gel chromatography to afford the intermediate ethyl 3-(3-(cyclohexylmethyl)-2-oxo-3,3a, 8,8a-tetrahydro-2H-indeno[1,2-d]oxazol-5-yl)-3-(1,4-dimethyl-1H-benzo[d][1,2,3]triazol-5-yl)propanoate. This intermediate was dissolved in methanol (4 mL) after which time 1.0 mL of a 2M solution of NaOH (2.00 mmol) was added. After being heated via microwave irradiation at 80° C. for 30 min, the reaction mixture was acidified with HCl (1 N) to pH~5, concentrated under reduced pressure, and purified with preparative HPLC to afford the title compound (58.1 mg, 0.119 mmol, 24.31% yield) as a solid. LC-MS m/z 489.2 (M+H)$^+$, 0.90 min (ret. time). $^1$H NMR (400 MHz, chloroform-d) b=0.90 (q, J=11.80 Hz, 2H), 1.09-1.27 (m, 3H), 1.48 (d, J=12.55 Hz, 1H), 1.61-1.76 (m, 5H), 2.76-2.87 (m, 4H), 3.03-3.29 (m, 4H), 3.34-3.46 (m, 1H), 4.23-4.30 (m, 3H), 4.96-5.07 (m, 2H), 5.29 (td, J=7.47, 2.64 Hz, 1H), 7.03-7.15 (m, 1H), 7.18-7.28 (m, 2H), 7.29-7.42 (m, 2H).

Example 21

3-(3-(7-Chloro-2,2-dimethyl-2,3-dihydrobenzo[f][1,4]oxazepin-4(5H)-yl)-2,3-dihydro-1H-inden-5-yl)-3-(1,4-dimethyl-1H-benzo[d][1,2,3]triazol-5-yl)propanoic Acid, Formic Acid Salt

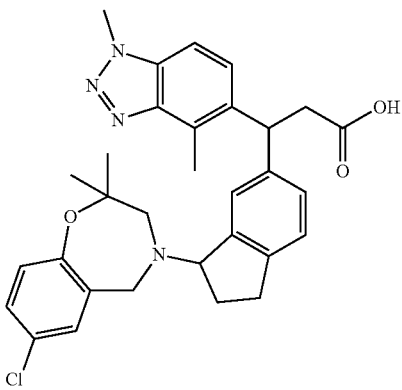 [SMILES: Cc1c(C(CC(=O)O)c2ccc3c(c2)C(N2Cc4cc(Cl)ccc4OC(C)(C)C2)CC3)ccc2c1nnn2C]

1,6-Dibromo-2,3-dihydro-1H-indene

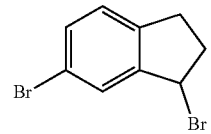

To a solution of 6-bromo-2,3-dihydro-1H-inden-1-ol (3 g, 14.08 mmol) in DCM (30 mL) was added PBr$_3$ (1.726 mL, 18.30 mmol) at 0° C. The reaction was stirred at ambient temperature for 30 min. The reaction mixture was then cooled to 0° C., quenched with saturated NaHCO$_3$, extracted with DCM (2×). The combined organics were washed with a brine solution, the organic layer was dried over anhydrous Na$_2$SO$_4$ and filtered. The filtrate was evaporated under reduced pressure to afford the title compound (3 g, 77% yield). $^1$H NMR (400 MHz, CDCl$_3$) b ppm=7.55 (d, J=1.5

Hz, 1H), 7.36 (dd, J=1.8, 8.1 Hz, 1H), 7.12 (d, J=7.9 Hz, 1H), 5.48 (dd, J=2.4, 6.6 Hz, 1H), 3.12 (td, J=7.8, 16.0 Hz, 1H), 2.83 (ddd, J=2.7, 7.7, 16.1 Hz, 1H), 2.67-2.45 (m, 2H).

1-((2-Bromo-5-chlorobenzyl)amino)-2-methylpropan-2-ol

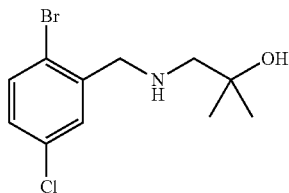

To a solution of 2-bromo-5-chlorobenzaldehyde (1 g, 4.56 mmol) in methanol (20 mL) was added 1-amino-2-methylpropan-2-ol (0.406 g, 4.56 mmol) and 1 N NaOH (0.5 mL, 0.500 mmol) under nitrogen atmosphere. NaBH$_4$ (0.345 g, 9.11 mmol) was added portion wise over 10 min at 0° C. and stirred at ambient temperature for 72 h. The reaction mixture was evaporated under reduced pressure before was purified with flash chromatography to afford 1-((2-bromo-5-chlorobenzyl)amino)-2-methylpropan-2-ol (1 g, 3.39 mmol, 74.4% yield). LC-MS m/z 291.9 (M+H)$^+$, 1.62 min (ret. time).

7-Chloro-2,2-dimethyl-2,3,4,5-tetrahydrobenzo[f][1,4]ioxazepine

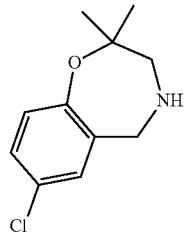

To a solution of 1-((2-bromo-5-chlorobenzyl)amino)-2-methylpropan-2-ol (500 mg, 1.709 mmol) in isopropanol (8 mL) was added Cs$_2$CO3 (472 mg, 3.42 mmol) and copper(l) iodide (32.5 mg, 0.171 mmol) and the reaction mixture was stirred at 130° C. in microwave reactor for 1 hr. The reaction mixture was quenched with water, extracted twice with EtOAc and washed with brine. The organic layer was dried with anhydrous Na$_2$SO$_4$ and filtered. The filtrate was concentrated and purified by flash chromatography to afford desired product 7-chloro-2,2-dimethyl-2,3,4,5-tetrahydrobenzo[f][1,4]oxazepine (450 mg, 1.213 mmol, 71.0% yield). LC-MS m/z 212.0 (M+H)$^+$, 3.49 min (ret. time).

The compounds in the following Table 2 were prepared by a method similar to the one described for the preparation of 7-chloro-2,2-dimethyl-2,3,4,5-tetrahydrobenzo[f][1,4]oxazepine. As is appreciated by those skilled in the art, these analogous examples may involve variations in general reaction conditions.

TABLE 2

| Reagent | Product Name | Product Structure | (M + H)$^+$ | Ret. Time (min) |
|---|---|---|---|---|
| | (S)-2-Methyl-2,3,4,5-tetrahydrobenzo[f][1,4]oxazepine | | 164.1 | 0.49 |
| | 2,2-Dimethyl-2,3,4,5-tetrahydrobenzo[f][1,4]oxazepine | | 178.19 | 2.72 |
| | (R)-2-Ethyl-2,3,4,5-tetrahydropyrido[3,4-f][1,4]oxazepine | | 179.0 | 2.78 |
| | (R)-2-Ethyl-2,3,4,5-tetrahydrobenzo[f][1,4]oxazepine hydrochloride | | 178.1 | 1.563 |

TABLE 2-continued

| Reagent | Product Name | Product Structure | (M + H)+ | Ret. Time (min) |
|---|---|---|---|---|
| 2-bromo-5-methoxybenzaldehyde | 7-Methoxy-2,2-dimethyl-2,3,4,5-tetrahydrobenzo[f][1,4]oxazepine | | 208.1 | 3.17 |
| 2-bromo-5-chlorobenzaldehyde | 7-Chloro-2,2-dimethyl-2,3,4,5-tetrahydrobenzo[f][1,4]oxazepine | | 212.0 | 3.49 |
| 2-bromo-5-methylbenzaldehyde | 2,2,8-Trimethyl-2,3,4,5-tetrahydrobenzo[f][1,4]oxazepine | | 192.20 | 1.36 |
| 2-bromo-5-fluorobenzaldehyde | 7-Fluoro-2,2-dimethyl-2,3,4,5-tetrahydrobenzo[f][1,4]oxazepine | | 196.11 | 1.22 |
| 2,5-dibromobenzaldehyde | 7-Bromo-2,2-dimethyl-2,3,4,5-tetrahydrobenzo[f][1,4]oxazepine | | 256.07 | 1.45 |
| 2,4-dibromobenzaldehyde | 8-Bromo-2,2-dimethyl-2,3,4,5-tetrahydrobenzo[f][1,4]oxazepine | | 256.15 | 1.52 |
| 4-bromonicotinaldehyde | 2,2-Dimethyl-2,3,4,5-tetrahydropyrido[3,4-f][1,4]oxazepine hydrochloride | | 179.0 | 2.7 |
| 2-bromobenzaldehyde | (R)-2-Methyl-2,3,4,5-tetrahydrobenzo[f][1,4]oxazepine hydrochloride | | 164.23 | 2.36 |
| 3-bromoisonicotinaldehyde | 2,2-dimethyl-2,3,4,5-tetrahydropyrido[4,3-f][1,4]oxazepine | | 179.0 | 3.33 |

4-(6-Bromo-2,3-dihydro-1H-inden-1-yl)-7-chloro-2,2-dimethyl-2,3,4,5-tetrahydrobenzo[f][1,4]oxazepine

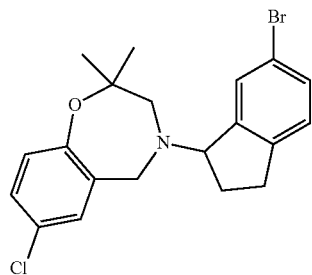 [SMILES: CC1(C)CN(C2CCc3ccc(Br)cc32)Cc2cc(Cl)ccc2O1]

To a solution of 1,6-dibromo-2,3-dihydro-1H-indene (500 mg, 1.812 mmol), and 7-chloro-2,2-dimethyl-2,3,4,5-tetrahydrobenzo[f][1,4]oxazepine (384 mg, 1.812 mmol) was added DIPEA (0.633 mL, 3.62 mmol) at ambient temperature. The reaction mixture was stirred in a microwave reactor at 90° C. for 1 h. The reaction mixture was cooled to 0° C., quenched with cold water, and extracted with EtOAc (2×). The combined organics were washed with a brine solution and the organic layer was dried over anhydrous Na$_2$SO$_4$ and filtered. The filtrate was evaporated under reduced pressure and the crude residue was purified by flash chromatography eluting with EtOAc:Hexane (4:96) to afford the title compound (500 mg, 67.8% yield). $^1$H NMR (400 MHz, CDCl$_3$) b ppm=7.39 (s, 1H), 7.34 (br d, J=7.9 Hz, 1H), 7.12-7.07 (m, 2H), 6.94 (d, J=2.4 Hz, 1H), 6.84 (d, J=8.3 Hz, 1H), 4.48 (br t, J=7.9 Hz, 1H), 3.58 (s, 2H), 2.94-2.86 (m, 1H), 2.81-2.67 (m, 3H), 2.22-2.12 (m, 1H), 2.04 (qd, J=8.8, 12.9 Hz, 1H), 1.24 (d, J=5.7 Hz, 6H).

7-Chloro-2,2-dimethyl-4-(6-(4,4,5,5-tetramethyl-1,3,2-dioxaborolan-2-yl)-2,3-dihydro-1H-inden-1-yl)-2,3,4,5-tetrahydrobenzo[f][1,4]oxazepine

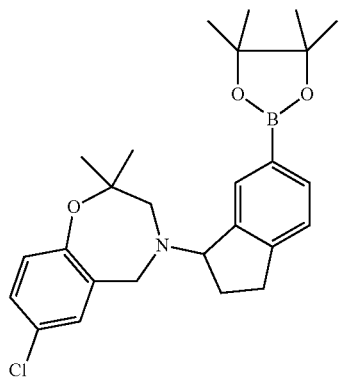 [SMILES: CC1(C)CN(C2CCc3ccc(B4OC(C)(C)C(C)(C)O4)cc32)Cc2cc(Cl)ccc2O1]

To a solution of 4-(6-bromo-2,3-dihydro-1H-inden-1-yl)-7-chloro-2,2-dimethyl-2,3,4,5-tetrahydrobenzo[f][1,4]oxazepine (500 mg, 1.229 mmol) in 1,4-dioxane (10 mL) was added bis(pinacolato)diboron (375 mg, 1.475 mmol) and potassium acetate (241 mg, 2.459 mmol). The reaction mixture was degassed with argon for 10 min then PdCl$_2$(dppf)-CH$_2$Cl$_2$ adduct (50.2 mg, 0.061 mmol) was added and the reaction mixture was heated to 90° C. for 16 h. The reaction mixture was cooled to 0° C., quenched with cold water, and extracted with EtOAc (2×). The combined organics were washed with a brine solution and the organic layer was dried over anhydrous Na$_2$SO$_4$ and filtered. The filtrate was evaporated under reduced pressure and the crude residue was purified by flash chromatography eluting with EtOAc:Hexane (5:95) to afford the title compound (350 mg, 62.7% yield). $^1$H NMR (400 MHz, CDCl3) δ ppm 7.73 (s, 1H), 7.68 (d, J=7.5 Hz, 1H), 7.15 (br dd, J=7.2, 19.3 Hz, 1H), 7.08 (dd, J=2.5, 8.4 Hz, 1H), 6.93 (d, J=2.4 Hz, 1H), 6.83 (d, J=8.3 Hz, 1H), 4.50 (br t, J=7.7 Hz, 1H), 3.65-3.54 (m, 2H), 3.00-2.91 (m, 1H), 2.88-2.71 (m, 2H), 2.21-2.12 (m, 1H), 2.06-1.96 (m, 2H), 1.35-1.27 (m, 12H), 1.24 (d, J=11.0 Hz, 6H).

Ethyl 3-(3-(7-chloro-2,2-dimethyl-2,3-dihydrobenzo[f][1,4]oxazepin-4(5H)-yl)-2,3-dihydro-1H-inden-5-yl)-3-(1,4-dimethyl-1H-benzo[d][1,2,3]triazol-5-yl)propanoate

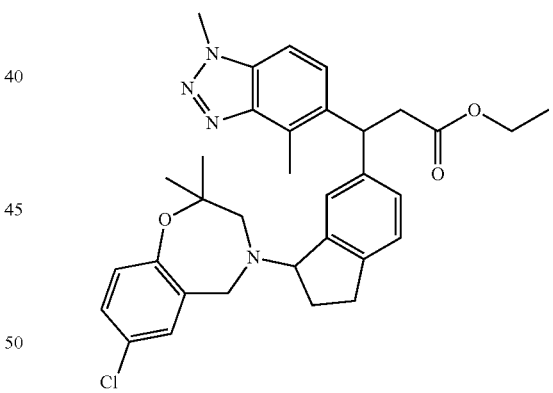

To solution of (E)-ethyl 3-(1,4-dimethyl-1H-benzo[d][1,2,3]triazol-5-yl)acrylate (200 mg, 0.815 mmol) in mixture of 1,4-dioxane (4 mL) and water 4 mL) in a sealed tube was added TEA (0.334 mL, 2.446 mmol). The reaction was degassed with nitrogen for 20 min, followed by the addition of chloro(1,5-cyclooctadiene)rhodium(l) dimer (40.2 mg, 0.082 mmol). The reaction mixture was stirred at 90° C. for 4 h. The reaction mixture was quenched with cold water and extracted with EtOAc (2×). The combined organics were washed with a brine solution and the organic layer was dried over anhydrous Na$_2$SO$_4$ and filtered. The filtrate was evaporated under reduced pressure to afford the title compound (250 mg, 53.5% yield). LC-MS m/z 573 (M+H)$^+$, 4.52 min (ret. time).

3-(3-(7-Chloro-2,2-dimethyl-2,3-di hydrobenzo[f][1,4]oxazepin-4(5H)-yl)-2,3-dihydro-1H-inden-5-yl)-3-(1,4-dimethyl-1H-benzo[d][1,2,3]triazol-5-yl)propanoic Acid, Formic Acid Salt

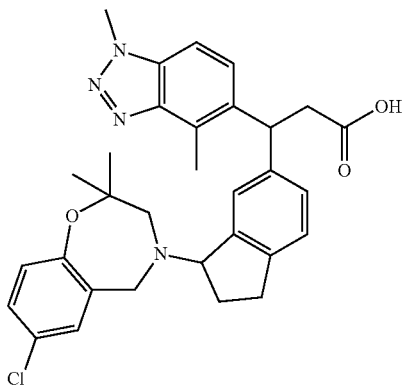 [SMILES: Cc1c(C(CC(=O)O)c2ccc3c(c2)C(N2Cc4cc(Cl)ccc4OC(C)(C)C2)CC3)ccc2c1nnn2C]

To a solution of ethyl 3-(3-(7-chloro-2,2-dimethyl-2,3-dihydrobenzo[f][1,4]oxazepin-4(5H)-yl)-2,3-dihydro-1H-inden-5-yl)-3-(1,4-dimethyl-1H-benzo[d][1,2,3]triazol-5-yl)propanoate (250 mg, 0.436 mmol) in ethanol (10 mL) was added 10% NaOH (10 mL, 0.436 mmol) at 0° C. The reaction was stirred at ambient temperature for 16 h. The reaction mixture was evaporated under reduced pressure, neutralized with 2N HCl, and extracted with DCM (2×). The combined organcis were washed with a brine solution and the organic layer was dried over anhydrous $Na_2SO_4$ and filtered. The filtrate was evaporated and purified by preparative HPLC to afford the title compound (23 mg, 9.56% yield). LC-MS m/z 545 (M+H)$^+$, 3.27 min (ret. time).

Example 22

3-(1,4-Dimethyl-1H-benzo[d][1,2,3]triazol-5-yl)-3-(3-(2,2,7-trimethyl-2,3-dihydrobenzo[f][1,4]oxazepin-4(5H)-yl)-2,3-dihydro-1H-inden-5-yl)propanoic Acid

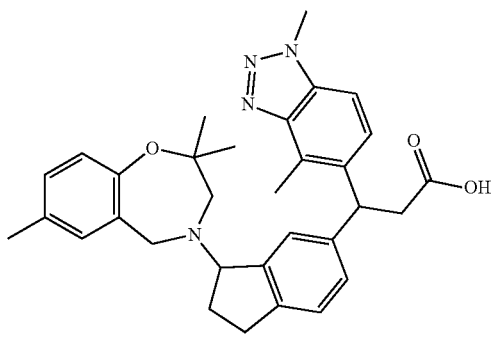 [SMILES: Cc1ccc2c(c1)CN(C1CCc3ccc(C(CC(=O)O)c4ccc5c(nnn5C)c4C)cc31)CC(C)(C)O2]

1-((2-Bromo-5-methylbenzyl)amino)-2-methylpropan-2-ol

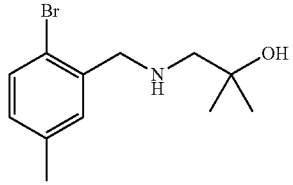

To a solution of 2-bromo-5-methylbenzaldehyde (2 g, 10.05 mmol) in methanol (5 mL) was added 1-amino-2-methylpropan-2-ol (0.896 g, 10.05 mmol) and NaOH (1.005 mL, 1.005 mmol). The resulting reaction mixture was stirred under nitrogen atmosphere for 1 hr then was added NaBH$_4$ (0.266 g, 7.03 mmol) slowly and the reaction stirred at ambient temperature for 72 hr. The reaction was evaporated down under vacuum, diluted with water (30 mL) and extracted with DCM (2×20 mL). The combined organic layer was washed with brine (20 mL), dried over $Na_2SO_4$, filtered and evaporated down under vacuum to afford desired product 1-((2-bromo-5-methylbenzyl)amino)-2-methylpropan-2-ol (2.4 g, 5.84 mmol, 58.2% yield). LC-MS m/z 272.2 (M+H)$^+$, 1.28 min (ret. time).

2,2,7-Trimethyl-2,3,4,5-tetrahydrobenzo[f][1,4]oxazepine

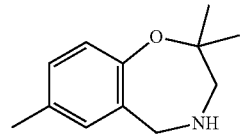

To a solution of 1-((2-bromo-5-methylbenzyl)amino)-2-methylpropan-2-ol (1.2 g, 4.41 mmol) in isopropanol (10 mL) was added Cs$_2$C03 (2.011 g, 6.17 mmol) and copper(l) iodide (0.084 g, 0.441 mmol) and the reaction mixture was stirred at 130° C. in microwave reactor for 1 hr. The reaction mixture was filtered and the filter cake was washed with isopropanol (10 mL). The combined filtrate was concentrated under vacuum before was purified on flash chromatography to afford desired product 2,2,7-trimethyl-2,3,4,5-tetrahydrobenzo[f][1,4]oxazepine (500 mg, 1.354 mmol, 30.7% yield). LC-MS m/z 192.1 (M+H)$^+$, 3.39 min (ret. time).

4-(6-Bromo-2,3-dihydro-1H-inden-1-yl)-2,2,7-trimethyl-2,3,4,5-tetrahydrobenzo[f][1,4]oxazepine

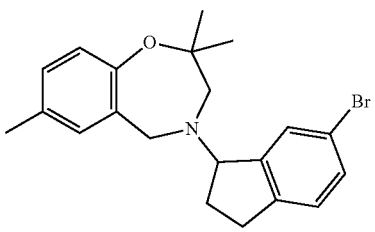 [SMILES: Cc1ccc2c(c1)CN(C1CCc3ccc(Br)cc31)CC(C)(C)O2]

121

To a solution of 2,2,7-trimethyl-2,3,4,5-tetrahydrobenzo[f][1,4]oxazepine (832 mg, 4.35 mmol) in acetonitrile (20 mL) was added 1,6-dibromo-2,3-dihydro-1H-indene (600 mg, 2.174 mmol) followed by addition of DIPEA (1.139 mL, 6.52 mmol). The reaction mixture was stirred at 120° C. on a microwave reactor for 1 h. The reaction was then diluted with ice water and extracted with EtOAc (2×20 mL). The combined organic layer was washed with brine solution (30 mL) and dried over anhydrous $Na_2SO_4$, filtered and the solvent was evaporated under vacuum. The crude residue was purified by flash column chromotography eluting with EtOAc:Hexane (1:9). The eluted fractions were concentrated under vacuum to afford title product (600 mg, 68.8% yield). LC-MS m/z 386 $(M+H)^+$, 2.41 min (ret. time).

2,2,7-Trimethyl-4-(6-(4,4,5,5-tetramethyl-1,3,2-dioxaborolan-2-yl)-2,3-dihydro-1H-inden-1-yl)-2,3,4,5-tetrahydrobenzo[f][1,4]oxazepine

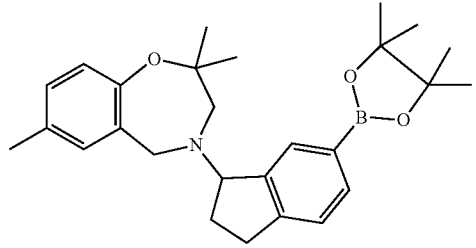

To a solution of 4-(6-bromo-2,3-dihydro-1H-inden-1-yl)-2,2,7-trimethyl-2,3,4,5-tetrahydrobenzo[f][1,4]oxazepine (600 mg, 1.553 mmol) in 1,4-dioxane (10 mL) was added bis(pinacolato)diboron (473 mg, 1.864 mmol) and potassium acetate (305 mg, 3.11 mmol). The reaction mixture was degassed with argon for 10 min then $PdCl_2(dppf)$-$CH_2Cl_2$ adduct (127 mg, 0.155 mmol) was added and the reaction mixture was heated to 90° C. for 3 h. The reaction mixture was filtered through celite and washed with EtOAc (100 mL). The filtrate was concentrated under reduced pressure to afford a crude residue. The crude residue was purified by column chromatography and eluted with 10% ethyl acetate in hexanes. The eluted fractions were concentrated under reduced pressure to afford the title compound (500 mg, 62.9% yield). LC-MS m/z 434 $(M+H)^+$, 2.33 min (ret. time).

122

Ethyl 3-(1,4-dimethyl-1H-benzo[d][1,2,3]triazol-5-yl)-3-(3-(2,2,7-trimethyl-2,3-dihydrobenzo[f][1,4]oxazepin-4(5H)-yl)-2,3-dihydro-1H-inden-5-yl)propanoate

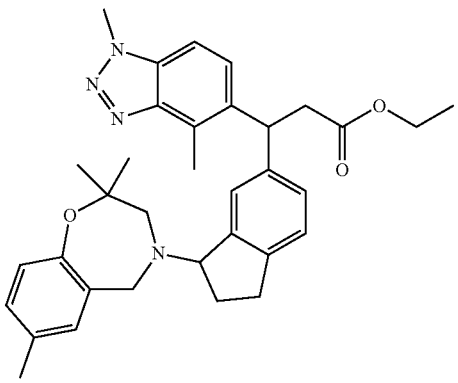 [SMILES: CCOC(=O)CC(c1ccc2c(c1)C(N1Cc3cc(C)ccc3OC(C)(C)C1)CC2)c1ccc2c(nnn2C)c1C]

To a solution of (E)-ethyl 3-(1,4-dimethyl-1H-benzo[d][1,2,3]triazol-5-yl)acrylate (250 mg, 1.019 mmol), and 2,2,7-trimethyl-4-(6-(4,4,5,5-tetramethyl-1,3,2-dioxaborolan-2-yl)-2,3-dihydro-1H-inden-1-yl)-2,3,4,5-tetrahydrobenzo[f][1,4]oxazepine (574 mg, 1.325 mmol) in 1,4-dioxane (5 mL) and water (5.00 mL) was added TEA (0.426 mL, 3.06 mmol) and chloro(1,5-cyclooctadiene)rhodium(I) dimer (50.3 mg, 0.102 mmol). The reaction mixture was degassed with argon for 10 min and then stirred at 100° C. for 2 h. The reaction mixture was cooled to ambient temperature, diluted with water and extracted with EtOAc (2×20 mL). The combined organic layers were washed with a brine solution (20 mL) and dried over $Na_2SO_4$, filtered and evaporated under vacuum. The crude residue was purified by flash column chromatography, using EtOAc:Hexane (5:5) as eluent to afford the title compound (200 mg, 29.3% yield). LC-MS m/z 553 $(M+H)^+$, 2.09 min (ret. time).

3-(1,4-Dimethyl-1H-benzo[d][1,2,3]triazol-5-yl)-3-(3-(2,2,7-trimethyl-2,3-dihydrobenzo[f][1,4]oxazepin-4(5H)-yl)-2,3-dihydro-1H-inden-5-yl)propanoic Acid

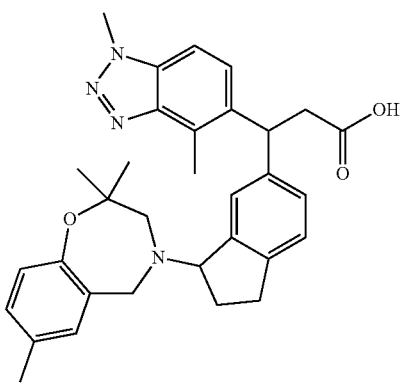 [SMILES: Cc1ccc2c(c1)CN(C1CCc3ccc(C(CC(=O)O)c4ccc5c(nnn5C)c4C)cc31)CC(C)(C)O2]

To a solution of ethyl 3-(1,4-dimethyl-1H-benzo[d][1,2,3]triazol-5-yl)-3-(3-(2,2,7-trimethyl-2,3-dihydrobenzo[f][1,4]oxazepin-4(5H)-yl)-2,3-dihydro-1H-inden-5-yl)propanoate (200 mg, 0.362 mmol) in ethanol (10 mL) and was added 1 M NaOH in water (10 mL, 10.00 mmol) at 0° C. The reaction was stirred for 4 h at ambient temperature. The reaction mixture was concentrated under reduced pressure, neutralised with 1 N HCl, extracted with DCM and dried over $Na_2SO_4$. The filtrate was evaporated under reduced pressure and was purified using reverse phase HPLC to afford the title compound (120 mg, 61.0% yield). LC-MS m/z 5253 (M+H)$^+$, 1.81 min (ret. time).

Example 23

3-(1,4-Dimethyl-1H-benzo[d][1,2,3]triazol-5-yl)-3-(3-(7-methoxy-2,2-dimethyl-2,3-dihydrobenzo[f][1,4]oxazepin-4(5H)-yl)-2,3-dihydro-1H-inden-5-yl) propanoic Acid

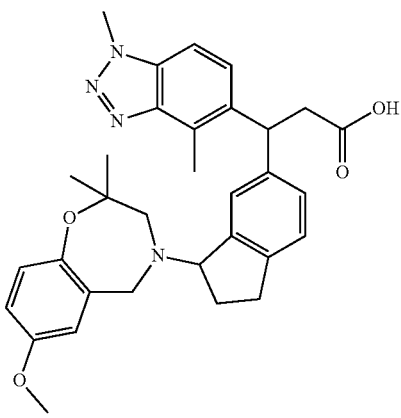 [SMILES: COc1ccc2c(c1)CN(C1CCc3ccc(C(CC(=O)O)c4ccc5c(nnn5C)c4C)cc31)CC(C)(C)O2]

4-(6-Bromo-2,3-dihydro-1H-inden-1-yl)-7-methoxy-2,2-dimethyl-2,3,4,5-tetrahydrobenzo[f][1,4]oxazepine

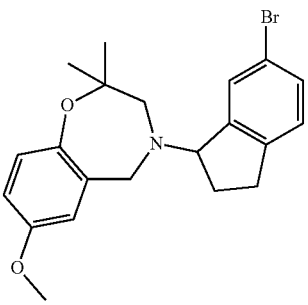 [SMILES: COc1ccc2c(c1)CN(C1CCc3ccc(Br)cc31)CC(C)(C)O2]

To a solution of 1,6-dibromo-2,3-dihydro-1H-indene (500 mg, 1.812 mmol), 7-methoxy-2,2-dimethyl-2,3,4,5-tetrahydrobenzo[f][1,4]oxazepine (376 mg, 1.812 mmol) in acetonitrile (10 mL) was added DIPEA (0.633 mL, 3.62 mmol) at ambient temperature. The reaction mixture was stirred in a microwave reactor at 90° C. for 1 h. The reaction mixture was cooled to 0° C., quenched with cold water, and extracted with EtOAc (2×). The combined organic layers were washed with a brine solution, the organic layer was dried over anhydrous $Na_2SO_4$ and filtered. The filtrate was evaporated under reduced pressure and the crude residue was purified by flash chromatography by using EtOAc:Hexane (4:96) as eluent to afford the title compound (400 mg, 54.9% yield). $^1$H NMR (400 MHz, CDCl$_3$) δ ppm=7.42 (s, 1H), 7.33 (br d, J=8.3 Hz, 1H), 7.09 (d, J=7.9 Hz, 1H), 6.83 (d, J=8.8 Hz, 1H), 6.66 (dd, J=3.1, 8.6 Hz, 1H), 6.48 (d, J=3.1 Hz, 1H), 4.48 (br t, J=8.0 Hz, 1H), 3.76 (s, 3H), 3.56 (s, 2H), 2.95-2.85 (m, 1H), 2.82-2.70 (m, 3H), 2.23-2.13 (m, 1H), 2.11-2.02 (m, 1H), 1.24 (d, J=18.2 Hz, 6H).

7-Methoxy-2,2-dimethyl-4-(6-(4,4,5,5-tetramethyl-1,3,2-dioxaborolan-2-yl)-2,3-dihydro-1H-inden-1-yl)-2,3,4,5-tetrahydrobenzo[f][1,4]oxazepine

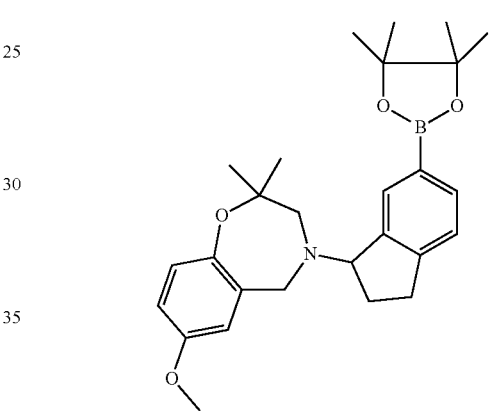

To a solution of 4-(6-bromo-2,3-dihydro-1H-inden-1-yl)-7-methoxy-2,2-dimethyl-2,3,4,5-tetrahydrobenzo[f][1,4]oxazepine (400 mg, 0.994 mmol) in 1,4-dioxane (10 mL) was added bis(pinacolato)diboron (303 mg, 1.193 mmol) and potassium acetate (195 mg, 1.988 mmol). The reaction mixture was degassed with argon for 10 min then PdCl$_2$(dppf)-CH$_2$Cl$_2$ adduct (40.6 mg, 0.050 mmol) was added and the reaction mixture was heated to 90° C. for 4 h. The reaction mixture was cooled to 0° C., quenched with cold water, and extracted with EtOAc (2×). The combined organic layers were washed with a brine solution, the organic layer was dried over anhydrous $Na_2SO_4$ and filtered. The filtrate was evaporated under reduced pressure and the crude residue was purified by flash column chromatography using EtOAc:Hexane (5:95) as eluent to afford the title compound (300 mg, 67.1% yield). $^1$H NMR (400 MHz, CDCl$_3$) δ ppm=7.76 (s, 1H), 7.67 (d, J=7.5 Hz, 1H), 7.15 (br dd, J=7.2, 19.3 Hz, 1H), 6.82 (d, J=8.6 Hz, 1H), 6.65 (dd, J=3.0, 8.7 Hz, 1H), 6.52 (d, J=2.9 Hz, 1H), 4.51 (br t, J=7.6 Hz, 1H), 3.74 (s, 3H), 3.69-3.58 (m, 2H), 3.00-2.90 (m, 1H), 2.82 (td, J=8.4, 16.4 Hz, 1H), 2.69 (q, J=12.6 Hz, 2H), 2.22-2.12 (m, 1H), 2.09-2.00 (m, 1H), 1.32-1.26 (m, 12H), 1.22 (d, J=6.4 Hz, 6H).

Ethyl 3-(1,4-dimethyl-1H-benzo[d][1,2,3]triazol-5-yl)-3-(3-(7-methoxy-2,2-dimethyl-2,3-dihydrobenzo[f][1,4]oxazepin-4(5H)-yl)-2,3-dihydro-1H-inden-5-yl)propanoate

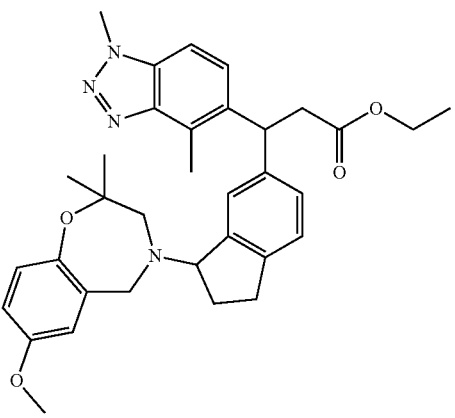 [SMILES: CCOC(=O)CC(c1ccc2c(c1)C(N1Cc3cc(OC)ccc3OC(C)(C)C1)CC2)c1ccc2c(nnn2C)c1C]

To solution of (E)-ethyl 3-(1,4-dimethyl-1H-benzo[d][1,2,3]triazol-5-yl)acrylate (200 mg, 0.815 mmol) in a mixture of 1,4-dioxane (4 mL) and water (4 mL) was added TEA (0.334 mL, 2.446 mmol). The solution was degassed with nitrogen for 20 min, followed by the addition of chloro(1,5-cyclooctadiene)rhodium(I) dimer (40.2 mg, 0.082 mmol). The reaction mixture was stirred at 90° C. for 4 h. The reaction mixture was then quenched with cold water, and extracted with EtOAc (2×). The combined organics were washed with a brine solution, the organic layer was dried over anhydrous $Na_2SO_4$ and filtered. The filtrate was evaporated under reduced pressure to afford the crude title compound which was carried on to the next step without further purification (300 mg, 64.7% yield). LC-MS m/z 569 $(M+H)^+$, 4.42 min (ret. time).

3-(1,4-Dimethyl-1H-benzo[d][1,2,3]triazol-5-yl)-3-(3-(7-methoxy-2,2-dimethyl-2,3-dihydrobenzo[f][1,4]oxazepin-4(5H)-yl)-2,3-dihydro-1H-inden-5-yl)propanoic Acid

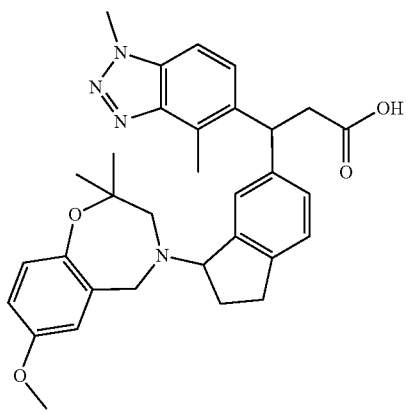 [SMILES: COc1ccc2c(c1)CN(C1CCc3ccc(C(CC(=O)O)c4ccc5c(nnn5C)c4C)cc31)CC(C)(C)O2]

To a solution of ethyl 3-(1,4-dimethyl-1H-benzo[d][1,2,3]triazol-5-yl)-3-(3-(7-methoxy-2,2-dimethyl-2,3-dihydrobenzo[f][1,4]oxazepin-4(5H)-yl)-2,3-dihydro-1H-inden-5-yl)propanoate (300 mg, 0.528 mmol) in ethanol (10 mL) was added 10% NaOH (10 mL, 0.528 mmol) at 0° C. The reaction was stirred at ambient temperature for 16 h. The reaction mixture was evaporated under reduced pressure, neutralized with 2N HCl, and extracted with DCM (2×). The combined organic layers were washed with a brine solution, the organic layer was dried over anhydrous $Na_2SO_4$ and filtered. The filtrate was evaporated and purified by preparative HPLC to afford the title compound (57 mg, 19.94% yield). LC-MS m/z 541 $(M+H)^+$, 1.78 min (ret. time).

Example 24

3-(1,4-Dimethyl-1H-benzo[d][1,2,3]triazol-5-yl)-3-(3-(2,2,8-trimethyl-2,3-dihydrobenzo[f][1,4]oxazepin-4(5H)-yl)-2,3-dihydro-1H-inden-5-yl)propanoic Acid, Formic Acid Salt

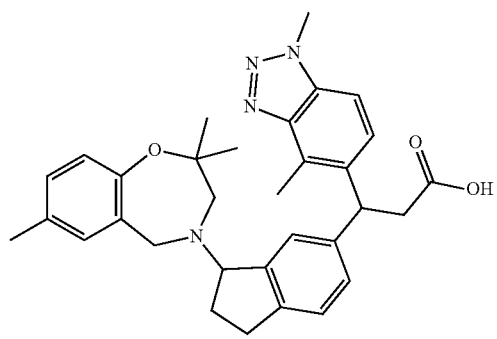 [SMILES: Cc1ccc2c(c1)CN(C1CCc3ccc(C(CC(=O)O)c4ccc5c(nnn5C)c4C)cc31)CC(C)(C)O2]

4-(6-Bromo-2,3-dihydro-1H-inden-1-yl)-2,2,8-trimethyl-2,3,4,5-tetrahydrobenzo[f][1,4]oxazepine

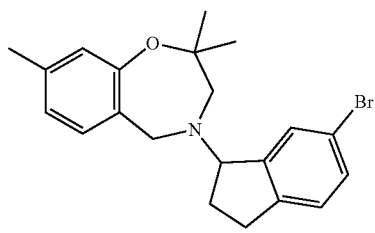 [SMILES: Cc1ccc2c(c1)OC(C)(C)CN(C1CCc3ccc(Br)cc31)C2]

To a solution of 2,2,8-trimethyl-2,3,4,5-tetrahydrobenzo[f][1,4]oxazepine (200 mg, 1.046 mmol) and 1,6-dibromo-2,3-dihydro-1H-indene (289 mg, 1.046 mmol) in acetonitrile (10 mL) was added DIPEA (0.365 mL, 2.091 mmol) at ambient temperature. The reaction mixture was stirred for 16 h at 70° C. The reaction mixture was then concentrated under reduced pressure, diluted with water and extracted with ethyl acetate. The organic layer was washed with brine solution, dried over $Na_2SO_4$ and filtered. The filtrate was concentrated and purified by column chromatography using (5:95) EtOAc:Hexane as eluent. The solvent was concentrated to afford the title compound (220 mg, 54.5% yield). $^1$H NMR (400 MHz, $CDCl_3$) δ ppm=7.41 (s, 1H), 7.32 (dd, J=1.3, 8.1 Hz, 1H), 7.08 (d, J=7.9 Hz, 1H), 6.86-6.72 (m, 3H), 4.48 (t, J=8.0 Hz, 1H), 3.58 (s, 2H), 2.93-2.83 (m, 1H), 2.79-2.67 (m, 3H), 2.28 (s, 3H), 2.21-2.04 (m, 2H), 1.25 (d, J=10.7 Hz, 6H).

2,2,8-Trimethyl-4-(6-(4,4,5,5-tetramethyl-1,3,2-dioxaborolan-2-yl)-2,3-dihydro-1H-inden-1-yl)-2,3,4,5-tetrahydrobenzo[f][1,4]oxazepine

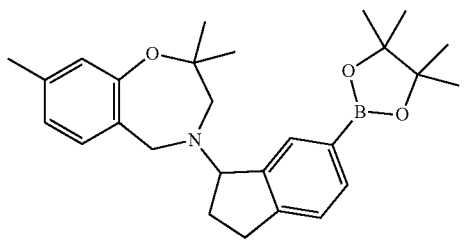

To a solution of 4-(6-bromo-2,3-dihydro-1H-inden-1-yl)-2,2,8-trimethyl-2,3,4,5-tetrahydrobenzo[f][1,4]oxazepine (300 mg, 0.777 mmol) in 1,4-dioxane (10 mL) in a sealed tube was added bis(pinacolato)diboron (256 mg, 1.010 mmol) and potassium acetate (191 mg, 1.941 mmol). The reaction was degassed with argon for 20 min, followed by the addition of $PdCl_2(dppf)$ (28.4 mg, 0.039 mmol). The reaction mixture was stirred at 90° C. for 2 h. The crude residue was purified by column chromatography using 20% ethyl acetate in hexanes as eluent. The eluted fractions were concentrated under reduced pressure to afford the title compound (250 mg, 69.2% yield). LC-MS m/z 434 (M+H)+, 4.97 min (ret. time).

Ethyl 3-(1,4-dimethyl-1H-benzo[d][1,2,3]triazol-5-yl)-3-(3-(2,2,8-trimethyl-2,3-dihydrobenzo[f][1,4]oxazepin-4(5H)-yl)-2,3-dihydro-1H-inden-5-yl)propanoate

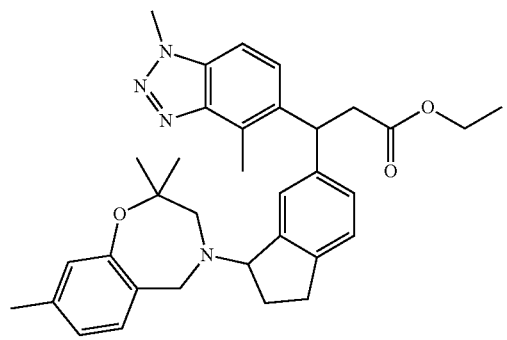 [SMILES: CCOC(=O)CC(c1ccc2c(c1)C(N1Cc3ccc(C)cc3OC(C)(C)C1)CC2)c1ccc2c(nnn2C)c1C]

To a solution of (E)-ethyl 3-(1,4-dimethyl-1H-benzo[d][1,2,3]triazol-5-yl)acrylate (50 mg, 0.204 mmol) in 1,4-dioxane (10 mL) and water (10.00 mL) in a sealed tube was added 2,2,8-trimethyl-4-(6-(4,4,5,5-tetramethyl-1,3,2-dioxaborolan-2-yl)-2,3-dihydro-1H-inden-1-yl)-2,3,4,5-tetrahydrobenzo[f][1,4]oxazepine (115 mg, 0.265 mmol). The reaction was degassed with argon for 20 min, followed by the addition of chloro(1,5-cyclooctadiene)rhodium(I) dimer (10.05 mg, 0.020 mmol). The reaction mixture was stirred at 95° C. for 16 h. The reaction mixture was then filtered through celite and washed with ethyl acetate. The filtrate was concentrated under reduced pressure and the crude residue was purified by column chromatography using 20% ethyl acetate in hexanes as eluent. The eluted fractions were concentrated under reduced pressure to afford the title compound (120 mg, 56.2% yield). LC-MS m/z 553 (M+H)+, 2.12 min (ret. time).

3-(1,4-Dimethyl-1H-benzo[d][1,2,3]triazol-5-yl)-3-(3-(2,2,8-trimethyl-2,3-dihydrobenzo[f][1,4]oxazepin-4(5H)-yl)-2,3-dihydro-1H-inden-5-yl)propanoic Acid, Formic Acid Salt

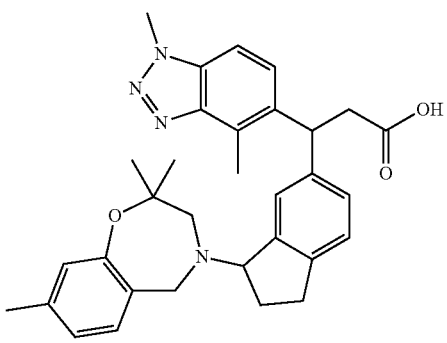 [SMILES: Cc1ccc2c(c1)OC(C)(C)CN(C1CCc3ccc(C(CC(=O)O)c4ccc5c(nnn5C)c4C)cc31)C2]

To a solution of ethyl 3-(1,4-dimethyl-1H-benzo[d][1,2,3]triazol-5-yl)-3-(3-(2,2,8-trimethyl-2,3-dihydrobenzo[f][1,4]oxazepin-4(5H)-yl)-2,3-dihydro-1H-inden-5-yl)propanoate (120 mg, 0.217 mmol) in ethanol (10 mL) and was added 1M NaOH (10 mL, 10.00 mmol) at 0° C. The reaction was stirred for 4 h at ambient temperature. The reaction mixture was concentrated under reduced pressure, neutralized with 1N HCl and extracted with (1:1) MeOH:DCM. The organic layers were dried over $Na_2SO_4$. The filtrate was evaporated under reduced pressure and was purified by preparative HPLC to afford the title compound (56 mg, 48% yield). LC-MS m/z 525 (M+H)+, 1.85 min (ret. time).

Example 25

3-(1,4-Dimethyl-1H-benzo[d][1,2,3]triazol-5-yl)-3-(3-(8-fluoro-2,2-dimethyl-2,3-dihydrobenzo[f][1,4]oxazepin-4(5H)-yl)-2,3-dihydro-1H-inden-5-yl)propanoic Acid

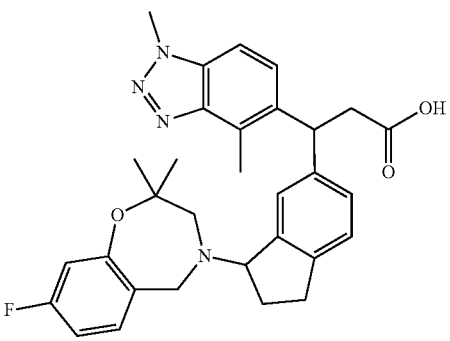

4-(6-Bromo-2,3-dihydro-1H-inden-1-yl)-8-fluoro-2,2-dimethyl-2,3,4,5-tetrahydrobenzo[f][1,4]oxazepine

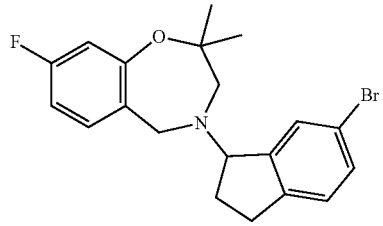 [SMILES: CC1(C)CN(C2CCc3ccc(Br)cc32)Cc2ccc(F)cc2O1]

To a solution of 8-fluoro-2,2-dimethyl-2,3,4,5-tetrahydrobenzo[f][1,4]oxazepine (150 mg, 0.768 mmol) and 1,6-dibromo-2,3-dihydro-1H-indene (212 mg, 0.768 mmol) in acetonitrile (10 mL) and was added DIPEA (0.268 mL, 1.537 mmol) at ambient temperature. The reaction mixture was stirred for 4 h at 70° C. The reaction mixture was concentrated under reduced pressure, diluted with water and extracted with ethyl acetate. The organic layer was washed with a brine solution dried over $Na_2SO_4$ and filtered. The filtrate was evaporated under vacuum and purified by colomn chromatography using EtOAc:Hexane (5:95) as eluent. The eluted fractions were concentrated to afford the title compound (200 mg, 66.7% yield). $^1$H NMR (400 MHz, $CDCl_3$) δ ppm=7.40 (s, 1H), 7.35-7.31 (m, 1H), 7.09 (d, J=7.9 Hz, 1H), 6.87-6.80 (m, 2H), 6.65 (dd, J=2.9, 8.6 Hz, 1H), 4.48 (t, J=7.9 Hz, 1H), 3.57 (s, 2H), 2.93-2.85 (m, 1H), 2.81-2.71 (m, 3H), 2.22-2.13 (m, 1H), 2.10-2.01 (m, 1H), 1.30-1.27 (m, 2H), 1.24 (dd, J=2.2, 9.9 Hz, H).

8-Fluoro-2,2-dimethyl-4-(6-(4,4,5,5-tetramethyl-1,3,2-dioxaborolan-2-yl)-2,3-dihydro-1H-inden-1-yl)-2,3,4,5-tetrahydrobenzo[f][1,4]oxazepine

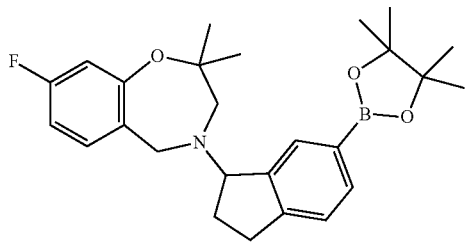 [SMILES: CC1(C)CN(C2CCc3ccc(B4OC(C)(C)C(C)(C)O4)cc32)Cc2ccc(F)cc2O1]

To a solution of 4-(6-bromo-2,3-dihydro-1H-inden-1-yl)-8-fluoro-2,2-dimethyl-2,3,4,5-tetrahydrobenzo[f][1,4]oxazepine (200 mg, 0.512 mmol) in 1,4-dioxane (10 mL) in a sealed tube was added bis(pinacolato)diboron (169 mg, 0.666 mmol) and potassium acetate (126 mg, 1.281 mmol). The reaction was degassed with argon for 20 min, followed by the addition of $PdCl_2$(dppf) (18.75 mg, 0.026 mmol). The reaction mixture was stirred at 90° C. for 4 h. The reaction mixture was passed through celite and washed with ethyl acetate. The reaction was diluted with water and extracted with EtOAc. The organic layer was dried over $Na_2SO_4$ and filtered. The filtrate was concentrated under reduced pressure and purified by column chromatography using (5:95) EtOAc:Hexane as eluent. The eluted fractions were evaporated to afford the title compound (215 mg, 87% yield). LC-MS m/z 438 (M+H)$^+$, 4.80 min (ret. time).

Ethyl 3-(1,4-dimethyl-1H-benzo[d][1,2,3]triazol-5-yl)-3-(3-(8-fluoro-2,2-dimethyl-2,3-dihydrobenzo[f][1,4]oxazepin-4(5H)-yl)-2,3-dihydro-1H-inden-5-yl)propanoate

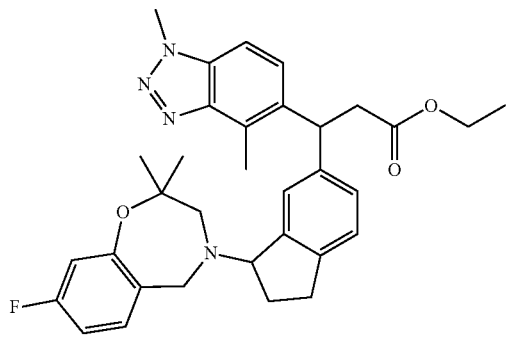 [SMILES: CCOC(=O)CC(c1ccc2c(c1)C(N1Cc3ccc(F)cc3OC(C)(C)C1)CC2)c1ccc2c(nnn2C)c1C]

To a solution of (E)-ethyl 3-(1,4-dimethyl-1H-benzo[d][1,2,3]triazol-5-yl)acrylate (50 mg, 0.204 mmol) in 1,4-dioxane (10 mL) and water (10.00 mL) in a sealed tube was added 8-fluoro-2,2-dimethyl-4-(6-(4,4,5,5-tetramethyl-1,3,2-dioxaborolan-2-yl)-2,3-dihydro-1H-inden-1-yl)-2,3,4,5-tetrahydrobenzo[f][1,4]oxazepine (116 mg, 0.265 mmol). The reaction was degassed with argon for 20 min followed by the addition of chloro(1,5-cyclooctadiene)rhodium(I) dimer (10.05 mg, 0.020 mmol). The reaction mixture was stirred at 95° C. for 16 h. The reaction mixture was filtered through celite and washed with ethyl acetate. The filtrate was concentrated under reduced pressure and the crude residue was purified by column chromatography using 20% ethyl acetate in hexanes as eluent. The eluted fractions were concentrated under reduced pressure to afford the title compound (150 mg, 42.7% yield). LC-MS m/z 557 (M+H)$^+$, 4.97 min (ret. time).

3-(1,4-Dimethyl-1H-benzo[d][1,2,3]triazol-5-yl)-3-(3-(8-fluoro-2,2-dimethyl-2,3-dihydrobenzo[f][1,4]oxazepin-4(5H)-yl)-2,3-dihydro-1H-inden-5-yl)propanoic Acid

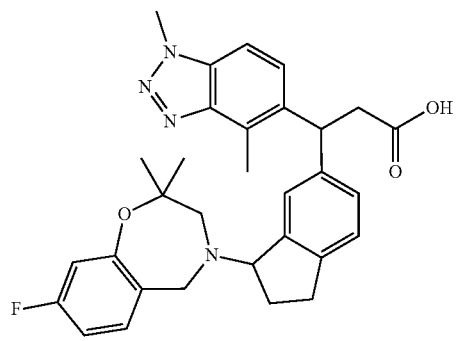

To a solution of ethyl 3-(1,4-dimethyl-1H-benzo[d][1,2,3]triazol-5-yl)-3-(3-(8-fluoro-2,2-dimethyl-2,3-dihydrobenzo[f][1,4]oxazepin-4(5H)-yl)-2,3-dihydro-1H-inden-5-yl)propanoate (150 mg, 0.269 mmol) in ethanol (10 mL) and was added NaOH in water (10.78 mg, 0.269 mmol) at 0° C. The reaction mixture was stirred for 16 h at ambient temperature. The reaction mixture was then concentrated under reduced pressure, quenched with 1 N HCl and extracted with MeOH:DCM (1:9). The organic layer was dried over Na₂SO₄ and filtered. The filtrate was evaporated under vacuum and the residue was purified through preparative HPLC to afford the title compound (60 mg, 41.6% yield). LC-MS m/z 529 (M+H)⁺, 3.19 min (ret. time).

Example 26

3-(3-(2,2-Dimethyl-2,3-dihydrobenzo[f][1,4]oxazepin-4(5H)-yl)-2,3-dihydro-1H-inden-5-yl)-3-(4-fluoro-2-methylphenyl)-2,2-dimethylpropanoic Acid

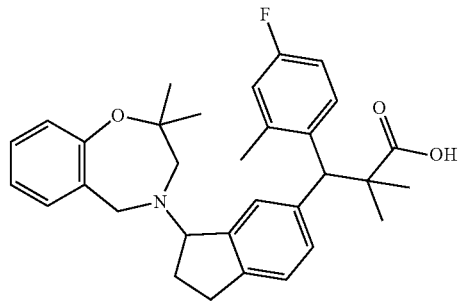 [SMILES: Cc1cc(F)ccc1C(c1ccc2c(c1)C(N1Cc3ccccc3OC(C)(C)C1)CC2)C(C)(C)C(=O)O]

4-(6-Bromo-2,3-dihydro-1H-inden-1-yl)-2,2-dimethyl-2,3,4,5-tetrahydrobenzo[f][1,4]oxazepine

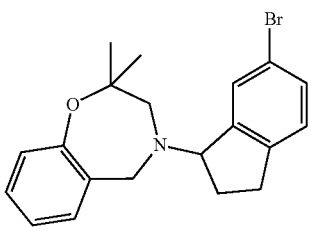 [SMILES: CC1(C)CN(C2CCc3ccc(Br)cc32)Cc2ccccc2O1]

To the solution of 1,6-dibromo-2,3-dihydro-1H-indene (800 mg, 2.90 mmol) and 2,2-dimethyl-2,3,4,5-tetrahydrobenzo[f][1,4]oxazepine (617 mg, 3.48 mmol) in acetonitrile (15 mL) was added DIPEA (0.506 mL, 2.90 mmol) and the reaction mixture was allowed to stir in a microwave at 90° C. for 1 h. The reaction mixture was diluted with ice water and extracted with EtOAc. The combined organic layers were washed with brine solution and dried over anhydrous Na₂SO₄ and filtered. The solvent was evaporated under vacuum and the crude residue was purified by flash chromatography using EtOAc:Hexane (2:8) as eluent. The solvent was concentrated under vacuum to afford the title compound (600 mg, 54.8% yield). LC-MS m/z 374 (M+H)⁺, 2.50 min (ret. time).

(3-(2,2-Dimethyl-2,3-dihydrobenzo[f][1,4]oxazepin-4(5H)-yl)-2,3-dihydro-1H-inden-5-yl)(4-fluoro-2-methylphenyl)methanol

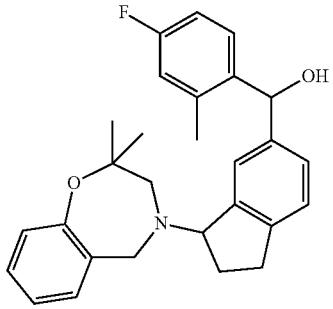 [SMILES: Cc1cc(F)ccc1C(O)c1ccc2c(c1)C(N1Cc3ccccc3OC(C)(C)C1)CC2]

To the solution of 4-(6-bromo-2,3-dihydro-1H-inden-1-yl)-2,2-dimethyl-2,3,4,5-tetrahydrobenzo[f][1,4]oxazepine (600 mg, 1.612 mmol) in THF (25 mL) at −78° C. was added 1.6 M BuLi in hexane (1.309 mL, 2.095 mmol). The reaction mixture was allowed to stir at −78° C. for 30 min. 4-Fluoro-2-methylbenzaldehyde (245 mg, 1.773 mmol) was then added in THF and the reaction mixture was stirred at ambient temperature for 1 h. The reaction mixture was quenched with saturated NH₄Cl, diluted with ice water and extracted with EtOAc. The combined organic layers were washed with brine solution and dried over anhydrous Na₂SO₄, filtered and evaporated under vacuum. The crude residue was purified by flash chromatography using EtOAc:Hexane (2:8) as eluent. The solvent was concentrated under vacuum to afford the title compound (300 mg, 31.1% yield). LC-MS m/z 432 (M+H)⁺, 4.34 min (ret. time).

Methyl 3-(3-(2,2-dimethyl-2,3-dihydrobenzo[f][1,4]oxazepin-4(5H)-yl)-2,3-dihydro-1H-inden-5-yl)-3-(4-fluoro-2-methylphenyl)-2,2-dimethylpropanoate

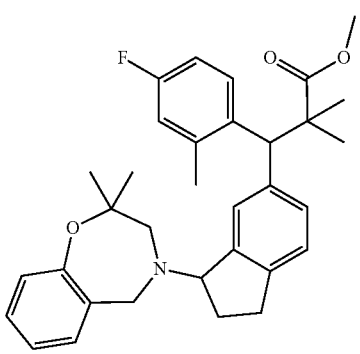 [SMILES: COC(=O)C(C)(C)C(c1ccc2c(c1)C(N1Cc3ccccc3OC(C)(C)C1)CC2)c1ccc(F)cc1C]

To the solution of (3-(2,2-dimethyl-2,3-dihydrobenzo[f][1,4]oxazepin-4(5H)-yl)-2,3-dihydro-1H-inden-5-yl)(4-fluoro-2-methylphenyl)methanol (180 mg, 0.417 mmol) in DCM (10 mL) was added ((1-methoxy-2-methylprop-1-en-1-yl)oxy)trimethylsilane (218 mg, 1.251 mmol) followed by the addition of TiCl₄ (6 mL, 6.00 mmol) and was allowed to stir at 0° C. for 30 min. The reaction mixture was diluted with saturated NaHCO₃ and extracted with EtOAc. The combined organic layers were washed with brine solution and dried over anhydrous Na₂SO₄, filtered and concentrated. The crude residue was purified by flash chromatography using EtOAc:Hexane (2:8) as eluent. The solvent was concentrated under vacuum to afford the title compound (150 mg, 67.1% yield). LC-MS m/z 516 (M+H)⁺, 4.83 min (ret. time).

3-(3-(2,2-Dimethyl-2,3-dihydrobenzo[f][1,4]oxazepin-4(5H)-yl)-2,3-dihydro-1H-inden-5-yl)-3-(4-fluoro-2-methylphenyl)-2,2-dimethylpropanoic Acid

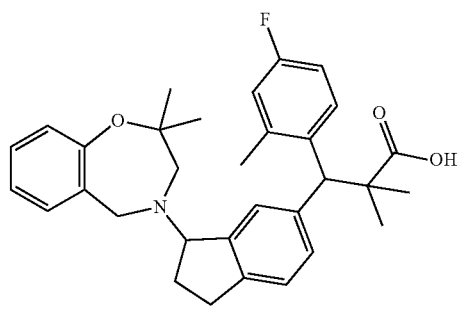 [SMILES: Cc1cc(F)ccc1C(c1ccc2c(c1)C(N1Cc3ccccc3OC(C)(C)C1)CC2)C(C)(C)C(=O)O]

To the solution of methyl 3-(3-(2,2-dimethyl-2,3-dihydrobenzo[f][1,4]oxazepin-4(5H)-yl)-2,3-dihydro-1H-inden-5-yl)-3-(4-fluoro-2-methylphenyl)-2,2-dimethylpropanoate (150 mg, 0.291 mmol) in dimethyl sulfoxide (DMSO) (3 mL), was added 2N NaOH (3 mL, 0.291 mmol) and methanol (3 mL) and the reaction mixture heated at 100° C. for 18 h. After completion of the reaction, the solvent was evaporated under vacuum and the residue was diluted with ice water and acidified with 1N HCl to pH 3. The resulting solid was filtered and was purified by preparative HPLC to afford the title compound (52 mg, 35.1% yield). LC-MS m/z 502 (M+H)⁺, 3.68 min (ret. time).

Example 27

3-(1,4-Dimethyl-1H-benzo[d][1,2,3]triazol-5-yl)-3-(3-(2,2-dimethyl-2,3-dihydrobenzo[f][1,4]oxazepin-4(5H)-yl)-2,3-dihydro-1H-inden-5-yl)-2,2-dimethylpropanoic Acid, 2 Formic Acid Salt

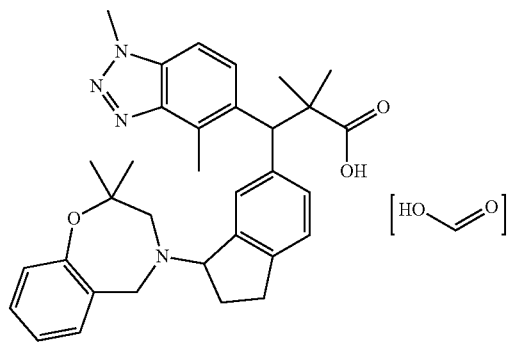

3-((4-Methoxybenzyl)oxy)-2,3-dihydro-1H-indene-5-carbaldehyde

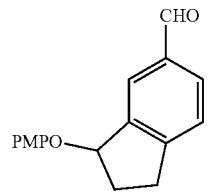

To a solution of 6-bromo-1-((4-methoxybenzyl)oxy)-2,3-dihydro-1H-indene (3.33 g, 9.99 mmol) in THF (70 mL) was added butyllithium (4.80 mL, 11.99 mmol) at −78° C. The mixture was stirred at −78° C. for half an hour under N₂ atmosphere, then DMF (3.87 mL, 50.0 mmol) was slowly added into the reaction. The resulting reaction mixture was stirred for 2 hours at −78° C. before being quenched with saturated NH₄Cl solution. The mixture was extracted with ethyl acetate three times. The combined organic layer was washed with brine, dried over anhydrous Na₂SO₄, filtered, evaporated down and purified by flash chromatography to afford desired product 3-((4-methoxybenzyl)oxy)-2,3-dihydro-1H-indene-5-carbaldehyde (2.3 g, 8.15 mmol, 82% yield). LC-MS m/z 305.2 (M+H)⁺, 2.07 min (ret. time).

(1,4-Dimethyl-1H-benzo[d][1,2,3]triazol-5-yl)(3-((4-methoxybenzyl)oxy)-2,3-dihydro-1H-inden-5-yl) methanol

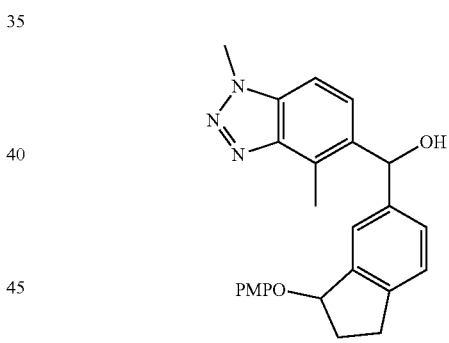

To a solution of 5-bromo-1,4-dimethyl-1H-benzo[d][1,2,3]triazole (2.26 g, 10.00 mmol) in THF (60 mL) was added tert-butyllithium (9.23 mL, 12.00 mmol) at −78° C. under N₂ atmosphere. The reaction mixture was stirred at −78° C. for one hour under N₂ atmosphere before 3-((4-methoxybenzyl)oxy)-2,3-dihydro-1H-indene-5-carbaldehyde (2.82 g, 10.00 mmol) in 20 ml THF was slowly added into the reaction. The resulting reaction mixture was stirred at −78° C. for 2 hours then slowly warmed up to ambient temperature and stirred for 8 hours. The reaction mixture was quenched with saturated NH₄Cl solution and extracted with ethyl acetate three times. The combined organic layer was washed with brine and dried over anhydrous Na₂SO₄. After filtration and concentration, the residue was purified with flash chromatography to afford desired product (1,4-dimethyl-1H-benzo[d][1,2,3]triazol-5-yl)(3-((4-methoxybenzyl)oxy)-2,3-dihydro-1H-inden-5-yl)methanol (3.2 g, 7.45 mmol, 74.5% yield). LC-MS m/z 514.2 (M+H)⁺, 2.24 min (ret. time).

Methyl 3-(1,4-dimethyl-1H-benzo[d][1,2,3]triazol-5-yl)-3-(3-((4-methoxybenzyl)oxy)-2,3-dihydro-1H-inden-5-yl)-2,2-dimethylpropanoate

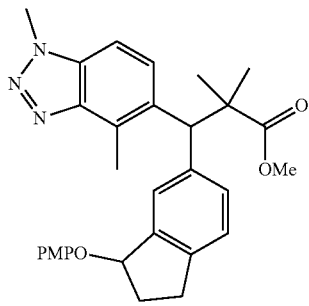

To a solution of (1,4-dimethyl-1H-benzo[d][1,2,3]triazol-5-yl)(3-((4-methoxybenzyl)oxy)-2,3-dihydro-1H-inden-5-yl)methanol (1 g, 2.328 mmol) in dry acetonitrile (40 mL) was slowly added DBU (7.02 µL, 0.047 mmol) and 2,2,2-trichloroacetonitrile (0.403 g, 2.79 mmol) under $N_2$ protection. The resulting mixture was stirred at ambient temperature for half an hour before adding ((1-methoxy-2-methylprop-1-en-1-yl)oxy)trimethylsilane (1.015 g, 5.82 mmol) then trifluoro-N-((trifluoromethyl)sulfonyl)methanesulfonamide (0.033 g, 0.116 mmol). The reaction mixture was stirred at ambient temperature for 2 hours then extracted with EtOAc (10 ml) three times and the organic layer was washed with brine, filtered and evaporated down to afford desired product methyl 3-(1,4-dimethyl-1H-benzo[d][1,2,3]triazol-5-yl)-3-(3-((4-methoxybenzyl)oxy)-2,3-dihydro-1H-inden-5-yl)-2,2-dimethylpropanoate (1.1 g, 2.14 mmol, 92% yield). LC-MS m/z 514.2 (M+H)$^+$, 2.24 min (ret. time).

Methyl 3-(1,4-dimethyl-1H-benzo[d][1,2,3]triazol-5-yl)-3-(3-hydroxy-2,3-dihydro-1H-inden-5-yl)-2,2-dimethylpropanoate

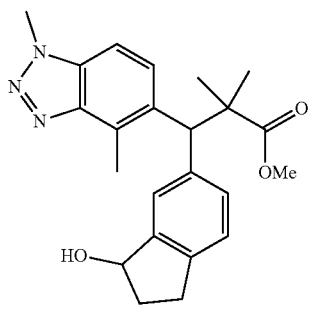 [SMILES: COC(=O)C(C)(C)C(c1ccc2c(c1)C(O)CC2)c1ccc2c(nnn2C)c1C]

To a solution of methyl 3-(1,4-dimethyl-1H-benzo[d][1,2,3]triazol-5-yl)-3-(3-((4-methoxybenzyl)oxy)-2,3-dihydro-1H-inden-5-yl)-2,2-dimethylpropanoate (5.9 g, 11.49 mmol) in chloroform (64 mL) and water (4 mL) was added DDQ (2.61 g, 11.49 mmol) at 0° C. The resulting mixture was stirred at 0° C. for two hours before adding EtOAc (120 mL) and NaHCO$_3$ (70 mL, sat. aq.). The organic layer was separated and the aqueous layer was extracted with ethyl acetate three times and the combined organic layer was washed with saturated NaHSO$_3$ aqueous solution, and brine. The solution was dried over anhydrous Na$_2$SO$_4$, filtered, evaporated down, purified with flash chromatography to afford desired product methyl 3-(1,4-dimethyl-1H-benzo[d][1,2,3]triazol-5-yl)-3-(3-hydroxy-2,3-dihydro-1H-inden-5-yl)-2,2-dimethylpropanoate (2.7 g, 6.70 mmol, 97.7% yield). LC-MS m/z 394.2 (M+H)$^+$, 1.86 min (ret. time).

3-(1,4-Dimethyl-1H-benzo[d][1,2,3]triazol-5-yl)-3-(3-(2,2-dimethyl-2,3-dihydrobenzo[f][1,4]oxazepin-4(5H)-yl)-2,3-dihydro-1H-inden-5-yl)-2,2-dimethylpropanoic Acid, 2 Formic Acid Salt

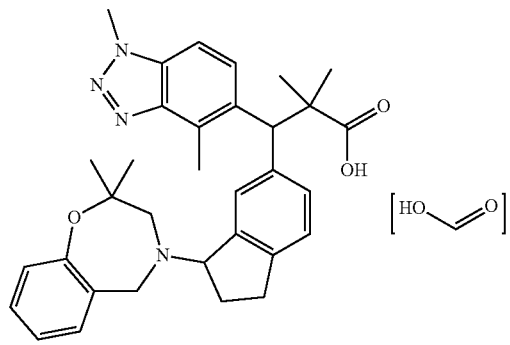

To a solution of methyl 3-(1,4-dimethyl-1H-benzo[d][1,2,3]triazol-5-yl)-3-(3-hydroxy-2,3-dihydro-1H-inden-5-yl)-2,2-dimethylpropanoate (79 mg, 0.2 mmol) in DCM (1.0 mL) was added SOCl$_2$ (0.029 mL, 0.400 mmol). The resulting reaction mixture was stirred at ambient temperature for 15 min, evaporated under vacuum and dissolved in acetonitrile (3 mL). To this solution was added 2,2-dimethyl-2,3,4,5-tetrahydrobenzo[f][1,4]oxazepine, hydrochloride (85 mg, 0.400 mmol), sodium iodide (14.99 mg, 0.100 mmol) and K$_2$CO$_3$ (83 mg, 0.600 mmol). The resulting reaction mixture was heated at 40° C. for 68 h. The reaction mixture was filtered. The filter cake was washed with MeCN (2 mL). The combined filtrate was evaporated down, dissolved in methanol (3 mL) after which NaOH (3 N) (0.533 mL, 1.600 mmol) was added. The resulting reaction mixture was heated with microwave at 130° C. for 1 h. The reaction mixture was acidified with HCl (3 N) to pH 4-5, evaporated under vacuum, and purified by reverse phase HPLC to afford product 3-(1,4-dimethyl-1H-benzo[d][1,2,3]triazol-5-yl)-3-(3-(2,2-dimethyl-2,3-dihydrobenzo[f][1,4]oxazepin-4(5H)-yl)-2,3-dihydro-1H-inden-5-yl)-2,2-dimethylpropanoic acid, 2 formic acid salt (21.6 mg, 0.034 mmol, 17.12% yield). LC-MS m/z 539.5 (M+H)$^+$, 0.80 min (ret. time).

Example 28

3-(3-(7-Cyano-2,2-dimethyl-2,3-di hydrobenzo[f][1,4]oxazepin-4(5H)-yl)-2,3-dihydro-1H-inden-5-yl)-3-(1,4-dimethyl-1H-benzo[d][1,2,3]triazol-5-yl)propanoic Acid, Formic Acid Salt

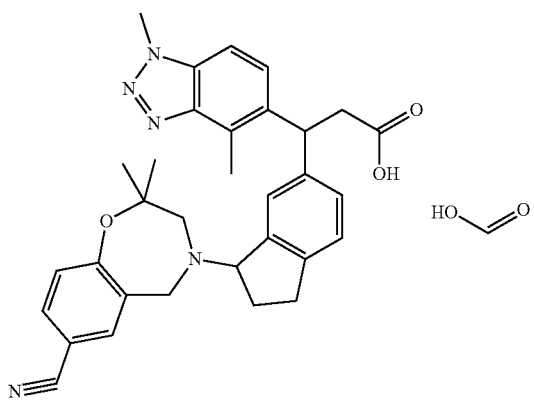 [SMILES: Cc1c(C(CC(=O)O)c2ccc3c(c2)C(N2Cc4cc(C#N)ccc4OC(C)(C)C2)CC3)ccc2c1nnn2C ; O=CO]

2,2-Dimethyl-2,3,4,5-tetrahydrobenzo[f][1,4]oxazepine-7-carbonitrile

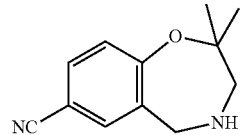

To a solution of tert-butyl 7-bromo-2,2-dimethyl-2,3-dihydrobenzo[f][1,4]oxazepine-4(5H)-carboxylate (300 mg, 0.842 mmol) in N,N-dimethylformamide (5 mL) at ambient temperature was added $Zn(CN)_2$ (99 mg, 0.842 mmol). The reaction mixture was degassed for 20 min, followed by the addition of tetrakis(triphenylphosphine)palladium(0) (97 mg, 0.084 mmol). The reaction mixture was heated in microwave reactor for 1 h at 95° C. The reaction mixture was concentrated and purified with silica gel chromatography to afford the title compound (90 mg, 0.101 mmol, 12.02% yield) as a liquid. LC-MS m/z 203.21 (M+H)$^+$, 1.22 min (ret. time).

The compounds in Table 3 were prepared by a method similar to the one described for the preparation of 2,2-dimethyl-2,3,4,5-tetrahydrobenzo[f][1,4]oxazepine-7-carbonitrile. As is appreciated by those skilled in the art, these analogous examples may involve variations in general reaction conditions.

TABLE 3

| Reagent | Product Name | Product Structure | (M + H)$^+$ | Ret. Time (min) |
|---|---|---|---|---|
| 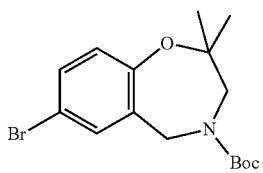 [SMILES: CC(C)(C)OC(=O)N1Cc2cc(Br)ccc2OC(C)(C)C1] | 2,2-dimethy1-2,3,4,5-tetrahydrobenzo[f][1,4]oxazepine-8-carbonitrile | 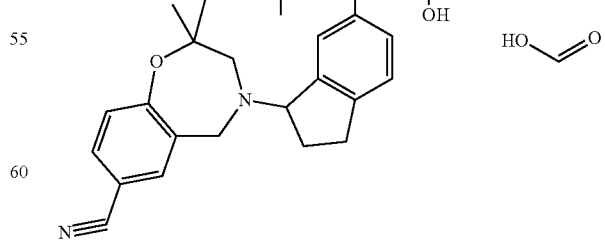 | 203.2 | 1.17 |

Tert-Butyl 7-bromo-2,2-dimethyl-2,3-dihydrobenzo[f][1,4]oxazepine-4(5H)-carboxylate To a solution of 7-bromo-2,2-dimethyl-2,3,4,5-tetrahydrobenzo[f][1,4]oxazepine (700 mg, 2.73 mmol) in DCM (5 mL) at ambient temperature was added TEA (0.381 mL, 2.73 mmol). Tert-butyl dicarbonate (596 mg, 2.73 mmol) was added at 0° C. The reaction mixture was stirred at ambient temperature for 1 h. It was diluted with water and extracted with ethyl acetate, dried over $Na_2SO_4$, filtered and concentrated. The crude residue was purified with silica gel chromatography to afford the title compound (900 mg, 2.444 mmol, 89% yield) as a liquid. LC-MS m/z 300.13 (M+H)$^+$, 4.23 min (ret. time)

3-(3-(7-Cyano-2,2-dimethyl-2,3-di hydrobenzo[f][1,4]oxazepin-4(5H)-yl)-2,3-dihydro-1H-inden-5-yl)-3-(1,4-dimethyl-1H-benzo[d][1,2,3]triazol-5-y)propanoic Acid, Formic Acid Salt To a solution of 2,2-dimethyl-2,3,4,5-tetrahydrobenzo[f][1,4]oxazepine-7-carbonitrile, hydrochloride (95 mg, 0.400 mmol) in methanol (3 mL) was added $K_2CO_3$ (55.3 mg, 0.400 mmol). The resulting reaction mixture was stirred at ambient temperature for 30 min, evaporated under vacuum. To the resulting residue was added acetonitrile (3 mL) and stirred at ambient temperature for 10 min before being filtered to afford acetonitrile solution A.

To a solution of ethyl 3-(1,4-dimethyl-1H-benzo[d][1,2,3]triazol-5-yl)-3-(3-hydroxy-2,3-dihydro-1H-inden-5-yl) propanoate (76 mg, 0.2 mmol) in DCM (1.000 mL) was added SOCl₂ (0.029 mL, 0.400 mmol). The resulting reaction mixture was stirred at ambient temperature for 20 min then was evaporated under vacuum before adding the above acetonitrile solution A, sodium iodide (14.99 mg, 0.100 mmol) and K₂CO₃ (55.3 mg, 0.400 mmol). The resulting reaction mixture was heated at 40° C. for 22 h. The reaction mixture was filtered. The filter cake was washed with MeCN (2 mL). The combined filtrate was evaporated under vacuum, dissolved in methanol (3 mL). NaOH (3 N) (0.533 mL, 1.600 mmol) was. The resulting reaction mixture was heated with microwave at 80° C. for 20 min. The reaction mixture was acidified with HCl (3 N) to pH 4-5, evaporated under vacuum, and purified by reverse phase HPLC to afford product 3-(3-(7-cyano-2,2-dimethyl-2,3-dihydrobenzo[f][1,4]oxazepin-4(5H)-yl)-2,3-dihydro-1H-inden-5-yl)-3-(1,4-dimethyl-1H-benzo[d][1,2,3]triazol-5-yl)propanoic acid, formic acid salt (36.3 mg, 0.064 mmol, 32.0% yield). LC-MS m/z 536.4 (M+H)⁺, 0.80 min (ret. time).

Example 29

3-(3-(2,2-Dimethyl-2,3-di hydrobenzo[f][1,4]oxazepin-4(5H)-yl)-2,3-dihydro-1H-inden-5-yl)-3-(7-methoxy-1,4-dimethyl-1H-benzo[d][1,2,3]triazol-5-yl)propanoic Acid, Formic Acid Salt

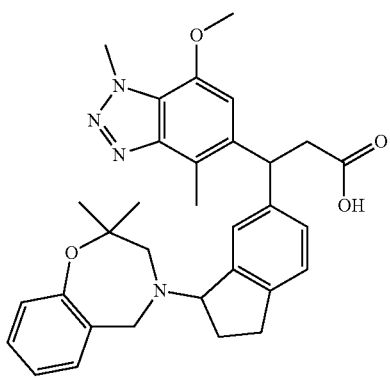 [SMILES: COc1cc(C(CC(=O)O)c2ccc3c(c2)C(N2Cc4ccccc4OC(C)(C)C2)CC3)c(C)c2nnn(C)c12]

5-Bromo-7-iodo-1,4-dimethyl-1H-benzo[d][1,2,3]triazole

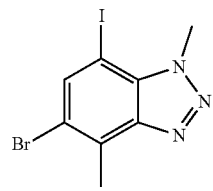

Sodium periodate (0.378 g, 1.769 mmol) was suspended in a stirred mixture of acetic acid (2 mL) with Ac₂O (2.98 mL, 31.5 mmol) cooled to 5-10° C. Concentrated H₂SO₄ (1.792 mL, 33.6 mmol) was very slowly added dropwise. 5-Bromo-1,4-dimethyl-1H-benzo[d][1,2,3]triazole (1 g, 4.42 mmol) was added, and the stirring was continued for 16 h at ambient temperature. The reaction mixture was poured into ice-water containing previously dissolved Na₂SO₃. After 15 minutes, the collected precipitate was worked up with EtOAc and Na₂SO₃ solution. The crude product was then purified on a silica cartridge (40 g) with a Combiflash Companion, eluting at 40 mL/min with a gradient running from 100% hexanes to 80% EtOAc/hexanes over 35 min to afford the title compound (286 mg, 18.34%). LC-MS m/z 351.9, 353.9 (M+H)⁺, 1.03 (ret. time).

5-Bromo-7-methoxy-1,4-dimethyl-1H-benzo[d][1,2,3]triazole

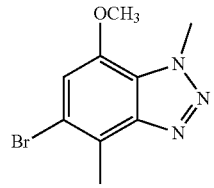

To a solution of 5-bromo-7-iodo-1,4-dimethyl-1H-benzo[d][1,2,3]triazole (286 mg, 0.813 mmol) in methanol (5 mL) at ambient temperature, copper(I) iodide (77 mg, 0.406 mmol) and Cs₂CO3 (530 mg, 1.625 mmol) were added. The reaction mixture was stirred at 110° C. for 40 minutes. The solvent was evaporated under reduced pressure. The crude product was then purified on a silica cartridge (12 g) with a Combiflash Companion, eluting at 20 mL/min with a gradient running from 100% hexanes to 80% EtOAc/hexanes over 35 min to afford the title compound (68 mg, 32.7%). LC-MS m/z 256.1, 258.0 (M+H)⁺, 0.91 (ret. time).

(E)-Ethyl 3-(7-methoxy-1,4-dimethyl-1H-benzo[d][1,2,3]triazol-5-yl)acrylate

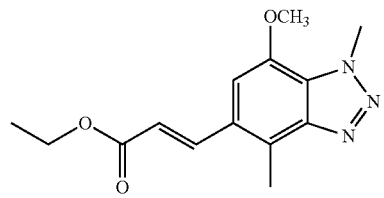 [SMILES: CCOC(=O)/C=C/c1cc(OC)c2c(nnn2C)c1C]

To a solution of 5-bromo-7-methoxy-1,4-dimethyl-1H-benzo[d][1,2,3]triazole (88 mg, 0.344 mmol) in N,N-dimethylformamide (1 mL), ethyl acrylate (206 mg, 2.062 mmol), DIPEA (0.240 mL, 1.374 mmol) and palladium(II) acetate (11.57 mg, 0.052 mmol) were added. The reaction mixture was heated in a microwave at 110° C. for 1 h. Water was added to quench the reaction. Ethyl acetate was added, and the layers were separated. The aqueous layer was extracted once with ethyl acetate, and the combined organic layers were washed once with brine. The organic layer was concentrated. The crude product was then purified on a silica cartridge (40 g) with a Combiflash Companion, eluting at 40 mL/min with a gradient running from 100% hexanes to 80% EtOAc/hexanes over 35 min to afford the title compound (90 mg, 95%). LC-MS m/z 276.1 (M+H)⁺, 0.93 (ret. time).

Methyl 3-(3-hydroxy-2,3-dihydro-1H-inden-5-yl)-3-(7-methoxy-,4-dimethyl-1H-benzo[d][1,2,3]triazol-5-yl)propanoate

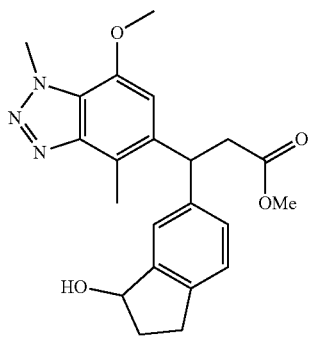 [SMILES: COC(=O)CC(c1ccc2c(c1)C(O)CC2)c1cc(OC)c2c(nnn2C)c1C]

To a solution of (E)-methyl 3-(7-methoxy-1,4-dimethyl-1H-benzo[d][1,2,3]triazol-5-yl)acrylate (0.653 g, 2.50 mmol) in 1,4-dioxane (12 mL) and water (4 mL) was added 6-(4,4,5,5-tetramethyl-1,3,2-dioxaborolan-2-yl)-2,3-dihydro-1H-inden-1-ol (0.976 g, 3.75 mmol), TEA (1.045 mL, 7.50 mmol) and [Rh(cod)Cl]₂ (0.062 g, 0.125 mmol). The resulting reaction mixture was stirred at 90° C. for 2 h. The reaction mixture was evaporated under vacuum and purified via flash chromatography to afford product methyl 3-(3-hydroxy-2,3-dihydro-1H-inden-5-yl)-3-(7-methoxy-1,4-dimethyl-1H-benzo[d][1,2,3]triazol-5-yl)propanoate (0.2238 g, 0.566 mmol, 22.64% yield). LC-MS m/z 396.1 (M+H)⁺, 0.92 min (ret. time).

Methyl 3-(3-chloro-2,3-dihydro-1H-inden-5-yl)-3-(7-methoxy-,4-dimethyl-1H-benzo[d][1,2,3]triazol-5-yl)propanoate

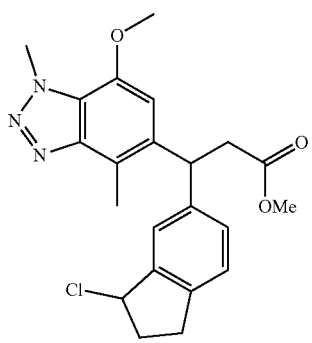 [SMILES: COC(=O)CC(c1ccc2c(c1)C(Cl)CC2)c1cc(OC)c2c(nnn2C)c1C]

To a solution of methyl 3-(3-hydroxy-2,3-dihydro-1H-inden-5-yl)-3-(7-methoxy-1,4-dimethyl-1H-benzo[d][1,2,3]triazol-5-yl)propanoate (0.158 g, 0.4 mmol) in DCM (2 mL) was added SOCl₂ (0.058 mL, 0.800 mmol). The resulting reaction mixture was stirred at ambient temperature for 2 h. The reaction was evaporated under vacuum to afford product methyl 3-(3-chloro-2,3-dihydro-1H-inden-5-yl)-3-(7-methoxy-1,4-dimethyl-1H-benzo[d][1,2,3]triazol-5-yl)propanoate (0.1959 g, 0.473 mmol, 118% yield). LC-MS m/z 410.1 (M−Cl+MeOH)⁺, 1.07 min (ret. time).

3-(3-(2,2-Dimethyl-2,3-di hydrobenzo[f][1,4]oxazepin-4(5H)-yl)-2,3-dihydro-1H-inden-5-yl)-3-(7-methoxy-1,4-dimethyl-1H-benzo[d][1,2,3]triazol-5-yl)propanoic Acid, Formic Acid Salt

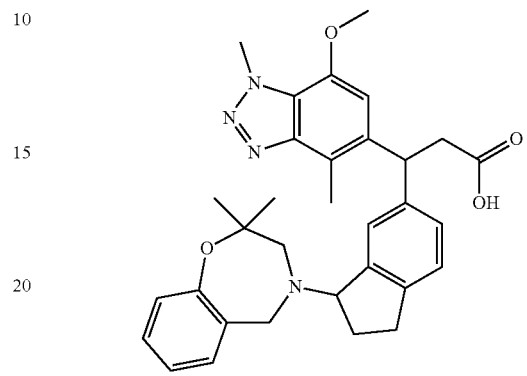

To a solution of 2,2-dimethyl-2,3,4,5-tetrahydrobenzo[f][1,4]oxazepine, hydrochloride (73.6 mg, 0.344 mmol) and K₂CO₃ (127 mg, 0.918 mmol) in acetonitrile (2 mL) was added sodium iodide (17.20 mg, 0.115 mmol) and methyl 3-(3-chloro-2,3-dihydro-1H-inden-5-yl)-3-(7-methoxy-1,4-dimethyl-1H-benzo[d][1,2,3]triazol-5-yl)propanoate (95 mg, 0.230 mmol). The resulting solution was heated at 50° C. for 16 h. The reaction mixture was filtered. The filter cake was washed with MeCN (2 mL). The combined filtrate was evaporated under vacuum before being diluted with methanol (2.000 mL) then NaOH (2 N) (0.552 mL, 0.230 mmol) was added. The resulting reaction mixture was heated with microwave at 80° C. for 15 min. The reaction mixture was acidified with HCl (1 N) to pH~5, evaporated under vacuum, and purified by reverse phase HPLC to afford product 3-(3-(2,2-dimethyl-2,3-dihydrobenzo[f][1,4]oxazepin-4(5H)-yl)-2,3-dihydro-1H-inden-5-yl)-3-(7-methoxy-1,4-dimethyl-1H-benzo[d][1,2,3]triazol-5-yl)propanoic acid, formic acid salt (51.8 mg, 0.096 mmol, 41.7% yield). LC-MS m/z 541.4 (M+H)⁺, 0.79 min (ret. time).

Example 30

3-(1,4-Dimethyl-1H-benzo[d][1,2,3]triazol-5-yl)-3-(3-((R)-2-ethyl-2,3-dihydrobenzo[f][1,4]oxazepin-4(5H)-yl)-2,3-dihydro-1H-inden-5-yl)-2,2-dimethylpropanoic Acid, Formic Acid Salt

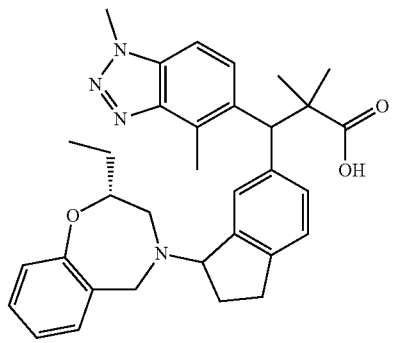 [SMILES: CC[C@@H]1CN(C2CCc3ccc(C(c4ccc5c(nnn5C)c4C)C(C)(C)C(=O)O)cc32)Cc2ccccc2O1]

3-(3-Chloro-2,3-dihydro-1H-inden-5-yl)-3-(1,4-dimethyl-1H-benzo[d][1,2,3]triazol-5-yl)-2,2-dimethylpropanoate

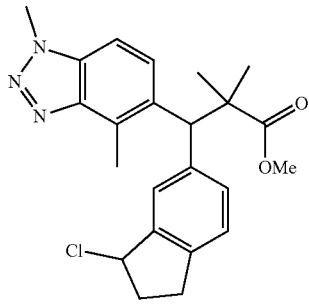 [SMILES: COC(=O)C(C)(C)C(c1ccc2c(c1)C(Cl)CC2)c1ccc2c(nnn2C)c1C]

To a solution of methyl 3-(1,4-dimethyl-1H-benzo[d][1,2,3]triazol-5-yl)-3-(3-hydroxy-2,3-dihydro-1H-inden-5-yl)-2,2-dimethylpropanoate (550 mg, 1.398 mmol) in DCM (3 mL) was added SOCl$_2$ (0.306 mL, 4.19 mmol). The resulting reaction mixture was stirred at ambient temperature for 2 h. The reaction was evaporated under vacuum to afford product methyl 3-(3-chloro-2,3-dihydro-1H-inden-5-yl)-3-(1,4-dimethyl-1H-benzo[d][1,2,3]triazol-5-yl)-2,2-dimethylpropanoate (598.6 mg, 1.453 mmol, 104% yield). LC-MS m/z 408.1 (M−Cl+MeOH)$^+$, 1.11 min (ret. time).

3-(1,4-Dimethyl-1H-benzo[d][1,2,3]triazol-5-yl)-3-(3-((R)-2-ethyl-2,3-dihydrobenzo[f][1,4]oxazepin-4(5H)-yl)-2,3-dihydro-1H-inden-5-yl)-2,2-dimethylpropanoate

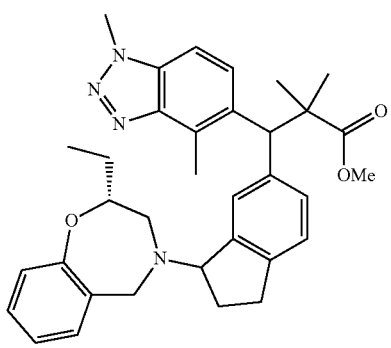 [SMILES: CC[C@@H]1CN(C2CCc3ccc(C(c4ccc5c(nnn5C)c4C)C(C)(C)C(=O)OC)cc32)Cc2ccccc2O1]

To a solution of (R)-2-ethyl-2,3,4,5-tetrahydrobenzo[f][1,4]oxazepine, hydrochloride (125 mg, 0.583 mmol) in acetonitrile (2 mL) was added K$_2$CO$_3$ (215 mg, 1.554 mmol). The resulting solution was stirred at ambient temperature for 20 min and followed by addition of sodium iodide (18.19 mg, 0.121 mmol) and a solution of methyl 3-(3-chloro-2,3-dihydro-1H-inden-5-yl)-3-(1,4-dimethyl-1H-benzo[d][1,2,3]triazol-5-yl)-2,2-dimethylpropanoate (160 mg, 0.388 mmol) in acetonitrile (2 mL). The resulting solution was heated with 50° C. for 19 h. The reaction mixture was filtered. The filter cake was washed with MeCN (3 mL).

Another reaction of (R)-2-ethyl-2,3,4,5-tetrahydrobenzo[f][1,4]oxazepine, hydrochloride (78 mg, 0.364 mmol) in acetonitrile (2.5 mL) was added K$_2$CO$_3$ (134 mg, 0.971 mmol). The resulting solution was stirred at ambient temperature for 20 min and added sodium iodide (18.19 mg, 0.121 mmol) and methyl 3-(3-chloro-2,3-dihydro-1H-inden-5-yl)-3-(1,4-dimethyl-1H-benzo[d][1,2,3]triazol-5-yl)-2,2-dimethylpropanoate (100 mg, 0.243 mmol). The resulting solution was heated with 50° C. for 16 h before being filtered.

The combined filtrate was evaporated under vacuum. The residue was purified via flash chromatography to afford product methyl 3-(1,4-dimethyl-1H-benzo[d][1,2,3]triazol-5-yl)-3-(3-((R)-2-ethyl-2,3-dihydrobenzo[f][1,4]oxazepin-4(5H)-yl)-2,3-dihydro-1H-inden-5-yl)-2,2-dimethylpropanoate (202.5 mg, 0.366 mmol, 39% yield). LC-MS m/z 553.3 (M+H)$^+$, 0.96 min (ret. time).

3-(1,4-Dimethyl-1H-benzo[d][1,2,3]triazol-5-yl)-3-(3-((R)-2-ethyl-2,3-dihydrobenzo[f][1,4]oxazepin-4(5H)-yl)-2,3-dihydro-1H-inden-5-yl)-2,2-dimethylpropanoic Acid

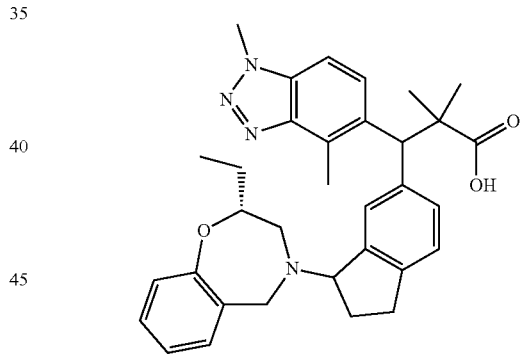

To a solution of methyl 3-(1,4-dimethyl-1H-benzo[d][1,2,3]triazol-5-yl)-3-(3-((R)-2-ethyl-2,3-di hydrobenzo[f][1,4]oxazepin-4(5H)-yl)-2,3-dihydro-1H-inden-5-yl)-2,2-dimethylpropanoate (202.5 mg, 0.366 mmol) in methanol (5 mL) was added NaOH (2 N) (73.3 mg, 1.832 mmol). The resulting solution was heated with microwave at 120° C. for 5 h. The reaction mixture was acidified with HCl (1 N) to pH~5, evaporated under vacuum, and purified by reverse phase HPLC to afford product 3-(1,4-dimethyl-1H-benzo[d][1,2,3]triazol-5-yl)-3-(3-((R)-2-ethyl-2,3-dihydrobenzo[f][1,4]oxazepin-4(5H)-yl)-2,3-dihydro-1H-inden-5-yl)-2,2-dimethylpropanoic acid (34 mg, 0.063 mmol, 17.23% yield). LC-MS m/z 539.5 (M+H)$^+$, 0.85 min (ret. time).

Example 31

3-(1,4-Dimethyl-1H-benzo[d][1,2,3]triazol-5-yl)-3-(3-((R)-2,7-dimethyl-2,3-dihydrobenzo[f][1,4]oxazepin-4(5H)-yl)-2,3-dihydro-1H-inden-5-yl)-2,2-dimethylpropanoic Acid, Formic Acid Salt

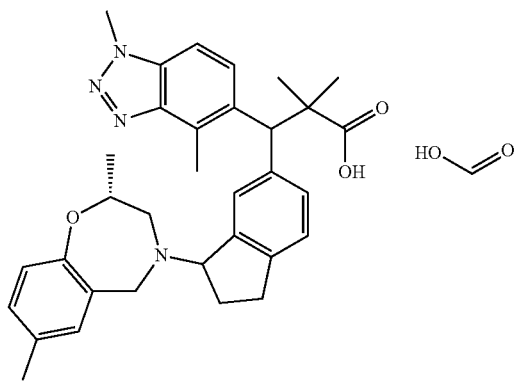 [SMILES: Cc1ccc2c(c1)CN(C1CCc3ccc(C(c4ccc5c(nnn5C)c4C)C(C)(C)C(=O)O)cc31)C[C@@H](C)O2 ; O=CO]

(R)-2,7-dimethyl-2,3,4,5-tetrahydrobenzo[f][1,4]oxazepine

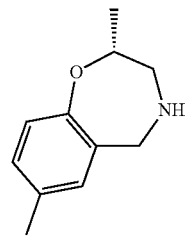

To a solution of (R)-1-aminopropan-2-ol (0.394 mL, 5.00 mmol) in methanol (25 mL) was added 2-bromo-5-methylbenzaldehyde (995 mg, 5 mmol). The resulting reaction mixture was stirred at ambient temperature for 15 min. before adding NaBH$_4$ (76 mg, 2.000 mmol) slowly. The resulting reaction mixture was stirred at ambient temperature for 67 h, evaporated under vacuum, redissolved in DCM (20 mL), dried over MgSO$_4$, filtered, evaporated under vacuum and dissolved in isopropanol (20 mL). Copper(I) iodide (95 mg, 0.500 mmol), and K$_2$CO$_3$ (1382 mg, 10.00 mmol) was added. The resulting reaction mixture was heated with microwave at 130° C. for 60 min. The reaction mixture was evaporated under vacuum, redissolved in DCM (20 mL), dried over MgSO$_4$, filtered, evaporated under vacuum to afford product (R)-2,7-dimethyl-2,3,4,5-tetrahydrobenzo[f][1,4]oxazepine (727.0 mg, 4.10 mmol, 82% yield). LC-MS m/z 178.0 (M+H)$^+$, 0.50 min (ret. time).

3-(1,4-Dimethyl-1H-benzo[d][1,2,3]triazol-5-yl)-3-(3-((R)-2,7-dimethyl-2,3-dihydrobenzo[f][1,4]oxazepin-4(5H)-yl)-2,3-dihydro-1H-inden-5-yl)-2,2-dimethylpropanoic Acid, Formic Acid Salt

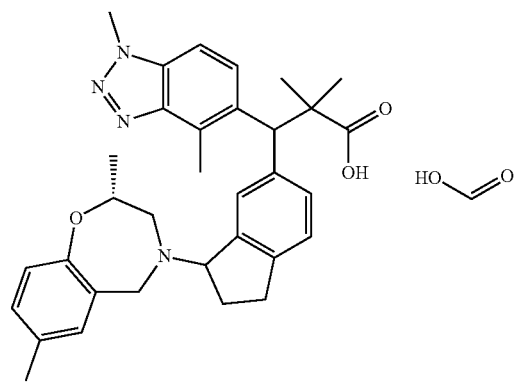 [SMILES: Cc1ccc2c(c1)CN(C1CCc3ccc(C(c4ccc5c(nnn5C)c4C)C(C)(C)C(=O)O)cc31)C[C@@H](C)O2 ; O=CO]

To a solution of methyl 3-(1,4-dimethyl-1H-benzo[d][1,2,3]triazol-5-yl)-3-(3-hydroxy-2,3-dihydro-1H-inden-5-yl)-2,2-dimethylpropanoate (79 mg, 0.2 mmol) in DCM (1.000 mL) was added SOCl$_2$ (0.029 mL, 0.400 mmol). The resulting reaction mixture was stirred at ambient temperature for 15 min, evaporated under vacuum, dissolved in acetonitrile (2 mL) then added (R)-2,7-dimethyl-2,3,4,5-tetrahydrobenzo[f][1,4]oxazepine (70.9 mg, 0.400 mmol), sodium iodide (14.99 mg, 0.100 mmol) and K$_2$CO$_3$ (55.3 mg, 0.400 mmol). The resulting reaction mixture was heated at 40° C. for 92 h. The reaction mixture was filtered. The filter cake was washed with MeCN (2 mL). The combined filtrate was evaporated under vacuum, dissolved in methanol (2 mL). NaOH (3 N) (0.533 mL, 1.600 mmol) was added. The resulting reaction mixture was heated with microwave at 120° C. for 2 h. The reaction mixture was acidified with HCl (3 N) to pH 4-5, evaporated under vacuum, and purified by reverse phase HPLC to afford product 3-(1,4-dimethyl-1H-benzo[d][1,2,3]triazol-5-yl)-3-(3-((R)-2,7-dimethyl-2,3-dihydrobenzo[f][1,4]oxazepin-4(5H)-yl)-2,3-dihydro-1H-inden-5-yl)-2,2-dimethylpropanoic acid, formic acid salt (36.8 mg, 0.065 mmol, 32.5% yield). LC-MS m/z 539.5 (M+H)$^+$, 0.82 min (ret. time).

Example 32

3-(1,4-Dimethyl-1H-benzo[d][1,2,3]triazol-5-yl)-2,2-dimethyl-3-(3-((R)-2-methyl-2,3-dihydrobenzo[f][1,4]oxazepin-4(5H)-yl)-2,3-dihydro-1H-inden-5-yl)propanoic Acid, Formic Acid Salt

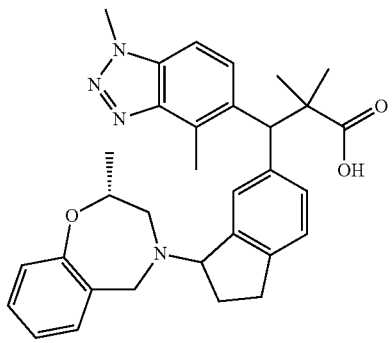 [SMILES: Cc1c(C(c2ccc3c(c2)C(N2Cc4ccccc4O[C@H](C)C2)CC3)C(C)(C)C(=O)O)ccc2c1nnn2C]

Methyl 3-(1,4-dimethyl-1H-benzo[d][1,2,3]triazol-5-yl)-2,2-dimethyl-3-(3-((R)-2-methyl-2,3-dihydrobenzo[f][1,4]oxazepin-4(5H)-yl)-2,3-dihydro-1H-inden-5-yl)propanoate

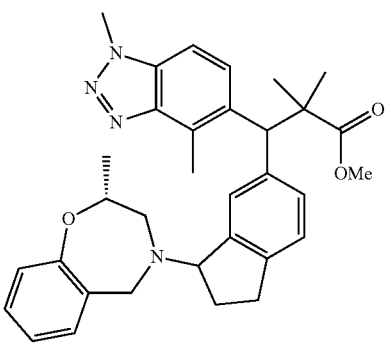 [SMILES: COC(=O)C(C)(C)C(c1ccc2c(c1)C(N1Cc3ccccc3O[C@H](C)C1)CC2)c1ccc2c(nnn2C)c1C]

To a solution of (R)-2-methyl-2,3,4,5-tetrahydrobenzo[f][1,4]oxazepine, hydrochloride (72.7 mg, 0.364 mmol) in acetonitrile (2.5 mL) was added $K_2CO_3$ (134 mg, 0.971 mmol). The resulting solution was stirred at ambient temperature for 20 min after which time sodium iodide (18.19 mg, 0.121 mmol) and methyl 3-(3-chloro-2,3-dihydro-1H-inden-5-yl)-3-(1,4-dimethyl-1H-benzo[d][1,2,3]triazol-5-yl)-2,2-dimethylpropanoate (100 mg, 0.243 mmol) were added. The resulting solution was heated at 50° C. for 16 h. The reaction mixture was filtered. The filter cake was washed with MeCN (2 mL). The combined filtrate was evaporated under vacuum and the residue was purified via flash chromatography to afford product methyl 3-(1,4-dimethyl-1H-benzo[d][1,2,3]triazol-5-yl)-2,2-dimethyl-3-(3-((R)-2-methyl-2,3-dihydrobenzo[f][1,4]oxazepin-4(5H)-yl)-2,3-dihydro-1H-inden-5-yl)propanoate (98.4 mg, 0.183 mmol, 75% yield). LC-MS m/z 539.2 (M+H)$^+$, 0.93 min (ret. time).

3-(1,4-Dimethyl-1H-benzo[d][1,2,3]triazol-5-yl)-2,2-dimethyl-3-(3-((R)-2-methyl-2,3-dihydrobenzo[f][1,4]oxazepin-4(5H)-yl)-2,3-dihydro-1H-inden-5-yl)propanoic Acid

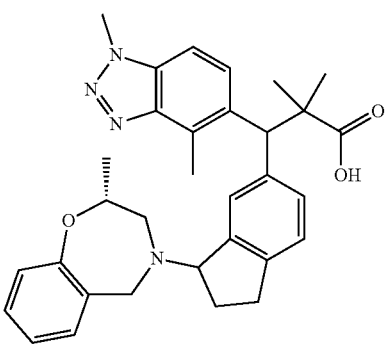 [SMILES: Cc1c(C(c2ccc3c(c2)C(N2Cc4ccccc4O[C@H](C)C2)CC3)C(C)(C)C(=O)O)ccc2c1nnn2C]

To a solution of methyl 3-(1,4-dimethyl-1H-benzo[d][1,2,3]triazol-5-yl)-2,2-dimethyl-3-(3-((R)-2-methyl-2,3-dihydrobenzo[f][1,4]oxazepin-4(5H)-yl)-2,3-dihydro-1H-inden-5-yl)propanoate (98 mg, 0.182 mmol) in methanol (3 mL) was added NaOH (2 N) (36.4 mg, 0.910 mmol). The resulting solution was heated with microwave at 120° C. for 7 h. The reaction mixture was acidified with HCl (1 N) to pH~5, evaporated under vacuum, and purified by reverse phase HPLC to afford product 3-(1,4-dimethyl-1H-benzo[d][1,2,3]triazol-5-yl)-2,2-dimethyl-3-(3-((R)-2-methyl-2,3-dihydrobenzo[f][1,4]oxazepin-4(5H)-yl)-2,3-dihydro-1H-inden-5-yl)propanoic acid (46.2 mg, 0.088 mmol), 48.4% yield. LC-MS m/z 525.6 (M+H)$^+$, 0.78 min (ret. time).

Example 33

3-(1,4-Dimethyl-1H-benzo[d][1,2,3]triazol-5-yl)-3-(3-(2,2-dimethyl-2,3-dihydropyrido[3,4-f][1,4]oxazepin-4(5H)-yl)-2,3-dihydro-1H-inden-5-yl)-2,2-dimethylpropanoic Acid, Trifluoroacetic Acid Salt

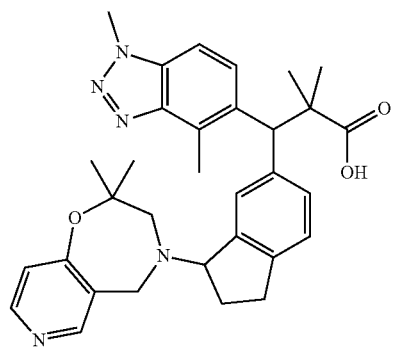 [SMILES: Cc1c(C(c2ccc3c(c2)C(N2Cc4cnccc4OC(C)(C)C2)CC3)C(C)(C)C(=O)O)ccc2c1nnn2C]

To a solution of 2,2-dimethyl-2,3,4,5-tetrahydropyrido[3,4-f][1,4]oxazepine, hydrochloride (86 mg, 0.400 mmol) in methanol (3 mL) was added $K_2CO_3$ (83 mg, 0.600 mmol). The resulting reaction mixture was stirred at ambient temperature for 50 min, evaporated under vacuum followed by addition of acetonitrile (3 mL), filtered to afford the acetonitrile solution A. To the solution of methyl 3-(1,4-dimethyl-1H-benzo[d][1,2,3]triazol-5-yl)-3-(3-hydroxy-2,3-dihydro-1H-inden-5-yl)-2,2-dimethylpropanoate (79 mg, 0.2 mmol) in DCM (1.0 mL) was added $SOCl_2$ (0.029 mL, 0.400 mmol). The resulting reaction mixture was stirred at ambient temperature for 25 min, evaporated under vacuum followed by addition of the above acetonitrile solution A, sodium iodide (14.99 mg, 0.100 mmol) and $K_2CO_3$ (83 mg, 0.600 mmol). The resulting reaction mixture was heated at 40° C. for 20 h. The reaction mixture was filtered. The filter cake was washed with MeCN (2 mL). The combined filtrate was evaporated under vacuum then was redissolved in methanol (3 mL) followed by addition of NaOH (3 N) (0.533 mL, 1.600 mmol). The resulting reaction mixture was heated with microwave at 130° C. for 1 h then was acidified with HCl (3 N) to pH 4-5, evaporated under vacuum, and purified by reverse phase HPLC to afford the desired product 3-(1,4-dimethyl-1H-benzo[d][1,2,3]triazol-5-yl)-3-(3-(2,2-dimethyl-2,3-dihydropyrido[3,4-f][1,4]oxazepin-4(5H)-yl)-2,3-dihydro-1H-inden-5-yl)-2,2-dimethylpropanoic acid, trifluoroacetic acid salt (56.9 mg, 0.105 mmol, 52.7% yield). LC-MS m/z 540.4 (M+H)$^+$, 0.85 min (ret. time).

Example 34

3-(1,4-Dimethyl-1H-benzo[d][1,2,3]triazol-5-yl)-3-(3-(2,2-dimethyl-2,3-dihydropyrido[3,2-f][1,4]oxazepin-4(5H)-yl)-2,3-dihydro-1H-inden-5-yl)-2,2-dimethylpropanoic Acid, Formic Acid Salt

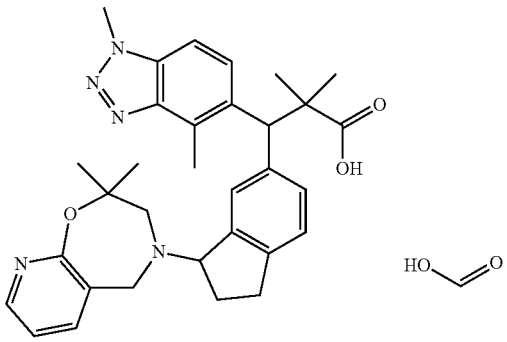 [SMILES: Cc1c(C(c2ccc3c(c2)C(N2Cc4cccnc4OC(C)(C)C2)CC3)C(C)(C)C(=O)O)ccc2c1nnn2C ; O=CO]

To a solution of methyl 3-(1,4-dimethyl-1H-benzo[d][1,2,3]triazol-5-yl)-3-(3-hydroxy-2,3-dihydro-1H-inden-5-yl)-2,2-dimethylpropanoate (79 mg, 0.2 mmol) in DCM (1.0 mL) was added $SOCl_2$ (0.029 mL, 0.400 mmol). The resulting reaction mixture was stirred at ambient temperature for 20 min, evaporated under vacuum before being redissolved in acetonitrile (3 mL) after which 2,2-dimethyl-2,3,4,5-tetrahydropyrido[3,2-f][1,4]oxazepine (71.3 mg, 0.400 mmol), sodium iodide (14.99 mg, 0.100 mmol) and $K_2CO_3$ (55.3 mg, 0.400 mmol) were added. The resulting reaction mixture was heated at 40° C. for 20 h before being filtered. The filter cake was washed with MeCN (2 mL). The combined filtrate was evaporated under vacuum before being redissolved in methanol (3 mL) and was added NaOH (3 N) (0.533 mL, 1.600 mmol) then was heated with microwave at 140° C. for 60 min, acidified with HCl (3 N) to pH 4-5, evaporated under vacuum and purified by reverse phase HPLC to afford product 3-(1,4-dimethyl-1H-benzo[d][1,2,3]triazol-5-yl)-3-(3-(2,2-dimethyl-2,3-dihydropyrido[3,2-f][1,4]oxazepin-4(5H)-yl)-2,3-dihydro-1H-inden-5-yl)-2,2-dimethylpropanoic acid, formic acid salt (9.4 mg, 0.017 mmol, 8.42% yield). LC-MS m/z 540.2 (M+H)+, 0.80 min (ret. time).

Example 35

3-(3-(8-Cyano-2,2-dimethyl-2,3-di hydrobenzo[f][1,4]oxazepin-4(5H)-yl)-2,3-dihydro-1H-inden-5-yl)-3-(1,4-dimethyl-1H-benzo[d][1,2,3]triazol-5-yl)propanoic Acid, Formic Acid Salt

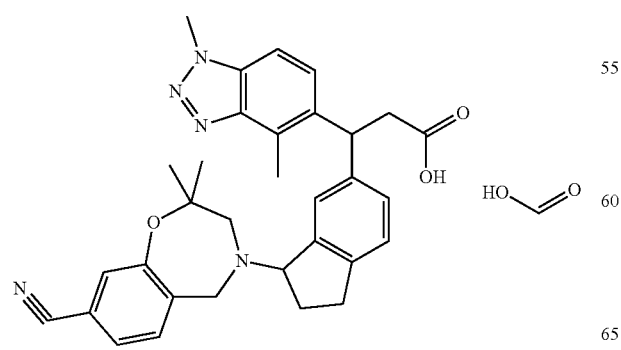

To a solution of 2,2-dimethyl-2,3,4,5-tetrahydrobenzo[f][1,4]oxazepine-8-carbonitrile, hydrochloride (0.063 g, 0.264 mmol) in methanol (2 mL) was added $K_2CO_3$ (0.036 g, 0.264 mmol). The resulting reaction mixture was stirred at ambient temperature for 30 min, evaporated under vacuum followed by addition of acetonitrile (2 mL) and stirred at ambient temperature for 10 min before being filter to afford the acetonitrile solution A.

To the solution of ethyl 3-(1,4-dimethyl-1H-benzo[d][1,2,3]triazol-5-yl)-3-(3-hydroxy-2,3-dihydro-1H-inden-5-yl)propanoate (0.050 g, 0.132 mmol) in DCM (1.0 mL) was added $SOCl_2$ (0.019 mL, 0.264 mmol). The resulting reaction mixture was stirred at ambient temperature for 15 min, evaporated down followed by addition of the above acetonitrile solution A, sodium iodide (9.88 mg, 0.066 mmol) and $K_2CO_3$ (0.036 g, 0.264 mmol). The resulting reaction mixture was heated at 40° C. for 19 h before being filtered. The filter cake was washed with MeCN (2 mL). The combined filtrate was evaporated under vacuum before being redissolved in methanol (2 mL) followed by addition of NaOH (3 N) (0.351 mL, 1.054 mmol). The resulting reaction mixture was heated with microwave at 80° C. for 20 min before being acidified with HCl (3 N) to pH 4-5, evaporated under vacuum, and purified by reverse phase HPLC to afford product 3-(3-(8-cyano-2,2-dimethyl-2,3-dihydrobenzo[f][1,4]oxazepin-4(5H)-yl)-2,3-dihydro-1H-inden-5-yl)-3-(1,4-dimethyl-1H-benzo[d][1,2,3]triazol-5-yl)propanoic acid, formic acid salt (8.5 mg, 0.015 mmol, 11.55% yield). LC-MS m/z 536.1 (M+H)+, 0.82 min (ret. time).

Example 36

3-(3-(2,2-Dimethyl-2,3-dihydropyrido[3,4-f][1,4]oxazepin-4(5H)-yl)-2,3-dihydro-1H-inden-5-yl)-3-(7-methoxy-1,4-dimethyl-1H-benzo[d][1,2,3]triazol-5-yl)propanoic Acid, Formic Acid Salt

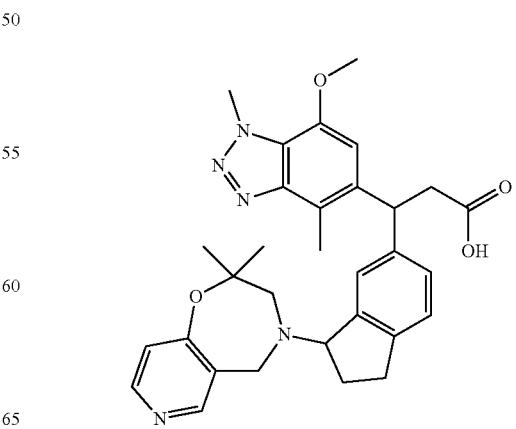

Methyl 3-(3-(2,2-dimethyl-2,3-dihydropyrido[3,4-f]
[1,4]oxazepin-4(5H)-yl)-2,3-dihydro-1H-inden-5-
yl)-3-(7-methoxy-1,4-dimethyl-1H-benzo[d][1,2,3]
triazol-5-yl)propanoate

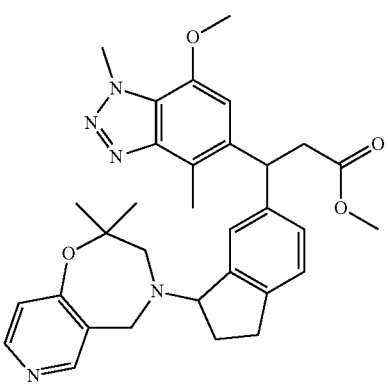 [SMILES: COC(=O)CC(c1ccc2c(c1)C(N1Cc3cnccc3OC(C)(C)C1)CC2)c1cc(OC)c2c(nnn2C)c1C]

To a solution of 2,2-dimethyl-2,3,4,5-tetrahydropyrido[3,4-f][1,4]oxazepine, hydrochloride (73.9 mg, 0.344 mmol) and $K_2CO_3$ (127 mg, 0.918 mmol) in acetonitrile (2 mL) was added sodium iodide (17.20 mg, 0.115 mmol) and methyl 3-(3-chloro-2,3-dihydro-1H-inden-5-yl)-3-(7-methoxy-1,4-dimethyl-1H-benzo[d][1,2,3]triazol-5-yl)propanoate (95 mg, 0.230 mmol). The resulting solution was heated with microwave at 50° C. for 16 h. The reaction mixture was evaporated down under vacuum and purified with flash chromatography to afford desired product methyl 3-(3-(2,2-dimethyl-2,3-dihydropyrido[3,4-f][1,4]oxazepin-4(5H)-yl)-2,3-dihydro-1H-inden-5-yl)-3-(7-methoxy-1,4-dimethyl-1H-benzo[d][1,2,3]triazol-5-yl)propanoate (41.9 mg, 0.075 mmol, 32.9% yield). LC-MS m/z 556.2 (M+H)$^+$, 0.96 min (ret. time).

3-(3-(2,2-Dimethyl-2,3-dihydropyrido[3,4-f][1,4]
oxazepin-4(5H)-yl)-2,3-dihydro-1H-inden-5-yl)-3-
(7-methoxy-1,4-dimethyl-1H-benzo[d][1,2,3]triazol-
5-yl)propanoic Acid, Formic Acid Salt

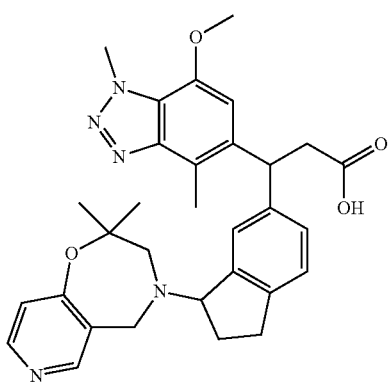 [SMILES: COc1cc(C(CC(=O)O)c2ccc3c(c2)C(N2Cc4cnccc4OC(C)(C)C2)CC3)c(C)c2nnn(C)c12]

To a solution of methyl 3-(3-(2,2-dimethyl-2,3-dihydropyrido[3,4-f][1,4]oxazepin-4(5H)-yl)-2,3-dihydro-1H-inden-5-yl)-3-(7-methoxy-1,4-dimethyl-1H-benzo[d][1,2,3]triazol-5-yl)propanoate (41.9 mg, 0.075 mmol) in methanol (2 mL) was added NaOH (2 N) (15.08 mg, 0.377 mmol). The resulting solution was heated with microwave at 80° C. for 15 min before being acidified with HCl (1 N) to pH~5, evaporated under vacuum, and purified by reverse phase HPLC to afford product 3-(3-(2,2-dimethyl-2,3-dihydropyrido[3,4-f][1,4]oxazepin-4(5H)-yl)-2,3-dihydro-1H-inden-5-yl)-3-(7-methoxy-1,4-dimethyl-1H-benzo[d][1,2,3]triazol-5-yl)propanoic acid, formic acid salt (32.9 mg, 0.061 mmol, 81% yield). LC-MS m/z 542.5 (M+H)$^+$, 0.82 min (ret. time).

Example 37

3-(1,4-Dimethyl-1H-benzo[d][1,2,3]triazol-5-yl)-3-
(3-((R)-2-ethyl-2,3-dihydropyrido[3,4-f][1,4]oxaze-
pin-4(5H)-yl)-2,3-dihydro-1H-inden-5-yl)-2,2-dim-
ethylpropanoic Acid, Formic Acid Salt

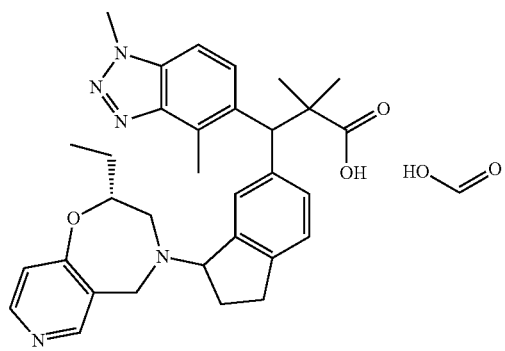 [SMILES: CC[C@@H]1CN(C2CCc3ccc(C(c4ccc5c(nnn5C)c4C)C(C)(C)C(=O)O)cc32)Cc2cnccc2O1 ; O=CO]

To a solution of (R)-2-ethyl-2,3,4,5-tetrahydropyrido[3,4-f][1,4]oxazepine, hydrochloride (86 mg, 0.400 mmol) in methanol (3 mL) was added $K_2CO_3$ (55.3 mg, 0.400 mmol). The resulting reaction mixture was stirred at ambient temperature for 30 min, evaporated under vacuum followed by addition of acetonitrile (3 mL) and stirred at ambient temperature for 20 min before being filter to afford the acetonitrile solution A.

To the solution of methyl 3-(1,4-dimethyl-1H-benzo[d][1,2,3]triazol-5-yl)-3-(3-hydroxy-2,3-dihydro-1H-inden-5-yl)-2,2-dimethylpropanoate (79 mg, 0.2 mmol) in DCM (1.000 mL) was added $SOCl_2$ (0.029 mL, 0.400 mmol). The resulting reaction mixture was stirred at ambient temperature for 10 min, evaporated under vacuum followed by addition of the above acetonitrile solution A, sodium iodide (14.99 mg, 0.100 mmol) and $K_2CO_3$ (55.3 mg, 0.400 mmol). The resulting reaction mixture was heated at 40° C. for 20 h before being filtered. The filter cake was washed with MeCN (2 mL). The combined filtrate was evaporated under vacuum before being redissolved in methanol (3 mL) followed by addition of NaOH (3 N) (0.533 mL, 1.600 mmol).

The resulting reaction mixture was heated with microwave at 140° C. for 60 min then was acidified with HCl (3 N) to pH 4-5, evaporated under vacuum, and purified by reverse phase HPLC to afford product 3-(1,4-dimethyl-1H-benzo[d][1,2,3]triazol-5-yl)-3-(3-((R)-2-ethyl-2,3-dihydropyrido[3,4-f][1,4]oxazepin-4(5H)-yl)-2,3-dihydro-1H-inden-5-yl)-2,2-dimethylpropanoic acid, formic acid salt (53.8 mg, 0.095 mmol, 47.4% yield). LC-MS m/z 540.5 (M+H)$^+$, 0.69, 0.73 min (ret. time).

Example 38

3-(3-(2,3-Dihydrobenzo[f][1,4]oxazepin-4(5H)-yl)-2,3-dihydro-1H-inden-5-yl)-3-(1,4-dimethyl-1H-benzo[d][1,2,3]triazol-5-yl)-2,2-dimethylpropanoic Acid, Formic Acid Salt

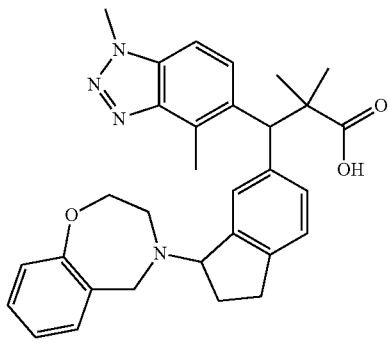 [SMILES: Cc1c(C(c2ccc3c(c2)C(N2CCOc4ccccc4C2)CC3)C(C)(C)C(=O)O)ccc2c1nnn2C]

Methyl 3-(3-(2,3-dihydrobenzo[f][1,4]oxazepin-4(5H)-yl)-2,3-dihydro-1H-inden-5-yl)-3-(1,4-dimethyl-1H-benzo[d][1,2,3]triazol-5-yl)-2,2-dimethylpropanoate

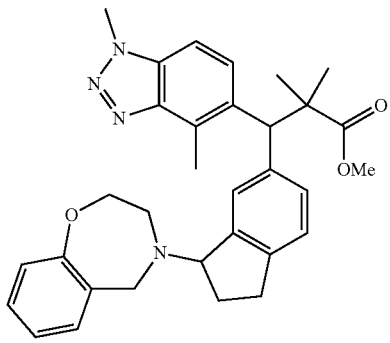 [SMILES: COC(=O)C(C)(C)C(c1ccc2c(c1)C(N1CCOc3ccccc3C1)CC2)c1ccc2c(nnn2C)c1C]

To a solution of 2,3,4,5-tetrahydrobenzo[f][1,4]oxazepine (54.3 mg, 0.364 mmol) in acetonitrile (2.5 mL) was added K$_2$CO$_3$ (101 mg, 0.728 mmol). The resulting solution was stirred at ambient temperature for 20 min before adding sodium iodide (18.19 mg, 0.121 mmol) and methyl 3-(3-chloro-2,3-dihydro-1H-inden-5-yl)-3-(1,4-dimethyl-1H-benzo[d][1,2,3]triazol-5-yl)-2,2-dimethylpropanoate (100 mg, 0.243 mmol). The resulting solution was heated at 50° C. for 16 h before being filtered. The filter cake was washed with MeCN (2 mL). The combined filtrate was evaporated under vacuum, purified via flash chromatography to afford product methyl 3-(3-(2,3-dihydrobenzo[f][1,4]oxazepin-4(5H)-yl)-2,3-dihydro-1H-inden-5-yl)-3-(1,4-dimethyl-1H-benzo[d][1,2,3]triazol-5-yl)-2,2-dimethylpropanoate (71 mg, 0.135 mmol, 55.7% yield). LC-MS m/z 525.1 (M+H)$^+$, 0.90, 0.91 min (ret. time).

3-(3-(2,3-Dihydrobenzo[f][1,4]oxazepin-4(5H)-yl)-2,3-dihydro-1H-inden-5-yl)-3-(1,4-dimethyl-1H-benzo[d][1,2,3]triazol-5-yl)-2,2-dimethylpropanoic Acid

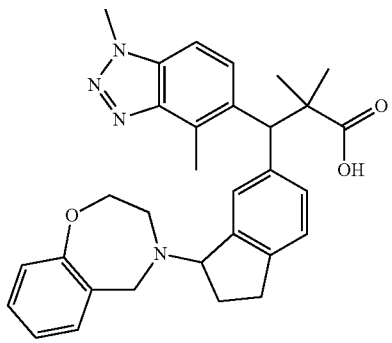 [SMILES: Cc1c(C(c2ccc3c(c2)C(N2CCOc4ccccc4C2)CC3)C(C)(C)C(=O)O)ccc2c1nnn2C]

To a solution of methyl 3-(3-(2,3-dihydrobenzo[f][1,4]oxazepin-4(5H)-yl)-2,3-dihydro-1H-inden-5-yl)-3-(1,4-dimethyl-1H-benzo[d][1,2,3]triazol-5-yl)-2,2-dimethylpropanoate (71 mg, 0.135 mmol) in methanol (2 mL) was added NaOH (2 N) (27.1 mg, 0.677 mmol). The resulting solution was heated with microwave at 120° C. for 6 h before being acidified with HCl (1 N) to pH~5, evaporated under vacuum, and purified by reverse phase HPLC to afford product 3-(3-(2,3-dihydrobenzo[f][1,4]oxazepin-4(5H)-yl)-2,3-dihydro-1H-inden-5-yl)-3-(1,4-dimethyl-1H-benzo[d][1,2,3]triazol-5-yl)-2,2-dimethylpropanoic acid (56.4 mg, 0.110 mmol, 82% yield). LC-MS m/z 511.5 (M+H)$^+$, 0.74 min (ret. time).

Example 39

3-(3-((R)-2,7-Dimethyl-2,3-dihydrobenzo[f][1,4]oxazepin-4(5H)-yl)-2,3-dihydro-1H-inden-5-yl)-3-(7-methoxy-1,4-dimethyl-1H-benzo[d][1,2,3]triazol-5-yl)propanoic Acid, Formic Acid Salt

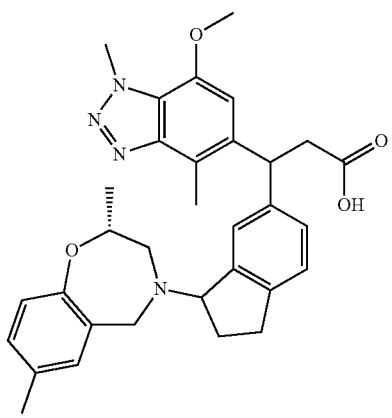 [SMILES: COc1cc(C(CC(=O)O)c2ccc3c(c2)C(N2Cc4cc(C)ccc4O[C@H](C)C2)CC3)c(C)c2nnn(C)c12]

To a solution of ethyl 3-(3-hydroxy-2,3-dihydro-1H-inden-5-yl)-3-(7-methoxy-1,4-dimethyl-1H-benzo[d][1,2,3]triazol-5-yl)propanoate (0.050 g, 0.122 mmol) in DCM (0.60 mL) was added SOCl$_2$ (0.018 mL, 0.244 mmol). The resulting reaction mixture was stirred at ambient temperature for 10 min, evaporated under vacuum and dissolved in acetonitrile (1.5 mL) followed by addition of (R)-2,7-dimethyl-2,3,4,5-tetrahydrobenzo[f][1,4]oxazepine (0.043 g, 0.244 mmol), sodium iodide (9.15 mg, 0.061 mmol) and K$_2$CO$_3$ (0.034 g, 0.244 mmol). The resulting reaction mixture was heated at 40° C. for 18 h before being filtered. The filter cake was washed with MeCN (2 mL). The combined filtrate was evaporated under vacuum then was redissolved in methanol (1.5 mL) followed by addition of NaOH (3 N) (0.204 mL, 0.611 mmol). The resulting reaction mixture was heated with microwave at 80° C. for 20 min before being acidified with HCl (3 N) to pH 4-5, evaporated under vacuum, and purified by reverse phase HPLC to afford product 3-(3-((R)-2,7-dimethyl-2,3-dihydrobenzo[f][1,4]oxazepin-4(5H)-yl)-2,3-dihydro-1H-inden-5-yl)-3-(7-methoxy-1,4-dimethyl-1H-benzo[d][1,2,3]triazol-5-yl)propanoic acid, formic acid salt (41.2 mg, 0.072 mmol, 58.9% yield). LC-MS m/z 541.4 (M+H)$^+$, 0.84 min (ret. time).

Example 40

3-(1,4-Dimethyl-1H-benzo[d][1,2,3]triazol-5-yl)-3-(3-(2,2-dimethyl-2,3-dihydrobenzo[f][1,4]oxazepin-4(5H)-yl)-2,3-dihydro-1H-inden-5-yl)propanoic Acid, Formic Acid Salt

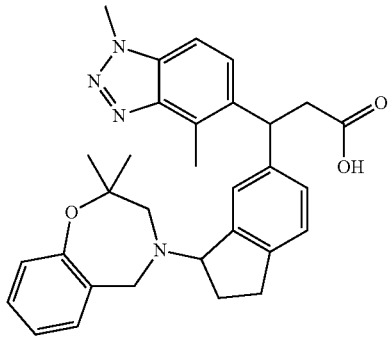 [SMILES: Cc1c(C(CC(=O)O)c2ccc3c(c2)C(N2Cc4ccccc4OC(C)(C)C2)CC3)ccc2c1nnn2C]

To a solution of ethyl 3-(1,4-dimethyl-1H-benzo[d][1,2,3]triazol-5-yl)-3-(3-hydroxy-2,3-dihydro-1H-inden-5-yl)propanoate (100 mg, 0.264 mmol) in DCM (0.5 mL) was added thionyl chloride (0.038 mL, 0.527 mmol). The resulting reaction mixture was stirred at ambient temperature for 55 min, evaporated under vacuum then dissolved in acetonitrile (2.5 mL) followed by addition of 2,2-dimethyl-2,3,4,5-tetrahydrobenzo[f][1,4]oxazepine, hydrochloride (113 mg, 0.527 mmol), K$_2$CO$_3$ (109 mg, 0.791 mmol), sodium iodide (7.90 mg, 0.053 mmol). The resulting reaction mixture was stirred at 40° C. for 69 h before being filtered, evaporated under vacuum followed by addition of NaOH (3 N) (0.439 mL, 1.318 mmol). The resulting reaction mixture was heated with microwave at 80° C. for 20 min then was acidified with HCl (3 N) to pH~6, evaporated under vacuum, purified by reverse phase HPLC to afford product 3-(1,4-dimethyl-1H-benzo[d][1,2,3]triazol-5-yl)-3-(3-(2,2-dimethyl-2,3-dihydrobenzo[f][1,4]oxazepin-4(5H)-yl)-2,3-dihydro-1H-inden-5-yl)propanoic acid (76.1 mg, 0.149 mmol, 56.6% yield). LC-MS m/z 511.5 (M+H)$^+$, 0.70 min (ret. time).

Example 41

3-(1,4-Dimethyl-1H-benzo[d][1,2,3]triazol-5-yl)-3-(3-(2,2-dimethyl-2,3-dihydrobenzo[f][1,4]oxazepin-4(5H)-yl)-2,3-dihydro-1H-inden-5-yl)propanoic Acid, Formic Acid Salt

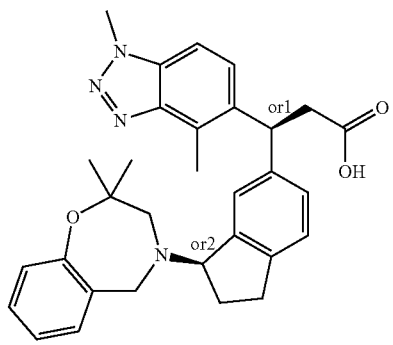

ISOMER 2

6-(4,4,5,5-Tetramethyl-1,3,2-dioxaborolan-2-yl)-2,3-dihydro-1H-inden-1-one

To the solution of 6-bromo-2,3-dihydro-1H-inden-1-one (1.688 g, 8 mmol) in N,N-dimethylformamide (16 mL) was added bis(pinacolato)diboron (3.05 g, 12.00 mmol), KOAc (1.570 g, 16.00 mmol) and PdCl$_2$(dppf) (0.293 g, 0.400 mmol). The resulting reaction mixture was heated with microwave at 100° C. for 1 h. The reaction mixture was diluted with H$_2$O (20 mL) and EtOAc (40 mL), stirred and filtered. The organic layer was separated and the aqueous layer was extracted with EtOAc (2×30 mL). The combined organic layer was washed with brine (40 mL), dried over MgSO$_4$, filtered, evaporated down under vacuum, purified with flash chromatography to afford desired product 6-(4,4,5,5-tetramethyl-1,3,2-dioxaborolan-2-yl)-2,3-dihydro-1H-inden-1-one (1.9623 g, 7.60 mmol, 95% yield). LC-MS m/z 259.1 (M+H)$^+$, 1.03 min (ret. time).

Ethyl 3-(1,4-dimethyl-1H-benzo[d][1,2,3]triazol-5-yl)-3-(3-oxo-2,3-dihydro-1H-inden-5-yl)propanoate

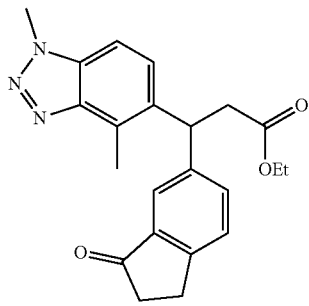 [SMILES: CCOC(=O)CC(c1ccc2c(c1)C(=O)CC2)c1ccc2c(nnn2C)c1C]

To the solution of (E)-ethyl 3-(1,4-dimethyl-1H-benzo[d][1,2,3]triazol-5-yl)acrylate (0.564 g, 2.3 mmol) in 1,4-dioxane (13 mL) and water (4 ml) was added 6-(4,4,5,5-tetramethyl-1,3,2-dioxaborolan-2-yl)-2,3-dihydro-1H-inden-1-one (0.891 g, 3.45 mmol), TEA (1.282 mL, 9.20 mmol) and [Rh(cod)Cl]$_2$ (0.057 g, 0.115 mmol). The resulting reaction mixture was stirred at 90° C. for 1 h. The reaction mixture was evaporated down under vacuum, purified with flash chromatography to afford desired product ethyl 3-(1,4-dimethyl-1H-benzo[d][1,2,3]triazol-5-yl)-3-(3-oxo-2,3-dihydro-1H-inden-5-yl)propanoate (0.6070 g, 1.608 mmol, 69.9% yield). LC-MS m/z 378.3 (M+H)$^+$, 0.87 min (ret. time).

Ethyl 3-(1,4-dimethyl-1H-benzo[d][1,2,3]triazol-5-yl)-3-(3-oxo-2,3-dihydro-1H-inden-5-yl)propanoate

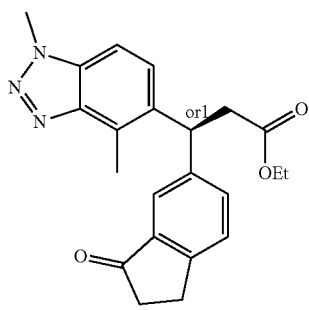 [SMILES: CCOC(=O)C[C@@H](c1ccc2c(c1)C(=O)CC2)c1ccc2c(nnn2C)c1C]

Ethyl 3-(1,4-dimethyl-1H-benzo[d][1,2,3]triazol-5-yl)-3-(3-oxo-2,3-dihydro-1H-inden-5-yl)propanoate (0.800 g, 2.120 mmol) was purified by chiral SFC to afford enantiomeric pure product ethyl 3-(1,4-dimethyl-1H-benzo[d][1,2,3]triazol-5-yl)-3-(3-oxo-2,3-dihydro-1H-inden-5-yl)propanoate (0.3393 g, 0.899 mmol, 42.4% yield). LC-MS m/z 378.3 (M+H)$^+$, 0.88 min (ret. time).

Ethyl 3-(1,4-dimethyl-1H-benzo[d][1,2,3]triazol-5-yl)-3-(3-hydroxy-2,3-dihydro-1H-inden-5-yl)propanoate

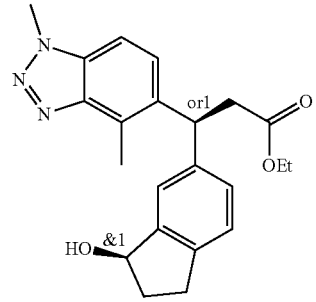 [SMILES: CCOC(=O)C[C@@H](c1ccc2c(c1)[C@H](O)CC2)c1ccc2c(nnn2C)c1C]

To a solution of ethyl 3-(1,4-dimethyl-1H-benzo[d][1,2,3]triazol-5-yl)-3-(3-oxo-2,3-dihydro-1H-inden-5-yl)propanoate (339 mg, 0.898 mmol) in methanol (5 mL) was added NaBH$_4$ (34.0 mg, 0.898 mmol). The resulting reaction mixture was stirred at ambient temperature for 140 min before adding more NaBH$_4$ (34.0 mg, 0.898 mmol). The resulting reaction mixture was stirred at ambient temperature for 90 min before adding more NaBH$_4$ (68.0 mg, 1.796 mmol). The resulting reaction mixture was stirred at ambient temperature for 1 h, evaporated under vacuum, purified via flash chromatography to afford product ethyl 3-(1,4-dimethyl-1H-benzo[d][1,2,3]triazol-5-yl)-3-(3-hydroxy-2,3-dihydro-1H-inden-5-yl)propanoate (0.3120 g, 0.822 mmol, 92% yield). LC-MS m/z 380.2 (M+H)$^+$, 0.87 min (ret. time).

Ethyl 3-(3-chloro-2,3-dihydro-1H-inden-5-yl)-3-(1,4-dimethyl-1H-benzo[d][1,2,3]triazol-5-yl)propanoate

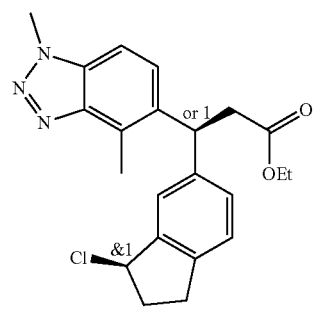 [SMILES: CCOC(=O)C[C@@H](c1ccc2c(c1)[C@H](Cl)CC2)c1ccc2c(nnn2C)c1C]

To a solution of ethyl 3-(1,4-dimethyl-1H-benzo[d][1,2,3]triazol-5-yl)-3-(3-hydroxy-2,3-dihydro-1H-inden-5-yl)propanoate (120 mg, 0.316 mmol) in DCM (2 mL) was added SOCl$_2$ (0.069 mL, 0.949 mmol). The resulting reaction mixture was stirred at ambient temperature for 5 h, evaporated under vacuum to afford product ethyl 3-(3-chloro-2,3-dihydro-1H-inden-5-yl)-3-(1,4-dimethyl-1H-benzo[d][1,2,3]triazol-5-yl)propanoate (125.8 mg, 0.316 mmol, 100% yield). LC-MS m/z 394.2 (M−Cl+MeOH)$^+$, 1.01 min (ret. time).

Ethyl 3-(1,4-dimethyl-1H-benzo[d][1,2,3]triazol-5-yl)-3-(3-(2,2-dimethyl-2,3-dihydrobenzo[f][1,4]oxazepin-4(5H)-yl)-2,3-dihydro-1H-inden-5-yl)propanoate

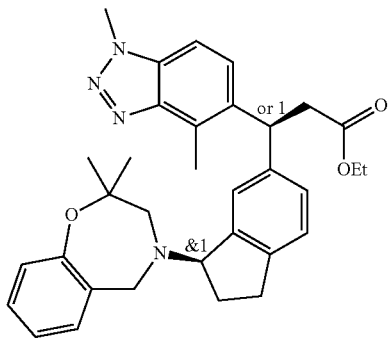 [SMILES: CCOC(=O)C[C@@H](c1ccc2c(c1)[C@H](N1Cc3ccccc3OC(C)(C)C1)CC2)c1ccc2c(nnn2C)c1C]

To a solution of 2,2-dimethyl-2,3,4,5-tetrahydrobenzo[f][1,4]oxazepine, hydrochloride (101 mg, 0.474 mmol) and K₂CO₃ (175 mg, 1.265 mmol) in acetonitrile (3 mL) was added sodium iodide (23.70 mg, 0.158 mmol) and ethyl 3-(3-chloro-2,3-dihydro-1H-inden-5-yl)-3-(1,4-dimethyl-1H-benzo[d][1,2,3]triazol-5-yl)propanoate (125.8 mg, 0.316 mmol). The resulting solution was heated with microwave at 60° C. for 16 h, evaporated under vacuum then purified via flash chromatography to afford product ethyl 3-(1,4-dimethyl-1H-benzo[d][1,2,3]triazol-5-yl)-3-(3-(2,2-dimethyl-2,3-dihydrobenzo[f][1,4]oxazepin-4(5H)-yl)-2,3-dihydro-1H-inden-5-yl)propanoate (118.4 mg, 0.220 mmol, 69.5% yield). LC-MS m/z 539.2 (M+H)⁺, 0.94 min (ret. time).

3-(1,4-Dimethyl-1H-benzo[d][1,2,3]triazol-5-yl)-3-(3-(2,2-dimethyl-2,3-dihydrobenzo[f][1,4]oxazepin-4(5H)-yl)-2,3-dihydro-1H-inden-5-yl)propanoic Acid, Formic Acid Salt

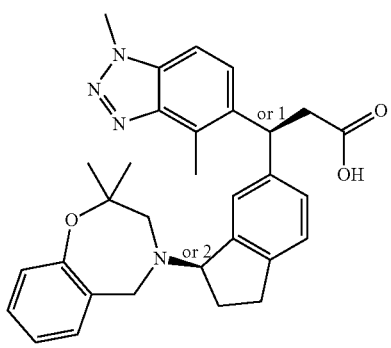

ISOMER 2

To a solution of ethyl 3-(1,4-dimethyl-1H-benzo[d][1,2,3]triazol-5-yl)-3-(3-(2,2-dimethyl-2,3-dihydrobenzo[f][1,4]oxazepin-4(5H)-yl)-2,3-dihydro-1H-inden-5-yl)propanoate (118.4 mg, 0.220 mmol) in methanol (3 mL) was added NaOH (2 N) (44.0 mg, 1.099 mmol). The resulting solution was heated with microwave at 80° C. for 15 min before being acidified with HCl (1 N) to pH~5, evaporated under vacuum, and purified by reverse phase HPLC then chiral SFC to afford product 3-(1,4-dimethyl-1H-benzo[d][1,2,3]triazol-5-yl)-3-(3-(2,2-dimethyl-2,3-dihydrobenzo[f][1,4]oxazepin-4(5H)-yl)-2,3-dihydro-1H-inden-5-yl)propanoic acid, formic acid salt (20 mg, 0.039 mmol, 17.82% yield). LC-MS m/z 511.6 (M+H)⁺, 0.70 min (ret. time).

Example 42

3-(1,4-Dimethyl-1H-benzo[d][1,2,3]triazol-5-yl)-2,2-dimethyl-3-(3-((R)-2-methyl-2,3-dihydropyrido[3,2-f][1,4]oxazepin-4(5H)-yl)-2,3-dihydro-1H-inden-5-yl)propanoic Acid, Formic Acid Salt

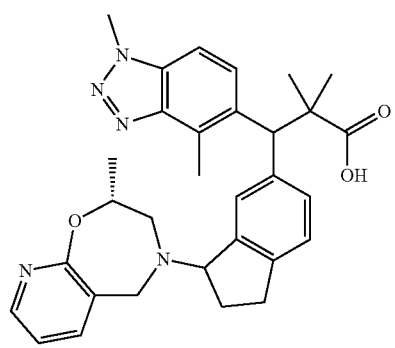 [SMILES: Cc1c(C(c2ccc3c(c2)C(N2Cc4cccnc4O[C@H](C)C2)CC3)C(C)(C)C(=O)O)ccc2c1nnn2C]

(R)-1-(((2-chloropyridin-3-yl)methyl)amino)propan-2-ol

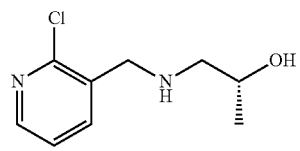

To a solution of 2-chloronicotinaldehyde (0.708 g, 5 mmol) in methanol (10 mL) was added (R)-1-aminopropan-2-ol (0.488 g, 6.50 mmol). The reaction mixture was stirred at ambient temperature for 1 h before adding NaBH₄ (0.378 g, 10.00 mmol) slowly then stirred at ambient temperature for an additional 1 h. The reaction mixture was quenched with NaHCO₃ (sat. aq.) (0.5 mL), then evaporated under vacuum. The residue was diluted with DCM (50 mL), dried over MgSO₄, filtered and evaporated under vacuum to afford product (R)-1-(((2-chloropyridin-3-yl)methyl)amino)propan-2-ol (1.3176 g, 6.57 mmol, 131% yield). LC-MS m/z 200.9 (M+H)⁺, 0.24 min (ret. time).

(R)-2-methyl-2,3,4,5-tetrahydropyrido[3,2-f][1,4]oxazepine

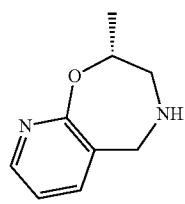

To a solution of (R)-1-(((2-chloropyridin-3-yl)methyl)amino)propan-2-ol (1.2176 g, 6.07 mmol) in N,N-dimethylformamide (60 mL) was added KOtBu (2.043 g, 18.20 mmol). The resulting solution was heated at 80° C. for 4 h then evaporated down under high vacuum before being diluted with DCM (50 mL), filtered. The solution was evaporated under vacuum to afford product (R)-2-methyl-2,3,4,5-tetrahydropyrido[3,2-f][1,4]oxazepine (0.7899 g, 4.81 mmol, 79% yield). LC-MS m/z 165.0 (M+H)$^+$, 0.16 min (ret. time).

Methyl 3-(1,4-dimethyl-1H-benzo[d][1,2,3]triazol-5-yl)-2,2-dimethyl-3-(3-((R)-2-methyl-2,3-dihydropyrido[3,2-f][1,4]oxazepin-4(5H)-yl)-2,3-dihydro-1H-inden-5-yl)propanoate

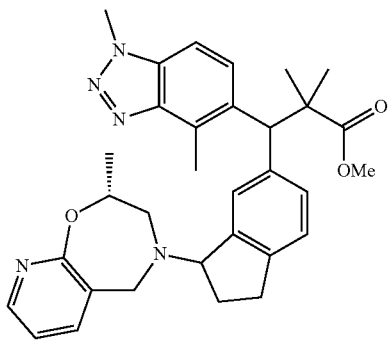 [SMILES: COC(=O)C(C)(C)C(c1ccc2c(c1)C(N1Cc3cccnc3O[C@H](C)C1)CC2)c1ccc2c(nnn2C)c1C]

To a solution of (R)-2-methyl-2,3,4,5-tetrahydropyrido[3,2-f][1,4]oxazepine (80 mg, 0.486 mmol) in acetonitrile (2.5 mL) was added K$_2$CO$_3$ (101 mg, 0.728 mmol). The resulting solution was stirred at ambient temperature for 20 min before adding sodium iodide (18.19 mg, 0.121 mmol) and methyl 3-(3-chloro-2,3-dihydro-1H-inden-5-yl)-3-(1,4-dimethyl-1H-benzo[d][1,2,3]triazol-5-yl)-2,2-dimethylpropanoate (100 mg, 0.243 mmol). The resulting solution was heated at 50° C. for 23 h then was filtered. The filter cake was washed with MeCN (2 mL). The combined filtrate was evaporated under vacuum and purified via flash chromatography to afford product methyl 3-(1,4-dimethyl-1H-benzo[d][1,2,3]triazol-5-yl)-2,2-dimethyl-3-(3-((R)-2-methyl-2,3-dihydropyrido[3,2-f][1,4]oxazepin-4(5H)-yl)-2,3-dihydro-1H-inden-5-yl)propanoate (73.8 mg, 0.137 mmol, 56.3% yield). LC-MS m/z 540.2 (M+H)$^+$, 0.87 min (ret. time).

3-(1,4-Dimethyl-1H-benzo[d][1,2,3]triazol-5-yl)-2,2-dimethyl-3-(3-((R)-2-methyl-2,3-dihydropyrido[3,2-f][1,4]oxazepin-4(5H)-yl)-2,3-dihydro-1H-inden-5-yl)propanoic Acid, Formic Acid Salt

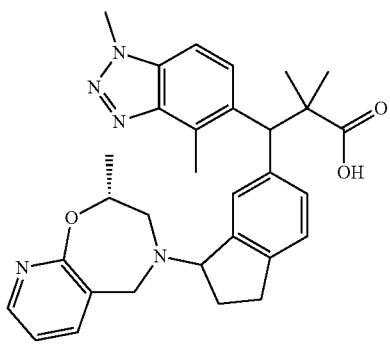 [SMILES: Cc1c(C(c2ccc3c(c2)C(N2Cc4cccnc4O[C@H](C)C2)CC3)C(C)(C)C(=O)O)ccc2c1nnn2C]

To a solution of methyl 3-(1,4-dimethyl-1H-benzo[d][1,2,3]triazol-5-yl)-2,2-dimethyl-3-(3-((R)-2-methyl-2,3-dihydropyrido[3,2-f][1,4]oxazepin-4(5H)-yl)-2,3-dihydro-1H-inden-5-yl)propanoate (73 mg, 0.135 mmol) in methanol (2.5 mL) was added NaOH (2 N) (27.1 mg, 0.676 mmol). The resulting solution was heated with microwave at 120° C. for 7 h before being acidified with HCl (1 N) to pH~5, evaporated under vacuum, and purified by reverse phase HPLC to afford product 3-(1,4-dimethyl-1H-benzo[d][1,2,3]triazol-5-yl)-2,2-dimethyl-3-(3-((R)-2-methyl-2,3-dihydropyrido[3,2-f][1,4]oxazepin-4(5H)-yl)-2,3-dihydro-1H-inden-5-yl)propanoic acid, formic acid salt (51.6 mg, 0.098 mmol, 72.6% yield). LC-MS m/z 526.6 (M+H)$^+$, 0.68 min (ret. time).

Example 43

3-(3-(2,2-Dimethyl-2,3-di hydrobenzo[f][1,4]oxazepin-4(5H)-yl)-2,3-dihydro-1H-inden-5-yl)-3-(7-methoxy-1-methyl-1H-benzo[d][1,2,3]triazol-5-yl)propanoic Acid, Formate Salt

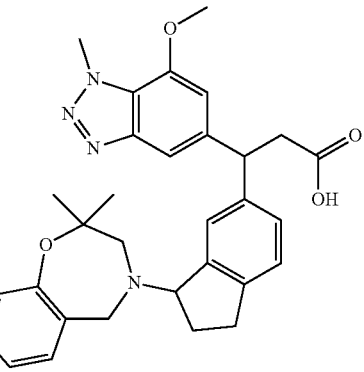

Ethyl 3-(3-hydroxy-2,3-dihydro-1H-inden-5-yl)-3-(7-methoxy-1-methyl-1H-benzo[d][1,2,3]triazol-5-yl)propanoate

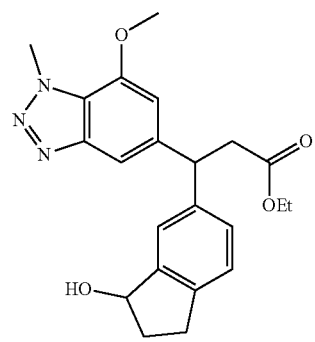 [SMILES: CCOC(=O)CC(c1ccc2c(c1)C(O)CC2)c1cc(OC)c2c(c1)nnn2C]

To a solution of (E)-ethyl 3-(7-methoxy-1-methyl-1H-benzo[d][1,2,3]triazol-5-yl)acrylate (653 mg, 2.50 mmol) in 1,4-dioxane (12 mL) and water (4 mL) was added 6-(4,4,5,5-tetramethyl-1,3,2-dioxaborolan-2-yl)-2,3-dihydro-1H-inden-1-ol (976 mg, 3.75 mmol), TEA (1.045 mL, 7.50 mmol) and [Rh(cod)Cl]$_2$ (61.6 mg, 0.125 mmol). The resulting reaction mixture was stirred at 90° C. for 3 h, evaporated under vacuum and purified via flash chromatography to afford product ethyl 3-(3-hydroxy-2,3-dihydro-1H-inden-5-yl)-3-(7-methoxy-1-methyl-1H-benzo[d][1,2,3]triazol-5-yl)propanoate (334.1 mg, 0.845 mmol, 33.8% yield). LC-MS m/z 396.1 (M+H)+, 0.90 min (ret. time).

Ethyl 3-(3-chloro-2,3-dihydro-1H-inden-5-yl)-3-(7-methoxy-1-methyl-1H-benzo[d][1,2,3]triazol-5-yl)propanoate

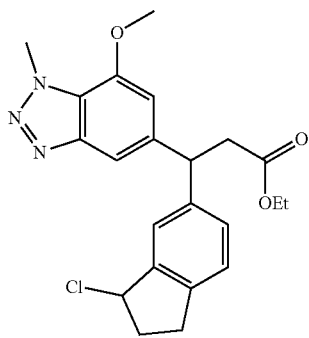 [SMILES: CCOC(=O)CC(c1ccc2c(c1)C(Cl)CC2)c1cc(OC)c2c(c1)nnn2C]

To a solution of ethyl 3-(3-hydroxy-2,3-dihydro-1H-inden-5-yl)-3-(7-methoxy-1-methyl-1H-benzo[d][1,2,3]triazol-5-yl)propanoate (280 mg, 0.708 mmol) in DCM (3 mL) was added SOCl₂ (0.103 mL, 1.416 mmol). The resulting reaction mixture was stirred at ambient temperature for 2 h, evaporated under vacuum to afford product ethyl 3-(3-chloro-2,3-dihydro-1H-inden-5-yl)-3-(7-methoxy-1-methyl-1H-benzo[d][1,2,3]triazol-5-yl)propanoate (0.3455 g, 0.835 mmol, 118% yield). LC-MS m/z 396.0 (M−Cl+ H₂O)+, 0.95 min (ret. time).

Ethyl 3-(3-(2,2-dimethyl-2,3-dihydrobenzo[f][1,4]oxazepin-4(5H)-yl)-2,3-dihydro-1H-inden-5-yl)-3-(7-methoxy-1-methyl-1H-benzo[d][1,2,3]triazol-5-yl)propanoate

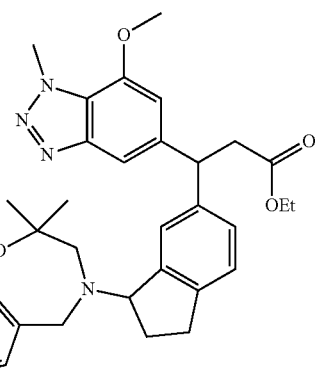

To a solution of 2,2-dimethyl-2,3,4,5-tetrahydrobenzo[f][1,4]oxazepine, hydrochloride (69.7 mg, 0.326 mmol) and K₂CO₃ (90 mg, 0.652 mmol) in acetonitrile (2 mL) was added sodium iodide (16.30 mg, 0.109 mmol) and ethyl 3-(3-chloro-2,3-dihydro-1H-inden-5-yl)-3-(7-methoxy-1-methyl-1H-benzo[d][1,2,3]triazol-5-yl)propanoate (90 mg, 0.217 mmol). The resulting solution was heated with microwave at 50° C. for 15 h, evaporated under vacuum, purified via flash chromatography to afford product ethyl 3-(3-(2,2-dimethyl-2,3-dihydrobenzo[f][1,4]oxazepin-4(5H)-yl)-2,3-dihydro-1H-inden-5-yl)-3-(7-methoxy-1-methyl-1H-benzo[d][1,2,3]triazol-5-yl)propanoate (58.1 mg, 0.105 mmol, 48.2% yield). LC-MS m/z 555.2 (M+H)+, 0.95 min (ret. time).

3-(3-(2,2-Dimethyl-2,3-dihydrobenzo[f][1,4]oxazepin-4(5H)-yl)-2,3-dihydro-1H-inden-5-yl)-3-(7-methoxy-1-methyl-1H-benzo[d][1,2,3]triazol-5-yl)propanoic Acid, Formic Acid Salt

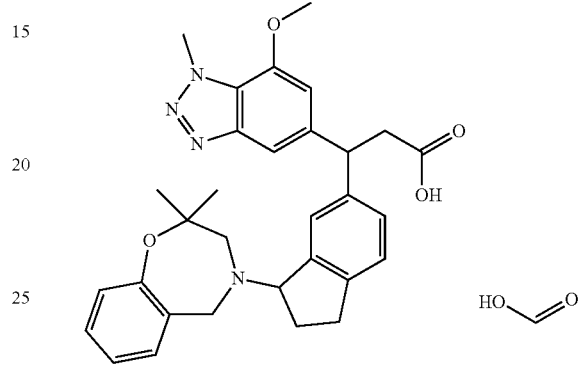

To a solution of ethyl 3-(3-(2,2-dimethyl-2,3-dihydrobenzo[f][1,4]oxazepin-4(5H)-yl)-2,3-dihydro-1H-inden-5-yl)-3-(7-methoxy-1-methyl-1H-benzo[d][1,2,3]triazol-5-yl)propanoate (58.1 mg, 0.105 mmol) in methanol (2 mL) was added NaOH (2 N) (20.95 mg, 0.524 mmol). The resulting solution was heated with microwave at 80° C. for 15 min then was acidified with HCl (1 N) to pH~5, evaporated under vacuum, and purified by reverse phase HPLC to afford product 3-(3-(2,2-dimethyl-2,3-dihydrobenzo[f][1,4]oxazepin-4(5H)-yl)-2,3-dihydro-1H-inden-5-yl)-3-(7-methoxy-1-methyl-1iH-benzo[d][1,2,3]triazol-5-yl)propanoic acid, formic acid salt (20.86 mg, 0.037 mmol, 35.0% yield). LC-MS m/z 527.2 (M+H)+, 0.82 min (ret. time).

Example 44

3-(3-(2,2-Dimethyl-2,3-dihydropyrido[3,2-f][1,4]oxazepin-4(5H)-yl)-2,3-dihydro-1H-inden-5-yl)-3-(7-methoxy-1,4-dimethyl-1H-benzo[d][1,2,3]triazol-5-yl)propanoic Acid, Formic Acid Salt

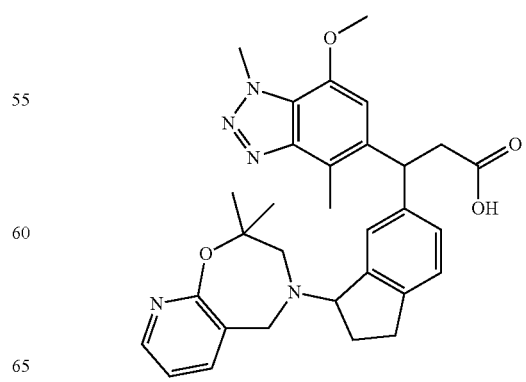

1-(((2-Chloropyridin-3-yl)methyl)amino)-2-methyl-propan-2-ol

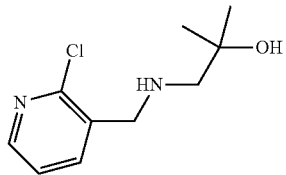

To a solution of 2-chloronicotinaldehyde (1.132 g, 8 mmol) in methanol (20 mL) was added 1-amino-2-methyl-propan-2-ol (0.927 g, 10.40 mmol). The reaction mixture was stirred at ambient temperature for 1 h. Then NaBH$_4$ (0.605 g, 16.00 mmol) was added to the reaction solution in two portions and the resulting solution was stirred at ambient temperature for an additional 1 h. The reaction mixture was quenched with NaHCO$_3$ (sat.) (0.7 ml), then evaporated down under vacuum. The residue was dissolved in DCM, dried over MgSO$_4$, filtered and evaporated under vacuum to afford desired product 1-(((2-chloropyridin-3-yl)methyl)amino)-2-methylpropan-2-ol (1.8329 g, 8.54 mmol, 107% yield). LC-MS m/z 214.9 (M+H)$^+$, 0.30 min (ret. time).

2,2-Dimethyl-2,3,4,5-tetrahydropyrido[3,2-f][1,4]oxazepine

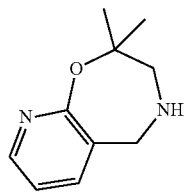

To a solution of 1-(((2-chloropyridin-3-yl)methyl)amino)-2-methylpropan-2-ol (1.6575 g, 7.72 mmol) in N,N-dimethylformamide (75 mL) was added NaH (0.371 g, 15.44 mmol). The resulting solution was heated at 80° C. for 1 h, concentrated then diluted with DCM (50 ml), and filtered. The solution was evaporated down under vacuum to afford desired product 2,2-dimethyl-2,3,4,5-tetrahydropyrido[3,2-f][1,4]oxazepine (1.3823 g, 7.76 mmol, 100% yield). LC-MS m/z 179.0 (M+H)$^+$, 0.21 min (ret. time).

Methyl 3-(3-(2,2-dimethyl-2,3-dihydropyrido[3,2-f][1,4]oxazepin-4(5H)-yl)-2,3-dihydro-1H-inden-5-yl)-3-(7-methoxy-1,4-dimethyl-1H-benzo[d][1,2,3]triazol-5-yl)propanoate

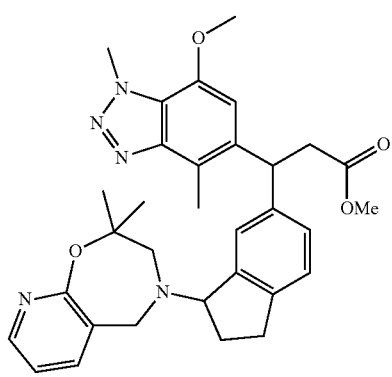 [SMILES: COC(=O)CC(c1ccc2c(c1)C(N1Cc3cccnc3OC(C)(C)C1)CC2)c1cc(OC)c2c(nnn2C)c1C]

To a solution of 2,2-dimethyl-2,3,4,5-tetrahydropyrido[3,2-f][1,4]oxazepine (134 mg, 0.750 mmol) in acetonitrile (2.5 mL) was added K$_2$CO$_3$ (69.1 mg, 0.500 mmol), sodium iodide (18.74 mg, 0.125 mmol) and methyl 3-(3-chloro-2,3-dihydro-1H-inden-5-yl)-3-(7-methoxy-1,4-dimethyl-1H-benzo[d][1,2,3]triazol-5-yl)propanoate (103 mg, 0.25 mmol). The resulting solution was heated with microwave at 60° C. for 3 h then evaporated under vacuum, purified via flash chromatography to afford product methyl 3-(3-(2,2-dimethyl-2,3-dihydropyrido[3,2-f][1,4]oxazepin-4(5H)-yl)-2,3-dihydro-1H-inden-5-yl)-3-(7-methoxy-1,4-dimethyl-1H-benzo[d][1,2,3]triazol-5-yl)propanoate (43.1 mg, 0.078 mmol, 31.0% yield). LC-MS m/z 556.2 (M+H)$^+$, 0.82 min (ret. time).

3-(3-(2,2-Dimethyl-2,3-dihydropyrido[3,2-f][1,4]oxazepin-4(5H)-yl)-2,3-dihydro-1H-inden-5-yl)-3-(7-methoxy-1,4-dimethyl-1H-benzo[d][1,2,3]triazol-5-yl)propanoic Acid, Formic Acid Salt

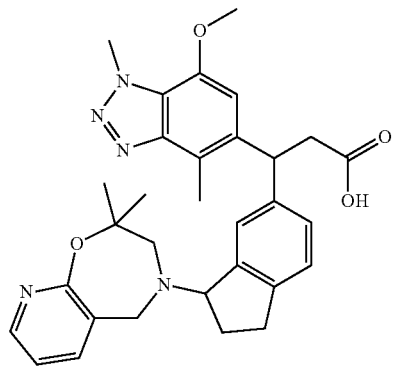 [SMILES: COc1cc(C(CC(=O)O)c2ccc3c(c2)C(N2Cc4cccnc4OC(C)(C)C2)CC3)c(C)c2nnn(C)c12]

To a solution of methyl 3-(3-(2,2-dimethyl-2,3-dihydropyrido[3,2-f][1,4]oxazepin-4(5H)-yl)-2,3-dihydro-1H-inden-5-yl)-3-(7-methoxy-1,4-dimethyl-1H-benzo[d][1,2,3]triazol-5-yl)propanoate (43 mg, 0.077 mmol) in methanol (1.5 mL) was added NaOH (2 N) (15.48 mg, 0.387 mmol). The resulting solution was heated with microwave at 80° C. for 15 min before being acidified with HCl (1 N) to pH~5, evaporated under vacuum, and purified by reverse phase HPLC to afford product 3-(3-(2,2-dimethyl-2,3-dihydropyrido[3,2-f][1,4]oxazepin-4(5H)-yl)-2,3-dihydro-1H-inden-5-yl)-3-(7-methoxy-1,4-dimethyl-1H-benzo[d][1,2,3]triazol-5-yl)propanoic acid, formic acid salt (14.1 mg, 0.026 mmol, 33.6% yield). LC-MS m/z 542.3 (M+H)$^+$, 0.75 min (ret. time).

Example 45

3-(3-((R)-2-Ethyl-2,3-dihydrobenzo[f][1,4]oxazepin-4(5H)-yl)-2,3-dihydro-1H-inden-5-yl)-3-(7-methoxy-1,4-dimethyl-1H-benzo[d][1,2,3]triazol-5-yl)propanoic Acid, Formic Acid Salt

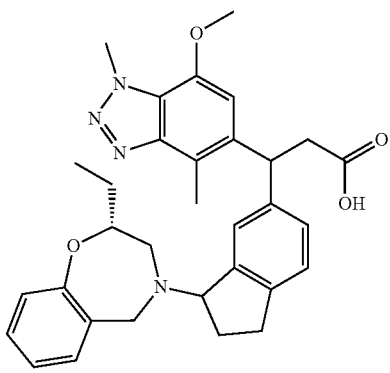 [SMILES: CC[C@@H]1CN(C2CCc3ccc(C(CC(=O)O)c4cc(OC)c5c(nnn5C)c4C)cc32)Cc2ccccc2O1]

Methyl 3-(3-((R)-2-ethyl-2,3-dihydrobenzo[f][1,4]oxazepin-4(5H)-yl)-2,3-dihydro-1H-inden-5-yl)-3-(7-methoxy-1,4-dimethyl-1H-benzo[d][1,2,3]triazol-5-yl)propanoate

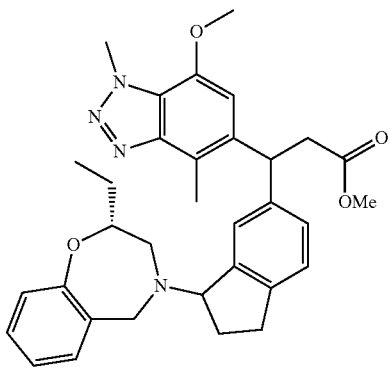 [SMILES: CC[C@@H]1CN(C2CCc3ccc(C(CC(=O)OC)c4cc(OC)c5c(nnn5C)c4C)cc32)Cc2ccccc2O1]

To a solution of (R)-2-ethyl-2,3,4,5-tetrahydrobenzo[f][1,4]oxazepine, hydrochloride (85 mg, 0.399 mmol) in acetonitrile (2.5 mL) was added K$_2$CO$_3$ (147 mg, 1.063 mmol). The resulting solution was stirred at ambient temperature for 20 min followed by addition of sodium iodide (19.92 mg, 0.133 mmol) and methyl 3-(3-chloro-2,3-dihydro-1H-inden-5-yl)-3-(7-methoxy-1,4-dimethyl-1H-benzo[d][1,2,3]triazol-5-yl)propanoate (110 mg, 0.266 mmol). The resulting solution was heated at 50° C. for 19 h before being filtered. The filter cake was washed with MeCN (2 mL). The combined filtrate was evaporated under vacuum and the residue was purified via flash chromatography to afford product methyl 3-(3-((R)-2-ethyl-2,3-dihydrobenzo[f][1,4]oxazepin-4(5H)-yl)-2,3-dihydro-1H-inden-5-yl)-3-(7-methoxy-1,4-dimethyl-1H-benzo[d][1,2,3]triazol-5-yl)propanoate (104.7 mg, 0.189 mmol, 71.0% yield). LC-MS m/z 555.2 (M+H)$^+$, 0.97 min (ret. 5 time).

3-(3-((R)-2-ethyl-2,3-dihydrobenzo[f][1,4]oxazepin-4(5H)-yl)-2,3-dihydro-1H-inden-5-yl)-3-(7-methoxy-1,4-dimethyl-1H-benzo[d][1,2,3]triazol-5-yl)propanoic Acid, Formic Acid Salt

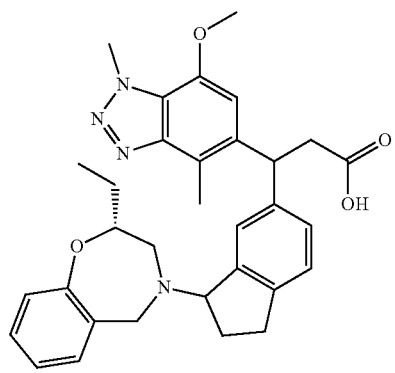 [SMILES: CC[C@@H]1CN(C2CCc3ccc(C(CC(=O)O)c4cc(OC)c5c(nnn5C)c4C)cc32)Cc2ccccc2O1]

To a solution of methyl 3-(3-((R)-2-ethyl-2,3-dihydrobenzo[f][1,4]oxazepin-4(5H)-yl)-2,3-dihydro-1H-inden-5-yl)-3-(7-methoxy-1,4-dimethyl-1H-benzo[d][1,2,3]triazol-5-yl)propanoate (104 mg, 0.187 mmol) in methanol (3 mL) was added NaOH (2 N) (37.5 mg, 0.937 mmol). The resulting solution was heated with microwave at 80° C. for 15 min before being acidified with HCl (1 N) to pH~5, evaporated under vacuum, and purified by reverse phase HPLC to afford the product 3-(3-((R)-2-ethyl-2,3-dihydrobenzo[f][1,4]oxazepin-4(5H)-yl)-2,3-dihydro-1H-inden-5-yl)-3-(7-methoxy-1,4-dimethyl-1H-benzo[d][1,2,3]triazol-5-yl)propanoic acid, formic acid salt (36.8 mg, 0.068 mmol, 36.3% yield). LC-MS m/z 541.4 (M+H)$^+$, 0.80 min (ret. time).

Example 46

3-(3-(2,2-Dimethyl-2,3-dihydropyrido[3,4-f][1,4]oxazepin-4(5H)-yl)-2,3-dihydro-1H-inden-5-yl)-3-(7-methoxy-1-methyl-1H-benzo[d][1,2,3]triazol-5-yl)propanoic Acid, Formic Acid Salt

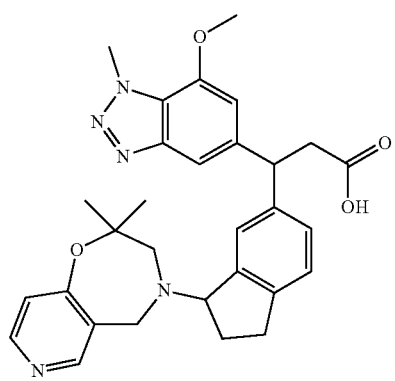 [SMILES: COc1cc(C(CC(=O)O)c2ccc3c(c2)C(N2Cc4cnccc4OC(C)(C)C2)CC3)cc2nnn(C)c12]

Ethyl 3-(3-(2,2-dimethyl-2,3-dihydropyrido[3,4-f][1,4]oxazepin-4(5H)-yl)-2,3-dihydro-1H-inden-5-yl)-3-(7-methoxy-1-methyl-1H-benzo[d][1,23]triazol-5-yl)propanoate

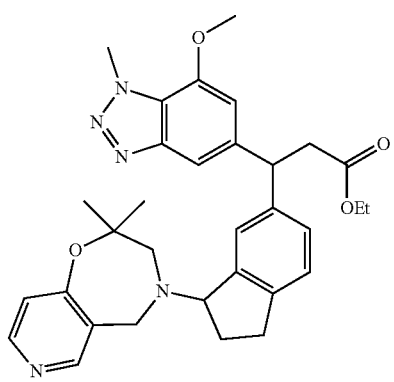

To a solution of 2,2-dimethyl-2,3,4,5-tetrahydropyrido[3,4-f][1,4]oxazepine, hydrochloride (124 mg, 0.580 mmol) in acetonitrile (2.0 mL) was added $K_2CO_3$ (214 mg, 1.546 mmol). The resulting solution was stirred at ambient temperature for 20 min before adding sodium iodide (29.0 mg, 0.193 mmol) and a solution of ethyl 3-(3-chloro-2,3-dihydro-1H-inden-5-yl)-3-(7-methoxy-1-methyl-1H-benzo[d][1,2,3]triazol-5-yl)propanoate (160 mg, 0.387 mmol) in acetonitrile (2.0 mL). The resulting solution was heated with microwave at 50° C. for 14 h then was filtered. The filter cake was washed with MeCN (2 mL). The combined filtrate was evaporated under vacuum and the residue was purified via flash chromatography to afford the desired product ethyl 3-(3-(2,2-dimethyl-2,3-dihydropyrido[3,4-f][1,4]oxazepin-4(5H)-yl)-2,3-dihydro-1H-inden-5-yl)-3-(7-methoxy-1-methyl-1H-benzo[d][1,2,3]triazol-5-yl)propanoate (17.6 mg, 0.032 mmol, 8.19% yield). LC-MS m/z 556.2 (M+H)$^+$, 1.02 min (ret. time).

3-(3-(2,2-Dimethyl-2,3-dihydropyrido[3,4-f][1,4]oxazepin-4(5H)-yl)-2,3-dihydro-1H-inden-5-yl)-3-(7-methoxy-1-methyl-1H-benzo[d][1,2,3]triazol-5-yl)propanoic Acid, Formic Acid Salt

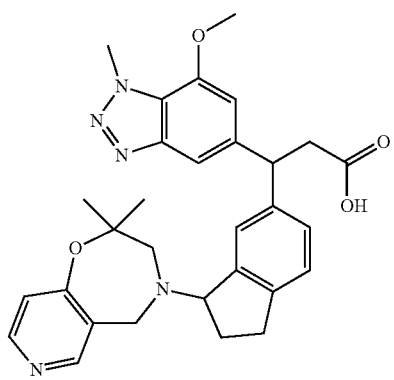 [SMILES: COc1cc(C(CC(=O)O)c2ccc3c(c2)C(N2Cc4cnccc4OC(C)(C)C2)CC3)cc2nnn(C)c12]

To a solution of ethyl 3-(3-(2,2-dimethyl-2,3-dihydropyrido[3,4-f][1,4]oxazepin-4(5H)-yl)-2,3-dihydro-1H-inden-5-yl)-3-(7-methoxy-1-methyl-1H-benzo[d][1,2,3]triazol-5-yl)propanoate (25.6 mg, 0.046 mmol) in methanol (1 mL) was added NaOH (2 N) (9.21 mg, 0.230 mmol). The resulting solution was heated with microwave at 80° C. for 15 min before being acidified with HCl (1 N) to pH~5, evaporated under vacuum, and purified by reverse phase HPLC to afford product 3-(3-(2,2-dimethyl-2,3-dihydropyrido[3,4-f][1,4]oxazepin-4(5H)-yl)-2,3-dihydro-1H-inden-5-yl)-3-(7-methoxy-1-methyl-1H-benzo[d][1,2,3]triazol-5-yl)propanoic acid, formic acid salt (8.4 mg, 0.016 mmol, 34.6% yield). LC-MS m/z 528.2 (M+H)$^+$, 0.84 min (ret. time).

Example 47

3-(1,4-Dimethyl-1H-benzo[d][1,2,3]triazol-5-yl)-3-(3-((R)-2,7-dimethyl-2,3-dihydrobenzo[f][1,4]oxazepin-4(5H)-yl)-2,3-dihydro-1H-inden-5-yl)propanoic Acid, Formic Acid Salt

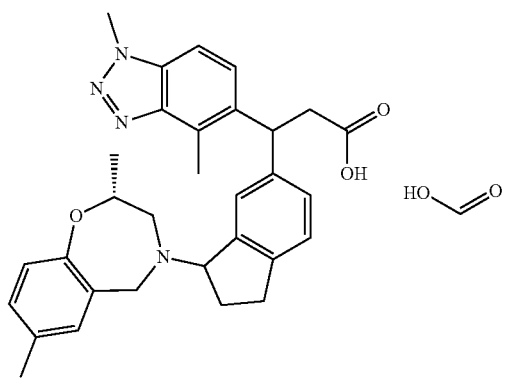 [SMILES: Cc1ccc2c(c1)CN(C1CCc3ccc(C(CC(=O)O)c4ccc5c(nnn5C)c4C)cc31)C[C@@H](C)O2 ; O=CO]

To a solution of ethyl 3-(1,4-dimethyl-1H-benzo[d][1,2,3]triazol-5-yl)-3-(3-hydroxy-2,3-dihydro-1H-inden-5-yl)propanoate (76 mg, 0.2 mmol) in DCM (1.000 mL) was added $SOCl_2$ (0.029 mL, 0.400 mmol). The resulting reaction mixture was stirred at ambient temperature for 15 min, evaporated under vacuum and dissolved in acetonitrile (2 mL) before adding (R)-2,7-dimethyl-2,3,4,5-tetrahydrobenzo[f][1,4]oxazepine (70.9 mg, 0.400 mmol), sodium iodide (14.99 mg, 0.100 mmol) and $K_2CO_3$ (55.3 mg, 0.400 mmol). The resulting reaction mixture was heated at 40° C. for 92 h then was filtered. The filter cake was washed with MeCN (2 mL). The combined filtrate was evaporated under vacuum and dissolved in methanol (2 mL) before adding NaOH (3 N) (0.333 mL, 1.000 mmol). The resulting reaction mixture was heated with microwave at 80° C. for 20 min before being acidified with HCl (3 N) to pH 4-5, evaporated under vacuum, and purified by reverse phase HPLC to afford the desired product 3-(1,4-dimethyl-1H-benzo[d][1,2,3]triazol-5-yl)-3-(3-((R)-2,7-dimethyl-2,3-di hydrobenzo[f][1,4]oxazepin-4(5H)-yl)-2,3-dihydro-1H-inden-5-yl)propanoic acid, formic acid salt (60.4 mg, 0.113 mmol, 56.4% yield). LC-MS m/z 511.5 (M+H)$^+$, 0.75 min (ret. time).

Example 48

3-(1,4-Dimethyl-1H-benzo[d][1,2,3]triazol-5-yl)-3-(3-(2,2-dimethyl-2,3-dihydropyrido[3,4-f][1,4]oxazepin-4(5H)-yl)-2,3-dihydro-1H-inden-5-yl)propanoic Acid, Formic Acid Salt

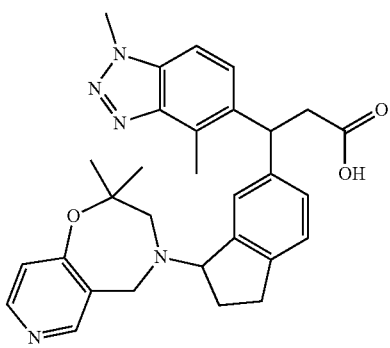 [SMILES: Cc1c(C(CC(=O)O)c2ccc3c(c2)C(N2Cc4cnccc4OC(C)(C)C2)CC3)ccc2c1nnn2C]

Ethyl 3-(1,4-dimethyl-1H-benzo[d][1,2,3]triazol-5-yl)-3-(3-(2,2-dimethyl-2,3-dihydropyrido[3,4-f][1,4]oxazepin-4(5H)-yl)-2,3-dihydro-1H-inden-5-yl)propanoate

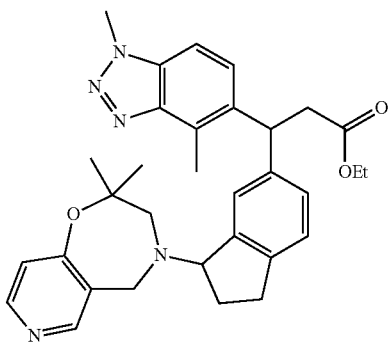

To a solution of 2,2-dimethyl-2,3,4,5-tetrahydropyrido[3,4-f][1,4]oxazepine (67.1 mg, 0.376 mmol) in acetonitrile (3 mL) was added K$_2$CO$_3$ (96 mg, 0.691 mmol), sodium iodide (25.9 mg, 0.173 mmol) and ethyl 3-(3-chloro-2,3-dihydro-1H-inden-5-yl)-3-(1,4-dimethyl-1H-benzo[d][1,2,3]triazol-5-yl)propanoate (137.5 mg, 0.346 mmol). The resulting solution was heated with microwave at 60° C. for 5 h then was evaporated under vacuum, purified via flash chromatography to afford desired product ethyl 3-(1,4-dimethyl-1H-benzo[d][1,2,3]triazol-5-yl)-3-(3-(2,2-dimethyl-2,3-dihydropyrido[3,4-f][1,4]oxazepin-4(5H)-yl)-2,3-dihydro-1H-inden-5-yl)propanoate (17 mg, 0.032 mmol, 9.12% yield). LC-MS m/z 540.2 (M+H)$^+$, 0.89 min (ret. time).

3-(1,4-Dimethyl-1H-benzo[d][1,2,3]triazol-5-yl)-3-(3-(2,2-dimethyl-2,3-dihydropyrido[3,4-f][1,4]oxazepin-4(5H)-yl)-2,3-dihydro-1H-inden-5-yl)propanoic Acid, Formic Acid Salt

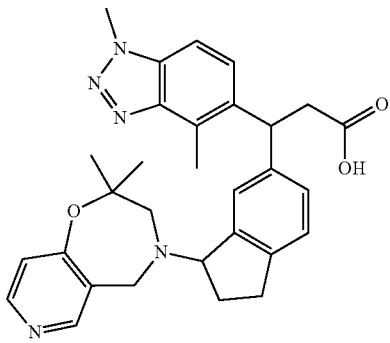 [SMILES: Cc1c(C(CC(=O)O)c2ccc3c(c2)C(N2Cc4cnccc4OC(C)(C)C2)CC3)ccc2c1nnn2C]

To a solution of ethyl 3-(1,4-dimethyl-1H-benzo[d][1,2,3]triazol-5-yl)-3-(3-(2,2-dimethyl-2,3-dihydropyrido[3,4-f][1,4]oxazepin-4(5H)-yl)-2,3-dihydro-1H-inden-5-yl)propanoate (17 mg, 0.032 mmol) in methanol (1 mL) was added NaOH (2 N) (6.30 mg, 0.158 mmol). The resulting solution was heated with microwave at 80° C. for 15 min then was acidified with HCl (1 N) to pH~5, evaporated under vacuum, and purified by reverse phase HPLC to afford product 3-(1,4-dimethyl-1H-benzo[d][1,2,3]triazol-5-yl)-3-(3-(2,2-dimethyl-2,3-dihydropyrido[3,4-f][1,4]oxazepin-4(5H)-yl)-2,3-dihydro-1H-inden-5-yl)propanoic acid, formic acid salt (10.5 mg, 0.021 mmol, 65.2% yield). LC-MS m/z 512.2 (M+H)$^+$, 0.78 min (ret. time).

Example 49

3-(1,4-Dimethyl-1H-benzo[d][1,2,3]triazol-5-yl)-2,2-dimethyl-3-(3-((S)-2-methyl-2,3-dihydropyrido[3,2-f][1,4]oxazepin-4(5H)-yl)-2,3-dihydro-1H-inden-5-yl)propanoic Acid, Formic Acid Salt

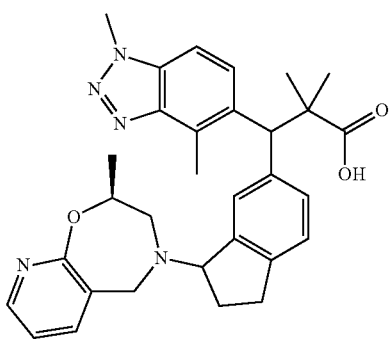 [SMILES: Cc1c(C(c2ccc3c(c2)C(N2Cc4cccnc4O[C@@H](C)C2)CC3)C(C)(C)C(=O)O)ccc2c1nnn2C]

(S)-1-(((2-chloropyridin-3-yl)methyl)amino)propan-2-ol

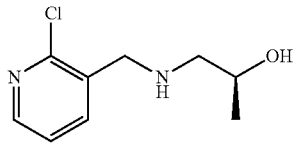

To a solution of 2-chloronicotinaldehyde (0.708 g, 5 mmol) in methanol (10 mL) was added (S)-1-aminopropan-2-ol (0.488 g, 6.50 mmol). The reaction mixture was stirred at ambient temperature for 1 h before adding NaBH$_4$ (0.378 g, 10.00 mmol) slowly and the resulting solution was stirred at ambient temperature for an additional 1 h then was quenched with NaHCO$_3$ (sat.), diluted with DCM (20 mL), dried over MgSO$_4$, filtered, evaporated under vacuum to afford product (S)-1-(((2-chloropyridin-3-yl)methyl)amino)propan-2-ol (1.0291 g, 5.13 mmol, 103% yield). LC-MS m/z 200.9 (M+H)$^+$, 0.19 min (ret. time).

(S)-2-Methyl-2,3,4,5-tetrahydropyrido[3,2-f][1,4]oxazepine

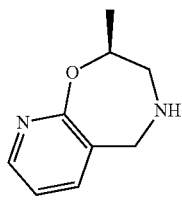

To a solution of (S)-1-(((2-chloropyridin-3-yl)methyl)amino)propan-2-ol (1.026 g, 5.11 mmol) in N,N-dimethylformamide (50 mL) was added KOtBu (1.721 g, 15.34 mmol). The resulting solution was heated at 80° C. for 4 h, evaporated by under high vacuum then diluted with DCM (50 mL), filtered evaporated under vacuum to afford product (S)-2-methyl-2,3,4,5-tetrahydropyrido[3,2-f][1,4]oxazepine (0.8617 g, 5.25 mmol, 103% yield). LC-MS m/z 164.9 (M+H)$^+$, 0.10 min (ret. time).

Methyl 3-(1,4-dimethyl-1H-benzo[d][1,2,3]triazol-5-yl)-2,2-dimethyl-3-(3-((S)-2-methyl-2,3-dihydropyrido[3,2-f][1,4]oxazepin-4(5H)-yl)-2,3-dihydro-1H-inden-5-yl)propanoate

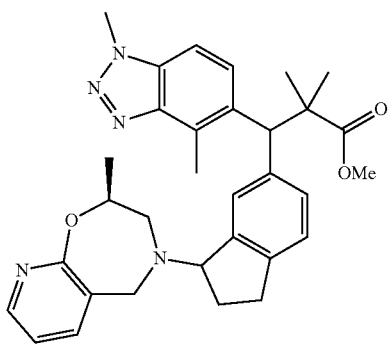 [SMILES: COC(=O)C(C)(C)C(c1ccc2c(c1)C(N1Cc3cccnc3O[C@@H](C)C1)CC2)c1ccc2c(nnn2C)c1C]

To a solution of (S)-2-methyl-2,3,4,5-tetrahydropyrido[3,2-f][1,4]oxazepine (80 mg, 0.486 mmol) in acetonitrile (2.5 mL) was added K$_2$CO$_3$ (101 mg, 0.728 mmol). The resulting solution was stirred at ambient temperature for 20 min followed by addition of sodium iodide (18.19 mg, 0.121 mmol) and methyl 3-(3-chloro-2,3-dihydro-1H-inden-5-yl)-3-(1,4-dimethyl-1H-benzo[d][1,2,3]triazol-5-yl)-2,2-dimethylpropanoate (100 mg, 0.243 mmol). The resulting solution was heated at 50° C. for 21 h before being filtered. The filter cake was washed with MeCN (2 mL). The combined filtrate was evaporated under vacuum then purified via flash chromatography to afford the desired product methyl 3-(1,4-dimethyl-1H-benzo[d][1,2,3]triazol-5-yl)-2,2-dimethyl-3-(3-((S)-2-methyl-2,3-dihydropyrido[3,2-f][1,4]oxazepin-4(5H)-yl)-2,3-dihydro-1H-inden-5-yl)propanoate (78.9 mg, 0.146 mmol, 60.2% yield). LC-MS m/z 540.2 (M+H)$^+$, 0.85 min (ret. time).

3-(1,4-Dimethyl-1H-benzo[d][1,2,3]triazol-5-yl)-2,2-dimethyl-3-(3-((S)-2-methyl-2,3-dihydropyrido[3,2-f][1,4]oxazepin-4(5H)-yl)-2,3-dihydro-1H-inden-5-yl)propanoic Acid, Formic Acid Salt

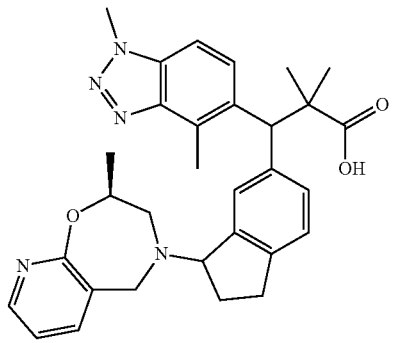 [SMILES: Cc1c(C(c2ccc3c(c2)C(N2Cc4cccnc4O[C@@H](C)C2)CC3)C(C)(C)C(=O)O)ccc2c1nnn2C]

To a solution of methyl 3-(1,4-dimethyl-1H-benzo[d][1,2,3]triazol-5-yl)-2,2-dimethyl-3-(3-((S)-2-methyl-2,3-dihydropyrido[3,2-f][1,4]oxazepin-4(5H)-yl)-2,3-dihydro-1H-inden-5-yl)propanoate (78 mg, 0.145 mmol) in methanol (2.5 mL) was added NaOH (2 N) (28.9 mg, 0.723 mmol). The resulting solution was heated with microwave at 120° C. for 7 h then was acidified with HCl (1 N) to pH~5, evaporated under vacuum, and purified by reverse phase HPLC to afford product 3-(1,4-dimethyl-1H-benzo[d][1,2,3]triazol-5-yl)-2,2-dimethyl-3-(3-((S)-2-methyl-2,3-dihydropyrido[3,2-f][1,4]oxazepin-4(5H)-yl)-2,3-dihydro-1H-inden-5-yl)propanoic acid, formic acid salt (54 mg, 0.103 mmol, 71.1% yield). LC-MS m/z 526.5 (M+H)$^+$, 0.69 min (ret. time).

Example 50

3-(1,4-Dimethyl-1H-benzo[d][1,2,3]triazol-5-yl)-3-(3-((R)-2-ethyl-2,3-dihydrobenzo[f][1,4]oxazepin-4(5H)-yl)-2,3-dihydro-1H-inden-5-yl)propanoic Acid, Formic Acid Salt

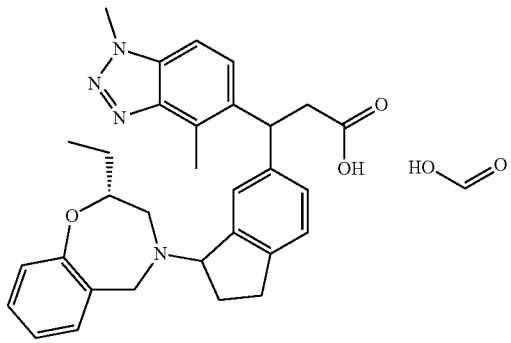 [SMILES: CC[C@@H]1CN(C2CCc3ccc(C(CC(=O)O)c4ccc5c(nnn5C)c4C)cc32)Cc2ccccc2O1 ; O=CO]

To a solution of ethyl 3-(1,4-dimethyl-1H-benzo[d][1,2,3]triazol-5-yl)-3-(3-hydroxy-2,3-dihydro-1H-inden-5-yl)propanoate (0.050 g, 0.132 mmol) in DCM (0.50 mL) was added SOCl2 (0.019 mL, 0.264 mmol). The resulting reaction mixture was stirred at ambient temperature for 15 min, evaporated under vacuum, dissolved in acetonitrile (1.5 mL) followed by addition of (R)-2-ethyl-2,3,4,5-tetrahydrobenzo[f][1,4]oxazepine, hydrochloride (0.042 g, 0.198 mmol), sodium iodide (9.88 mg, 0.066 mmol) and $K_2CO_3$ (0.055 g, 0.395 mmol). The resulting reaction mixture was heated at 40° C. for 17 h then was filtered. The filter cake was washed with MeCN (2 mL). The combined filtrate was evaporated under vacuum and dissolved in methanol (1.5 mL) followed by addition of NaOH (3 N) (0.220 mL, 0.659 mmol). The resulting reaction mixture was heated with microwave at 80° C. for 20 min before being acidified with HCl (3 N) to pH 4-5, evaporated under vacuum, and purified by reverse phase HPLC to afford product 3-(1,4-dimethyl-1H-benzo[d][1,2,3]triazol-5-yl)-3-(3-((R)-2-ethyl-2,3-dihydrobenzo[f][1,4]oxazepin-4(5H)-yl)-2,3-dihydro-1H-inden-5-yl)propanoic acid, formic acid salt (22.7 mg, 0.042 mmol, 32.0% yield) (78.7 mg, 0.158 mmol, 67.5% yield). LC-MS m/z 511.5 (M+H)+, 0.75 min (ret. time).

Example 51

3-(1,4-Dimethyl-1H-benzo[d][1,2,3]triazol-5-yl)-3-(3-((2,2-dimethyl-2,3-dihydropyrido[3,2-f][1,4]oxazepin-4(5H)-yl)methyl)-4-methylphenyl)propanoic Acid

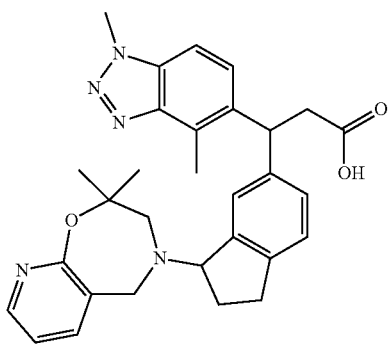 [SMILES: Cc1c(C(CC(=O)O)c2ccc3c(c2)C(N2Cc4cccnc4OC(C)(C)C2)CC3)ccc2c1nnn2C]

To a solution of ethyl 3-(1,4-dimethyl-1H-benzo[d][1,2,3]triazol-5-yl)-3-(3-hydroxy-2,3-dihydro-1H-inden-5-yl)propanoate (76 mg, 0.2 mmol) in DCM (1.000 mL) was added SOCl2 (0.029 mL, 0.400 mmol). The resulting reaction mixture was stirred at ambient temperature for 20 min, evaporated under vacuum before being redissolved in acetonitrile (3 mL) followed by addition of 2,2-dimethyl-2,3,4,5-tetrahydropyrido[3,2-f][1,4]oxazepine (71.3 mg, 0.400 mmol), sodium iodide (14.99 mg, 0.100 mmol) and $K_2CO_3$ (55.3 mg, 0.400 mmol). The resulting reaction mixture was heated at 40° C. for 21 h before being filtered. The filter cake was washed with MeCN (2 mL). The combined filtrate was evaporated under vacuum and dissolved in methanol (3 mL) before adding NaOH (3 N) (0.533 mL, 1.600 mmol). The resulting reaction mixture was heated with microwave at 80° C. for 20 min before being acidified with HCl (3 N) to pH 4-5, evaporated under vacuum, and purified by reverse phase HPLC to afford the desired product 3-(1,4-dimethyl-1H-benzo[d][1,2,3]triazol-5-yl)-3-(3-(2,2-dimethyl-2,3-dihydropyrido[3,2-f][1,4]oxazepin-4(5H)-yl)-2,3-dihydro-1H-inden-5-yl)propanoic acid (40.5 mg, 0.079 mmol, 39.6% yield). LC-MS m/z 512.1 (M+H)+, 0.72 min (ret. time).

Example 52

3-(3-(2,3-Dihydrobenzo[f][1,4]oxazepin-4(5H)-yl)-2,3-dihydro-1H-inden-5-yl)-3-(7-methoxy-1,4-dimethyl-1H-benzo[d][1,2,3]triazol-5-yl)propanoic Acid, Formic Acid Salt

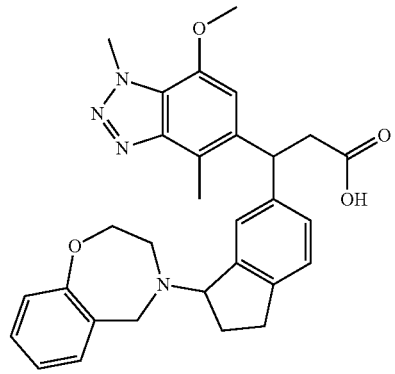 [SMILES: COc1cc(C(CC(=O)O)c2ccc3c(c2)C(N2CCOc4ccccc4C2)CC3)c(C)c2nnn(C)c12]

Methyl 3-(3-(2,3-dihydrobenzo[f][1,4]oxazepin-4(5H)-yl)-2,3-dihydro-1H-inden-5-yl)-3-(7-methoxy-1,4-dimethyl-1H-benzo[d][1,2,3]triazol-5-yl)propanoate

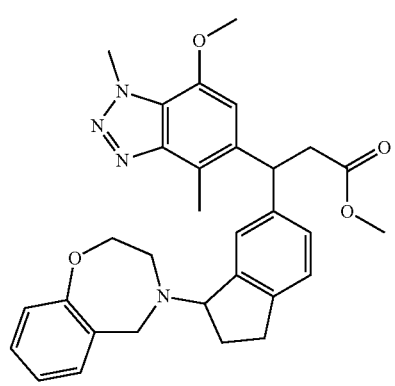 [SMILES: COC(=O)CC(c1ccc2c(c1)C(N1CCOc3ccccc3C1)CC2)c1cc(OC)c2c(nnn2C)c1C]

To a solution of 2,3,4,5-tetrahydrobenzo[f][1,4]oxazepine (59.5 mg, 0.399 mmol) in acetonitrile (2.5 mL) was added K₂CO₃ (110 mg, 0.797 mmol). The resulting solution was stirred at ambient temperature for 20 min before adding sodium iodide (19.92 mg, 0.133 mmol) and methyl 3-(3-chloro-2,3-dihydro-1H-inden-5-yl)-3-(7-methoxy-1,4-dimethyl-1H-benzo[d][1,2,3]triazol-5-yl)propanoate (110 mg, 0.266 mmol). The resulting solution was heated at 50° C. for 19 h. The reaction mixture was filtered. The filter cake was washed with MeCN (2 mL). The combined filtrate was evaporated under vacuum and the residue was purified via flash chromatography to afford product methyl 3-(3-(2,3-dihydrobenzo[f][1,4]oxazepin-4(5H)-yl)-2,3-dihydro-1H-inden-5-yl)-3-(7-methoxy-1,4-dimethyl-1H-benzo[d][1,2,3]triazol-5-yl)propanoate (50.8 mg, 0.096 mmol, 36.3% yield). LC-MS m/z 527.3 (M+H)⁺, 0.82 min (ret. time).

3-(3-(2,3-Dihydrobenzo[f][1,4]oxazepin-4(5H)-yl)-2,3-dihydro-1H-inden-5-yl)-3-(7-methoxy-1,4-dimethyl-1H-benzo[d][1,2,3]triazol-5-yl)propanoic Acid, Formic Acid Salt

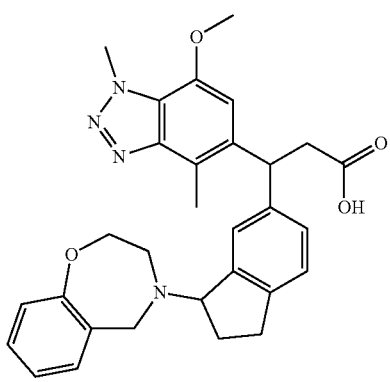 [SMILES: COc1cc(C(CC(=O)O)c2ccc3c(c2)C(N2CCOc4ccccc4C2)CC3)c(C)c2nnn(C)c12]

To a solution of methyl 3-(3-(2,3-dihydrobenzo[f][1,4]oxazepin-4(5H)-yl)-2,3-dihydro-1H-inden-5-yl)-3-(7-methoxy-1,4-dimethyl-1H-benzo[d][1,2,3]triazol-5-yl)propanoate (50.8 mg, 0.096 mmol) in methanol (2 mL) was added NaOH (2 N) (19.29 mg, 0.482 mmol). The resulting solution was heated with microwave at 80° C. for 15 min. The reaction mixture was acidified with HCl (1 N) to pH~5, evaporated under vacuum, and purified by reverse phase HPLC to afford the desired product 3-(3-(2,3-dihydrobenzo[f][1,4]oxazepin-4(5H)-yl)-2,3-dihydro-1H-inden-5-yl)-3-(7-methoxy-1,4-dimethyl-1H-benzo[d][1,2,3]triazol-5-yl)propanoic acid, formic acid salt (39.8 mg, 0.078 mmol, 80% yield). LC-MS m/z 513.6 (M+H)⁺, 0.71 min (ret. time).

Example 53

3-(1,4-Dimethyl-1H-benzo[d][1,2,3]triazol-5-yl)-3-(3-((R)-2-methyl-2,3-dihydrobenzo[f][1,4]oxazepin-4(5H)-yl)-2,3-dihydro-1H-inden-5-yl)propanoic Acid

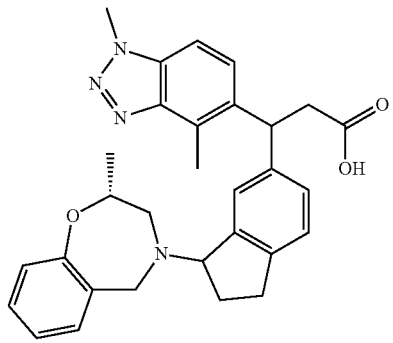 [SMILES: Cc1c(C(CC(=O)O)c2ccc3c(c2)C(N2Cc4ccccc4O[C@H](C)C2)CC3)ccc2c1nnn2C]

6-Bromo-1-chloro-2,3-dihydro-1H-indene

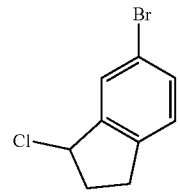 [SMILES: ClC1CCc2ccc(Br)cc21]

To a solution of 6-bromo-2,3-dihydro-1H-inden-1-ol (1.50 g, 7.04 mmol) in DCM (3.5 mL) was added thionyl chloride (1.028 mL, 14.08 mmol). The resulting reaction mixture was stirred at ambient temperature for 1 h. The reaction mixture was evaporated under vacuum to afford product 6-bromo-1-chloro-2,3-dihydro-1H-indene (1.6225 g, 7.01 mmol, 100% yield). ¹H NMR (400 MHz, CHLOROFORM-d): ppm 2.33-2.44 (m, 1H) 2.63 (dq, J=14.24, 7.22 Hz, 1H) 2.86 (ddd, J=16.00, 7.97, 4.14 Hz, 1H) 3.13 (dt, J=15.81, 7.65 Hz, 1H) 5.37 (dd, J=6.53, 3.51 Hz, 1H) 7.14 (d, J=8.03 Hz, 1H) 7.39 (d, J=8.03 Hz, 1H) 7.57 (s, 1H).

((2R)-4-(6-Bromo-2,3-dihydro-1H-inden-1-yl)-2-methyl-2,3,4,5-tetrahydrobenzo[f][1,4]oxazepine

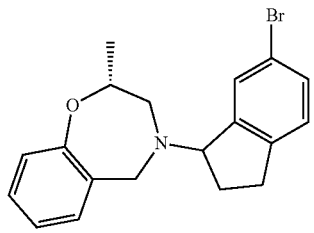 [SMILES: C[C@@H]1CN(C2CCc3ccc(Br)cc32)Cc2ccccc2O1]

To a solution of 6-bromo-1-chloro-2,3-dihydro-1H-indene (185 mg, 0.8 mmol) in acetonitrile (8 mL) was added (R)-2-methyl-2,3,4,5-tetrahydrobenzo[f][1,4]oxazepine (261 mg, 1.600 mmol), K$_2$CO$_3$ (221 mg, 1.600 mmol) and sodium iodide (23.98 mg, 0.160 mmol). The resulting reaction mixture was heated at 60° C. for 68 h. The reaction mixture was evaporated under vacuum, purified via flash chromatography to afford product (2R)-4-(6-bromo-2,3-dihydro-1H-inden-1-yl)-2-methyl-2,3,4,5-tetrahydrobenzo[f][1,4]oxazepine (191.5 mg, 0.535 mmol, 66.8% yield). LC-MS m/z 358.1 (M+H)$^+$, 0.77 min (ret. time).

(2R)-2-Methyl-4-(6-(4,4,5,5-tetramethyl-1,3,2-dioxaborolan-2-yl)-2,3-dihydro-1H-inden-1-yl)-2,3,4,5-tetrahydrobenzo[f][1,4]oxazepine

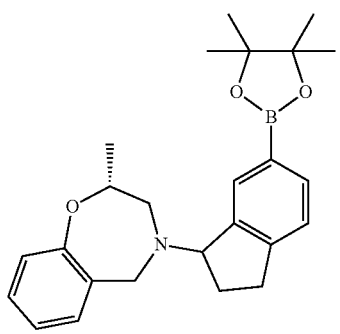 [SMILES: C[C@@H]1CN(C2CCc3ccc(B4OC(C)(C)C(C)(C)O4)cc32)Cc2ccccc2O1]

To a solution of (2R)-4-(6-bromo-2,3-dihydro-1H-inden-1-yl)-2-methyl-2,3,4,5-tetrahydrobenzo[f][1,4]oxazepine (190 mg, 0.530 mmol) in N,N-dimethylformamide (3 mL) was added bis(pinacolato)diboron (202 mg, 0.795 mmol), KOAc (104 mg, 1.061 mmol) and PdCl$_2$(dppf) (19.40 mg, 0.027 mmol). The resulting reaction mixture was heated with microwave at 100° C. for 1 h. The reaction mixture was evaporated under vacuum, purified via flash chromatography to afford product (2R)-2-methyl-4-(6-(4,4,5,5-tetramethyl-1,3,2-dioxaborolan-2-yl)-2,3-dihydro-1H-inden-1-yl)-2,3,4,5-tetrahydrobenzo[f][1,4]oxazepine (164.1 mg, 0.405 mmol, 76% yield). LC-MS m/z 406.2 (M+H)$^+$, 0.94 min (ret. time).

3-(1,4-Dimethyl-1H-benzo[d][1,2,3]triazol-5-yl)-3-(3-((R)-2-methyl-2,3-dihydrobenzo[f][1,4]oxazepin-4(5H)-yl)-2,3-dihydro-1H-inden-5-yl)propanoic Acid

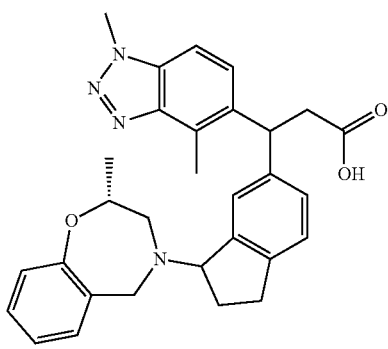 [SMILES: Cc1c(C(CC(=O)O)c2ccc3c(c2)C(N2Cc4ccccc4O[C@H](C)C2)CC3)ccc2c1nnn2C]

To a solution of (2R)-2-methyl-4-(6-(4,4,5,5-tetramethyl-1,3,2-dioxaborolan-2-yl)-2,3-dihydro-1H-inden-1-yl)-2,3,4,5-tetrahydrobenzo[f][1,4]oxazepine (165 mg, 0.408 mmol) in 1,4-dioxane (2 mL) and water (0.7 mL) was added (E)-ethyl 3-(1,4-dimethyl-1H-benzo[d][1,2,3]triazol-5-yl)acrylate (50 mg, 0.204 mmol), TEA (0.085 mL, 0.612 mmol) and [RhCl(cod)]$_2$ (5.03 mg, 10.19 μmol). The resulting reaction mixture was heated at 90° C. for 90 min. The reaction mixture was evaporated under vacuum before being redissolved in methanol (2 mL) followed by addition of NaOH (3 N) (0.340 mL, 1.019 mmol). The resulting reaction mixture was heated with microwave at 80° C. for 20 min. The reaction mixture was acidified with HCl (3 N) to pH 3-4, evaporated under vacuum, and purified by reverse phase HPLC to afford product 3-(1,4-dimethyl-1H-benzo[d][1,2,3]triazol-5-yl)-3-(3-((R)-2-methyl-2,3-di hydrobenzo[f][1,4]oxazepin-4(5H)-yl)-2,3-dihydro-1H-inden-5-yl)propanoic acid (11.0 mg, 0.022 mmol, 10.87% yield). LC-MS m/z 497.2 (M+H)$^+$, 0.74 min (ret. time).

Example 54

3-(3-(2,3-Dihydropyrido[3,2-f][1,4]oxazepin-4(5H)-yl)-2,3-dihydro-1H-inden-5-yl)-3-(1,4-dimethyl-1H-benzo[d][1,2,3]triazol-5-yl)-2,2-dimethylpropanoic Acid, Formic Acid Salt, Formic Acid Salt

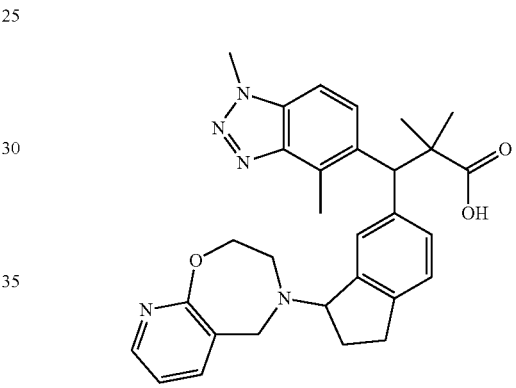

2,3,4,5-Tetrahydropyrido[3,2-f][1,4]oxazepine

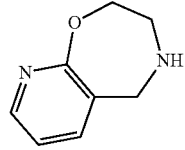 [SMILES: c1cnc2c(c1)CNCCO2]

To a solution of 2-chloronicotinaldehyde (425 mg, 3 mmol) in methanol (5 mL) was added 2-aminoethanol (476 mg, 3.90 mmol). The reaction mixture was stirred at ambient temperature for 1 h then NaBH$_4$ (227 mg, 6.00 mmol) was added. The resulting solution was stirred at ambient temperature for an additional 1 h. The reaction mixture was quenched with NaHCO$_3$ (sat.) (0.5 mL) and evaporated down. The residue was diluted with DCM (20 mL), dried over MgSO$_4$, filtered and then evaporated under vacuum before being diluted with N,N-dimethylformamide (30.00 mL) followed by addition of KOtBu (673 mg, 6.00 mmol). The resulting solution was heated at 80° C. for 4 h before adding more KOtBu (337 mg, 3.00 mmol) then was heated at 80° C. for an additional 3 h. The reaction mixture was filtered and the filter cake was washed with N,N-dimethylformamide (5.00 mL). The combined filtrate was evaporated down under vacuum. The residue was diluted with DCM (30 mL), dried over MgSO₄ and evaporated down to afford product 2,3,4,5-tetrahydropyrido[3,2-f][1,4]oxazepine (679 mg, 4.52 mmol, 151% yield). LC-MS m/z 150.8 (M+H)⁺, 0.11 min (ret. time).

Tert-butyl 2,3-dihydropyrido[3,2-f][1,4]oxazepine-4 (5H)-carboxylate

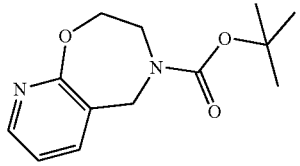 [SMILES: CC(C)(C)OC(=O)N1CCOc2ncccc2C1]

To a solution of di-tert-butyl dicarbonate (2.099 mL, 9.04 mmol) in THF (5.0 mL) was added a solution of 2,3,4,5-tetrahydropyrido[3,2-f][1,4]oxazepine (679 mg, 4.52 mmol) in THF (5.0 mL) under argon atmosphere. The resulting solution was stirred at ambient temperature for 21 h. The reaction was then evaporated under vacuum, purified via flash chromatography to afford product tert-butyl 2,3-dihydropyrido[3,2-f][1,4]oxazepine-4(5H)-carboxylate (390.8 mg, 1.561 mmol, 34.5% yield). LC-MS m/z 250.9 (M+H)⁺, 0.69 min (ret. time).

2,3,4,5-Tetrahydropyrido[3,2-f][1,4]oxazepine, Hydrochloride

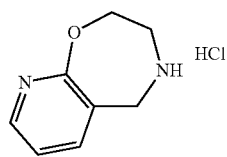 [SMILES: c1cnc2c(c1)CNCCO2 ; Cl]

To a solution of tert-butyl 2,3-dihydropyrido[3,2-f][1,4] oxazepine-4(5H)-carboxylate (390 mg, 1.558 mmol) in 1,4-dioxane (3 mL) was added HCl (4 M in 1,4-dioxane) (1.169 mL, 4.67 mmol). The resulting solution was stirred at ambient temperature for 2 h before adding more HCl (4M in 1,4-dioxane) (2.73 mL, 10.91 mmol). The resulting solution was stirred at ambient temperature for additional 20 h. The reaction solution was evaporated under vacuum to afford product 2,3,4,5-tetrahydropyrido[3,2-f][1,4]oxazepine, hydrochloride (290.4 mg, 1.556 mmol, 100% yield). LC-MS m/z 150.8 (M+H)⁺, 0.13 min (ret. time).

Methyl 3-(3-(2,3-dihydropyrido[3,2-f][1,4]oxazepin-4(5H)-yl)-2,3-dihydro-1H-inden-5-yl)-3-(1,4-dimethyl-1H-benzo[d][1,2,3]triazol-5-yl)-2,2-dimethylpropanoate

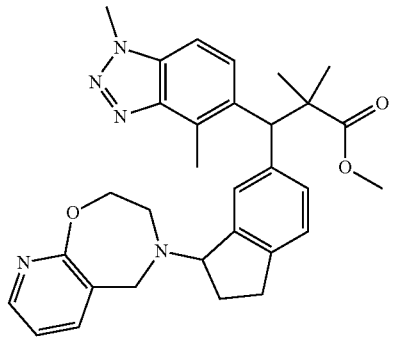 [SMILES: COC(=O)C(C)(C)C(c1ccc2c(c1)C(N1CCOc3ncccc3C1)CC2)c1ccc2c(nnn2C)c1C]

To a solution of 2,3,4,5-tetrahydropyrido[3,2-f][1,4]oxazepine, hydrochloride (68.0 mg, 0.364 mmol) in acetonitrile (2.5 mL) was added K₂CO₃ (134 mg, 0.971 mmol). The resulting solution was stirred at ambient temperature for 20 min before adding sodium iodide (18.19 mg, 0.121 mmol) and methyl 3-(3-chloro-2,3-dihydro-1H-inden-5-yl)-3-(1,4-dimethyl-1H-benzo[d][1,2,3]triazol-5-yl)-2,2-dimethylpropanoate (100 mg, 0.243 mmol). The resulting solution was heated at 50° C. for 16 h. The reaction mixture was filtered. The filter cake was washed with MeCN (2 mL). The combined filtrate was evaporated under vacuum and the residue was purified via flash chromatography to afford product methyl 3-(3-(2,3-dihydropyrido[3,2-f][1,4]oxazepin-4(5H)-yl)-2,3-dihydro-1H-inden-5-yl)-3-(1,4-dimethyl-1H-benzo[d][1,2,3]triazol-5-yl)-2,2-dimethylpropanoate (64.2 mg, 0.122 mmol, 50.3% yield). LC-MS m/z 526.2 (M+H)⁺, 0.79 min (ret. time).

3-(3-(2,3-Dihydropyrido[3,2-f][1,4]oxazepin-4(5H)-yl)-2,3-dihydro-1H-inden-5-yl)-3-(1,4-dimethyl-1H-benzo[d][1,2,3]triazol-5-yl)-2,2-dimethylpropanoic Acid, Formic Acid Salt

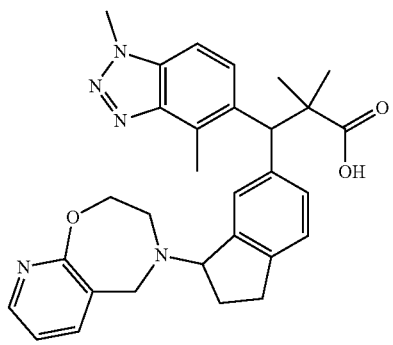

To a solution of methyl 3-(3-(2,3-dihydropyrido[3,2-f][1, 4]oxazepin-4(5H)-yl)-2,3-dihydro-1H-inden-5-yl)-3-(1,4-dimethyl-1H-benzo[d][1,2,3]triazol-5-yl)-2,2-dimethylpropanoate (64 mg, 0.122 mmol) in methanol (2.5 mL) was added NaOH (2 N) (24.35 mg, 0.609 mmol). The resulting solution was heated with microwave at 120° C. for 7 h. The reaction mixture was acidified with HCl (1 N) to pH~5, evaporated under vacuum, purified reverse phase HPLC to afford product 3-(3-(2,3-dihydropyrido[3,2-f][1,4]oxazepin-4(5H)-yl)-2,3-dihydro-1H-inden-5-yl)-3-(1,4-dimethyl-1H-benzo[d][1,2,3]triazol-5-yl)-2,2-dimethylpropanoic acid, formic acid salt (24.5 mg, 0.048 mmol, 39.3% yield). LC-MS m/z 512.6 (M+H)+, 0.66 min (ret. time).

Example 55

3-(3-(2,2-Dimethyl-2,3-dihydropyrido[3,2-f][1,4]oxazepin-4(5H)-yl)-2,3-dihydro-1H-inden-5-yl)-3-(7-methoxy-1-methyl-1H-benzo[d][1,2,3]triazol-5-yl)propanoic Acid, Formic Acid Salt

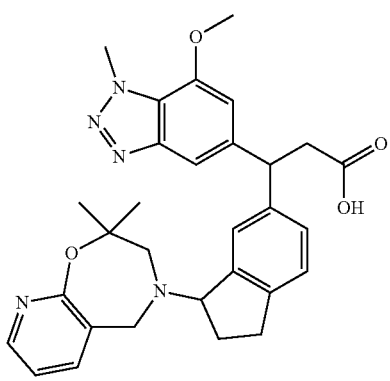 [SMILES: COc1cc(C(CC(=O)O)c2ccc3c(c2)C(N2Cc4cccnc4OC(C)(C)C2)CC3)cc2nnn(C)c12]

Ethyl 3-(3-(2,2-dimethyl-2,3-dihydropyrido[3,2-f][1,4]oxazepin-4(5H)-yl)-2,3-dihydro-1H-inden-5-yl)-3-(7-methoxy-1-methyl-1H-benzo[d][1,2,3]triazol-5-yl)propanoate

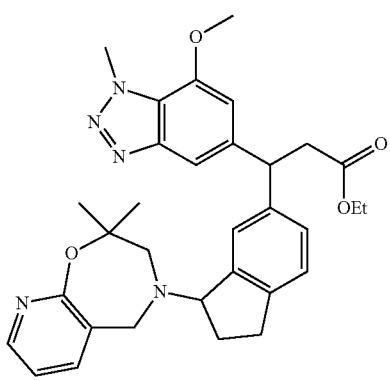 [SMILES: CCOC(=O)CC(c1ccc2c(c1)C(N1Cc3cccnc3OC(C)(C)C1)CC2)c1cc(OC)c2c(c1)nnn2C]

To a solution of 2,2-dimethyl-2,3,4,5-tetrahydropyrido[3,2-f][1,4]oxazepine, hydrochloride (93 mg, 0.435 mmol) and K$_2$CO$_3$ (120 mg, 0.870 mmol) in acetonitrile (3 mL) was added sodium iodide (21.73 mg, 0.145 mmol) and ethyl 3-(3-chloro-2,3-dihydro-1H-inden-5-yl)-3-(7-methoxy-1-methyl-1H-benzo[d][1,2,3]triazol-5-yl)propanoate (120 mg, 0.290 mmol). The resulting solution was heated with microwave at 50° C. for 19 h. The reaction mixture was evaporated under vacuum, purified via flash chromatography to afford product ethyl 3-(3-(2,2-dimethyl-2,3-dihydropyrido[3,2-f][1,4]oxazepin-4(5H)-yl)-2,3-dihydro-1H-inden-5-yl)-3-(7-methoxy-1-methyl-1H-benzo[d][1,2,3]triazol-5-yl)propanoate (62.6 mg, 0.113 mmol, 38.9% yield). LC-MS m/z 556.3 (M+H)+, 0.84 min (ret. time).

3-(3-(2,2-Dimethyl-2,3-dihydropyrido[3,2-f][1,4]oxazepin-4(5H)-yl)-2,3-dihydro-1H-inden-5-yl)-3-(7-methoxy-1-methyl-1H-benzo[d][1,2,3]triazol-5-yl)propanoic Acid, Formic Acid Salt

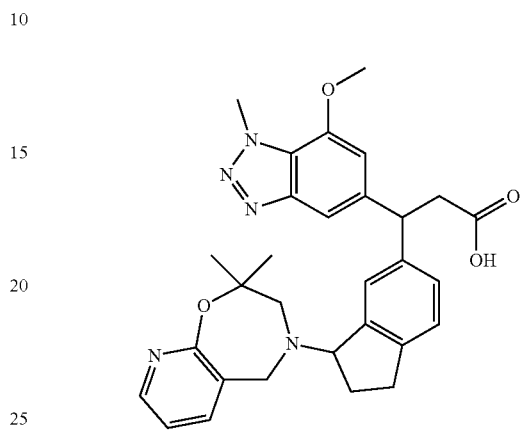

To a solution of ethyl 3-(3-(2,2-dimethyl-2,3-dihydropyrido[3,2-f][1,4]oxazepin-4(5H)-yl)-2,3-dihydro-1H-inden-5-yl)-3-(7-methoxy-1-methyl-1H-benzo[d][1,2,3]triazol-5-yl)propanoate (62.6 mg, 0.113 mmol) in methanol (2 mL) was added NaOH (2N) (22.53 mg, 0.563 mmol). The resulting solution was heated with microwave at 80° C. for 15 min. The reaction mixture was acidified with HCl (1 N) to pH~5, evaporated under vacuum, and purified by reverse phase HPLC to afford product 3-(3-(2,2-dimethyl-2,3-dihydropyrido[3,2-f][1,4]oxazepin-4(5H)-yl)-2,3-dihydro-1H-inden-5-yl)-3-(7-methoxy-1-methyl-1H-benzo[d][1,2,3]triazol-5-yl)propanoic acid, formic acid salt (38 mg, 0.072 mmol, 63.9% yield). LC-MS m/z 528.3 (M+H)+, 0.68 min (ret. time).

Example 56

3-(1,4-Dimethyl-1H-benzo[d][1,2,3]triazol-5-yl)-3-(3-((S)-2-methyl-2,3-dihydrobenzo[f][1,4]oxazepin-4(5H)-yl)-2,3-dihydro-1H-inden-5-yl)propanoic Acid, Formic Acid Salt

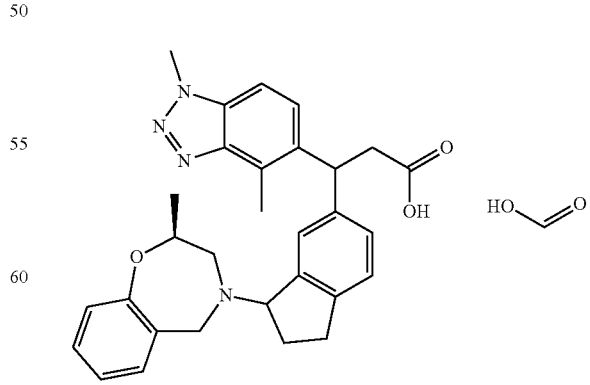

To a solution of ethyl 3-(3-chloro-2,3-dihydro-1H-inden-5-yl)-3-(1,4-dimethyl-1H-benzo[d][1,2,3]triazol-5-yl)propanoate (40 mg, 0.101 mmol) in acetonitrile (1 mL) was added (S)-2-methyl-2,3,4,5-tetrahydrobenzo[f][1,4]oxazepine (32.8 mg, 0.201 mmol), K$_2$CO$_3$ (27.8 mg, 0.201 mmol) and sodium iodide (3.01 mg, 0.020 mmol). The resulting reaction mixture was stirred at 40° C. for 23 h. The reaction mixture was filtered. The filter cake was washed with MeCN (1 mL). The combined filtrate was evaporated under vacuum, dissolved in methanol (1.5 mL) followed by addition of NaOH (3 N) (0.168 mL, 0.503 mmol). The resulting reaction mixture was heated with microwave at 80° C. for 20 min then was acidified with HCl (3 N) to pH~6, evaporated under vacuum, and purified by reverse phase HPLC to afford product 3-(1,4-dimethyl-1H-benzo[d][1,2,3]triazol-5-yl)-3-(3-((S)-2-methyl-2,3-di hydrobenzo[f][1,4]oxazepin-4(5H)-yl)-2,3-dihydro-1H-inden-5-yl)propanoic acid, formic acid salt (26.5 mg, 0.049 mmol, 48.6% yield) (40.5 mg, 0.079 mmol, 39.6% yield). LC-MS m/z 497.2 (M+H)$^+$, 0.73 min (ret. time).

Example 57

3-(1,4-Dimethyl-1H-benzo[d][1,2,3]triazol-5-yl)-3-(3-((R)-2-ethyl-2,3-dihydropyrido[3,4-f][1,4]oxazepin-4(5H)-yl)-2,3-dihydro-1H-inden-5-yl)propanoic Acid, Formic Acid Salt

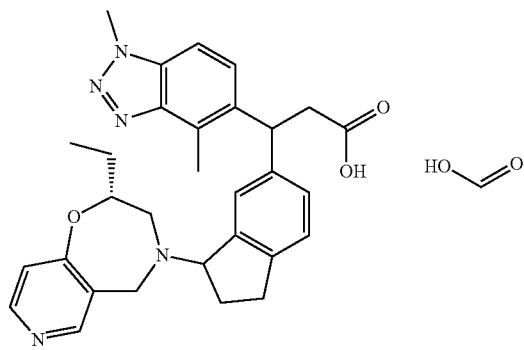 [SMILES: CC[C@@H]1CN(C2CCc3ccc(C(CC(=O)O)c4ccc5c(nnn5C)c4C)cc32)Cc2cnccc2O1 ; O=CO]

To a solution of (R)-2-ethyl-2,3,4,5-tetrahydropyrido[3,4-f][1,4]oxazepine, hydrochloride (86 mg, 0.400 mmol) in methanol (3 mL) was added K$_2$CO$_3$ (55.3 mg, 0.400 mmol). The resulting reaction mixture was stirred at ambient temperature for 30 min, evaporated under vacuum. The resulting residue was added acetonitrile (3 mL) and stirred at ambient temperature for 10 min before being filtered for later use as acetonitrile solution A.

To the solution of ethyl 3-(1,4-dimethyl-1H-benzo[d][1,2,3]triazol-5-yl)-3-(3-hydroxy-2,3-dihydro-1H-inden-5-yl)propanoate (76 mg, 0.2 mmol) in DCM (1.000 mL) was added SOCl$_2$ (0.029 mL, 0.400 mmol). The resulting reaction mixture was stirred at ambient temperature for 20 min, evaporated under vacuum and dissolved in acetonitrile (3 mL). To this solution was added the previous acetonitrile solution A, sodium iodide (14.99 mg, 0.100 mmol) and K$_2$CO$_3$ (55.3 mg, 0.400 mmol). The resulting reaction mixture was heated at 40° C. for 22 h before being filtered. The filter cake was washed with MeCN (2 mL). The combined filtrate was evaporated under vacuum before being dissolved in methanol (3 mL) followed by addition of NaOH (3 N) (0.533 mL, 1.600 mmol). The resulting reaction mixture was heated with microwave at 80° C. for 20 min. The reaction mixture was acidified with HCl (3 N) to pH 4-5, evaporated under vacuum, and purified by reverse phase HPLC to afford product 3-(1,4-dimethyl-1H-benzo[d][1,2,3]triazol-5-yl)-3-(3-((R)-2-ethyl-2,3-dihydropyrido[3,4-f][1,4]oxazepin-4(5H)-yl)-2,3-dihydro-1H-inden-5-yl)propanoic acid, formic acid salt (33.2 mg, 0.061 mmol, 30.5% yield). LC-MS m/z 512.6 (M+H)$^+$, 0.69 min (ret. time).

Example 58

3-(3-(2,3-Dihydrobenzo[f][1,4]oxazepin-4(5H)-yl)-2,3-dihydro-1H-inden-5-yl)-3-(1,4-dimethyl-1H-benzo[d][1,2,3]triazol-5-yl)propanoic Acid, Formic Acid Salt

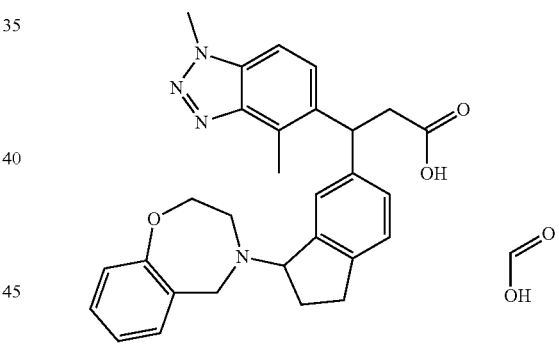

To a solution of ethyl 3-(3-chloro-2,3-dihydro-1H-inden-5-yl)-3-(1,4-dimethyl-1H-benzo[d][1,2,3]triazol-5-yl)propanoate (40 mg, 0.101 mmol) in acetonitrile (1 mL) was added 2,3,4,5-tetrahydrobenzo[f][1,4]oxazepine (30.0 mg, 0.201 mmol), K$_2$CO$_3$ (27.8 mg, 0.201 mmol) and sodium iodide (7.53 mg, 0.050 mmol). The resulting reaction mixture was stirred at 40° C. for 21 h. The reaction mixture was filtered. The filter cake was washed with MeCN (1 mL). The combined filtrate was evaporated under vacuum, dissolved in methanol (1.5 mL) followed by addition of NaOH (3 N) (0.168 mL, 0.503 mmol). The resulting reaction mixture was heated with microwave at 80° C. for 20 min before being acidified with HCl (3 N) to pH~6, evaporated under vacuum, and purified by reverse phase HPLC to afford product 3-(3-(2,3-dihydrobenzo[f][1,4]oxazepin-4(5H)-yl)-2,3-dihydro-1H-inden-5-yl)-3-(1,4-dimethyl-1H-benzo[d][1,2,3]triazol-5-yl)propanoic acid, formic acid salt (15.0 mg, 0.029 mmol, 28.7% yield). LC-MS m/z 483.4 (M+H)$^+$, 0.66 min (ret. time).

Example 59

3-(4-Cyano-2-methylphenyl)-3-(3-(2,2-dimethyl-2,3-dihydropyrido[3,2-f][1,4]oxazepin-4(5H)-yl)-2,3-dihydro-1H-inden-5-y)propanoic Acid, Formic Acid Salt

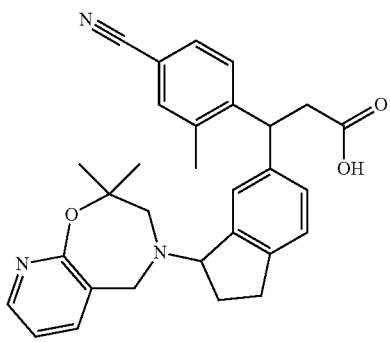 [SMILES: Cc1cc(C#N)ccc1C(CC(=O)O)c1ccc2c(c1)C(N1Cc3cccnc3OC(C)(C)C1)CC2]

4-(6-Bromo-2,3-dihydro-1H-inden-1-yl)-2,2-dimethyl-2,3,4,5-tetrahydropyrido[3,2-f][1,4]oxazepine

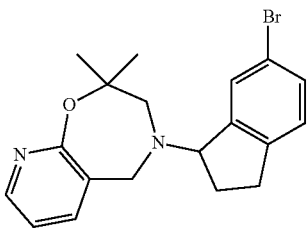 [SMILES: CC1(C)CN(C2CCc3ccc(Br)cc32)Cc2cccnc2O1]

To a solution of 2,2-dimethyl-2,3,4,5-tetrahydropyrido[3,2-f][1,4]oxazepine (0.927 g, 5.20 mmol) in acetonitrile (40 mL) was added $K_2CO_3$ (1.382 g, 10.00 mmol), sodium iodide (0.300 g, 2.000 mmol) and 6-bromo-1-chloro-2,3-dihydro-1H-indene (0.926 g, 4.00 mmol). The resulting solution was heated at 60° C. for 21 h, evaporated under vacuum, purified via flash chromatography to afford desired product 4-(6-bromo-2,3-dihydro-1H-inden-1-yl)-2,2-dimethyl-2,3,4,5-tetrahydropyrido[3,2-f][1,4]oxazepine (1.159 g, 3.10 mmol, 78% yield). LC-MS m/z 373.1 (M+H)$^+$, 0.87 min (ret. time).

2,2-Dimethyl-4-(6-(4,4,5,5-tetramethyl-1,3,2-dioxaborolan-2-yl)-2,3-dihydro-1H-inden-1-yl)-2,3,4,5-tetrahydropyrido[3,2-f][1,4]oxazepine

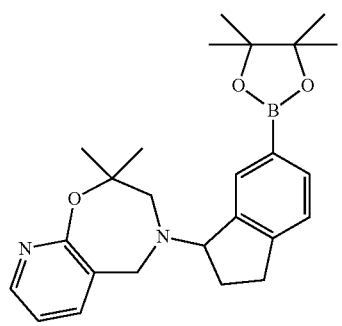 [SMILES: CC1(C)CN(C2CCc3ccc(B4OC(C)(C)C(C)(C)O4)cc32)Cc2cccnc2O1]

To a solution of 4-(6-bromo-2,3-dihydro-1H-inden-1-yl)-2,2-dimethyl-2,3,4,5-tetrahydropyrido[3,2-f][1,4]oxazepine (1.158 g, 3.10 mmol) in N,N-dimethylformamide (10 mL) was added bis(pinacolato)diboron (1.182 g, 4.65 mmol), PdCl$_2$(dppf) (0.113 g, 0.155 mmol) and KOAc (0.609 g, 6.20 mmol). The resulting reaction mixture was heated with microwave at 100° C. for 1 h, evaporated under vacuum, purified via flash chromatography to afford product 2,2-dimethyl-4-(6-(4,4,5,5-tetramethyl-1,3,2-dioxaborolan-2-yl)-2,3-dihydro-1H-inden-1-yl)-2,3,4,5-tetrahydropyrido[3,2-f][1,4]oxazepine (1.527 g, 3.63 mmol, 117% yield). LC-MS m/z 421.2 (M+H)$^+$, 0.87 min (ret. time).

(E)-methyl 3-(4-cyano-2-methylphenyl)acrylate

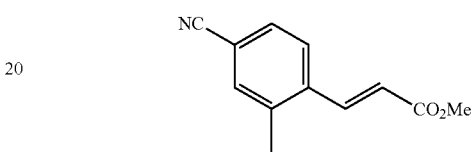

To a solution of 4-bromo-3-methylbenzonitrile (0.784 g, 4 mmol) in N,N-dimethylformamide (20 mL) was added methyl acrylate (1.812 mL, 20.00 mmol), DIPEA (1.747 mL, 10.00 mmol), palladium(II) acetate (0.090 g, 0.400 mmol) and tri-o-tolylphosphine (0.243 g, 0.800 mmol). The reaction mixture was then heated with microwave at 150° C. under N$_2$ atmosphere for 1 h. The reaction mixture was evaporated under vacuum to remove remaining methyl acrylate, then diluted with H$_2$O (20 mL), extracted with EtOAc (3×40 mL). The combined organic layer was washed with brine (50 ml), dried over MgSO$_4$, filtered, evaporated down under vacuum, purified with flash chromatography to afford desired product (E)-methyl 3-(4-cyano-2-methylphenyl)acrylate (0.8815 g, 4.38 mmol, 110% yield). $^1$H-NMR (400 MHz, CHLOROFORM-d) □ ppm 2.47 (s, 3H) 3.84 (s, 3H) 6.43 (d, J=15.81 Hz, 1H) 7.47-7.55 (m, 2H) 7.61 (d, J=8.53 Hz, 1H) 7.92 (d, J=15.81 Hz, 1H).

Methyl 3-(4-cyano-2-methylphenyl)-3-(3-(2,2-dimethyl-2,3-dihydropyrido[3,2-f][1,4]oxazepin-4(5H)-yl)-2,3-dihydro-1H-inden-5-yl)propanoate

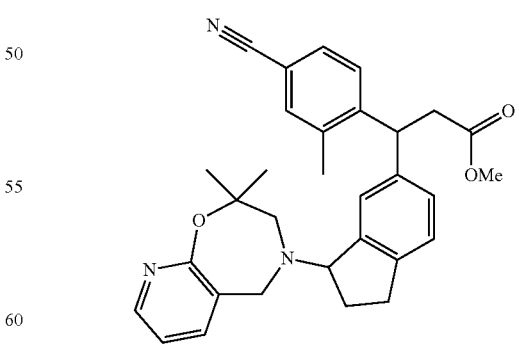

To a solution of (E)-methyl 3-(4-cyano-2-methylphenyl)acrylate (0.101 g, 0.5 mmol) in 1,4-dioxane (1.5 mL) and water (0.5 mL) were added 2,2-dimethyl-4-(6-(4,4,5,5-tetramethyl-1,3,2-dioxaborolan-2-yl)-2,3-dihydro-1H-inden-1-yl)-2,3,4,5-tetrahydropyrido[3,2-f][1,4]oxazepine (0.420 g, 1.000 mmol), TEA (0.209 mL, 1.500 mmol) and [Rh(cod)Cl]$_2$ (0.012 g, 0.025 mmol). The resulting reaction mixture was stirred at 90° C. for 1 h, evaporated under vacuum and purified via flash chromatography to afford methyl 3-(4-cyano-2-methylphenyl)-3-(3-(2,2-dimethyl-2,3-dihydropyrido[3,2-f][1,4]oxazepin-4(5H)-yl)-2,3-dihydro-1H-inden-5-yl)propanoate (0.1297 g, 0.262 mmol, 52.3% yield). LC-MS m/z 496.3 (M+H)$^+$, 0.92 min (ret. time).

3-(4-Cyano-2-methylphenyl)-3-(3-(2,2-dimethyl-2,3-dihydropyrido[3,2-f][1,4]oxazepin-4(5H)-yl)-2,3-dihydro-1H-inden-5-yl)propanoic Acid, Formic Acid Salt

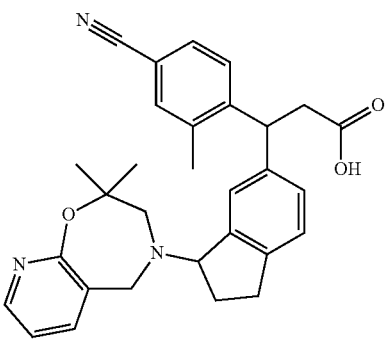 [SMILES: Cc1cc(C#N)ccc1C(CC(=O)O)c1ccc2c(c1)C(N1Cc3cccnc3OC(C)(C)C1)CC2]

To a solution of methyl 3-(4-cyano-2-methylphenyl)-3-(3-(2,2-dimethyl-2,3-dihydropyrido[3,2-f][1,4]oxazepin-4(5H)-yl)-2,3-dihydro-1H-inden-5-yl)propanoate (129.7 mg, 0.254 mmol) in methanol (3 mL) was added NaOH (2 N) (50.9 mg, 1.272 mmol). The resulting solution was heated with microwave at 80° C. for 15 min. The reaction mixture was acidified with HCl (1 N) to pH~5, evaporated under vacuum, and purified by reverse phase HPLC to afford product 3-(4-cyano-2-methylphenyl)-3-(3-(2,2-dimethyl-2,3-dihydropyrido[3,2-f][1,4]oxazepin-4(5H)-yl)-2,3-dihydro-1H-inden-5-yl)propanoic acid, formic acid salt (51.5 mg, 0.107 mmol, 42.0% yield). LC-MS m/z 482.2 (M+H)$^+$, 0.76 min (ret. time).

Example 60

3-(3-(2,2-Dimethyl-2,3-dihydropyrido[3,2-f][1,4]oxazepin-4(5H)-yl)-2,3-dihydro-1H-inden-5-yl)-3-(4-fluoro-2-methylphenyl)propanoic Acid, Formic Acid Salt

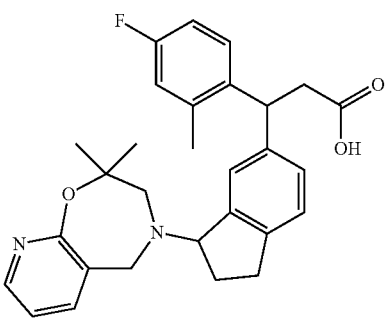 [SMILES: Cc1cc(F)ccc1C(CC(=O)O)c1ccc2c(c1)C(N1Cc3cccnc3OC(C)(C)C1)CC2]

(E)-Methyl 3-(4-fluoro-2-methylphenyl)acrylate

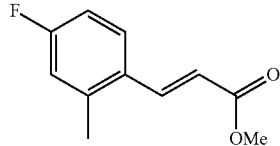

To a solution of 1-bromo-4-fluoro-2-methylbenzene (0.756 g, 4 mmol) in N,N-dimethylformamide (10 mL) was added methyl acrylate (1.812 mL, 20.00 mmol), DIPEA (1.747 mL, 10.00 mmol), palladium(II) acetate (0.090 g, 0.400 mmol) and tri-o-tolylphosphine (0.243 g, 0.800 mmol). The reaction mixture was heated with microwave at 130° C. under argon atmosphere for 6 h. The reaction mixture was concentrated then diluted with EtOAc (20 ml), washed with H$_2$O and extracted with EtOAc (20 ml×3). The organic phase was concentrated and purified with flash chromatography to afford desired product (E)-methyl 3-(4-fluoro-2-methylphenyl)acrylate (0.5479 g, 2.82 mmol, 70.5% yield). LC-MS m/z 195.0 (M+H)$^+$, 1.01 min (ret. time).

Methyl 3-(3-(2,2-dimethyl-2,3-dihydropyrido[3,2-f][1,4]oxazepin-4(5H)-yl)-2,3-dihydro-1H-inden-5-yl)-3-(4-fluoro-2-methylphenyl)propanoate

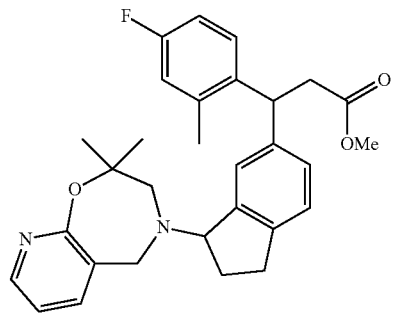 [SMILES: COC(=O)CC(c1ccc2c(c1)C(N1Cc3cccnc3OC(C)(C)C1)CC2)c1ccc(F)cc1C]

To a solution of (E)-methyl 3-(4-fluoro-2-methylphenyl)acrylate (104 mg, 0.5 mmol) in 1,4-dioxane (1.5 mL) and water (0.5 mL) were added 2,2-dimethyl-4-(6-(4,4,5,5-tetramethyl-1,3,2-dioxaborolan-2-yl)-2,3-dihydro-1H-inden-1-yl)-2,3,4,5-tetrahydropyrido[3,2-f][1,4]oxazepine (420 mg, 1.000 mmol), TEA (0.209 mL, 1.500 mmol) and [Rh(cod)Cl]$_2$ (12.33 mg, 0.025 mmol). The resulting reaction mixture was stirred at 90° C. for 1 h, evaporated under vacuum and purified via flash chromatography to afford product methyl 3-(3-(2,2-dimethyl-2,3-dihydropyrido[3,2-f][1,4]oxazepin-4(5H)-yl)-2,3-dihydro-1H-inden-5-yl)-3-(4-fluoro-2-methylphenyl)propanoate (52.3 mg, 0.104 mmol, 20.81% yield). LC-MS m/z 489.4 (M+H)$^+$, 1.00 min (ret. time).

191

3-(3-(2,2-Dimethyl-2,3-dihydropyrido[3,2-f][1,4]
oxazepin-4(5H)-yl)-2,3-dihydro-1H-inden-5-yl)-3-
(4-fluoro-2-methylphenyl)propanoic Acid, Formic
Acid Salt

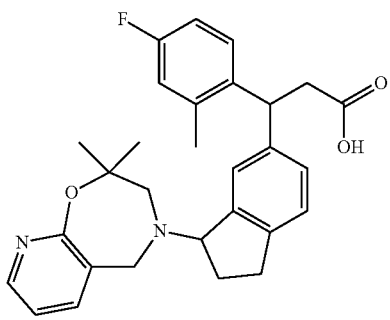 [SMILES: Cc1cc(F)ccc1C(CC(=O)O)c1ccc2c(c1)C(N1Cc3cccnc3OC(C)(C)C1)CC2]

To a solution of methyl 3-(3-(2,2-dimethyl-2,3-dihydropyrido[3,2-f][1,4]oxazepin-4(5H)-yl)-2,3-dihydro-1H-inden-5-yl)-3-(4-fluoro-2-methylphenyl)propanoate (52.3 mg, 0.104 mmol) in methanol (1.5 mL) was added NaOH (2 N) (20.81 mg, 0.520 mmol). The resulting solution was heated with microwave at 80° C. for 15 min before being acidified with HCl (1 N) to pH~5, evaporated under vacuum, and purified by reverse phase HPLC to afford product 3-(3-(2,2-dimethyl-2,3-dihydropyrido[3,2-f][1,4]oxazepin-4(5H)-yl)-2,3-dihydro-1H-inden-5-yl)-3-(4-fluoro-2-methylphenyl)propanoic acid, formic acid salt (34.4 mg, 0.072 mmol, 69.7% yield). LC-MS m/z 475.2 (M+H)$^+$, 0.81 min (ret. time).

Example 61

3-(1,4-Dimethyl-1H-benzo[d][1,2,3]triazol-5-yl)-3-
(3-((R)-2-methyl-2,3-dihydropyrido[3,2-f][1,4]ox-
azepin-4(5H)-yl)-2,3-dihydro-1H-inden-5-yl)pro-
panoic Acid, Formic Acid Salt

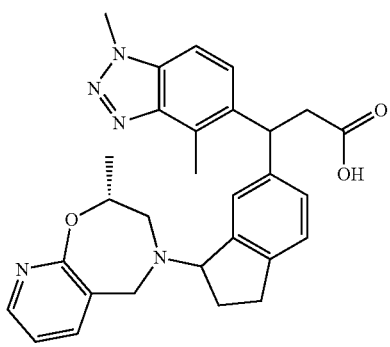 [SMILES: Cc1c(C(CC(=O)O)c2ccc3c(c2)C(N2Cc4cccnc4O[C@H](C)C2)CC3)ccc2c1nnn2C]

192

(R)-1-(((2-chloropyridin-3-yl)methyl)amino)propan-
2-ol

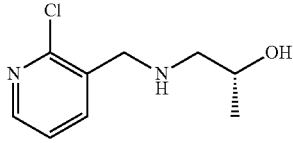

To a solution of 2-chloronicotinaldehyde (0.708 g, 5 mmol) in methanol (10 mL) was added (R)-1-aminopropan-2-ol (0.488 g, 6.50 mmol). The reaction mixture was stirred at ambient temperature for 1 h before adding NaBH$_4$ (0.378 g, 10.00 mmol) then was stirred at ambient temperature for an additional 1 h. To the reaction mixture was added NaHCO$_3$ (sat.) (0.5 mL) then evaporated under vacuum. The residue was diluted with DCM (50 mL), dried over MgSO$_4$, filtered and evaporated under vacuum to afford product (R)-1-(((2-chloropyridin-3-yl)methyl)amino)propan-2-ol (1.3176 g, 6.57 mmol, 131% yield). LC-MS m/z 200.9 (M+H)$^+$, 0.18 min (ret. time).

(R)-2-methyl-2,3,4,5-tetrahydropyrido[3,2-f][1,4]
oxazepine

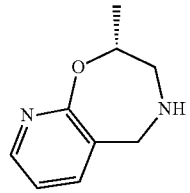

To a solution of (R)-1-(((2-chloropyridin-3-yl)methyl)amino)propan-2-ol (100 mg, 0.5 mmol) in N,N-dimethylformamide (5 mL) was added KOtBu (168 mg, 1.500 mmol) and the resulting solution was heated with microwave at 80° C. for 2 h. The reaction mixture was then evaporated under vacuum, diluted with DCM (20 mL) and filtered then evaporated under vacuum to afford product (R)-2-methyl-2,3,4,5-tetrahydropyrido[3,2-f][1,4]oxazepine (71.2 mg, 0.434 mmol, 87% yield). LC-MS m/z 164.9 (M+H)$^+$, 0.10 min (ret. time).

Ethyl 3-(1,4-dimethyl-1H-benzo[d][1,2,3]triazol-5-
yl)-3-(3-((R)-2-methyl-2,3-dihydropyrido[3,2-f][1,4]
oxazepin-4(5H)-yl)-2,3-dihydro-1H-inden-5-yl)pro-
panoate

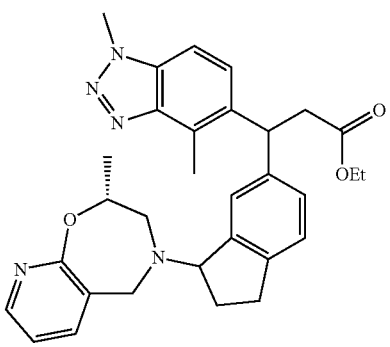

To a solution of (R)-2-methyl-2,3,4,5-tetrahydropyrido[3,2-f][1,4]oxazepine (71.2 mg, 0.434 mmol) in acetonitrile (3 mL) was added K$_2$CO$_3$ (120 mg, 0.867 mmol), sodium iodide (13.00 mg, 0.087 mmol) and ethyl 3-(3-chloro-2,3-dihydro-1H-inden-5-yl)-3-(1,4-dimethyl-1H-benzo[d][1,2,3]triazol-5-yl)propanoate (173 mg, 0.434 mmol). The resulting solution was heated with microwave at 60° C. for 2 h, evaporated under vacuum, purified via flash chromatography to afford product ethyl 3-(1,4-dimethyl-1H-benzo[d][1,2,3]triazol-5-yl)-3-(3-((R)-2-methyl-2,3-dihydropyrido[3,2-f][1,4]oxazepin-4(5H)-yl)-2,3-dihydro-1H-inden-5-yl)propanoate (57 mg, 0.108 mmol, 25.01% yield). LC-MS m/z 526.1 (M+H)$^+$, 0.77 min (ret. time).

3-(1,4-Dimethyl-1H-benzo[d][1,2,3]triazol-5-yl)-3-(3-((R)-2-methyl-2,3-dihydropyrido[3,2-f][1,4]oxazepin-4(5H)-yl)-2,3-dihydro-1H-inden-5-yl)propanoic Acid, Formic Acid Salt

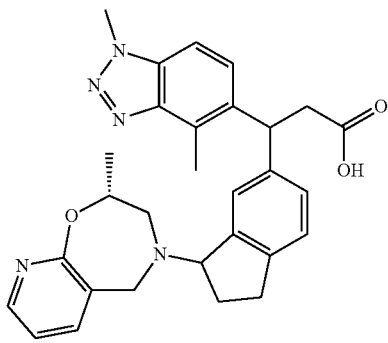 [SMILES: Cc1c(C(CC(=O)O)c2ccc3c(c2)C(N2Cc4cccnc4O[C@H](C)C2)CC3)ccc2c1nnn2C]

To a solution of ethyl 3-(1,4-dimethyl-1H-benzo[d][1,2,3]triazol-5-yl)-3-(3-((R)-2-methyl-2,3-dihydropyrido[3,2-f][1,4]oxazepin-4(5H)-yl)-2,3-dihydro-1H-inden-5-yl)propanoate (57 mg, 0.108 mmol) in methanol (1.500 mL) was added NaOH (2 N) (21.69 mg, 0.542 mmol). The resulting solution was heated with microwave at 80° C. for 15 min before being acidified with HCl (1 N) to pH~5, evaporated under vacuum, and purified by reverse phase HPLC to afford product 3-(1,4-dimethyl-1H-benzo[d][1,2,3]triazol-5-yl)-3-(3-((R)-2-methyl-2,3-dihydropyrido[3,2-f][1,4]oxazepin-4(5H)-yl)-2,3-dihydro-1H-inden-5-yl)propanoic acid, formic acid salt (41.6 mg, 0.084 mmol, 77% yield). LC-MS m/z 498.2 (M+H)$^+$, 0.65 min (ret. time).

Example 62

3-(3-(2,2-Dimethyl-2,3-dihydropyrido[3,2-f][1,4]oxazepin-4(5H)-yl)-2,3-dihydro-1H-inden-5-yl)-3-(3-methyl-3H-[1,2,3]triazolo[4,5-c]pyridin-6-yl)propanoic Acid, Formic Acid Salt

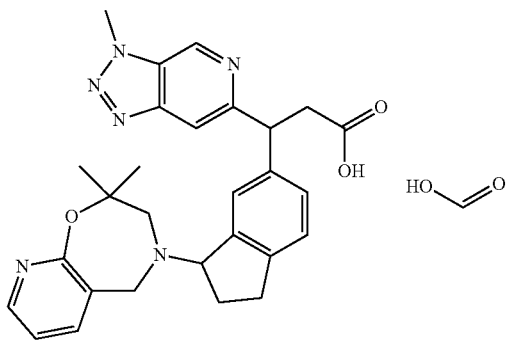 [SMILES: Cn1nnc2cc(C(CC(=O)O)c3ccc4c(c3)C(N3Cc5cccnc5OC(C)(C)C3)CC4)ncc21 ; O=CO]

2-Chloro-5-fluoropyridine 1-oxide

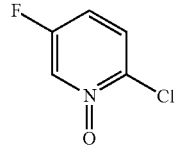

To 2-chloro-5-fluoro-pyridine (20 g, 152 mmol) in trifluoroacetic acid (150 mL) was added H$_2$O$_2$ (78 mL, 760 mmol) slowly under nitrogen at 70° C. The reaction mixture was stirred at 70° C. for 16 h and concentrated. Water and DCM were added to the residue. It was adjusted to pH 7 with 28% ammonium hydroxide solution and was extracted with DCM, dried with MgSO$_4$, concentrated to afford the title compound 2-chloro-5-fluoro-pyridine 1-oxide (20.1 g, 136 mmol, 90% yield) which was carried to the next step without further purification. LC-MS m/z 147.6 (M+H)$^+$, 0.78 min (ret. time).

2-Chloro-5-fluoro-4-nitropyridine 1-oxide

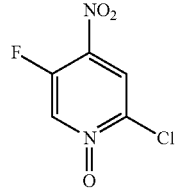

To 2-chloro-5-fluoro-pyridine 1-oxide (5 g, 33.9 mol) in H$_2$SO$_4$ (50 mL, 938 mmol) was added potassium nitrate acid (13.71 g, 136 mol) slowly under nitrogen at ambient temperature. The reaction mixture was stirred at 110° C. for 16 h. Then it was poured into 50 mL of ice/water. The solid was filtered and dried with high vacuum to afford the 2-chloro-5-fluoro-3-methyl-4-nitropyridine 1-oxide (5.1 g, 21.99 mmol, 64.9% yield) as a yellow solid. LC-MS m/z 203.9 (M+H)$^+$, 1.29 min (ret. time).

2-Chloro-5-(methylamino)-4-nitropyridine 1-oxide

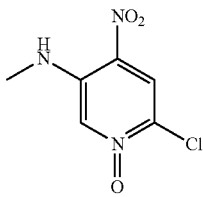

A mixture of 2-chloro-5-fluoro-4-nitropyridine 1-oxide (5.3 g, 27.5 mmol) and methylamine (50 mL, 425 mmol) was stirred at 20° C. for 3 h. After the solvent was evaporated, 50 mL of water was added. The solid was filtered and dried with high vacuum to afford the title compound 2-chloro-5-(methylamino)-4-nitropyridine 1-oxide (5.1 g, 18.54 mmol, 67.3% yield) as a yellow solid. LC-MS $_{m/z}$ 203.9 (M+H)$^+$, 1.29 min (ret. time).

6-Chloro-N3-methylpyridine-3,4-diamine

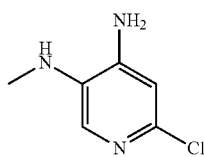

To 2-chloro-5-(methylamino)-4-nitropyridine 1-oxide (160 mg, 0.786 mmol) in ethanol (10 mL) was added nickel (46.1 mg, 0.786 mmol) slowly under nitrogen at 20° C. It was hydrogenated at 40 psi in a Parr vessel at ambient temperature for 16 h. The mixture was filtered and the filtrate was concentrated to afford the title compound 6-chloro-N3-methylpyridine-3,4-diamine (120 mg, 0.647 mmol, 82% yield) as a dark solid. LC-MS m/z 158.0 (M+H)$^+$, 0.68 min (ret. time).

6-Chloro-3-methyl-3H-[1,2,3]triazolo[4,5-c]pyridine

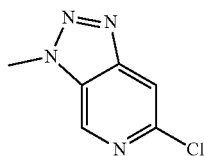

To a solution of 6-chloro-N3-methylpyridine-3,4-diamine (3.2 g, 20.30 mmol) in H$_2$SO$_4$ (3 mL, 56.3 mmol) solution in 50 mL of water was added sodium nitrite (2.80 g, 40.6 mmol) in water (30 mL) slowly under nitrogen at 0° C. The reaction mixture was stirred at 0° C. for 4 h after which the pH was adjusted to 8 with Na$_2$CO$_3$ (aq.). The solid was filtered to afford the title compound 6-chloro-3-methyl-3H-[1,2,3]triazolo[4,5-c]pyridine (3.2 g, 18.98 mmol, 93% yield) which was carried over to next step without further purification. LC-MS m/z 169.0 (M+H)$^+$, 1.33 min (ret. time).

(E)-Ethyl 3-(3-methyl-3H-[1,2,3]triazolo[4,5-c]pyridin-6-yl)acrylate

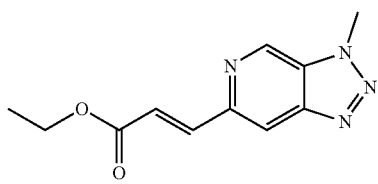 [SMILES: CCOC(=O)/C=C/c1cc2nnn(C)c2cn1]

A mixture of 6-chloro-3-methyl-3H-[1,2,3]triazolo[4,5-c]pyridine (3.000 g, 17.80 mmol), (E)-ethyl 3-(4,4,5,5-tetramethyl-1,3,2-dioxaborolan-2-yl)acrylate (9.90 mL, 89 mmol), TEA (12.40 mL, 89 mmol), tetrakis(triphenylphosphine)palladium(0) (1.453 g, 1.780 mmol) in N,N-dimethylformamide (50 mL) was stirred at 140° C. for 12 h. The reaction mixture was filtered and the filtrate was purified by silica gel chromatography (hexane:ethyl acetate=4:1) to afford the title compound (E)-ethyl 3-(3-methyl-3H-[1,2,3]triazolo[4,5-c]pyridin-6-yl)acrylate (710 mg, 2.97 mmol, 16.66% yield). LC-MS m/z 233.0 (M+H)$^+$, 1.51 min (ret. time).

Ethyl 3-(3-hydroxy-2,3-dihydro-1H-inden-5-yl)-3-(3-methyl-3H-[1,2,3]triazolo[4,5-c]pyridin-6-yl)propanoate

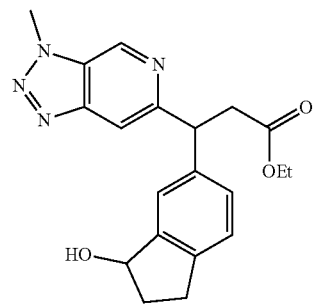 [SMILES: CCOC(=O)CC(c1ccc2c(c1)C(O)CC2)c1cc2nnn(C)c2cn1]

To a solution of (E)-ethyl 3-(3-methyl-3H-[1,2,3]triazolo[4,5-c]pyridin-6-yl)acrylate (0.232 g, 1 mmol) in 1,4-dioxane (9 mL) and water (3 mL) was added 6-(4,4,5,5-tetramethyl-1,3,2-dioxaborolan-2-yl)-2,3-dihydro-1H-inden-1-ol (0.390 g, 1.500 mmol), TEA (0.418 mL, 3.00 mmol) and [Rh(cod)Cl]$_2$ (0.025 g, 0.050 mmol). The resulting reaction mixture was stirred at 90° C. for 3 h, evaporated under vacuum, purified via flash chromatography to afford product ethyl 3-(3-hydroxy-2,3-dihydro-1H-inden-5-yl)-3-(3-methyl-3H-[1,2,3]triazolo[4,5-c]pyridin-6-yl)propanoate (0.1139 g, 0.311 mmol, 31.1% yield). LC-MS m/z 367.0 (M+H)$^+$, 0.79 min (ret. time).

Ethyl 3-(3-chloro-2,3-dihydro-1H-inden-5-yl)-3-(3-methyl-3H-[1,2,3]triazolo[4,5-c]pyridin-6-yl)propanoate

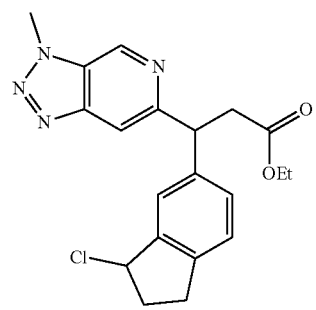 [SMILES: CCOC(=O)CC(c1ccc2c(c1)C(Cl)CC2)c1cc2nnn(C)c2cn1]

To a solution of ethyl 3-(3-hydroxy-2,3-dihydro-1H-inden-5-yl)-3-(3-methyl-3H-[1,2,3]triazolo[4,5-c]pyridin-6-yl)propanoate (0.1139 g, 0.311 mmol) in DCM (1.5 mL) was added SOCl$_2$ (0.045 mL, 0.622 mmol). The resulting reaction mixture was stirred at ambient temperature for 3 h, evaporated under vacuum to afford product ethyl 3-(3-chloro-2,3-dihydro-1H-inden-5-yl)-3-(3-methyl-3H-[1,2,3]triazolo[4,5-c]pyridin-6-yl)propanoate (0.1349 g, 0.351 mmol, 113% yield). LC-MS m/z 381.1 (M−Cl+MeOH)$^+$, 0.95 min (ret. time).

Ethyl 3-(3-(2,2-dimethyl-2,3-dihydropyrido[3,2-f][1,4]oxazepin-4(5H)-yl)-2,3-dihydro-1H-inden-5-yl)-3-(3-methyl-3H-[1,2,3]triazolo[4,5c]pyridin-6-yl)propanoate

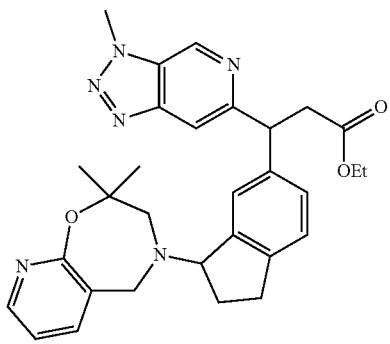 [SMILES: CCOC(=O)CC(c1ccc2c(c1)C(N1Cc3cccnc3OC(C)(C)C1)CC2)c1cc2nnn(C)c2cn1]

To a solution of 2,2-dimethyl-2,3,4,5-tetrahydropyrido[3,2-f][1,4]oxazepine (0.222 g, 1.247 mmol) in acetonitrile (3 mL) was added K$_2$CO$_3$ (0.086 g, 0.624 mmol), sodium iodide (9.35 mg, 0.062 mmol) and ethyl 3-(3-chloro-2,3-dihydro-1H-inden-5-yl)-3-(3-methyl-3H-[1,2,3]triazolo[4,5-c]pyridin-6-yl)propanoate (0.12 g, 0.312 mmol). The resulting solution was heated with microwave at 60° C. for 2 h. The reaction mixture was then evaporated under vacuum and purified via flash chromatography to afford product ethyl 3-(3-(2,2-dimethyl-2,3-dihydropyrido[3,2-f][1,4]oxazepin-4(5H)-yl)-2,3-dihydro-1H-inden-5-yl)-3-(3-methyl-3H-[1,2,3]triazolo[4,5-c]pyridin-6-yl)propanoate (0.1253 g, 0.238 mmol, 76% yield). LC-MS m/z 527.3 (M+H)$^+$, 0.77 min (ret. time).

3-(3-(2,2-Dimethyl-2,3-dihydropyrido[3,2-f][1,4]oxazepin-4(5H)-yl)-2,3-dihydro-1H-inden-5-yl)-3-(3-methyl-3H-[1,2,3]triazolo[4,5-c]pyridin-6-yl)propanoic Acid, Formic Acid Salt

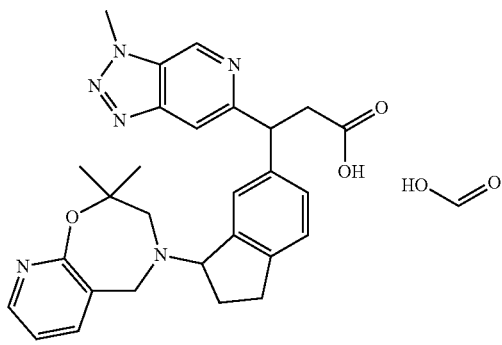 [SMILES: Cn1nnc2cc(C(CC(=O)O)c3ccc4c(c3)C(N3Cc5cccnc5OC(C)(C)C3)CC4)ncc21 ; O=CO]

To a solution of ethyl 3-(3-(2,2-dimethyl-2,3-dihydropyrido[3,2-f][1,4]oxazepin-4(5H)-yl)-2,3-dihydro-1H-inden-5-yl)-3-(3-methyl-3H-[1,2,3]triazolo[4,5-c]pyridin-6-yl)propanoate (125.3 mg, 0.238 mmol) in methanol (4 mL) was added NaOH (2 N) (47.6 mg, 1.190 mmol). The resulting solution was heated with microwave at 80° C. for 15 min. The reaction mixture was acidified with HCl (1 N) to pH~5, evaporated under vacuum, and purified by reverse phase HPLC to afford product 3-(3-(2,2-dimethyl-2,3-dihydropyrido[3,2-f][1,4]oxazepin-4(5H)-yl)-2,3-dihydro-1H-inden-5-yl)-3-(3-methyl-3H-[1,2,3]triazolo[4,5-c]pyridin-6-yl)propanoic acid, formic acid salt (52.9 mg, 0.102 mmol, 42.7% yield). LC-MS m/z 499.5 (M+H)$^+$, 0.57 min (ret. time).

Example 63

3-(3-(2,2-Dimethyl-2,3-dihydrobenzo[f][1,4]oxazepin-4(5H)-yl)-2,3-dihydro-1H-inden-5-yl)-5-(4-propyl-1H-1,2,3-triazol-1-yl)pentanoic Acid, Trifluoroacetic Acid Salt

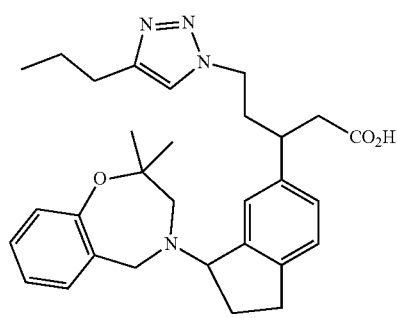 [SMILES: CCCc1cn(CCC(CC(=O)O)c2ccc3c(c2)C(N2Cc4ccccc4OC(C)(C)C2)CC3)nn1]

3-((Tert-butyldimethylsilyl)oxy)propan-1-ol

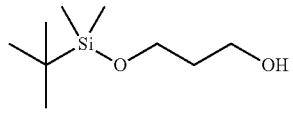

To an argon flushed flask containing NaH-60% dispersion in mineral oil (4.4 g) was added THF (200 mL). The reaction was stirred vigorously and propanediol (7.61 g, 100 mmol) was added slowly at 0° C. The reaction was allowed to stir for 45 min at ambient temperature over which time the initial grey suspension became white. Next, TBSCI (16.58 g, 110 mmol) was added in several portions to the flask being careful to avoid overflow by the vigorous release of gases. The reaction was then allowed to stir for another 45 min. The reaction was quenched slowly with 50 mL of 10% aqueous Na$_2$CO$_3$ solution, forming two layers. The two layers were separated and the aqueous layer was extracted with Et$_2$O. The combined organics were washed with brine and dried over Na$_2$SO$_4$. After concentration under reduced pressure the crude title compound (21 g, 110% yield) was of sufficient purity. $^1$H NMR (400 MHz, CHLOROFORM-d): ppm 0.10 (s, 6H) 0.87-0.97 (m, 9H) 1.76-1.85 (m, 2H) 3.79-3.94 (m, 4H)

3-((Tert-butyldimethylsilyl)oxy)propanal

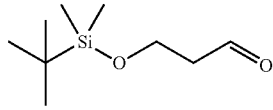

A solution of 3-((tert-butyldimethylsilyl)oxy)propan-1-ol (4.48 mL, 21.01 mmol) and TEA (29.1 mL, 210 mmol) in dimethyl sulfoxide (DMSO) (10 mL) was treated with a solution of pyridine*sulfur trioxide (10.03 g, 63.0 mmol) in dimethyl sulfoxide (DMSO) (10 mL) at 22° C. and the reaction was stirred under argon for 4 h. The reaction was combined with 1M HCl (1×100 mL) and extracted with EtOAc (2×100 mL). The combined EtOAc was washed with water (2×100 mL), brine (100 mL), dried over $Na_2SO_4$, and concentrated under reduced pressure. The crude title compound (4.13 g, 104% yield) was collected as a golden yellow oil which was used without purification. $^1$H NMR (400 MHz, CHLOROFORM-d): ppm 0.06 (br. s., 6H) 0.89 (s, 9H) 2.54-2.59 (m, 2H) 3.94-3.99 (m, 2H) 9.73-9.81 (m, 1H).

(E)-Ethyl 5-((tert-butyldimethylsilyl)oxy)pent-2-enoate

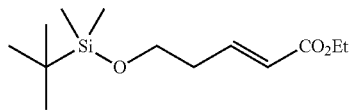 [SMILES: CCOC(=O)/C=C/CCO[Si](C)(C)C(C)(C)C]

3-((Tert-butyldimethylsilyl)oxy)propanal (2.667 g, 14.16 mmol) in DCM (10 mL) was combined with ethyl 2-(triphenylphosphoranylidene)acetate (5.30 g, 15.21 mmol) and the mixture was refluxed for 22 h and then cooled to 22° C. The reaction turned from a golden yellow to a light red after refluxing for 25 min. The reaction was diluted with DCM (1×100 mL), washed with water (2×50 mL), brine (50 mL), dried over $Na_2SO_4$ and concentrated under reduced pressure. The crude product was purified on a silica cartridge (40 g) using flash chromatography with a gradient running from 0-25% EtOAc/hexanes to yield the title compound (1.197 g, 32.7% yield) as a slightly yellowish liquid. LC-MS m/z 259.1 (M+H)$^+$, 1.43 min (ret. time).

(E)-ethyl 5-((methylsulfonyl)oxy)pent-2-enoate

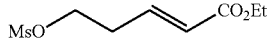

To a solution of (E)-ethyl 5-((tert-butyldimethylsilyl)oxy) pent-2-enoate (1.391 g, 5.38 mmol) in THF (15.00 mL) under argon, was added 1M TBAF in THF (5.87 mL, 5.87 mmol) and stirred for 45 min. The solvent was concentrated and the crude residue was dissolved in DCM (15 mL). TEA (0.970 mL, 7.00 mmol) was added and mixture was cooled to 0° C. Methanesulfonyl chloride (0.583 mL, 7.54 mmol) was added and the reaction mixture allowed to stir for 4 hours. An additional 0.5 mL of methanesulfonyl chloride was added and the reaction stirred for 17 hours. An additional 2.5 mL of methanesulfonyl chloride and 3 mL of TEA were added and the reaction stirred for 1 hour. The reaction was then diluted with DCM (60 mL), washed with water (4×50 mL), brine (25 mL), dried over $Na_2SO_4$, and concentrated under reduced pressure to yield the title compound (2.168 g, 65% yield) which was used without further purification. LC-MS m/z of 245.0 (M+Na)$^+$, 0.71 min (ret. time).

(E)-Ethyl 5-(4-propyl-1H-1,2,3-triazol-1-yl)pent-2-enoate

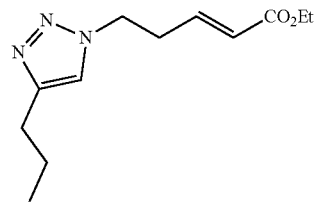 [SMILES: CCCc1cn(CC/C=C/C(=O)OCC)nn1]

Crude (E)-ethyl 5-((methylsulfonyl)oxy)pent-2-enoate (2.168 g, 9.75 mmol) was dissolved in N,N-dimethylformamide (25 mL) and sodium azide (0.761 g, 11.71 mmol) was added and reaction mixture allowed to stir at 70° C. for 2 h. The reaction mixture was allowed to cool to ambient temperature. water 25.00 mL) added to the reaction mixture and the mixture placed under argon atmosphere. To the stirring reaction mixture was added copper (II) sulfate (1.401 g, 8.78 mmol), pentyne (1.346 mL, 13.66 mmol), and sodium ascorbate (1.739 g, 8.78 mmol). The reaction mixture was concentrated under reduced pressure. EtOAc added and reaction filtered through disposable frit to remove salts. The crude mixture was purified using reverse phase preparative HPLC to yield the title compound (120 mg, 5.18% yield) as a slightly yellow liquid. LC-MS m/z 238.0 (M+H)$^+$, 260.1 (M+Na)$^+$, 0.78 (ret. time).

2,2-Dimethyl-4-(6-(4,4,5,5-tetramethyl-1,3,2-dioxaborolan-2-yl)-2,3-dihydro-1H-inden-1-yl)-2,3,4,5-tetrahydrobenzo[f][1,4]oxazepine

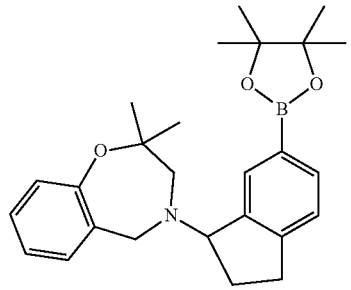 [SMILES: CC1(C)CN(C2CCc3ccc(B4OC(C)(C)C(C)(C)O4)cc32)Cc2ccccc2O1]

To a solution of 4-(6-bromo-2,3-dihydro-1H-inden-1-yl)-2,2-dimethyl-2,3,4,5-tetrahydrobenzo[f][1,4]oxazepine (3.5 g, 9.40 mmol) in 1,4-dioxane (35 mL) was added bis (pinacolato)diboron (2.86 g, 11.28 mmol) and potassium acetate (1.845 g, 18.80 mmol). The reaction mixture was degassed with argon for 10 min then added $PdCl_2$(dppf)-$CH_2Cl_2$ (0.384 g, 0.470 mmol) and heated to 90° C. for 16 h. The reaction mixture was filtered through celite and washed with EtOAc (2×100 ml). The filtrate was concentrated under reduced pressure then purified by flash chromatography to afford 2,2-dimethyl-4-(6-(4,4,5,5-tetramethyl-1,3,2-dioxaborolan-2-yl)-2,3-dihydro-1H-inden-1-yl)-2,3,4,5-tetrahydrobenzo[f][1,4]oxazepine (2.52 g, 5.98 mmol, 63.6% yield). LC-MS m/z 420.3 (M+H)$^+$, 4.80 min (ret. time).

Ethyl 3-(3-(2,2-dimethyl-2,3-dihydrobenzo[f][1,4]oxazepin-4(5H)-yl)-2,3-dihydro-1H-inden-5-yl)-5-(4-propyl-1H-1,2,3-triazol-1-yl)pentanoate

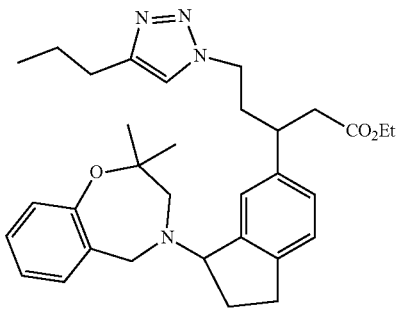 [SMILES: CCCc1cn(CCC(CC(=O)OCC)c2ccc3c(c2)C(N2Cc4ccccc4OC(C)(C)C2)CC3)nn1]

To a solution of (E)-ethyl 5-(4-propyl-1H-1,2,3-triazol-1-yl)pent-2-enoate (35 mg, 0.147 mmol) in 1,4-dioxane (2 mL) and water (1.000 mL) was added 2,2-dimethyl-4-(6-(4,4,5,5-tetramethyl-1,3,2-dioxaborolan-2-yl)-2,3-dihydro-1H-inden-1-yl)-2,3,4,5-tetrahydrobenzo[f][1,4]oxazepine (93 mg, 0.221 mmol), chloro(1,5-cyclooctadiene)rhodium(I) dimer (3.86 mg, 7.83 µmol), and TEA (0.020 mL, 0.147 mmol). A stream of Ar was passed through the mixture for ~5 min and then the reaction was heated under Ar at 90° C. for 2.5 h. The mixture was cooled slowly to 23° C. over 16 h. The residue was combined with EtOAc (5 mL) and water (5 mL). The aqueous layer was extracted again with EtOAc (10 mL) and the combined EtOAc layers were concentrated. The crude product was purified on reverse phase preparative HPLC to yield the title compound (12 mg, 15.33% yield) as a dark orange oil. LC-MS m/z 531.4 (M+H)$^+$, 0.95 min (ret. time).

3-(3-(2,2-Dimethyl-2,3-dihydrobenzo[f][1,4]oxazepin-4(5H)-yl)-2,3-dihydro-1H-inden-5-yl)-5-(4-propyl-1H-1,2,3-triazol-1-yl)pentanoic Acid, Trifluoroacetic Acid Salt

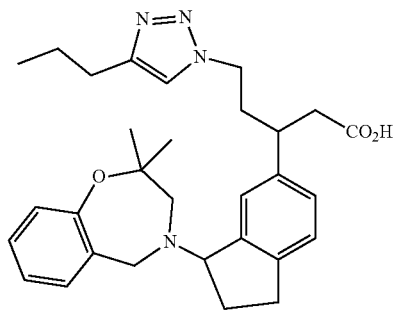 [SMILES: CCCc1cn(CCC(CC(=O)O)c2ccc3c(c2)C(N2Cc4ccccc4OC(C)(C)C2)CC3)nn1]

Ethyl 3-(3-(2,2-dimethyl-2,3-dihydrobenzo[f][1,4]oxazepin-4(5H)-yl)-2,3-dihydro-1H-inden-5-yl)-5-(4-propyl-1H-1,2,3-triazol-1-yl)pentanoate (22 mg, 0.041 mmol) was dissolved in THF (1.4 mL) and a solution of lithium hydroxide (2.98 mg, 0.124 mmol) in water (1.400 mL) was added. Methanol (0.5 mL) was added and the reaction was stirred for 16 h at 23° C. The solvents were then concentrated and the crude product was purified on reverse phase preparative HPLC to afford the title compound (31 mg, 121% yield). LC-MS m/z 503.3 (M+H)$^+$, 0.91 (ret. time).

Example 64

3-(3-(2,2-dimethyl-2,3-dihydrobenzo[f][1,4]oxazepin-4(5H)-yl)-2,3-dihydro-1H-inden-5-yl)-5-(2-ethyl-2H-tetrazol-5-yl)-2,2-dimethylpentanoic Acid, Trifluoroacetic Acid Salt

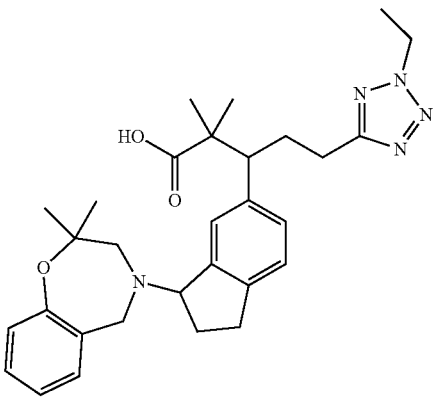 [SMILES: CCn1nnc(CCC(c2ccc3c(c2)C(N2Cc4ccccc4OC(C)(C)C2)CC3)C(C)(C)C(=O)O)n1]

6-bromo-2,3-dihydro-1H-inden-1-ol

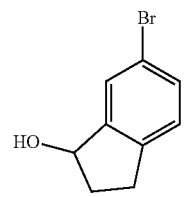

With ice bath cooling (10° C.), NaBH4 (1.344 g, 35.5 mmol) was added in one portion to 6-bromo-2,3-dihydro-1H-inden-1-one (5.0 g, 23.69 mmol) in methanol (100 mL). The ice bath was removed and the reaction was stirred for 3 h. The reaction was poured into water (250 mL) and extracted with EtOAc (250 mL and 100 mL) The combined extract was washed with water (100 mL) and saturated aqueous NaCl (50 mL) and dried over Na$_2$SO$_4$ and concentrated to a small volume and a precipitate was filtered off to afford an off white solid which was washed liberally with several portions of hexane to afford a first crop. The filtrate was concentrated. The filtrate had more precipitate formed in it, diluted with hexane and refiltered to afford more off white solid. The two crops were combined to afford the title compound (4.15 g, 82%) as an off white solid. LC-MS m/z 194 (M−OH)$^+$, 0.84 min (ret. time).

6-Bromo-1-((4-methoxybenzyl)oxy)-2,3-dihydro-1H-indene

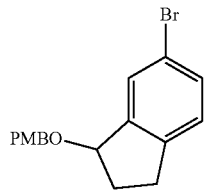

6-Bromo-2,3-dihydro-1H-inden-1-ol (4.1 g, 19.24 mmol) was dissolved in N,N-dimethylformamide (22 mL) and the solution was cooled via an ice water bath (10° C.) and 60% sodium hydride (1.539 g, 38.5 mmol) was added in one portion. The reaction bubbled and spontaneously warmed to 15° C. The ice bath was removed and the mixture was stirred for 1 h, cooled in an ice water bath to 10° C. and 1-(chloromethyl)-4-methoxybenzene (3.93 mL, 28.9 mmol was added. The resulting mixture was stirred at 23° C. for 2 h. The excess NaH was carefully quenched by the dropwise addition of water (5 mL) and it was diluted with EtOAc (200 mL) and water (75 mL) the phases were shaken and separated and the water was extracted with more EtOAc (75 mL) and then saturated aqueous NaCl (25 mL), dried (Na$_2$SO$_4$) and concentrated in vacuo to afford a yellow oil. The mixture was injected neat on a hexane equilibrated silica cartridge (120 g) and purified with a flash chromatography, eluting at 85 mL/min with a gradient running from hexanes to 10% EtOAc/hexanes over 25 min to afford the title compound (5.85 g, 91%) as a clear oil. $^1$H NMR (400 MHz, CDCl$_3$) □ ppm 2.09-2.20 (m, 1H) 2.33-2.44 (m, 1H) 2.71-2.82 (m, 1H) 2.99-3.09 (m, 1H) 3.84 (s, 3H) 4.56 (d, J=12.0 Hz, 1H) 4.62 (d, J=12.0 Hz, 1H) 4.98 (t, J=5.7 Hz, 1H) 6.93 (d, J=8.4 Hz, 2H) 7.13 (d, J=8.0 Hz, 1H) 7.34 (d, J=8.4 Hz, 2H) 7.38 (d, J=8.0 Hz, 1H) 7.52 (s, 1H).

3-((4-Methoxybenzyl)oxy)-2,3-dihydro-1H-indene-5-carbaldehyde

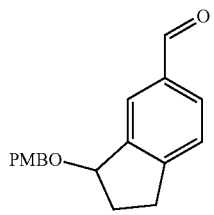

6-Bromo-1-((4-methoxybenzyl)oxy)-2,3-dihydro-1H-indene (5.85 g, 17.56 mmol) was dissolved in anhydrous THF (140 mL) and cooled on a dry-ice acetone bath. 2 M n-butyllithium (10.97 mL, 21.94 mmol) was added and the reaction was stirred with dry-ice acetone cooling for 0.5 h. DMF (6.80 mL, 88 mmol) was added and the reaction was stirred for 2 h. The reaction was diluted with saturated aqueous NH$_4$Cl (10 mL) and then additional (50 mL) water and EtOAc (100 mL). The aqueous layer was extracted with an additional portion of EtOAc (50 mL) and the combined EtOAc was washed with water (50 mL) and saturated aqueous NaCl (50 mL), dried over Na$_2$SO$_4$ and concentrated. The crude product was purified on a silica cartridge (120 g) with a flash chromatography, eluting at 85 mL/min with a gradient running from hexanes to 50% EtOAc/hexanes over 30 min. The desired fractions eluted were pooled based on tlc (4:1 heptane/EtOAc) and concentrated to afford 4.1 g (83%) of the title compound as a light yellow clear oil. $^1$H NMR (400 MHz, CDCl$_3$) δ ppm 2.13-2.26 (m, 1H) 2.36-2.49 (m, 1H) 2.82-2.94 (m, 1H) 3.10-3.24 (m, 1H) 3.82 (s, 3H) 4.58 (d, J=12.0 Hz, 1H) 4.64 (d, J=12.0 Hz, 1H) 5.04 (dd, J=5.6 Hz, 1H) 6.91 (d, J=8.4 Hz, 2H) 7.33 (d, J=8.4 Hz, 2H) 7.40 (d, J=7.8 Hz, 1H) 7.79 (d, J=7.8 Hz, 1H) 7.90 (s, 1H) 10.00 (s, 1H).

(E)-methyl 3-(3-((4-methoxybenzyl)oxy)-2,3-dihydro-1H-inden-5-yl)acrylate

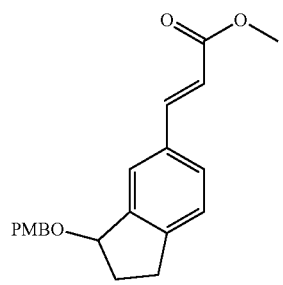

Methyl 2-(triphenylphosphoranylidene)acetate (5.34 g, 15.97 mmol) and 3-((4-methoxybenzyl)oxy)-2,3-dihydro-1H-indene-5-carbaldehyde (4.1 g, 14.52 mmol) were dissolved in DCM (105 mL) and heated reflux for 16 h. The reaction was cooled to 23° C. and stirred for 2 days. The crude product was preabsorbed on isolute and purified on a silica cartridge (120 g) 20 with a flash chromatography, eluting at 85 mL/min with a gradient running from hexanes to 30% EtOAc/hexanes over 25 min. The desired fractions were pooled and concentrated to afford 4.94 g (101%) of the title compound. LC-MS m/z 339 (M+H)$^+$, 1.20 min (ret. time).

Dimethyl 3-(3-((4-methoxybenzyl)oxy)-2,3-dihydro-1H-inden-5-yl)-2,2-dimethylpentanedioate

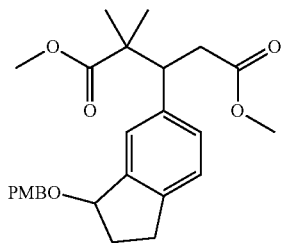

To an ice water cooled solution of (E)-methyl 3-(3-((4-methoxybenzyl)oxy)-2,3-dihydro-1H-inden-5-yl)acrylate (4.9 g, 14.48 mmol), tetrabutylammonium benzoate (0.263 g, 0.724 mmol) and THF (72 mL) was added ((1-methoxy-2-methylprop-1-en-1-yl)oxy)trimethylsilane (5.05 g, 29.0 mmol). The ice bath was removed and the solution was stirred for 3 h. The reaction was concentrated and preabsorbed on to isolute and the crude product was purified on a silica cartridge (120 g) with a flash chromatography, eluting at 85 mL/min with a gradient running from hexanes to 100% EtOAc over 30 min. The desired fractions were pooled and concentrated to afford 6.4 g (100%) of the title compound. LC-MS m/z 463 (M+Na)+, 1.26 min (ret. time).

Methyl 5-hydroxy-3-(3-((4-methoxybenzyl)oxy)-2,3-dihydro-1H-inden-5-yl)-2,2-dimethylpentanoate

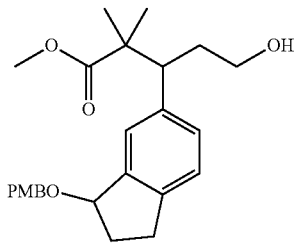

To a solution of dimethyl 3-(3-((4-methoxybenzyl)oxy)-2,3-dihydro-1H-inden-5-yl)-2,2-dimethylpentanedioate (5.2639 g, 11.95 mmol) in THF (72.4 mL), water (18.10 mL) and methanol (36.2 mL) was added LiOH (2.86 g, 119 mmol) at 23° C. After stirring for 18 hours, the reaction was diluted with DCM, and washed with 1N HCl. The aqueous layer was extracted with DCM (3×). The combined organic layers were washed with water and saturated aqueous NaCl, dried with MgSO$_4$ and concentrated in vacuo. The crude product was dissolved in THF (72.4 mL) and trimethyl borate (4.01 mL, 35.8 mmol) at 23° C. To this solution was added 2 M BH$_3$*DMS (29.9 mL, 59.7 mmol) dropwise over 60 min. After one hour of additional stirring methanol (36.2 mL) was added and the reaction stirred for an additional hour. The solvents were removed in vacuo, and the residue was dissolved in EtOAc. The organic layer was washed with saturated aqueous NaHCO$_3$, water, and saturated aqueous NaCl. The organic layer was dried with MgSO$_4$, and concentrated in vacuo. The crude product was then purified on a silica cartridge (40 g) with a flash chromatography, eluting at 40 mL/min with a gradient running from 100% hexanes to 80% EtOAc/hexanes over 25 min to give 4.12 g (84%) of the title compound. LC-MS m/z 435 (M+Na)+, 1.17 min (ret. time).

Methyl 5-bromo-3-(3-((4-methoxybenzyl)oxy)-2,3-dihydro-1H-inden-5-yl)-2,2-dimethylpentanoate

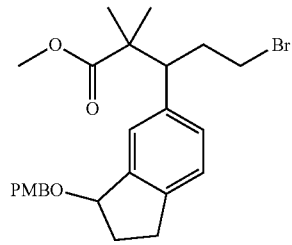

Polymer supported triphenylphosphine (2.71 g, 5.20 mmol) and carbon tetrabromide (1.812 g, 5.47 mmol) was successively added to a solution of methyl 5-hydroxy-3-(3-((4-methoxybenzyl)oxy)-2,3-dihydro-1H-inden-5-yl)-2,2-dimethylpentanoate (2.1471 g, 5.20 mmol) in DCM (26.0 mL) at ice bath cooling. After 18 h the reaction was filtered through a disposable frit, and the volatiles were removed in vacuo. The crude product was then perabsorbed on isolute and purified on a silica cartridge (24 g) with a flash chromatography to afford the title compound (1.5299 g, 3.22 mmol, 61.8% yield). LC-MS m/z 497 (M+Na)+, 1.50 min (ret. time).

Methyl 5-cyano-3-(3-((4-methoxybenzyl)oxy)-2,3-dihydro-1H-inden-5-yl)-2,2-dimethylpentanoate

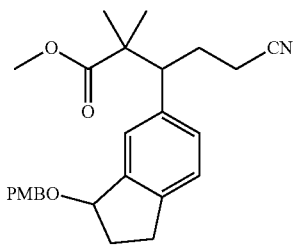

NaCN (0.173 g, 3.54 mmol) was added to methyl 5-bromo-3-(3-((4-methoxybenzyl)oxy)-2,3-dihydro-1H-inden-5-yl)-2,2-dimethylpentanoate (1.5299 g, 3.22 mmol) in ethanol (6.03 mL)/water (2.011 mL). The reaction warmed to 75° C. for 3 days. The reaction was then diluted with water and saturated aqueous NaHCO$_3$ and extracted with EtOAc. The organic layers were dried over MgSO$_4$, and concentrated in vacuo. The crude product was then purified on a silica cartridge (40 g) with a flash chromatography to afford the title compound (927.2 mg, 68.4%). LC-MS m/z 444 (M+Na)+, 1.26 min (ret. time).

Methyl 3-(3-((4-methoxybenzyl)oxy)-2,3-dihydro-1H-inden-5-yl)-2,2-dimethyl-5-(2H-tetrazol-5-yl)pentanoate

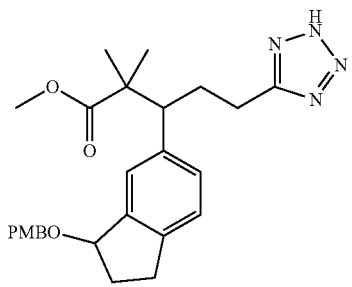

TMS-N$_3$ (1.168 mL, 8.80 mmol) and TBAF.3H$_2$O (398 mg, 1.523 mmol) were added to methyl 5-cyano-3-(3-((4-methoxybenzyl)oxy)-2,3-dihydro-1H-inden-5-yl)-2,2-dimethylpentanoate (917.2 mg, 2.176 mmol) neat in a sealed vial. After stirring for 45 min at 23° C., no reaction had occurred, so the reaction was heated to 130° C. After 4 h the reaction was cooled to 23° C. and the reaction mixture was taken up in EtOAc and washed with water and saturated aqueous NaCl. The aqueous layers were extracted with EtOAc (3×) and the organic layers were dried over MgSO$_4$ and concentrated in vacuo to afford the title compound (1.18 g, 117%). LC-MS m/z 487 (M+Na)+, 1.15 min (ret. time).

Methyl 5-(2-ethyl-2H-tetrazol-5-yl)-3-(3-((4-methoxybenzyl)oxy)-2,3-dihydro-1H-inden-5-yl)-2,2-dimethylpentanoate

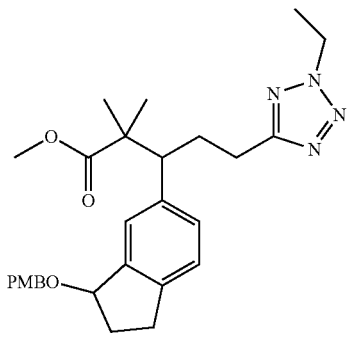

Iodoethane (261 μL, 3.26 mmol) was added to a solution of methyl 3-(3-((4-methoxybenzyl)oxy)-2,3-dihydro-1H-inden-5-yl)-2,2-dimethyl-5-(1H-tetrazol-5-yl)pentanoate (1011 mg, 2.176 mmol) and TEA (531 μL, 3.81 mmol) in THF (11 mL). The reaction was heated to 50° C. for 21 hours. The reaction was quenched by the addition of water, and extracted with EtOAc (3×). The organic layers were dried over MgSO$_4$ and concentrated in vacuo. The crude product was then purified on a silica cartridge (24 g) with a flash chromatography, eluting at 35 mL/min with a gradient running from 100% hexanes to 100% EtOAc over 20 min to afford the title compound (480.9 mg, 44.9%). LC-MS m/z 493 (M+H)$^+$, 1.27 min (ret. time).

Methyl 5-(2-ethyl-2H-tetrazol-5-yl)-3-(3-hydroxy-2,3-dihydro-1H-inden-5-yl)-2,2-dimethylpentanoate

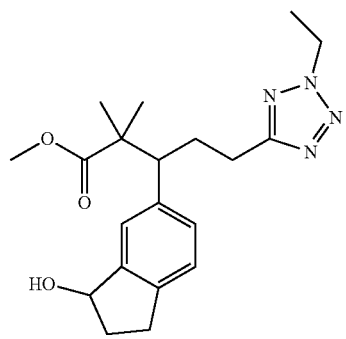 [SMILES: CCn1nnc(CCC(c2ccc3c(c2)C(O)CC3)C(C)(C)C(=O)OC)n1]

To a solution of methyl 5-(2-ethyl-2H-tetrazol-5-yl)-3-(3-((4-methoxybenzyl)oxy)-2,3-dihydro-1H-inden-5-yl)-2,2-dimethylpentanoate (480.9 mg, 0.976 mmol) in DCM (4.768 mL) and water (0.238 mL) was added DDQ (244 mg, 1.074 mmol) at 23° C. After 40 min the reaction was quenched by the addition of saturated aqueous NaHCO$_3$ and extracted with DCM 3 times. The organic layers were dried with MgSO$_4$ and concentrated in vacuo. The crude product was then purified on a silica cartridge (12 g) with a flash chromatography, eluting at 20 mL/min with a gradient running from 100% hexanes to 100% EtOAc over 20 min to afford the title compound (224.9 mg, 61.9%). LC-MS m/z 395 (M+Na)$^+$, 1.00 min (ret. time).

3-(3-(2,2-dimethyl-2,3-dihydrobenzo[f][1,4]oxazepin-4(5H)-yl)-2,3-dihydro-1H-inden-5-yl)-5-(2-ethyl-2H-tetrazol-5-yl)-2,2-dimethylpentanoic Acid, Trifluoroacetic Acid Salt

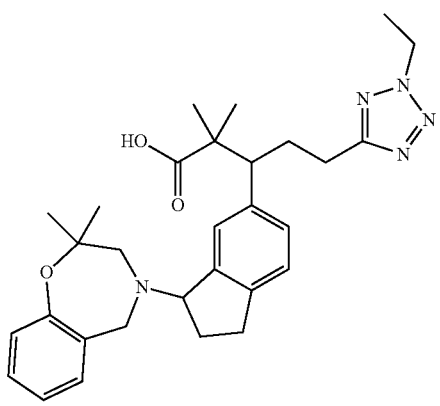 [SMILES: CCn1nnc(CCC(c2ccc3c(c2)C(N2Cc4ccccc4OC(C)(C)C2)CC3)C(C)(C)C(=O)O)n1]

PBr$_3$ (0.057 mL, 0.601 mmol) was added to a solution of methyl 5-(2-ethyl-2H-tetrazol-5-yl)-3-(3-hydroxy-2,3-dihydro-1H-inden-5-yl)-2,2-dimethylpentanoate (112 mg, 0.301 mmol) in DCM (1.203 mL) at −10° C. The reaction was stirred at −10° C. for 20 minutes. After 20 minutes, TLC analysis did not show any starting material, and the reaction was quenched with saturated aqueous NaHCO$_3$. The aqueous layer was extracted with DCM (3×), and the organic layers were combined and washed with saturated aqueous NaCl. The organic layers were dried over MgSO$_4$ and concentrated in vacuo to give a clear yellow oil. This crude residue was dissolved in acetonitrile (1.203 mL) and transferred to a Biotage microwave vial. 2,2-dimethyl-2,3,4,5-tetrahydrobenzo[f][1,4]oxazepine hydrochloride (77 mg, 0.361 mmol) and DIPEA (0.158 mL, 0.902 mmol) were added to this solution, and heated in a Biotage microwave reactor for 1 hour at 90° C. (high absorption). The volatiles was removed in vacuo, and the mixture was dissolved in methanol (0.601 mL), and transferred to a Biotage microwave vial. 3M NaOH (0.501 mL, 1.504 mmol) was added, and the reaction was heated in a Biotage microwave at 120° C. for 3 h at high absorption. 1 mL of DMSO was added, and the volatiles were removed in vacuo. The DMSO solution was acidified to ~pH 5 with 1N HCl. The water was removed in vacuo, and the mixture was filtered through a 0.45 micron syringe filter into a clean vial. The product was purified on a Gilson HPLC (Sunfire C18, 5 m 19×100 mm), eluting at 18 mL/min with a linear gradient running from 15% CH$_3$CN/H$_2$O (0.1% TFA) to 55% CH$_3$CN/H$_2$O (0.1% TFA) to give 18 mg (10%) the title compound. LC-MS m/z 518 (M+H)$^+$, 0.82 min (ret. time).

Example 65

3-(3-(2,2-Dimethyl-2,3-dihydrobenzo[f][1,4]oxazepin-4(5H)-yl)-2,3-dihydro-1H-inden-5-yl)-2,2-dimethyl-5-(4-propyl-1H-1,2,3-triazol-1-yl)pentanoic Acid, Trifluoroacetic Acid Salt

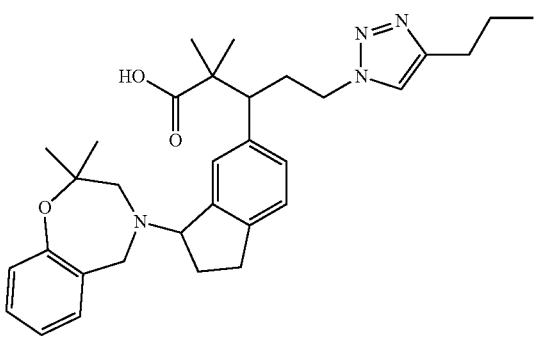 [SMILES: CCCc1cn(CCC(c2ccc3c(c2)C(N2Cc4ccccc4OC(C)(C)C2)CC3)C(C)(C)C(=O)O)nn1]

3-((4-Methoxybenzyl)oxy)-2,3-dihydro-1H-indene-5-carbaldehyde

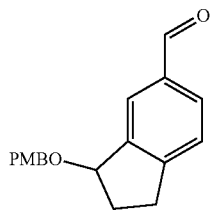

6-Bromo-1-((4-methoxybenzyl)oxy)-2,3-dihydro-1H-indene (3.4 g, 10.20 mmol) was dissolved in anhydrous THF (80 mL) and cooled to −78° C. in a dry-ice acetone bath. 2 M n-butyllithium (6.38 mL, 12.75 mmol) was added and the reaction was stirred at −78° C. for 0.5 h. DMF (3.95 mL, 51.0 mmol) was added and the reaction was stirred at −78° C. for 2 h. The reaction was diluted with saturated aqueous NH$_4$Cl (10 mL) and then additional (50 mL) water and EtOAc (100 mL). The aqueous layer was extracted with an additional portion of EtOAc (50 mL) and the combined EtOAc layers were washed with water (50 mL) and saturated aqueous NaCl (50 mL), dried over Na$_2$SO$_4$ and concentrated in vacuo. The crude product was purified on a silica cartridge (80 g) with a flash chromatography, eluting at 65 mL/min with a gradient running from hexanes to 50% EtOAc/hexanes over 30 min to afford the title compound (2.4 g, 83%). $^1$H NMR (400 MHz, CDCl$_3$) δ ppm 2.13-2.26 (m, 1H) 2.36-2.49 (m, 1H) 2.82-2.94 (m, 1H) 3.10-3.24 (m, 1H) 3.82 (s, 3H) 4.58 (d, J=12.0 Hz, 1H) 4.64 (d, J=12.0 Hz, 1H) 5.04 (dd, J=5.6 Hz, 1H) 6.91 (d, J=8.4 Hz, 2H) 7.33 (d, J=8.4 Hz, 2H) 7.40 (d, J=7.8 Hz, 1H) 7.79 (d, J=7.8 Hz, 1H) 7.90 (s, 1H) 10.00 (s, 1H).

(E)-allyl 3-(3-((4-methoxybenzyl)oxy)-2,3-dihydro-1H-inden-5-yl)acrylate

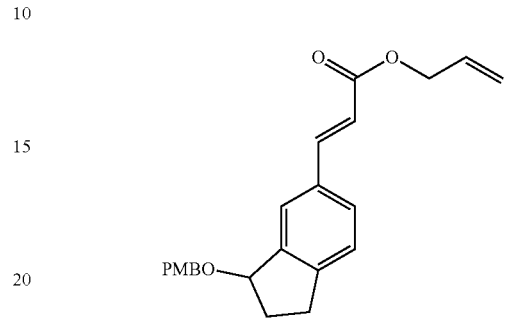

Allyl 2-(triphenylphosphoranylidene)acetate (3.19 g, 8.84 mmol) and 3-((4-methoxybenzyl)oxy)-2,3-dihydro-1H-indene-5-carbaldehyde (2.269 g, 8.04 mmol) were dissolved in DCM (65 mL) and heated to reflux for 23 h. The crude product was preabsorbed on isolute and purified on a silica cartridge (80 g) with a flash chromatography, eluting at 65 mL/min with a gradient running from hexanes to 25% EtOAc/hexanes over 25 min to afford the title compound (2.71 g, 93%). LC-MS m/z 430 (M+H$_2$O)$^+$, 1.17 min (ret. time).

5-allyl 1-methyl 3-(3-((4-methoxybenzyl)oxy)-2,3-dihydro-1H-inden-5-yl)-2,2-dimethylpentanedioate

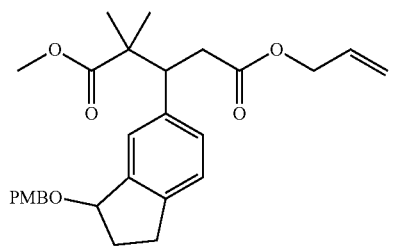

To a solution of (E)-allyl 3-(3-((4-methoxybenzyl)oxy)-2,3-dihydro-1H-inden-5-yl)acrylate (2.8128 g, 7.72 mmol) and tetrabutylammonium benzoate (0.101 g, 0.278 mmol) in THF (31.5 mL) was added ((1-methoxy-2-methylprop-1-en-1-yl)oxy)trimethylsilane (1.882 mL, 9.26 mmol) at 0° C. After 4 hours the reaction was diluted with water, and the aqueous layer extracted with EtOAc, dried over Na$_2$SO$_4$ and concentrate to afford the title compound (3.48 g, 97%). LC-MS m/z 489 (M+Na)$^+$, 1.37 min (ret. time).

5-Methoxy-3-(3-((4-methoxybenzyl)oxy)-2,3-di-hydro-1H-inden-5-yl)-4,4-dimethyl-5-oxopentanoic Acid

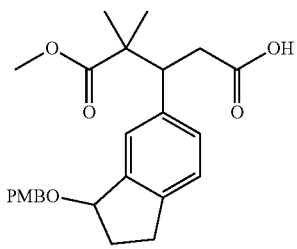

To a solution of 5-allyl 1-methyl 3-(3-((4-methoxybenzyl)oxy)-2,3-dihydro-1H-inden-5-yl)-2,2-dimethylpentanedioate (3.60 g, 7.72 mmol) in THF (386 mL) under argon was added 0.120 g of tetrakis(triphenylphosphine)palladium(0) (0.270 g, 0.234 mmol). To this morpholine (6.66 mL, 77 mmol) was added dropwise. After 3 days the reaction was not complete, and another 150 mg of tetrakis(triphenylphosphine)palladium(0) was added. After 5 days the solvent removed in vacuo. The residue was dissolved in EtOAc, and washed twice with 1N HCl and once with water. The organic layer was dried with $MgSO_4$ and concentrated in vacuo to afford the title compound (3.49 g, 106%). LC-MS m/z 444 $(M+H_2O)^+$ 449 $(M+Na)^+$, 1.15 min (ret. time).

Methyl 5-hydroxy-3-(3-((4-methoxybenzyl)oxy)-2,3-dihydro-1H-inden-5-yl)-2,2-dimethylpentanoate

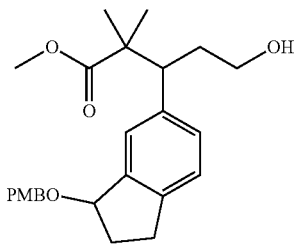

To a solution of 5-methoxy-3-(3-((4-methoxybenzyl)oxy)-2,3-dihydro-1H-inden-5-yl)-4,4-dimethyl-5-oxopentanoic acid (3.29 g, 7.72 mmol) in THF (18.00 mL) was added trimethyl borate (2.58 mL, 23.16 mmol) at 23° C. To this solution was added $BH_3$*DMS (19.30 mL, 38.6 mmol) dropwise over 60 min. After stirring for one hour, methanol (9.00 mL) was added and the reaction was stirred for 1 hour. The solvents were removed in vacuo, and the residue was dissolved in EtOAc. The organic layer was washed with saturated aqueous $NaHCO_3$, $H_2O$ and saturated aqueous NaCl. The organic layer was dried with $MgSO_4$, and concentrated in vacuo. The crude product was then purified on a silica cartridge (40 g) with a flash chromatography, eluting at 40 mL/min with a gradient running from 100% hexanes to 50% EtOAc/Hexanes over 25 min to afford the title compound (1.61 g, 50.6%). LC-MS m/z 430 $(M+H_2O)^+$, 1.17 min (ret. time).

Methyl 3-(3-((4-methoxybenzyl)oxy)-2,3-dihydro-1H-inden-5-yl)-2,2-dimethyl-5-((methylsulfonyl)oxy)pentanoate

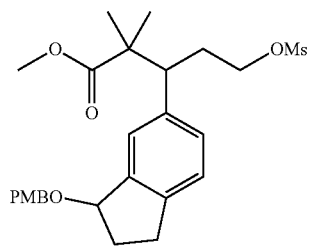

To a solution of methyl 5-hydroxy-3-(3-((4-methoxybenzyl)oxy)-2,3-dihydro-1H-inden-5-yl)-2,2-dimethylpentanoate (833.3 mg, 2.020 mmol) in DCM (10.100 mL) was added TEA (0.366 mL, 2.63 mmol) and methanesulfonyl chloride (0.173 mL, 2.222 mmol) at 0° C. The reaction was allowed to warm slowly, and after 60 minutes the reaction was diluted with DCM, washed with 1N HCl, $H_2O$, and saturated aqueous NaCl. The combined aqueous layers were extracted with DCM (3×). The organic layers were combined, dried with $MgSO_4$, and loaded on to Isolute. The crude product was then purified on a silica cartridge (12 g) with a flash chromatography, eluting at 20 mL/min with a gradient running from 100% hexanes to 50% EtOAc/hexanes over 22 min to afford the title compound (752.8 mg, 76%). LC-MS m/z 513 $(M+Na)^+$, 1.22 min (ret. time).

Methyl 3-(3-((4-methoxybenzyl)oxy)-2,3-dihydro-1H-inden-5-yl)-2,2-dimethyl-5-(4-propyl-1H-1,2,3-triazol-1-yl)pentanoate

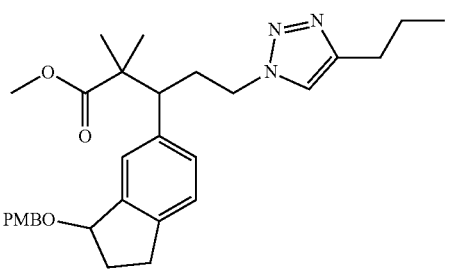

To a solution of methyl 3-(3-((4-methoxybenzyl)oxy)-2,3-dihydro-1H-inden-5-yl)-2,2-dimethyl-5-((methylsulfonyl)oxy)pentanoate (752.8 mg, 1.534 mmol) in DMF (12.787 mL) was added sodium azide (110 mg, 1.688 mmol), the reaction was heated to 60° C. After 2 hours the DMF was removed under vacuum, and the crude residue was taken up in THF (12.79 mL). Pentyne (0.756 mL, 7.67 mmol), N-ethyl-N-isopropylpropan-2-amine (0.080 mL, 0.460 mmol) and copper(I) iodide (58.4 mg, 0.307 mmol) were added and the reaction was allowed to stir at ambient temperature. After 18 h the THF was removed under reduced pressure. The crude product was then purified on a silica cartridge (24 g) with a flash chromatography, eluting at 35 mL/min with a gradient running from 100% hexanes to 100% EtOAc over 20 min to afford the title compound (259 mg, 33.4%). LC-MS m/z 506 (M+H)+, 1.34 min (ret. time).

Methyl 3-(3-hydroxy-2,3-dihydro-1H-inden-5-yl)-2,2-dimethyl-5-(4-propyl-1H-1,2,3-triazol-1-yl)pentanoate

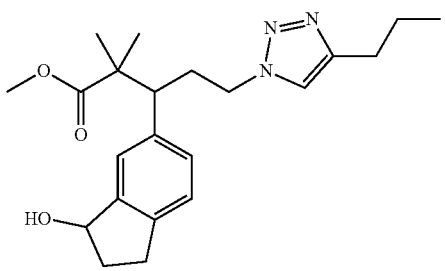 [SMILES: CCCc1cn(CCC(c2ccc3c(c2)C(O)CC3)C(C)(C)C(=O)OC)nn1]

To a solution of methyl 3-(3-((4-methoxybenzyl)oxy)-2,3-dihydro-1H-inden-5-yl)-2,2-dimethyl-5-(4-propyl-1H-1,2,3-triazol-1-yl)pentanoate (259 mg, 0.512 mmol) in DCM (2.567 mL) and water (0.128 mL) was added DDQ (128 mg, 0.563 mmol) at 23° C. After 45 min, the reaction was quenched by the addition of saturated aqueous NaHCO₃ and extracted with DCM. The organic layers were dried with MgSO₄ and reduced in vacuo. The crude product was then purified on a silica cartridge (4 g) with a flash chromatography, eluting at 18 mL/min with a gradient running from 100% hexanes to 100% EtOAc over 20 min to afford the title compound (89.5 mg, 45.3%). LC-MS m/z 384 (M+H)+, 0.99 min (ret. time).

3-(3-(2,2-dimethyl-2,3-dihydrobenzo[f][1,4]oxazepin-4(5H)-yl)-2,3-dihydro-1H-inden-5-yl)-2,2-dimethyl-5-(4-propyl-1H-1,2,3-triazol-1-yl)pentanoic Acid, Trifluoroacetic Acid Salt PBr₃ (0.066 ml, 0.698 mmol) was added to a solution of methyl 3-(3-hydroxy-2,3-dihydro-1H-inden-5-yl)-2,2-dimethyl-5-(4-propyl-1H-1,2,3-triazol-1-yl)pentanoate (134.5 mg, 0.349 mmol) in DCM (1.133 mL) at −10° C. The reaction was stirred at −10° C. for 20 minutes. After 20 minutes, TLC analysis did not show any starting material, and the reaction was quenched with NaHCO₃. The aqueous layer was extracted with DCM (3×) and the organic layers were combined and washed with sat. NaCl. The organic layers were dried over MgSO₄ and concentrated to give a clear yellow oil which was dissolved in acetonitrile (1.133 mL) and transferred to a microwave vial. 2,2-dimethyl-2,3,4,5-tetrahydrobenzo[f][1,4]oxazepine hydrochloride (89 mg, 0.419 mmol) and DIPEA (0.183 ml, 1.047 mmol) were added to this solution, and heated in the microwave for 1 hour at 90° C. at high absorption. After 1 hour LC-MS showed no more starting material, and product formation (LC-MS m/z 545 (M+H)+, 1.01 min (ret. time)). The solvent was removed in vacuo, and the mixture was dissolved in methanol (1.133 mL), and transferred to a microwave vial. 3M NaOH (0.581 mL, 1.744 mmol) was added, and the reaction was heated in the microwave at 120° C. for 3 hours. 1 mL of DMSO was added, and the volatiles were removed in vacuo. The DMSO solution was acidified to ~pH 5 with 1N HCl. The water was removed on in vacuo, and the mixture was filtered through a 0.45 micron syringe filter into a clean vial. The product was purified on a Gilson HPLC (Sunfire C18, 5 m 19×100 mm), eluting at 18 mL/min with a linear gradient running from 20% CH₃CN/H₂O (0.1% TFA) to 50% CH₃CN/H₂O (0.1% TFA) to afford the title compound (18 mg, 10%). LC-MS m/z 531 (M+H)+, 0.81 min (ret. time).

Example 66

3-(1,4-Dimethyl-1H-benzo[d][1,2,3]triazol-5-yl)-3-(8-((R)-2-methyl-2,3-dihydrobenzo[f][1,4]oxazepin-4(5H)-yl)-5,6,7,8-tetrahydronaphthalen-2-yl)propanoic Acid

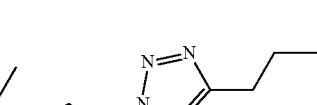

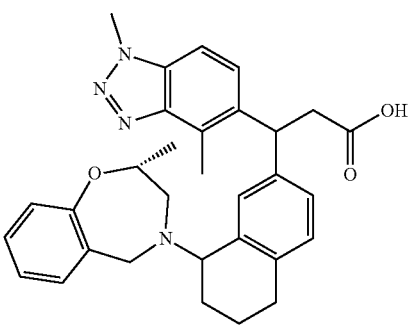 [SMILES: Cc1c(C(CC(=O)O)c2ccc3c(c2)C(N2Cc4ccccc4O[C@H](C)C2)CCC3)ccc2c1nnn2C]

7-Bromo-1,2,3,4-tetrahydronaphthalen-1-ol

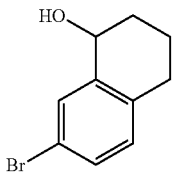 [SMILES: OC1CCCc2ccc(Br)cc21]

To a solution of 7-bromo-3,4-dihydronaphthalen-1(2H)-one (2000 mg, 8.89 mmol) in methanol (20 mL) at 25° C., NaBH₄ (672 mg, 17.77 mmol) was added. After the reaction mixture was stirred for 2 h, 1N HCl solution was added to quench the reaction and extracted with ethyl acetate (3×50 mL). The combined organic layer was washed with brine (50 mL), dried over MgSO₄, and concentrated to obtain the title compound 7-bromo-1,2,3,4-tetrahydronaphthalen-1-ol (1800 mg, 7.93 mmol, 89% yield) as an oil. $^1$H NMR (400 MHz, CDCl₃) b=7.58 (d, J=1.2 Hz, 1H), 7.3-7.26 (m, 1H), 6.97 (d, J=7.2 Hz 1H), 4.72 (s, 1H), 2.74 (m, 2H), 2.04-1.87 (m, 5H).

7-(4,4,5,5-Tetramethyl-1,3,2-dioxaborolan-2-y)-1,2,3,4-tetrahydronaphthalen-1-ol

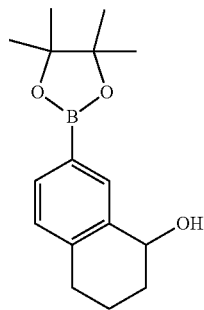 [SMILES: CC1(C)OB(c2ccc3c(c2)C(O)CCC3)OC1(C)C]

To a solution of 7-bromo-1,2,3,4-tetrahydronaphthalen-1-ol (1000 mg, 4.40 mmol) in 1,4-dioxane (20 mL) was added 4,4,4',4',5,5,5',5'-octamethyl-2,2'-bi(1,3,2-dioxaborolane) (1342 mg, 5.28 mmol), potassium acetate (648 mg, 6.61 mmol), and PdCl₂(dppf)-CH₂Cl₂ adduct (180 mg, 0.220 mmol) slowly under nitrogen. The reaction mixture was stirred at 90° C. for 16 hours. Water (50 mL) was added and the mixture extracted with ethyl acetate (3×50 mL). The combined organic layer was dried over MgSO₄ and concentrated under a stream of nitrogen at 50° C. The crude product was purified by silica gel chromatography (hexane:ethyl acetate=1:1) to obtain the title compound 7-(4,4,5,5-tetramethyl-1,3,2-dioxaborolan-2-yl)-1,2,3,4-tetrahydronaphthalen-1-ol (800 mg, 2.92 mmol, 66.3% yield) as a solid. $^1$H NMR (400 MHz, CDCl₃) δ=7.87 (d, J=1.2 Hz, 1H), 7.62 (d, J=1.2 Hz, 1H), 7.08 (d, J=7.2 Hz 1H), 4.80 (t, 1H), 2.83-2.73 (m, 2H), 1.95-1.76 (m, 4H), 1.34 (s, 12H).

Ethyl 3-(1,4-dimethyl-1H-benzo[d][1,2,3]triazol-5-yl)-3-(8-hydroxy-5,6,7,8-tetrahydronaphthalen-2-yl)propanoate

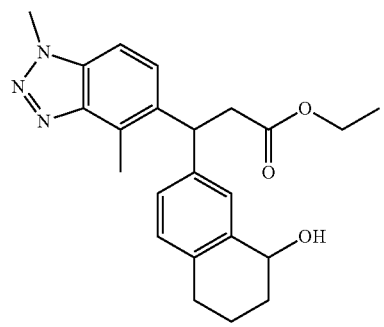 [SMILES: CCOC(=O)CC(c1ccc2c(c1)C(O)CCC2)c1ccc2c(nnn2C)c1C]

To a solution of (E)-ethyl 3-(1,4-dimethyl-1H-benzo[d][1,2,3]triazol-5-yl)acrylate (300 mg, 1.223 mmol) in 1,4-dioxane (10 mL) and water (5 mL) was added 7-(4,4,5,5-tetramethyl-1,3,2-dioxaborolan-2-yl)-1,2,3,4-tetrahydronaphthalen-1-ol (800 mg, 2.92 mmol) and TEA (0.341 mL, 2.446 mmol). The reaction mixture was stirred for 10 min followed by addition of chloro(1,5-cyclooctadiene)rhodium(I) dimer (30.2 mg, 0.061 mmol) under the protection of nitrogen. The reaction mixture was stirred at 90° C. for 16 h. Then the reaction mixture was extracted with EtOAc (3×10 mL). The combined organic layer was dried with MgSO₄ and concentrated. The crude product was purified by silica gel chromatography (petroleum ether/ethyl acetate=1:1) to obtain the title compound ethyl 3-(1,4-dimethyl-1H-benzo[d][1,2,3]triazol-5-yl)-3-(8-hydroxy-5,6,7,8-tetrahydronaphthalen-2-yl)propanoate (300 mg, 0.762 mmol, 62.3% yield) as a solid. LCMS m/z 394.2 (M+H)⁺, 1.85 min (ret. time).

Ethyl 3-(1,4-dimethyl-1H-benzo[d][1,2,3]triazol-5-yl)-3-(8-((R)-2-methyl-2,3-dihydrobenzo[f][1,4]oxazepin-4(5H)-yl)-5,6,7,8-tetrahydronaphthalen-2-yl)propanoate

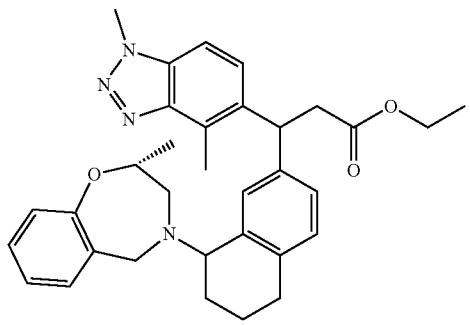 [SMILES: CCOC(=O)CC(c1ccc2c(c1)C(N1Cc3ccccc3O[C@H](C)C1)CCC2)c1ccc2c(nnn2C)c1C]

The mixture of ethyl 3-(1,4-dimethyl-1H-benzo[d][1,2,3]triazol-5-yl)-3-(8-hydroxy-5,6,7,8-tetrahydronaphthalen-2-yl)propanoate (250 mg, 0.635 mmol), DIPEA (0.222 mL, 1.271 mmol) in dichloromethane (DCM) (10 mL) was stirred at 0° C. Methanesulfonyl chloride (0.074 mL, 0.953 mmol) was added and stirred for 2 h. The reaction mixture was concentrated. The residue was dissolved into N,N-dimethylformamide (DMF) (2 mL) and (R)-2-methyl-2,3,4,5-tetrahydrobenzo[f][1,4]oxazepine (311 mg, 1.906 mmol) was added. Then it was stirred at 90° C. for 2 h. The reaction mixture was poured onto ice-water and extracted with ethyl acetate (3×30 mL), dried over MgSO$_4$ and concentrated. The crude product was purified by silica gel chromatography (petroleum ether/ethyl acetate=1:1) to obtain the title compound ethyl 3-(1,4-dimethyl-1H-benzo[d][1,2,3]triazol-5-yl)-3-(8-((R)-2-methyl-2,3-dihydrobenzo[f][1,4]oxazepin-4(5H)-yl)-5,6,7,8-tetrahydronaphthalen-2-yl)propanoate (300 mg, 0.557 mmol, 88% yield) as an oil which was carried to the next step without further purification. LCMS m/z 539.2 (M+H)$^+$, 1.70 min (ret. time)

3-(1,4-Dimethyl-1H-benzo[d][1,2,3]triazol-5-yl)-3-(8-((R)-2-methyl-2,3-dihydrobenzo[f][1,4]oxazepin-4(5H)-yl)-5,6,7,8-tetrahydronaphthalen-2-yl)propanoic Acid

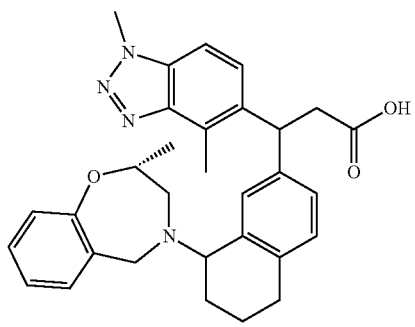 [SMILES: Cc1c(C(CC(=O)O)c2ccc3c(c2)C(N2Cc4ccccc4O[C@H](C)C2)CCC3)ccc2c1nnn2C]

To a solution of ethyl 3-(1,4-dimethyl-1H-benzo[d][1,2,3]triazol-5-yl)-3-(8-((R)-2-methyl-2,3-dihydrobenzo[f][1,4]oxazepin-4(5H)-yl)-5,6,7,8-tetrahydronaphthalen-2-yl)propanoate (200 mg, 0.371 mol) in MeOH (2 mol), NaOH (59.4 mg, 1.485 mmol) and water (2.0 mL) were added. The reaction mixture was stirred at 50° C. for 2 h. The mixture was concentrated and dissolved into water (5 mL). Then it was neutralized with 1N HCl aqueous solution to pH 6. The residue was concentrated and purified by reverse-phase HPLC (20% MeCN/H$_2$O) to obtain the title compound 3-(1,4-dimethyl-1H-benzo[d][1,2,3]triazol-5-yl)-3-(8-((R)-2-methyl-2,3-dihydrobenzo[f][1,4]oxazepin-4(5H)-yl)-5,6, 7,8-tetrahydronaphthalen-2-yl)propanoic acid (100 mg, 0.186 mmol, 50.1% yield) as a solid. LCMS m/z 511.2 (M+H)$^+$, 1.5 min (ret. Time).

Example 67 rac-(R)-3-(1,4-Dimethyl-1H-benzo[d][1,2,3]triazol-5-yl)-3-(rac-(S)-3-(2,2-dimethyl-2,3-dihydropyrido[2,3-f][1,4]oxazepin-4(5H)-yl)-2,3-dihydro-1H-inden-5-yl)-2,2-dimethylpropanoic Acid, Trifluoroacetic Acid Salt

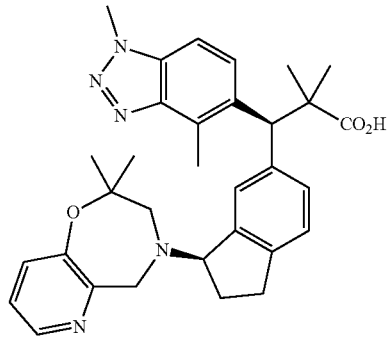 [SMILES: Cc1c([C@H](c2ccc3c(c2)[C@H](N2Cc4ncccc4OC(C)(C)C2)CC3)C(C)(C)C(=O)O)ccc2c1nnn2C]

To a mixture of methyl 3-(1,4-dimethyl-1H-benzo[d][1,2,3]triazol-5-yl)-3-(3-hydroxy-2,3-dihydro-1H-inden-5-yl)-2,2-dimethylpropanoate (0.060 g, 0.152 mmol) in dichloromethane (0.50 mL) was added SOCl$_2$ (0.022 mL, 0.305 mmol). The resulting reaction mixture was stirred at ambient temperature for 10 min then concentrated under reduced pressure. This residue was dissolved in acetonitrile (1.5 mL) and tetrahydrofuran (0.50 mL) after which 2,2-dimethyl-2,3,4,5-tetrahydropyrido[2,3-f][1,4]oxazepine, hydrochloride (0.049 g, 0.229 mmol), sodium iodide (0.011 g, 0.076 mmol) and K$_2$CO$_3$ (0.063 g, 0.457 mmol) were added. The resulting reaction mixture was heated at 40° C. for 24 h. The reaction mixture was filtered. The filter cake was washed with MeCN (2 mL). The combined filtrate was concentrated under reduced pressure. The residue was dissolved in methanol (1.5 mL) before adding NaOH (3 N) (0.254 mL, 0.762 mmol). The resulting reaction mixture was heated with microwave at 130° C. for 60 min before acidifying with HCl (3 N) (0.254 mL, 0.762 mmol). The reaction mixture was concentrated under reduced pressure and purified by reverse HPLC to give the title compound (9.3 mg, 0.014 mmol, 9.33% yield) as a solid. LCMS m/z 540.5 (M+H)$^+$, 0.84 min (ret. Time). The compounds in Table 4 were prepared by a method similar to the one described for the preparation of rac-(R)-3-(1,4-Dimethyl-1H-benzo[d][1,2,3]triazol-5-yl)-3-(rac-(S)-3-(2,2-dimethyl-2,3-dihydropyrido[2,3-f][1,4]oxazepin-4(5H)-yl)-2,3-dihydro-1H-inden-5-yl)-2,2-dimethylpropanoic acid. As is appreciated by those skilled in the art, these analogous examples may involve variations in general reaction conditions.

TABLE 4

| Ex # | Structure | Name | LCMS [M + H]+ | Retention Time (min) |
|---|---|---|---|---|
| 68 | 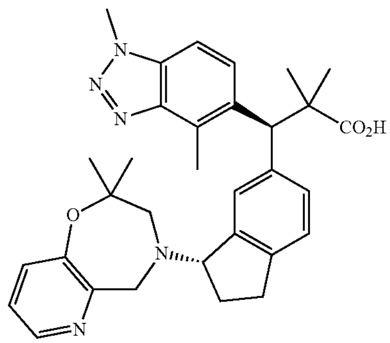 [SMILES: Cc1c([C@H](c2ccc3c(c2)[C@@H](N2Cc4ncccc4OC(C)(C)C2)CC3)C(C)(C)C(=O)O)ccc2c1nnn2C] | rac-(R)-3-(1,4-Dimethyl-1H-benzo[d][1,2,3]triazol-5-yl)-3-(rac-(R)-3-(2,2-dimethyl-2,3-dihydropyrido[2,3-f][1,4]oxazepin-4(5H)-yl)-2,3-dihydro-1H-inden-5-yl)-2,2-dimethylpropanoic acid | 540.3 | 0.90 |
| 689 | 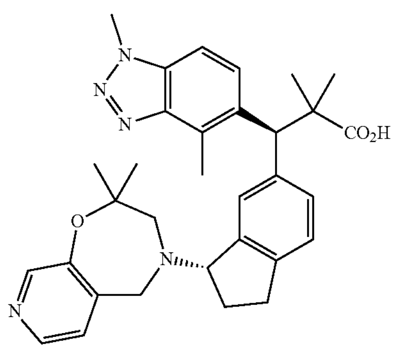 [SMILES: Cc1c([C@H](c2ccc3c(c2)[C@@H](N2Cc4ccncc4OC(C)(C)C2)CC3)C(C)(C)C(=O)O)ccc2c1nnn2C] | rac-(R)-3-(1,4--1H-benzo[d][1,2,3]triazol-5-yl)-3-(rac-(R)-3-(2,2-dimethyl-2,3-dihydropyrido[4,3-f][1,4]oxazepin-4(5H)-yl)-2,3-dihydro-1H-inden-5-yl)-2,2-dimethylpropanoic acid, Trifluoroacetic acid salt | 540.5 | 0.88 |
| 70 | 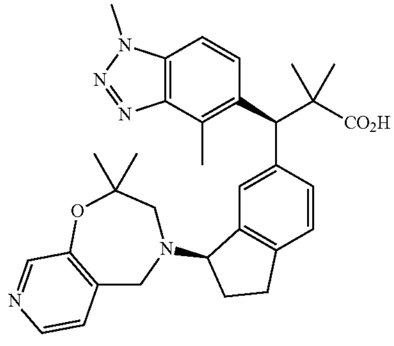 [SMILES: Cc1c([C@H](c2ccc3c(c2)[C@H](N2Cc4ccncc4OC(C)(C)C2)CC3)C(C)(C)C(=O)O)ccc2c1nnn2C] | rac-(R)-3-(1,4-Dimethyl-1H-benzo[d][1,2,3]triazol-5-yl)-3-(rac-(S)-3-(2,2-dimethyl-2,3-dihydropyrido[4,3-f][1,4]oxazepin-4(5H)-yl)-2,3-dihydro-1H-inden-5-yl)-2,2-dimethylpropanoic acid, Trifluoroacetic acid salt | 540.5 | 0.89 |

Example 69 rel-(S)-3-(1,4-Dimethyl-1H-benzo[d][1,2,3]triazol-5-yl)-3-(rel-(R)-3-((R)-2-ethyl-2,3-dihydropyrido[3,4-f][1,4]oxazepin-4(5H)-yl)-2,3-dihydro-1H-inden-5-yl)-2,2-dimethylpropanoic Acid

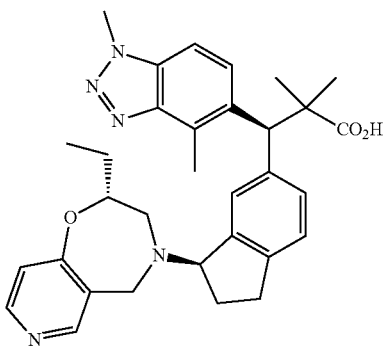 [SMILES: CC[C@@H]1CN([C@@H]2CCc3ccc([C@@H](c4ccc5c(nnn5C)c4C)C(C)(C)C(=O)O)cc32)Cc2cnccc2O1]

rel-(S)-3-(1,4-Dimethyl-1H-benzo[d][1,2,3]triazol-5-yl)-3-(rel-(R)-3-((R)-2-ethyl-2,3-dihydropyrido[3,4-f][1,4]oxazepin-4(5H)-yl)-2,3-dihydro-1H-inden-5-yl)-2,2-dimethylpropanoate

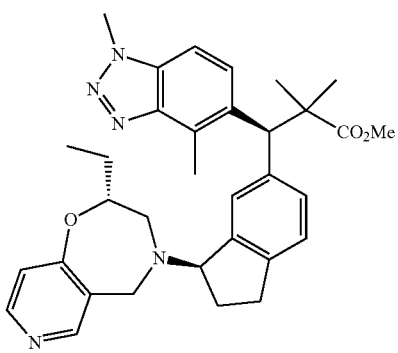 [SMILES: CC[C@@H]1CN([C@@H]2CCc3ccc([C@@H](c4ccc5c(nnn5C)c4C)C(C)(C)C(=O)OC)cc32)Cc2cnccc2O1]

To a mixture of (R)-2-ethyl-2,3,4,5-tetrahydropyrido[3,4-f][1,4]oxazepine, hydrochloride (344 mg, 1.600 mmol) in methanol (12 mL) was added $K_2CO_3$ (332 mg, 2.400 mmol). The resulting reaction mixture was stirred at ambient temperature for 60 min then filtered, concentrated, and taken into acetonitrile (12 mL) to afford the intermediate solution.

To the mixture of methyl 3-(1,4-dimethyl-1H-benzo[d][1,2,3]triazol-5-yl)-3-(3-hydroxy-2,3-dihydro-1H-inden-5-yl)-2,2-dimethylpropanoate (315 mg, 0.8 mmol) in DCM (4.0 mL) was added $SOCl_2$ (0.117 mL, 1.600 mmol). The resulting reaction mixture was stirred at ambient temperature for 20 min then concentrated under reduced pressure after which the above intermediate solution, sodium iodide (60.0 mg, 0.400 mmol) and $K_2CO_3$ (332 mg, 2.400 mmol) was added. The resulting reaction mixture was heated at 40° C. for 20 h then filtered. The filter cake was washed with MeCN (6 mL). The combined filtrate was concentrated under reduced pressure, purified via flash chromatography followed by purification via reverse phase HPLC (TFA modifier) then further purified with chiral SFC (Column: Chiralpak AD 20×250 mm, 5u; Co-solvent: 25% EtOH; Flowrate: 50 g/min; Back pressure: 100Bar) to give the title compound (42.3 mg, 0.076 mmol, 9.55% yield). LCMS m/z 554.3 $(M+H)^+$, 0.91 min (ret. time).

rel-(S)-3-(1,4-Dimethyl-1H-benzo[d][1,2,3]triazol-5-yl)-3-(rel-(R)-3-((R)-2-ethyl-2,3-dihydropyrido[3,4-f][1,4]oxazepin-4(5H)-yl)-2,3-dihydro-1H-inden-5-yl)-2,2-dimethylpropanoic Acid

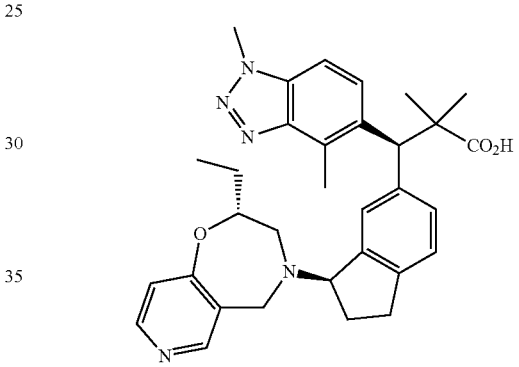

To a mixture of methyl rel-(S)-3-(1,4-dimethyl-1H-benzo[d][1,2,3]triazol-5-yl)-3-(rel-(R)-3-((R)-2-ethyl-2,3-dihydropyrido[3,4-f][1,4]oxazepin-4(5H)-yl)-2,3-dihydro-1H-inden-5-yl)-2,2-dimethylpropanoate (42.3 mg, 0.076 mmol) in methanol (1.5 mL) was added NaOH (3.0 N) (0.127 mL, 0.382 mmol). The resulting reaction mixture was heated 4 times with microwave at 120° C. for 1 h before acidifying with HCl (3.0 N) (0.127 mL, 0.382 mmol) The reaction mixture was concentrated under reduced pressure, and purified by reverse phase HPLC (formic acid modifier) to give the title compound (28.6 mg, 0.049 mmol, 63.9% yield). LCMS m/z 540.5 $(M+H)^+$, 0.82 min (ret. time).

The compounds in Table 5 were prepared by a method similar to the one described for the preparation of rel-(S)-3-(1,4-Dimethyl-1H-benzo[d][1,2,3]triazol-5-yl)-3-(rel-(R)-3-((R)-2-ethyl-2,3-dihydropyrido[3,4-f][1,4]oxazepin-4(5H)-yl)-2,3-dihydro-1H-inden-5-yl)-2,2-dimethylpropanoic acid. As is appreciated by those skilled in the art, these analogous examples may involve variations in general reaction conditions.

TABLE 5

| Ex # | Structure | Name | LCMS [M + H]+ | Retention Time (min) |
|---|---|---|---|---|
| 72 | 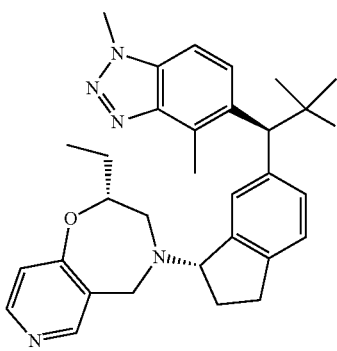 | rel-(S)-3-(1,4-Dimethyl-1H-benzo[d][1,2,3]triazol-5-yl)-3-(rel-(S)-3-((R)-2-ethyl -2,3-dihydropyrido[3,4-f][1,4]oxazepin-4(5H)-yl)-2,3-dihydro-1H-inden-5-yl)-2,2-dimethylpropanoic acid | 540.5 | 0.96 |
| 73 | 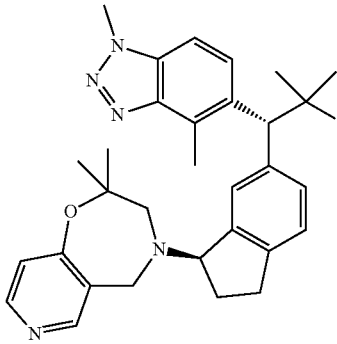 | rel-(R)-3-(1,4-Dimethyl-1H-benzo[d][1,2,3]triazol-5-yl)-3-(rel-(R)-3-((R)-2-ethyl-2,3-dihydropyrido[3,4-f][1,4]oxazepin-4(5H)-yl)-2,3-dihydro-1H-inden-5-yl)-2,2-dimethylpropanoic acid | 540.5 | 0.99 |
| 74 | 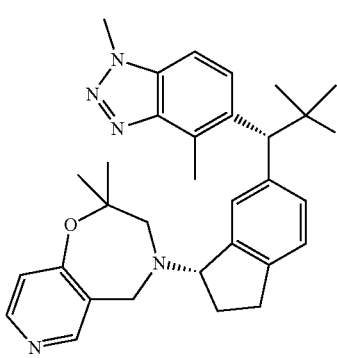 | rel-(R)-3-(1,4-Dimethyl-1H-benzo[d][1,2,3]triazol-5-yl)-3-(rel-(S)-3-((R)-2-ethyl-2,3-dihydropyrido[3,4-f][1,4]oxazepin-4(5H)-yl)-2,3-dihydro-1H-inden-5-yl)-2,2-dimethylpropanoic acid | 540.6 | 0.99 |

TABLE 5-continued

| Ex # | Structure | Name | LCMS [M + H]+ | Retention Time (min) |
|---|---|---|---|---|
| 75 | 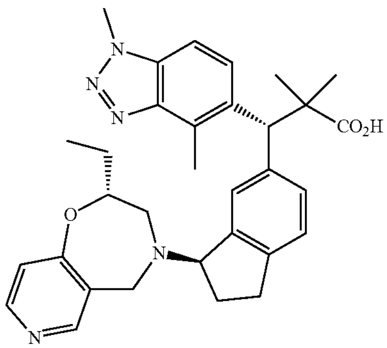 [SMILES: CC[C@@H]1CN([C@@H]2CCc3ccc([C@H](c4ccc5c(nnn5C)c4C)C(C)(C)C(=O)O)cc32)Cc2cnccc2O1] | rel-(S)-3-(1,4-Dimethyl-1H-benzo[d][1,2,3]triazol-5-yl)-3-(rel-(R)-3-((R)-2-ethyl-2,3-dihydropyrido[3,4-f][1,4]oxazepin-4(5H)-yl)-2,3-dihydro-1H-inden-5-yl)-2,2-dimethylpropanoic acid | 540.4 | 0.81 |
| 76 | 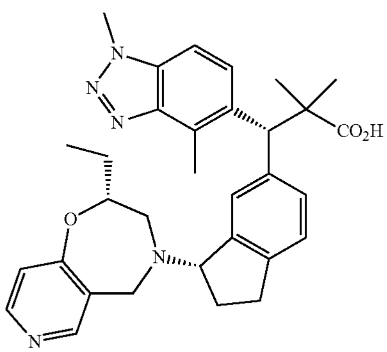 [SMILES: CC[C@@H]1CN([C@H]2CCc3ccc([C@H](c4ccc5c(nnn5C)c4C)C(C)(C)C(=O)O)cc32)Cc2cnccc2O1] | rel-(R)-3-(1,4-Dimethyl-1H-benzo[d][1,2,3]triazol-5-yl)-3-(rel-(S)-3-((R)-2-ethyl-2,3-dihydropyrido[3,4-f][1,4]oxazepin-4(5H)-yl)-2,3-dihydro-1H-inden-5-yl)-2,2-dimethylpropanoic acid | 540.5 | 0.84 |

Example 70 rel-(S)-3-(1,4-Dimethyl-1H-benzo[d][1,2,3]triazol-5-yl)-3-(rel-(R)-3-(2,2-dimethyl-2,3-dihydrobenzo[f][1,4]oxazepin-4(5H)-yl)-2,3-dihydro-1H-inden-5-yl)-2,2-dimethylpropanoic Acid

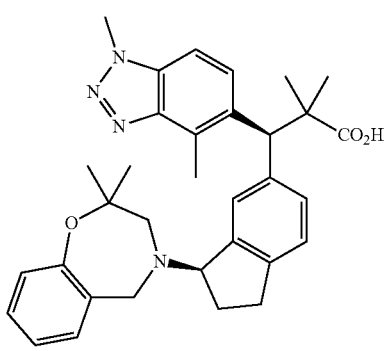 [SMILES: Cc1c([C@H](c2ccc3c(c2)[C@H](N2Cc4ccccc4OC(C)(C)C2)CC3)C(C)(C)C(=O)O)ccc2c1nnn2C]

Methyl 3-(1,4-dimethyl-1H-benzo[d][1,2,3]triazol-5-yl)-2,2-dimethyl-3-(3-oxo-2,3-dihydro-1H-inden-5-yl)propanoate

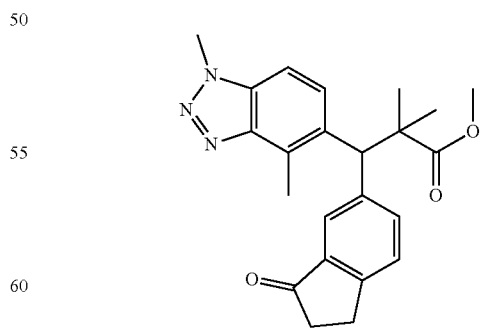

To a solution of methyl 3-(1,4-dimethyl-1H-benzo[d][1,2,3]triazol-5-yl)-3-(3-hydroxy-2,3-dihydro-1H-inden-5-yl)-2,2-dimethylpropanoate (650 mg, 1.652 mmol) in dichloromethane (50 mL) was added Dess-Martin periodinane (1401 mg, 3.30 mmol) and one drop of water. The reaction mixture was stirred at 25° C. for 8 h after which the mixture was filtered and the filtrate was concentrated. The crude product was purified by silica gel chromatography (petroleum ether:ethyl acetate=1:1) to provide the title compound methyl 3-(1,4-dimethyl-1H-benzo[d][1,2,3]triazol-5-yl)-2,2-dimethyl-3-(3-oxo-2,3-dihydro-1H-inden-5-yl)propanoate (570 mg) as a yellow oil. LC/MS m/z 392.2 (M+H)+, 1.65 (ret. time).

rel-(R)-Methyl 3-(1,4-dimethyl-1H-benzo[d][1,2,3]triazol-5-yl)-2,2-dimethyl-3-(3-oxo-2,3-dihydro-1H-inden-5-yl)propanoate

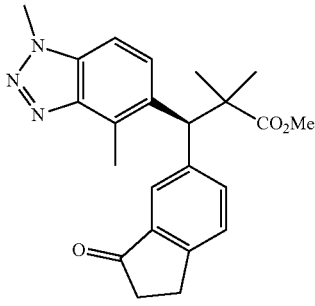 [SMILES: COC(=O)C(C)(C)[C@@H](c1ccc2c(c1)C(=O)CC2)c1ccc2c(nnn2C)c1C]

Methyl 3-(1,4-dimethyl-1H-benzo[d][1,2,3]triazol-5-yl)-2,2-dimethyl-3-(3-oxo-2,3-dihydro-1H-inden-5-yl)propanoate (0.57 g, 1.456 mmol) was purified by chiral SFC (Column: Chiralpak IA 20×250 mm, 5u; Co-solvent: 20% EtOH; Flowrate: 50 g/min; Back pressure: 100Bar) to give the title compound (177.9 mg, 0.454 mmol, 31.2% yield). LCMS m/z 392.2 (M+H)+, 0.99 min (ret. time).

rel-(3S)-Methyl 3-(1,4-dimethyl-1H-benzo[d][1,2,3]triazol-5-yl)-3-(3-hydroxy-2,3-dihydro-1H-inden-5-yl)-2,2-dimethylpropanoate

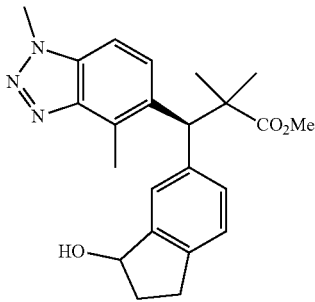 [SMILES: COC(=O)C(C)(C)[C@@H](c1ccc2c(c1)C(O)CC2)c1ccc2c(nnn2C)c1C]

To a solution of rel-(R)-methyl 3-(1,4-dimethyl-1H-benzo[d][1,2,3]triazol-5-yl)-2,2-dimethyl-3-(3-oxo-2,3-dihydro-1H-inden-5-yl)propanoate (177 mg, 0.452 mmol) in methanol (3.5 mL) was added NaBH4 (17.11 mg, 0.452 mmol). The reaction was stirred at ambient temperature for 30 min then concentrated under reduced pressure, extracted with DCM (2×5 mL), dried over Na2SO4, filtered, and concentrated under reduced pressure to give the title compound (203.9 mg, 0.518 mmol, 115% yield). LCMS m/z 394.2 (M+H)+, 0.96 min (ret. time).

rel-(S)-3-(1,4-Dimethyl-1H-benzo[d][1,2,3]triazol-5-yl)-3-(rel-(R)-3-(2,2-dimethyl-2,3-dihydrobenzo[f][1,4]oxazepin-4(5H)-yl)-2,3-dihydro-1H-inden-5-yl)-2,2-dimethylpropanoic Acid

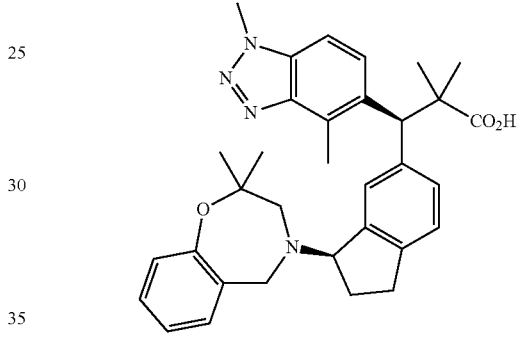

To a mixture of rel-(3S)-methyl 3-(1,4-dimethyl-1H-benzo[d][1,2,3]triazol-5-yl)-3-(3-hydroxy-2,3-dihydro-1H-inden-5-yl)-2,2-dimethylpropanoate (100 mg, 0.254 mmol) in dichloromethane (1.0 mL) was added SOCl2 (0.037 mL, 0.508 mmol). The resulting reaction mixture was stirred at ambient temperature for 20 min then concentrated under reduced pressure. This residue was dissolved in acetonitrile (3.0 mL) and tetrahydrofuran (1.0 mL) before adding 2,2-dimethyl-2,3,4,5-tetrahydrobenzo[f][1,4]oxazepine, hydrochloride (109 mg, 0.508 mmol), sodium iodide (19.05 mg, 0.127 mmol) and K2CO3 (140 mg, 1.017 mmol). The resulting reaction mixture was heated at 40° C. for 17 h then filtered. The filter cake was washed with MeCN (3 mL). The combined filtrate was concentrated under reduced pressure and dissolved in methanol (3.0 mL). NaOH (3 N) (0.678 mL, 2.033 mmol) was added. The resulting reaction mixture was heated twice with microwave at 130° C. for 1 h then was acidified with HCl (3 N) (0.678 mL, 2.033 mmol), concentrated under reduced pressure, and purified by reverse HPLC to give the title compound (28.7 mg, 0.053 mmol, 20.96% yield). LCMS m/z 539.4 (M+H)+, 0.86 min (ret. time). The compounds in Table 6 were prepared by a method similar to the one described for the preparation of rel-(S)-3-(1,4-Dimethyl-1H-benzo[d][1,2,3]triazol-5-yl)-3-(rel-(R)-3-((R)-2-ethyl-2,3-dihydropyrido[3,4-f][1,4]oxazepin-4(5H)-yl)-2,3-dihydro-1H-inden-5-yl)-2,2-dimethylpropanoic acid. As is appreciated by those skilled in the art, these analogous examples may involve variations in general reaction conditions.

TABLE 6

| Ex # | Structure | Name | LCMS [M + H]+ | Retention Time (min) |
|---|---|---|---|---|
| 78 | 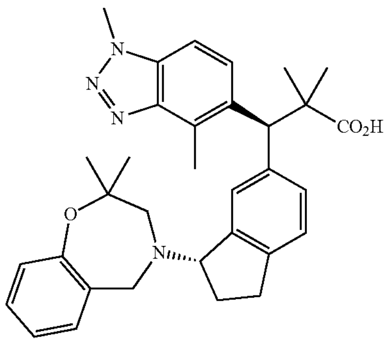 [SMILES: Cc1c([C@H](c2ccc3c(c2)[C@@H](N2Cc4ccccc4OC(C)(C)C2)CC3)C(C)(C)C(=O)O)ccc2c1nnn2C] | rel-(S)-3-(1,4-Dimethyl-1H-benzo[d][1,2,3]triazol-5-yl)-3-(rel-(S)-3-(2,2-dimethyl-2,3-dihydrobenzo[f][1,4]oxazepin-4(5H)-yl)-2,3-dihydro-1H-inden-5-yl)-2,2-dimethylpropanoic acid | 539.5 | 0.86 |
| 79 | 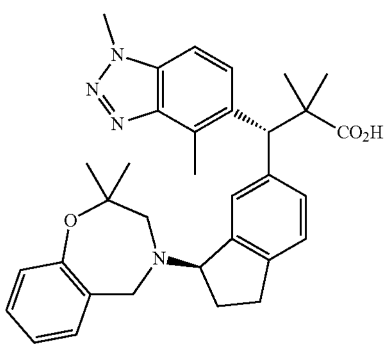 [SMILES: Cc1c([C@@H](c2ccc3c(c2)[C@H](N2Cc4ccccc4OC(C)(C)C2)CC3)C(C)(C)C(=O)O)ccc2c1nnn2C] | rel-(R)-3-(1,4-Dimethyl-1H-benzo[d][1,2,3]triazol-5-yl)-3-(rel-(R)-3-(2,2-dimethyl-2,3-dihydrobenzo[f][1,4]oxazepin-4(5H)-yl)-2,3-dihydro-1H-inden-5-yl)-2,2-dimethylpropanoic acid | 539.5 | 0.83 |
| 80 | 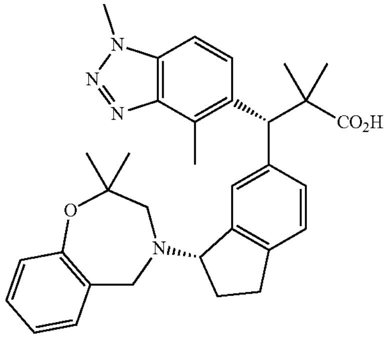 [SMILES: Cc1c([C@@H](c2ccc3c(c2)[C@@H](N2Cc4ccccc4OC(C)(C)C2)CC3)C(C)(C)C(=O)O)ccc2c1nnn2C] | rel-(R)-3-(1,4-Dimethyl-1H-benzo[d][1,2,3]triazol-5-yl)-3-(rel-(S)-3-(2,2-dimethyl-2,3-dihydrobenzo[f][1,4]oxazepin-4(5H)-yl)-2,3-dihydro-1H-inden-5-yl)-2,2-dimethylpropanoic acid | 539.4 | 0.86 |

Example 71 rel-(S)-3-(1,4-Dimethyl-1H-benzo[d][1,2,3]triazol-5-yl)-3-(rel-(S)-3-((R)-2-ethyl-2,3-dihydrobenzo[f][1,4]oxazepin-4(5H)-yl)-2,3-dihydro-1H-inden-5-yl)propanoic Acid

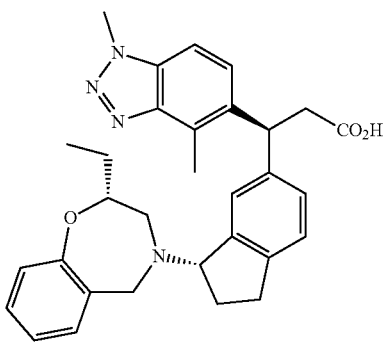 [SMILES: CC[C@@H]1CN([C@H]2CCc3ccc([C@H](CC(=O)O)c4ccc5c(nnn5C)c4C)cc32)Cc2ccccc2O1]

rel-(R)-Ethyl 3-(1,4-dimethyl-1H-benzo[d][1,2,3]triazol-5-yl)-3-(3-oxo-2,3-dihydro-1H-inden-5-yl)propanoate

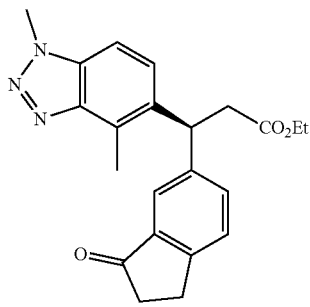 [SMILES: CCOC(=O)C[C@@H](c1ccc2c(c1)C(=O)CC2)c1ccc2c(nnn2C)c1C]

To a mixture of (E)-ethyl 3-(1,4-dimethyl-1H-benzo[d][1,2,3]triazol-5-yl)acrylate (564 mg, 2.3 mmol) in 1,4-dioxane (13 mL) and water (4 ml) was added 6-(4,4,5,5-tetramethyl-1,3,2-dioxaborolan-2-yl)-2,3-dihydro-1H-inden-1-one (891 mg, 3.45 mmol), triethylamine (1.282 mL, 9.20 mmol) and [Rh(cod)Cl]$_2$ (56.7 mg, 0.115 mmol). The resulting reaction mixture was stirred at 90° C. for 17 h then concentrated under reduced pressure, purified via flash chromatography and then further purified by chiral SFC (Column: Chiralpak AD, 20×250, 5u; Co-solvent: 30% Reagent alcohol (90% EtOH, 5% MeOH, 5% IPA); Total flow rate: 50 g/min; Back pressure: 100 bar) to give the title compound (168.0 mg, 0.445 mmol, 19.35% yield). LCMS m/z 378.3 (M+H)$^+$, 0.88 min (ret. time).

rel-(3R)-Ethyl 3-(1,4-dimethyl-1H-benzo[d][1,2,3]triazol-5-yl)-3-(3-hydroxy-2,3-dihydro-1H-inden-5-yl)propanoate

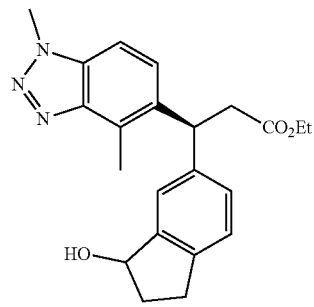 [SMILES: CCOC(=O)C[C@@H](c1ccc2c(c1)C(O)CC2)c1ccc2c(nnn2C)c1C]

To a solution of rel-(R)-ethyl 3-(1,4-dimethyl-1H-benzo[d][1,2,3]triazol-5-yl)-3-(3-oxo-2,3-dihydro-1H-inden-5-yl)propanoate (168 mg, 0.445 mmol) in methanol (3.0 mL) was added NaBH$_4$ (16.84 mg, 0.445 mmol). The resulting reaction was stirred at ambient temperature for 2 h before adding more NaBH$_4$ (8.42 mg, 0.223 mmol). After 1 h, the reaction mixture was concentrated under reduced pressure, apurified via flash chromatography to give the title compound (127.3 mg, 0.335 mmol, 75% yield). LCMS m/z 380.3 (M+H)$^+$, 0.90 min (ret. time).

rel-(S)-Ethyl 3-(1,4-dimethyl-1H-benzo[d][1,2,3]triazol-5-yl)-3-(rel-(S)-3-((R)-2-ethyl-2,3-dihydrobenzo[f][1,4]oxazepin-4(5H yl)-2,3-dihydro-1H-inden-5-yl)propanoate

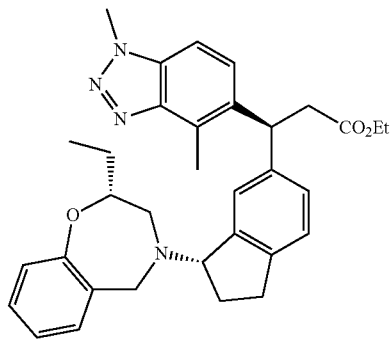 [SMILES: CCOC(=O)C[C@@H](c1ccc2c(c1)[C@@H](N1Cc3ccccc3O[C@H](CC)C1)CC2)c1ccc2c(nnn2C)c1C]

To a mixture of (R)-2-ethyl-2,3,4,5-tetrahydrobenzo[f][1,4]oxazepine, hydrochloride (141 mg, 0.659 mmol) in methanol (5.0 mL) was added K$_2$CO$_3$ (91 mg, 0.659 mmol). The resulting reaction mixture was stirred at ambient temperature for 30 min then filtered, and the filtrated concentrated under reduced pressure. The resulting residue was taken into acetonitrile (5.0 mL) to afford the intermediate solution.

To the mixture of rel-(3R)-ethyl 3-(1,4-dimethyl-1H-benzo[d][1,2,3]triazol-5-yl)-3-(3-hydroxy-2,3-dihydro-1H-inden-5-yl)propanoate (125 mg, 0.329 mmol) in dichloromethane (1.5 mL) was added SOCl$_2$ (0.048 mL, 0.659 mmol). The resulting reaction mixture was stirred at ambient temperature for 10 min then concentrated under reduced pressure. The above intermediate solution, sodium iodide (24.69 mg, 0.165 mmol), sodium and K$_2$CO$_3$ (91 mg, 0.659 mmol) were added. The resulting reaction mixture was heated at 40° C. for 18 h then filtered. The filter cake was washed with MeCN (2 mL). The combined filtrate was concentrated under reduced pressure, purified via flash chromatography then further purified by chiral HPLC to give the title compound (48.0 mg, 0.089 mmol, 27.0% yield). LCMS m/z 539.5 (M+H)+, 0.93 min (ret. time).

rel-(S)-3-(1,4-Dimethyl-1H-benzo[d][1,2,3]triazol-5-yl)-3-(rel-(S)-3-((R)-2-ethyl-2,3-dihydrobenzo[f][1,4]oxazepin-4(5H)-yl)-2,3-dihydro-1H-inden-5-yl)propanoic Acid

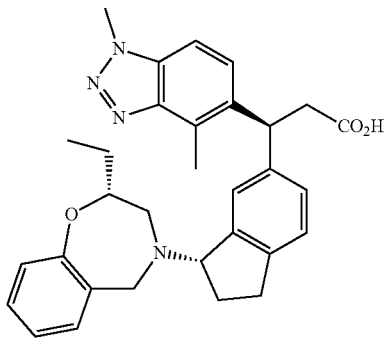 [SMILES: CC[C@@H]1CN([C@H]2CCc3ccc([C@H](CC(=O)O)c4ccc5c(nnn5C)c4C)cc32)Cc2ccccc2O1]

To a solution of rel-(S)-ethyl 3-(1,4-dimethyl-1H-benzo[d][1,2,3]triazol-5-yl)-3-(rel-(S)-3-((R)-2-ethyl-2,3-dihydrobenzo[f][1,4]oxazepin-4(5H)-yl)-2,3-dihydro-1H-inden-5-yl)propanoate (48 mg, 0.089 mmol) in methanol (2.0 mL) was added NaOH (3.0 N) (0.149 mL, 0.446 mmol). The resulting reaction mixture was heated with microwave at 80° C. for 20 min before acidifying with HCl (3.0 N) (0.149 mL, 0.446 mmol). The reaction mixture was concentrated under reduced pressure, and, extracted with DCM (3×2 mL). The combined organic layer was dried over MgSO4, filtered, and concentrated under reduced pressure, and to give the title compound (42.7 mg, 0.084 mmol, 94% yield). LCMS m/z 511.5 (M+H)+, 0.80 min (ret. time).

The compounds in Table 7 were prepared by a method similar to the one described for the preparation of rel-(S)-3-(1,4-Dimethyl-1H-benzo[d][1,2,3]triazol-5-yl)-3-(rel-(S)-3-((R)-2-ethyl-2,3-dihydrobenzo[f][1,4]oxazepin-4(5H)-yl)-2,3-dihydro-1H-inden-5-yl)propanoic acid. As is appreciated by those skilled in the art, these analogous examples may involve variations in general reaction conditions.

TABLE 7

| Ex # | Structure | Name | LCMS [M + H]+ | Retention Time (min) |
|---|---|---|---|---|
| 82 | 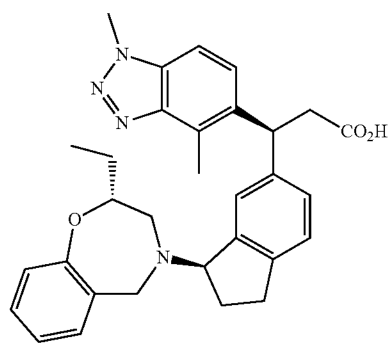 [SMILES: CC[C@@H]1CN([C@@H]2CCc3ccc([C@H](CC(=O)O)c4ccc5c(nnn5C)c4C)cc32)Cc2ccccc2O1] | rel-(S)-3-(1,4-Dimethyl-1H-benzo[d][1,2,3]triazol-5-yl)-3-(rel-(R)-3-((R)-2-ethyl-2,3-dihydrobenzo[f][1,4]oxazepin-4(5H)-yl)-2,3-dihydro-1H-inden-5-yl)propanoic acid | 511.6 | 0.81 |
| 83 | 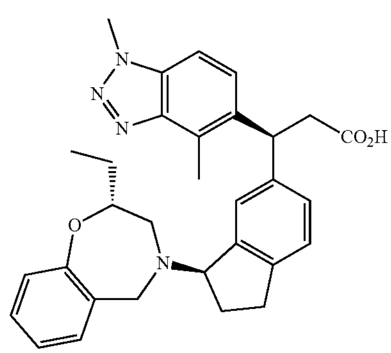 [SMILES: CC[C@@H]1CN([C@@H]2CCc3ccc([C@H](CC(=O)O)c4ccc5c(nnn5C)c4C)cc32)Cc2ccccc2O1] | rel-(R)-3-(1,4-Dimethyl-1H-benzo[d][1,2,3]triazol-5-yl)-3-(rel-(S)-3-((R)-2-ethyl-2,3-dihydrobenzo[f][1,4]oxazepin-4(5H)-yl)-2,3-dihydro-1H-inden-5-yl)propanoic acid | 511.5 | 0.77 |

TABLE 7-continued

| Ex # | Structure | Name | LCMS [M + H]+ | Retention Time (min) |
|---|---|---|---|---|
| 84 | 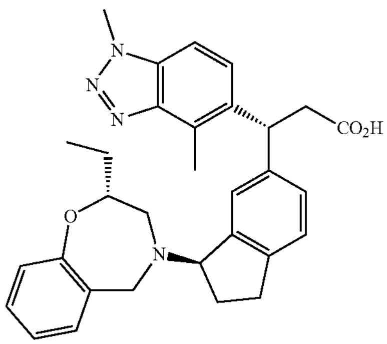 [SMILES: CC[C@@H]1CN([C@@H]2CCc3ccc([C@@H](CC(=O)O)c4ccc5c(nnn5C)c4C)cc32)Cc2ccccc2O1] | rel-(R)-3-(1,4-Dimethyl-1H-benzo[d][1,2,3]triazol-5-yl)-3-(rel-(R)-3-((R)-2-ethyl-2,3-dihydrobenzo[f][1,4]oxazepin-4(5H)-yl)-2,3-dihydro-1H-inden-5-yl)propanoic acid | 511.5 | 0.79 |

Example 85 rel-(S)-3-(1,4-Dimethyl-1H-benzo[d][1,2,3]triazol-5-yl)-3-(rel-(S)-3-((R)-2-ethyl-2,3-dihydropyrido[3,4-f][1,4]oxazepin-4(5H)-yl)-2,3-dihydro-1H-inden-5-yl)-2,2-dimethylpropanoic Acid

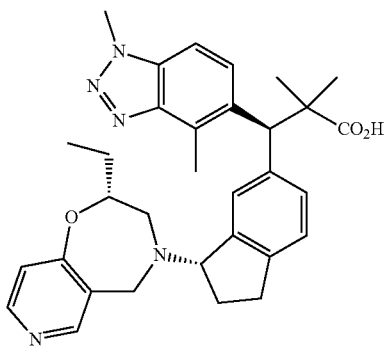 [SMILES: CC[C@@H]1CN([C@H]2CCc3ccc([C@@H](c4ccc5c(nnn5C)c4C)C(C)(C)C(=O)O)cc32)Cc2cnccc2O1]

rel-(S)-Methyl 3-(1,4-dimethyl-1H-benzo[d][1,2,3]triazol-5-yl)-3-(rel-(S)-3-((R)-2-ethyl-2,3-dihydropyrido[3,4-f][1,4]oxazepin-4(5H)-yl)-2,3-dihydro-1H-inden-5-yl)-2,2-dimethylpropanoate

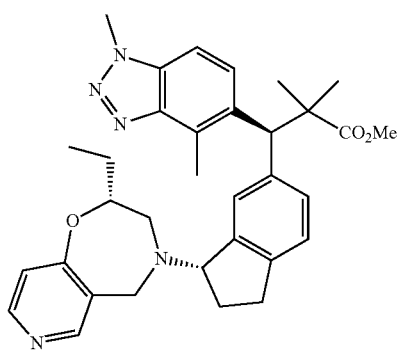 [SMILES: CC[C@@H]1CN([C@H]2CCc3ccc([C@@H](c4ccc5c(nnn5C)c4C)C(C)(C)C(=O)OC)cc32)Cc2cnccc2O1]

To the mixture of (R)-2-ethyl-2,3,4,5-tetrahydropyrido[3,4-f][1,4]oxazepine, hydrochloride (344 mg, 1.600 mmol) in methanol (12 mL) was added K₂CO₃ (332 mg, 2.400 mmol). The resulting reaction mixture was stirred at ambient temperature for 60 min and was filtered, The filtrate was concentrated and the residue taken into acetonitrile (12 mL) to afford the intermediate solution. To the mixture of methyl 3-(1,4-dimethyl-1H-benzo[d][1,2,3]triazol-5-yl)-3-(3-hydroxy-2,3-dihydro-1H-inden-5-yl)-2,2-dimethylpropanoate (315 mg, 0.8 mmol) in dichloromethane (4.0 mL) was added SOCl₂ (0.117 mL, 1.600 mmol). The resulting reaction mixture was stirred at ambient temperature for 20 min then concentrated. The above intermediate solution, sodium iodide (60.0 mg, 0.400 mmol) and K₂CO₃ (332 mg, 2.400 mmol) were added. The resulting reaction mixture was heated at 40° C. for 20 h then filtered. The filter cake was washed with MeCN (6 mL). The combined filtrate was concentrated and purified via flash chromatography, followed by purification with reverse phase HPLC (TFA modifier) then further purified with chiral SFC (Column: Chiralpak AD 20×250 mm, 5u; Co-solvent: 25% EtOH; Flowrate: 50 g/min; Back pressure: 100Bar) to give the title compound (49.1 mg, 0.089 mmol, 11.08% yield). LC/MS: m/z 554.3 (M+H)⁺, 0.88 min (ret. time).

rel-(S)-3-(1,4-Dimethyl-1H-benzo[d][1,2,3]triazol-5-yl)-3-(rel-(S)-3-((R)-2-ethyl-2,3-dihydropyrido[3,4-f][1,4]oxazepin-4(5H)-yl)-2,3-dihydro-1H-inden-5-yl)-2,2-dimethylpropanoic Acid

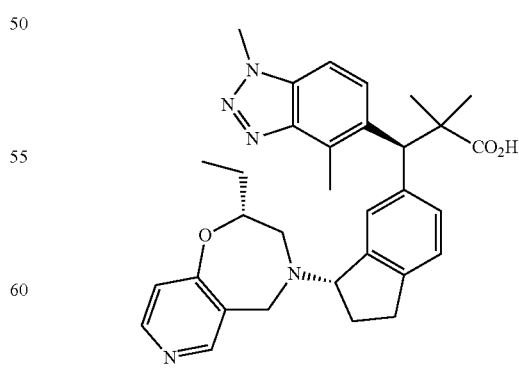

To the solution of methyl 3-(1,4-dimethyl-1H-benzo[d][1,2,3]triazol-5-yl)-3-(3-((R)-2-ethyl-2,3-dihydropyrido[3,4-f][1,4]oxazepin-4(5H)-yl)-2,3-dihydro-1H-inden-5-yl)-2, 2-dimethylpropanoate (49 mg, 0.088 mmol) in methanol (1.5 mL) was added NaOH (3.0 N) (0.147 mL, 0.442 mmol). The resulting reaction mixture was heated twice via microwave at 120° C. for 1 h then acidified with HCl (3.0 N) (0.147 mL, 0.442 mmol), concentrated, and purified by reverse phase to give the title compound (6.9 mg, 0.013 mmol, 14.45% yield). LC/MS: m/z 540.5 (M+H)$^+$, 0.76 min (ret. time).

Example 86

3-(1,4-Dimethyl-1H-benzo[d][1,2,3]triazol-5-yl)-3-(3-(2,2-dimethyl-2,3-dihydropyrido[3,4-f][1,4]oxazepin-4(5H)-yl)-2,3-dihydro-1H-inden-5-yl)-2,2-dimethylpropanoic Acid

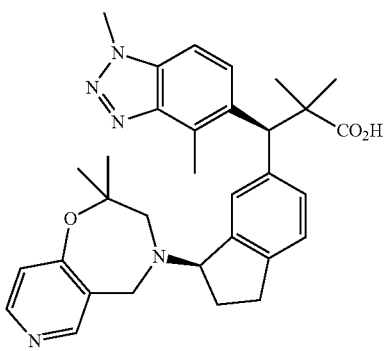 [SMILES: Cc1c([C@H](c2ccc3c(c2)[C@H](N2Cc4cnccc4OC(C)(C)C2)CC3)C(C)(C)C(=O)O)ccc2c1nnn2C]

Methyl 3-(1,4-dimethyl-1H-benzo[d][1,2,3]triazol-5-yl)-3-(3-(2,2-dimethyl-2,3-dihydropyrido[3,4-f][1,4]oxazepin-4(5H)-yl)-2,3-dihydro-1H-inden-5-yl)-2,2-dimethylpropanoate

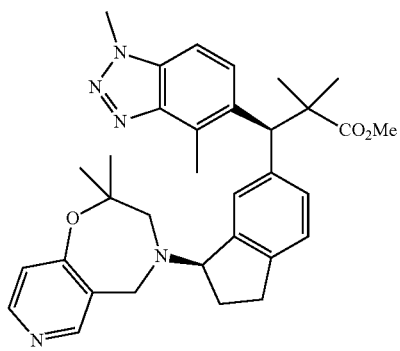 [SMILES: COC(=O)C(C)(C)[C@@H](c1ccc2c(c1)[C@H](N1Cc3cnccc3OC(C)(C)C1)CC2)c1ccc2c(nnn2C)c1C]

To the mixture of 2,2-dimethyl-2,3,4,5-tetrahydropyrido[3,4-f][1,4]oxazepine, hydrochloride (0.344 g, 1.600 mmol) in methanol (12 mL) was added $K_2CO_3$ (0.332 g, 2.400 mmol). The resulting reaction mixture was stirred at ambient temperature for 60 min and was filtered. The filtrate was concentrated and the residue taken into acetonitrile (12 mL) to afford intermediate solution.

To the mixture of methyl 3-(1,4-dimethyl-1H-benzo[d][1,2,3]triazol-5-yl)-3-(3-hydroxy-2,3-dihydro-1H-inden-5-yl)-2,2-dimethylpropanoate (0.315 g, 0.8 mmol) in dichloromethane (4.0 mL) was added $SOCl_2$ (0.117 mL, 1.600 mmol). The resulting reaction mixture was stirred at ambient temperature for 40 min after which the above intermediate solution, sodium iodide (0.060 g, 0.400 mmol) and $K_2CO_3$ (0.332 g, 2.400 mmol) were added. The resulting reaction mixture was heated at 40° C. for 67 h. The reaction mixture was filtered. The filter cake was washed with MeCN (6 mL). The combined filtrate was concentrated and purified with reverse phase HPLC (TFA modifier) and further with chiral SFC (Column: Chiralpak AD 20×250 mm, 5u; Co-solvent; 5% EtOH; Flowrate: 50 g/min; Back pressure: 100Bar) to give the title compound (52.9 mg, 0.096 mmol, 11.94% yield). LC/MS: m/z 554.4 (M+H)$^+$, 0.96 min (ret. time).

3-(1,4-Dimethyl-1H-benzo[d][1,2,3]triazol-5-yl)-3-(3-(2,2-dimethyl-2,3-dihydropyrido[3,4-f][1,4]oxazepin-4(5H)-yl)-2,3-dihydro-1H-inden-5-yl)-2,2-dimethylpropanoic Acid

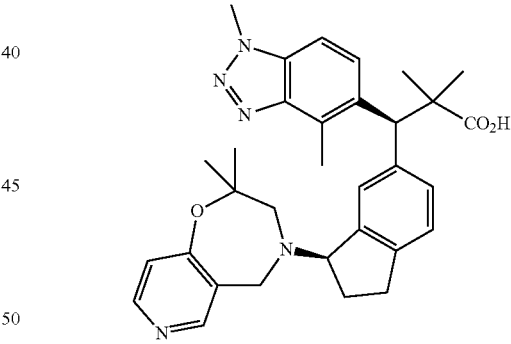

To the solution of methyl 3-(1,4-dimethyl-1H-benzo[d][1,2,3]triazol-5-yl)-3-(3-(2,2-dimethyl-2,3-dihydropyrido[3,4-f][1,4]oxazepin-4(5H)-yl)-2,3-dihydro-1H-inden-5-yl)-2,2-dimethylpropanoate (52.9 mg, 0.096 mmol) in methanol (1.2 mL) was added NaOH (3.0 N) (0.159 mL, 0.478 mmol) and the reaction heated 3 times via microwave at 130° C. for 1 h. The reaction mixture was acidified with HCl (3.0 N) (0.159 mL, 0.478 mmol), concentrated, and purified with reverse phase HPLC (formic acid modifier) to give the title compound (35.8 mg, 0.061 mmol, 64.0% yield). LC/MS: m/z 540.5 (M+H)$^+$, 0.97 min (ret. time).

Example 87

5-(1-Ethyl-1H-1,2,3-triazol-4-yl)-3-(3-((R)-2-ethyl-2,3-dihydropyrido[3,4-f][1,4]oxazepin-4(5H)-yl)-2,3-dihydro-1H-inden-5-yl)-2,2-dimethylpentanoic Acid

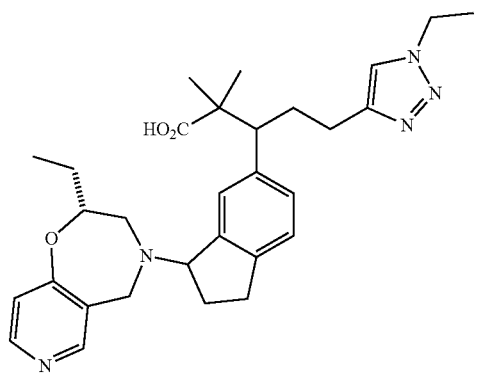 [SMILES: CC[C@@H]1CN(C2CCc3ccc(C(CCc4cn(CC)nn4)C(C)(C)C(=O)O)cc32)Cc2cnccc2O1]

6-Bromo-1-((4-methoxybenzyl)oxy)-2,3-dihydro-1H-indene

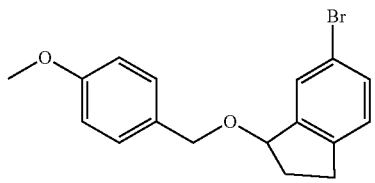 [SMILES: COc1ccc(COC2CCc3ccc(Br)cc32)cc1]

6-Bromo-2,3-dihydro-1H-inden-1-ol (8.6 g, 40.4 mmol) was dissolved in DMF (50 mL) and cooled to 4° C. and 60% sodium hydride (3.23 g, 81 mmol) was added in one portion. Stir at 23° C. for 1 h and then cooled again to 10° C. with the ice bath and 1-(chloromethyl)-4-methoxybenzene (9.48 g, 60.5 mmol) was added. Stirred at 23° C. for 14 h. The reaction was quenched with water 25 mL stirred 3 min and then diluted with EtOAc (200 mL) and more water (25 mL). Phases were separated and the aq was extracted with an additional 2×75 mL EtOAc. The combined EtOAc was washed with water (75 mL) and then satd aq NaCl (50 mL), dried (Na₂SO₄), concentrated and the residual amber oil was purified on an ISCO silica cartridge (120 g) with a Combiflash Companion, eluting at 85 mL/min with a gradient running from hexanes to 10% EtOAc/hexanes over 30 min. The desired fractions were pooled to afford 6-bromo-1-((4-methoxybenzyl)oxy)-2,3-dihydro-1H-indene (11.76 g, 35.3 mmol, 87% yield) as a clear oil. ¹H NMR (400 MHz, CHLOROFORM-d) δ 7.46-7.61 (m, 1H), 7.23-7.44 (m, 3H), 7.06-7.18 (m, 1H), 6.81-7.00 (m, 2H), 4.89-5.08 (m, 1H), 4.38-4.74 (m, 2H), 3.84 (s, 3H), 2.95-3.18 (m, 1H), 2.92-3.15 (m, 1H), 2.65-2.89 (m, 1H), 2.30-2.50 (m, 1H), 2.05-2.22 (m, 1H).

1-(3-((4-Methoxybenzyl)oxy)-2,3-dihydro-1H-inden-5-yl)-5-(trimethylsilyl)pent-4-yn-1-ol

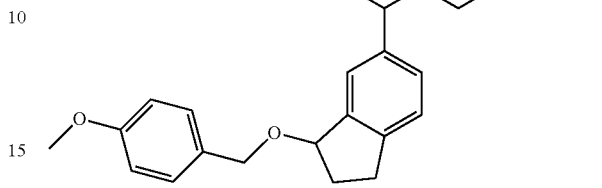

6-Bromo-1-((4-methoxybenzyl)oxy)-2,3-dihydro-1H-indene (3.3005 g, 9.90 mmol) was dissolved in THF (66.0 ml) and cooled to −70° C. 1.6M butyllithium (8.05 ml, 12.88 mmol) was added dropwise. The resulting mixture was stirred at −65--75° C. for 30 min and then 5-(trimethylsilyl)pent-4-ynal (2.978 g, 19.30 mmol) in THF (3 mL) was added (T<−65° C.) and the mixture was stirred at −75° C. for 2 h. The reaction was diluted with water, and EtOAc. The phases were shaken together and the aq was extracted again with EtOAc and the combined EtOAc was washed with water and satd aq NaCl, dried (MgSO4) and filtered. The filtrate was concentrated and purified on an ISCO silica cartridge (40 g) with an ISCO Combiflash Companion, with a gradient running from hexanes to 30% EtOAc/hexanes over 20 min. The desired fractions were pooled to afford 1-(3-((4-methoxybenzyl)oxy)-2,3-dihydro-1H-inden-5-yl)-5-(trimethylsilyl)pent-4-yn-1-ol (3.6339 g, 8.89 mmol, 90% yield) as a yellow oil. ¹H NMR (400 MHz, CHLOROFORM-d) δ 7.39-7.44 (m, 1H), 7.31-7.37 (m, 2H), 7.15-7.30 (m, 2H), 6.76-6.96 (m, 2H), 4.98-5.08 (m, 1H), 4.76-4.90 (m, 1H), 4.53-4.68 (m, 2H), 3.81-3.88 (m, 3H), 3.02-3.19 (m, 1H), 2.75-2.90 (m, 1H), 2.26-2.47 (m, 3H), 2.08-2.19 (m, 4H), 0.19 (s, 9H).

(5-Bromo-5-(3-((4-methoxybenzyl)oxy)-2,3-dihydro-1H-inden-5-yl)pent-1-yn-1-yl)trimethylsilane

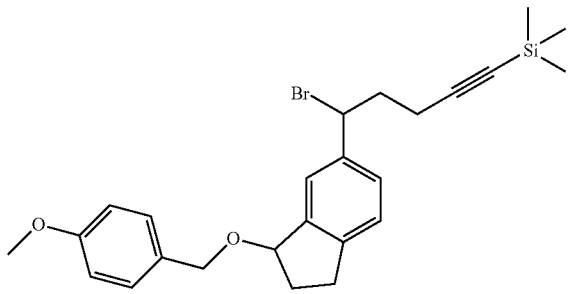

To a solution of 1-(3-((4-methoxybenzyl)oxy)-2,3-dihydro-1H-inden-5-yl)-5-(trimethylsilyl)pent-4-yn-1-ol (3.6339 g, 8.89 mmol) in DCM (44.5 ml) was added in succession polymer bound PPh₃ (2.39 mmol/g) (3.72 g, 8.89 mmol) and carbon tetrabromide (3.54 g, 10.67 mmol). Stirred 3 days and more CBr4 (2.95 g, 8.89 mmol) was added. After an additional 1 h the reaction was concentrated and filtered and the crude product was purified on an ISCO silica cartridge (40 g) with a flash chromatograph, eluting at 35 mL/min with a gradient from hexanes to 10% EtOAc/hexanes. The desired fractions were pooled and concentrated to afford (5-bromo-5-(3-((4-methoxybenzyl)oxy)-2,3-dihydro-1H-inden-5-yl)pent-1-yn-1-yl)trimethylsilane (1.31 g, 2.78 mmol, 31.2% yield) as a clear oil. $^1$H NMR (400 MHz, CHLOROFORM-d) δ 7.17-7.50 (m, 5H), 6.85-7.00 (m, 2H), 5.10-5.21 (m, 1H), 4.92-5.04 (m, 1H), 4.51-4.70 (m, 2H), 3.72-3.92 (m, 3H), 3.01-3.17 (m, 1H), 2.72-2.90 (m, 1H), 2.22-2.60 (m, 5H), 2.06-2.21 (m, 1H).

Benzyl 3-(3-((4-methoxybenzyl)oxy)-2,3-dihydro-1H-inden-5-yl)-2,2-dimethyl-7-(trimethylsilyl)hept-6-ynoate

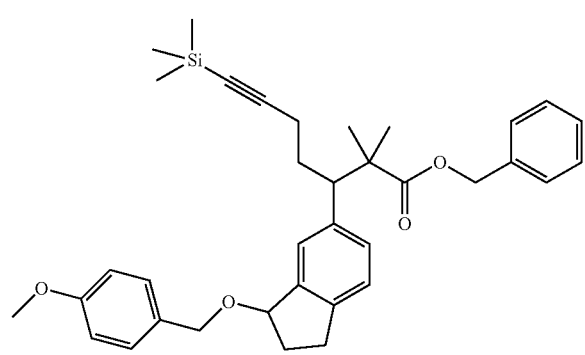 [SMILES: COc1ccc(COC2CCc3ccc(C(CCC#C[Si](C)(C)C)C(C)(C)C(=O)OCc4ccccc4)cc32)cc1]

A −70° C. solution of diisopropylamine (4.06 ml, 28.5 mmol) in THF (23.75 ml) was treated with 1.6 M n-butyllithium (8.91 ml, 14.25 mmol) and stirred at −70° C. for 15 min. Benzyl isobutyrate (4.22 ml, 23.75 mmol) was added to the −70° C. solution dropwise. Stirred at −70° C. for 45 min, then warmed to −45 C for 5 min, and cooled back down to −70° C. (5-bromo-5-(3-((4-methoxybenzyl)oxy)-2,3-dihydro-1H-inden-5-yl)pent-1-yn-1-yl)trimethylsilane (2.24 g, 4.75 mmol) in THF (3 mL) was added dropwise to the enolate followed by dry 1,3-dimethyltetrahydropyrimidin-2(1H)-one (5.06 ml, 42.0 mmol). After 1 hour stirring at −78° C. the reaction was warmed to −45° C. After 2.5 hours at −45, the reaction was quenched by the addition of NH$_4$Cl, and the aqueous layer was extracted 3× with EtOAc. The crude oil purified on a 24 g silica cartridge with 0-20% hex/(3:1 EtOAc:EtOH) over 20 min. Rechromatography with a second 24 g silica cartridge with 0-20% hex/EtOAc over 20 min afforded the purified. benzyl 3-(3-((4-methoxybenzyl)oxy)-2,3-dihydro-1H-inden-5-yl)-2,2-dimethyl-7-(trimethylsilyl)hept-6-ynoate (1.2886 g, 2.265 mmol, 47.7% yield) as a clear oil. $^1$H NMR (400 MHz, CHLOROFORM-d) δ 7.26-7.45 (m, 9H), 7.12-7.23 (m, 2H), 7.02-7.10 (m, 1H), 6.85-6.96 (m, 2H), 5.02-5.15 (m, 2H), 4.94-5.00 (m, 1H), 4.40-4.66 (m, 2H), 3.74-3.95 (m, 3H), 3.02-3.17 (m, 2H), 2.68-2.90 (m, 1H), 2.28-2.43 (m, 1H), 1.76-2.21 (m, 5H), 1.18-1.25 (m, 3H), 1.06-1.16 (m, 3H), 0.10-0.32 (m, 9H); LC/MS (ES+) [M+Na]$^+$=591.3 (1.82 min)

Benzyl 3-(3-((4-methoxybenzyl)oxy)-2,3-dihydro-1H-inden-5-yl)-2,2-dimethylhept-6-ynoate

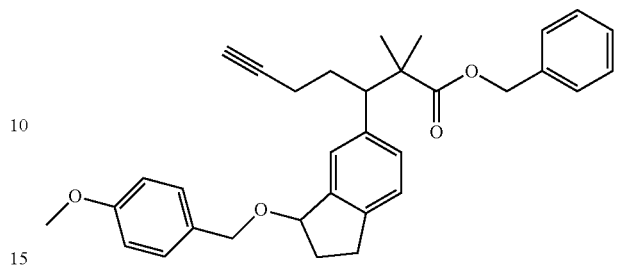

K$_2$CO$_3$ (1.230 g, 8.90 mmol) was added to a solution of benzyl 3-(3-((4-methoxybenzyl)oxy)-2,3-dihydro-1H-inden-5-yl)-2,2-dimethyl-7-(trimethylsilyl)hept-6-ynoate (1.260 g, 2.215 mmol) in Methanol (11.08 ml). After 3 h the reaction was diluted with water, and extracted 3× with DCM. The organic layers were dried with MgSO$_4$, and concentrated to afford benzyl 3-(3-((4-methoxybenzyl)oxy)-2,3-dihydro-1H-inden-5-yl)-2,2-dimethylhept-6-ynoate (1.11 g, 2.235 mmol, 101% yield) as a colorless oil. LC/MS (ES+) [M+Na]$^+$=519.3 (1.61 min).

Benzyl 5-(1-ethyl-1H-1,2,3-triazol-4-yl)-3-(3-((4-methoxybenzyl)oxy)-2,3-dihydro-1H-inden-5-yl)-2,2-dimethylpentanoate

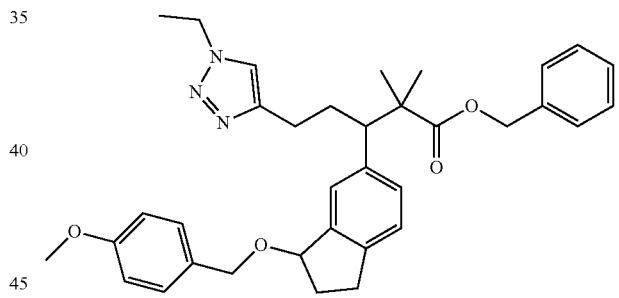

Sodium azide (0.363 g, 5.59 mmol), iodoethane (0.449 ml, 5.59 mmol), copper(I) iodide (0.064 g, 0.335 mmol) and N-ethyl-N-isopropylpropan-2-amine (0.078 ml, 0.447 mmol) were added to a solution of benzyl 3-(3-((4-methoxybenzyl)oxy)-2,3-dihydro-1H-inden-5-yl)-2,2-dimethylhept-6-ynoate (1.11 g, 2.235 mmol) in tert-butanol (5.6 ml)/water (5.6 ml). This mixture was heated via microwave to 70° C. for 1 hour. The reaction was diluted with water and EtOAc. The aqueous was extracted 3× with EtOAc, and the combined organic layers were dried over MgSO$_4$ and concentrated and the crude oil was purified on an ISCO 24 g silica gel cartridge eluting with 0-90% hex/EtOAc over 20 min. The desired fractions were collected to give benzyl 5-(1-ethyl-1H-1,2,3-triazol-4-yl)-3-(3-((4-methoxybenzyl)oxy)-2,3-dihydro-1H-inden-5-yl)-2,2-dimethylpentanoate (1.0147 g, 1.787 mmol, 80% yield) as a yellow oil. LC/MS (ES$^+$) [M+H]$^+$=568.4 (1.46 min).

Benzyl 5-(1-ethyl-1H-1,2,3-triazol-4-yl)-3-(3-hydroxy-2,3-dihydro-1H-inden-5-yl)-2,2-dimethylpentanoate

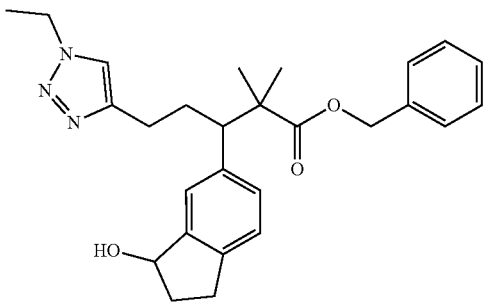 [SMILES: CCn1cc(CCC(c2ccc3c(c2)C(O)CC3)C(C)(C)C(=O)OCc2ccccc2)nn1]

Ceric ammonium nitrate (1.936 g, 3.53 mmol) was added to a solution of benzyl 5-(1-ethyl-1H-1,2,3-triazol-4-yl)-3-(3-((4-methoxybenzyl)oxy)-2,3-dihydro-1H-inden-5-yl)-2,2-dimethylpentanoate (1.0023 g, 1.765 mmol) in acetonitrile (7.94 ml) and water (0.883 ml). After 18 h the mixture was diluted with DCM and NaHCO$_3$. The aqueous layers were extracted 3x with DCM. The combined organic layers were dried with MgSO$_4$ and concentrated. The crude oil was purified on a 24 g ISCO silica column, 0-100% hex/EtOAc to give benzyl 5-(1-ethyl-1H-1,2,3-triazol-4-yl)-3-(3-hydroxy-2,3-dihydro-1H-inden-5-yl)-2,2-dimethylpentanoate (150 mg, 0.335 mmol, 18.98% yield). LC/MS (ES+) [M−OH]$^+$=430.2 (1.04 min).

5-(1-Ethyl-1H-1,2,3-triazol-4-yl)-3-(3-((R)-2-ethyl-2,3-di hydropyrido[3,4-f][1,4]oxazepin-4(5H)-yl)-2,3-dihydro-1H-inden-5-yl)-2,2-dimethylpentanoic Acid

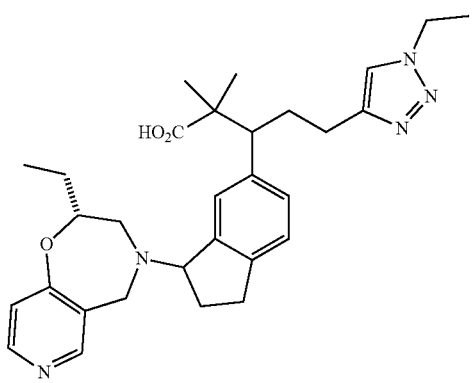 [SMILES: CC[C@@H]1CN(C2CCc3ccc(C(CCc4cn(CC)nn4)C(C)(C)C(=O)O)cc32)Cc2cnccc2O1]

K$_2$CO$_3$ (46.3 mg, 0.335 mmol) was added to a solution of (R)-2-ethyl-2,3,4,5-tetrahydropyrido[3,4-f][1,4]oxazepine hydrochloride (39.8 mg, 0.223 mmol) in methanol (1 mL). The mixture was stirred for 20 minutes, and the solids were filtered off. The filtrate was then concentrated under vacuum. The concentrated free base was then dissolved in acetonitrile (2.000 mL) to afford solution A. SOCl$_2$ (8.15 µl, 0.112 mmol) was added to a solution of benzyl 5-(1-ethyl-1H-1,2,3-triazol-4-yl)-3-(3-hydroxy-2,3-dihydro-1H-inden-5-yl)-2,2-dimethylpentanoate (50 mg, 0.112 mmol) in DCM (1.000 mL). After 20 minutes the solution was concentrated under vacuum to give intermediate benzyl 3-(3-chloro-2,3-dihydro-1H-inden-5-yl)-5-(1-ethyl-1H-1,2,3-triazol-4-yl)-2,2-dimethylpentanoate. The Acetonitrile (2.000 mL) and the free base (R)-2-ethyl-2,3,4,5-tetrahydropyrido[3,4-f][1,4]oxazepine (39.8 mg, 0.223 mmol) solution (solution A) was added to the benzyl 3-(3-chloro-2,3-dihydro-1H-inden-5-yl)-5-(1-ethyl-1H-1,2,3-triazol-4-yl)-2,2-dimethylpentanoate intermediate, along with K$_2$CO$_3$ (46.3 mg, 0.335 mmol) and sodium iodide (8.37 mg, 0.056 mmol). The mixture was warmed to 40° C. and the reaction was stirred for 18 h, the reaction was diluted with water, and the aqueous layer was extracted 3x with EtOAc. The organic layers were dried over MgSO$_4$, and concentrated. The crude residue was dissolved in 10 mL of MeOH, 3 M NaOH (0.186 mL, 0.559 mmol) was added, and the reaction was heated in the microwave to 100° C. for 5H, 1 mL of DMSO was added, and the volatiles were removed under reduced pressure. The DMSO solution was acidified to ~pH 5 with 1N HCl. The water was were removed under reduced pressure, and the mixture was filtered through a 0.45 micron syringe filter and purified reverse phase preparative HPLC using neutral conditions. The resulting purified product was further purified by reverse phase preparative HPLC using formic acid as a solvent modifier to afford 5-(1-ethyl-1H-1,2,3-triazol-4-yl)-3-(3-((R)-2-ethyl-2,3-dihydropyrido[3,4-f][1,4]oxazepin-4(5H)-yl)-2,3-dihydro-1H-inden-5-yl)-2,2-dimethylpentanoic acid (4 mg, 7.73 µmol, 6.92% yield). LC/MS (ES$^+$) [M+H]$^+$=518.4 (0.78 min).

What is claimed is:

1. A method of treating a neurologic disease which is Parkinson's disease (PD), Alzheimer's disease (AD), Friedreich's Ataxia (FA), amyotrophic lateral sclerosis (ALS), or multiple sclerosis comprising administering to a human in need thereof a therapeutically effective amount of a compound of Formula (I):

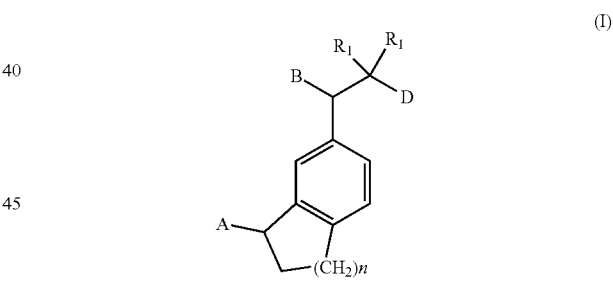

wherein:
- B is benzotriazolyl, phenyl, triazolopyridinyl, or —(CH$_2$)$_2$ triazolyl each of which is unsubstituted or substituted by 1, 2, or 3 substituents independently selected from —C$_{1-3}$alkyl, —O—C$_{1-3}$alkyl, CN, —(CH$_2$)$_2$—O—(CH$_2$)$_2$—OR$_4$ and halo;
- D is —C(O)OH, —C(O)NHSO$_2$CH$_3$, —SO$_2$NHC(O)CH$_3$, 5-(trifluoromethyl)-4H-1,2,4-triazol-2-yl, or tetrazolyl;
- R$_1$ is independently hydrogen, C$_{1-3}$ alkyl, F, C$_{3-6}$spirocycloalkyl, oxetane, or the two R$_1$ groups together with the carbon to which they are attached form a cyclopropyl group;
- R$_4$ is hydrogen or C$_{1-3}$ alkyl;
- A is tetrahydrobenzoxazepinyl, tetrahydrobenzazepinyl, tetrahydroimidazodiazepinyl, or tetrahydro-pyrido-oxazepinyl, each of which is unsubstituted or substituted by 1, 2, or 3 substituents independently selected from —C$_{1-3}$ alkyl, halo, CN, —OC$_{1-3}$alkyl, —CH$_2$—O—CH$_3$, C$_{3-6}$spirocycloalkyl, and OH;
n is 1 or 2;
or a pharmaceutically acceptable salt thereof.

2. A method of treating a neurologic disease which is Parkinson's disease (PD), Alzheimer's disease (AD), Friedreich's Ataxia (FA), amyotrophic lateral sclerosis (ALS), or multiple sclerosis comprising administering to a human in need thereof a therapeutically effective amount of a compound of Formula (II):

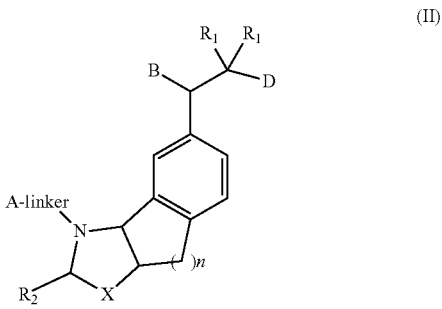

wherein:
B is benzotriazolyl, phenyl, triazolopyridinyl, or —(CH$_2$)$_2$ triazolyl each of which may be unsubstituted or substituted by 1, 2, or 3 substituents independently chosen from —C$_{1-3}$alkyl, —O—C$_{1-3}$alkyl, CN, —(CH$_2$)$_2$—O—(CH$_2$)$_2$—OR$_4$ and halo;
D is —C(O)OH, —C(O)NHSO$_2$CH$_3$, —SO$_2$NHC(O)CH$_3$, 5-(trifluoromethyl)-4H-1,2,4-triazol-2-yl, or tetrazolyl;
R$_1$ is independently hydrogen, C$_{1-3}$ alkyl, F, C$_{3-6}$spirocycloalkyl, oxetane, or the two R, groups together with the carbon to which they are attached form a cyclopropyl group;
R$_2$ is =O or hydrogen;
R$_4$ is hydrogen or C$_{1-3}$ alkyl;
Linker is —CH$_2$—, —O—C(O)—, —CH$_2$—C(O)—, —C(O)—, —CH(CH$_3$)—C(O)—, or —N(CH$_3$)—C(O)—;
A is cyclohexyl, cyclopentyl, phenyl or decahydronapthalenyl; all of which may be unsubstituted or independently substituted by C$_{1-3}$ alkyl, CN, and halo;
or A is C$_{4-5}$ alkyl which may be substituted by —OC$_{1-3}$ alkyl;
n is 1 or 2;
X is CH$_2$ or O;
or a pharmaceutically acceptable salt thereof.

3. The method of claim 1 wherein:
B is benzotriazolyl or —(CH$_2$)$_2$ triazolyl each of which may be unsubstituted or substituted by 1, 2, or 3 substituents independently chosen from —C$_{1-3}$alkyl and halo;
D is —C(O)OH;
R$_1$ is independently hydrogen or methyl or the two R1 groups together with the carbon to which they are attached form a cyclopropyl group;
A is tetrahydrobenzoxazepinyl, tetrahydrobenzazepinyl, or tetrahydro-pyrido-oxazepinyl, all of which may be unsubstituted or substituted by 1, 2, or 3 substituents chosen from: —C$_{1-3}$ alkyl, halo, CN, and —OC$_{1-3}$alkyl; and
n is 1 or 2
or a pharmaceutically acceptable salt thereof.

4. The method of claim 1, wherein:
B is benzotriazolyl or phenyl each of which may be unsubstituted or substituted by 1, 2, or 3 substituents independently chosen from —C$_{1-3}$alkyl, halo and CN;
D is —C(O)OH;
R$_1$ is independently hydrogen or C$_{1-3}$ alkyl;
A is tetrahydrobenzoxazepinyl, tetrahydrobenzazepinyl, tetrahydroimidazodiazepinyl, or tetrahydro-pyrido-oxazepinyl, all of which may be unsubstituted or substituted by 1, 2, or 3 substituents independently chosen from —C$_{1-3}$ alkyl, halo, CN, —OC$_{1-3}$alkyl, —CH$_2$—O—CH$_3$, C$_{3-6}$spirocycloalkyl, and OH; and
n is 1;
or a pharmaceutically acceptable salt thereof.

5. The method of claim 1, wherein:
B is benzotriazolyl which may be unsubstituted or substituted by 1, 2, or 3 substituents independently chosen from —C$_{1-3}$alkyl;
D is —C(O)OH;
R$_1$ is independently hydrogen or C$_{1-3}$ alkyl;
A is tetrahydrobenzoxazepinyl which may be unsubstituted or substituted by 1, 2, or 3 substituents independently chosen from —C$_{1-3}$ alkyl, —OC$_{1-3}$alkyl, CN and halo; and
n is 1;
or a pharmaceutically acceptable salt thereof.

6. The method of claim 2 wherein:
B is benzotriazolyl or —(CH$_2$)$_2$ triazolyl each of which may be unsubstituted or substituted by 1, 2, or 3 substituents independently chosen from —C$_{1-3}$alkyl and halo;
D is —C(O)OH;
R$_1$ is independently hydrogen or methyl or the two R$_1$ groups together with the carbon to which they are attached form a cyclopropyl group;
R$_2$ is =O or hydrogen;
Linker is —CH$_2$—, —O—C(O)—, —CH(CH$_3$)—C(O)—, or —N(CH$_3$)—C(O)—;
A is cyclohexyl or cyclopentyl, all of which may be unsubstituted or independently substituted by C$_{1-3}$ alkyl, CN, and halo;
n is 1; and
X is CH$_2$ or O;
or a pharmaceutically acceptable salt thereof.

7. The method of claim 2, wherein:
B is benzotriazolyl or —(CH$_2$)$_2$ triazolyl each of which may be unsubstituted or substituted by 1, 2, or 3 substituents independently chosen from —C$_{1-3}$alkyl and —O—C$_{1-3}$alkyl;
D is —C(O)OH;
R$_1$ is independently hydrogen;
R$_2$ is hydrogen;
Linker is —CH$_2$—, —O—C(O)—, —CH$_2$—C(O)—;
A is cyclohexyl, phenyl or decahydronapthalenyl; all of which may be unsubstituted or independently substituted by C$_{1-3}$ alkyl, CN, and halo;
or A is C$_{4-5}$ alkyl which may be substituted by —OC$_{1-3}$ alkyl;
n is 1; and
X is CH$_2$;
or a pharmaceutically acceptable salt thereof.

8. The method of claim 2, wherein:
B is benzotriazolyl or —(CH$_2$)$_2$ triazolyl each of which may be unsubstituted or substituted by 1, 2, or 3 substituents independently chosen from —C$_{1-3}$alkyl and —O—C$_{1-3}$alkyl;
D is —C(O)OH;

$R_1$ is independently hydrogen;
$R_2$ is =O;
Linker is —CH$_2$—, —O—C(O)—, —CH$_2$—C(O)—;
A is cyclohexyl, phenyl or decahydronapthalenyl; all of which may be unsubstituted or independently substituted by $C_{1-3}$ alkyl, CN, and halo;
or A is $C_{4-5}$ alkyl which may be substituted by —OC$_{1-3}$ alkyl;
n is 1; and
X is CH$_2$ or O;
or a pharmaceutically acceptable salt thereof.

9. A method of treating a neurologic disease which is Parkinson's disease (PD), Alzheimer's disease (AD), Friedreich's Ataxia (FA), amyotrophic lateral sclerosis (ALS), or multiple sclerosis comprising administering to a human in need thereof a therapeutically effective amount of a compound which is 3-(3-{2,2-dimethyl-2H,3H,4H,5H-pyrido[3,2-f][1,4]oxazepin-4-yl}-2,3-dihydro-1H-inden-5-yl)-3-(4-fluoro-2-methylphenyl)propanoic acid, or a pharmaceutically acceptable salt thereof.

10. A method of treating a neurologic disease which is Parkinson's disease (PD), Alzheimer's disease (AD), Friedreich's Ataxia (FA), amyotrophic lateral sclerosis (ALS), or multiple sclerosis comprising administering to a human in need thereof a therapeutically effective amount of a compound which is 3-[3-(2,2-dimethyl-2,3,4,5-tetrahydro-1,4-benzoxazepin-4-yl)-2,3-dihydro-1H-inden-5-yl]-3-(4-fluoro-2-methylphenyl)-2,2-dimethylpropanoic acid, or a pharmaceutically acceptable salt thereof.

* * * * *